(12) United States Patent
Marder et al.

(10) Patent No.: US 7,842,830 B2
(45) Date of Patent: Nov. 30, 2010

(54) TRANSITION-METAL CHARGE-TRANSPORT MATERIALS, METHODS OF FABRICATION THEREOF, AND METHODS OF USE THEREOF

(75) Inventors: Seth Marder, Atlanta, GA (US); Jian-Yang Cho, Blue Bell, PA (US); Bernard Kippelen, Decatur, GA (US); Benoit Domercq, Atlanta, GA (US); Steve Barlow, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 546 days.

(21) Appl. No.: 11/629,268

(22) PCT Filed: Jun. 14, 2005

(86) PCT No.: PCT/US2005/020872

§ 371 (c)(1),
(2), (4) Date: Jan. 7, 2008

(87) PCT Pub. No.: WO2005/123754

PCT Pub. Date: Dec. 29, 2005

(65) Prior Publication Data

US 2008/0121870 A1    May 29, 2008

Related U.S. Application Data

(60) Provisional application No. 60/579,376, filed on Jun. 14, 2004.

(51) Int. Cl.
*C07F 15/00* (2006.01)
*B32B 9/00* (2006.01)
*H01L 51/00* (2006.01)

(52) U.S. Cl. .................. 556/146; 136/252; 136/256; 252/301.16; 252/301.36; 257/40; 313/504; 313/506; 428/690; 428/917; 525/13; 525/17; 526/90; 526/161; 549/3; 549/206; 556/113; 556/136; 556/137

(58) Field of Classification Search ............... 136/252, 136/256; 252/301.16, 301.36; 257/40; 313/504, 313/506; 428/690, 917; 525/13, 17; 526/90, 526/161; 556/113, 136, 137, 146; 549/3, 549/206

See application file for complete search history.

(56) References Cited

U.S. PATENT DOCUMENTS

| 3,398,167 | A | | 8/1968 | Mahler et al. |
| 3,875,199 | A | | 4/1975 | Bloom |
| 3,928,477 | A | * | 12/1975 | Field et al. .................. 568/798 |

FOREIGN PATENT DOCUMENTS

| DE | 4202037 | 7/1993 |
| WO | WO 91/12555 | 8/1991 |

OTHER PUBLICATIONS

Int'l Search Report, Jul. 22, 2006.

* cited by examiner

*Primary Examiner*—Porfirio Nazario Gonzalez
(74) *Attorney, Agent, or Firm*—Thomas, Kayden, Horstemeyer & Risley, LLP

(57) ABSTRACT

Briefly described, embodiments of this disclosure include transition-metal charge-transport materials, methods of forming transition-metal charge-transport materials, and methods of using the transition-metal charge-transport materials.

20 Claims, 71 Drawing Sheets

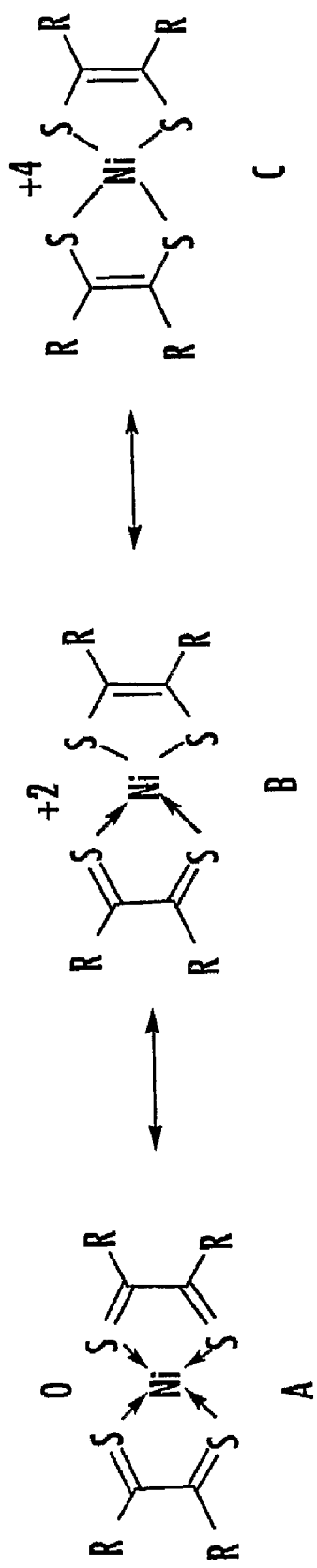

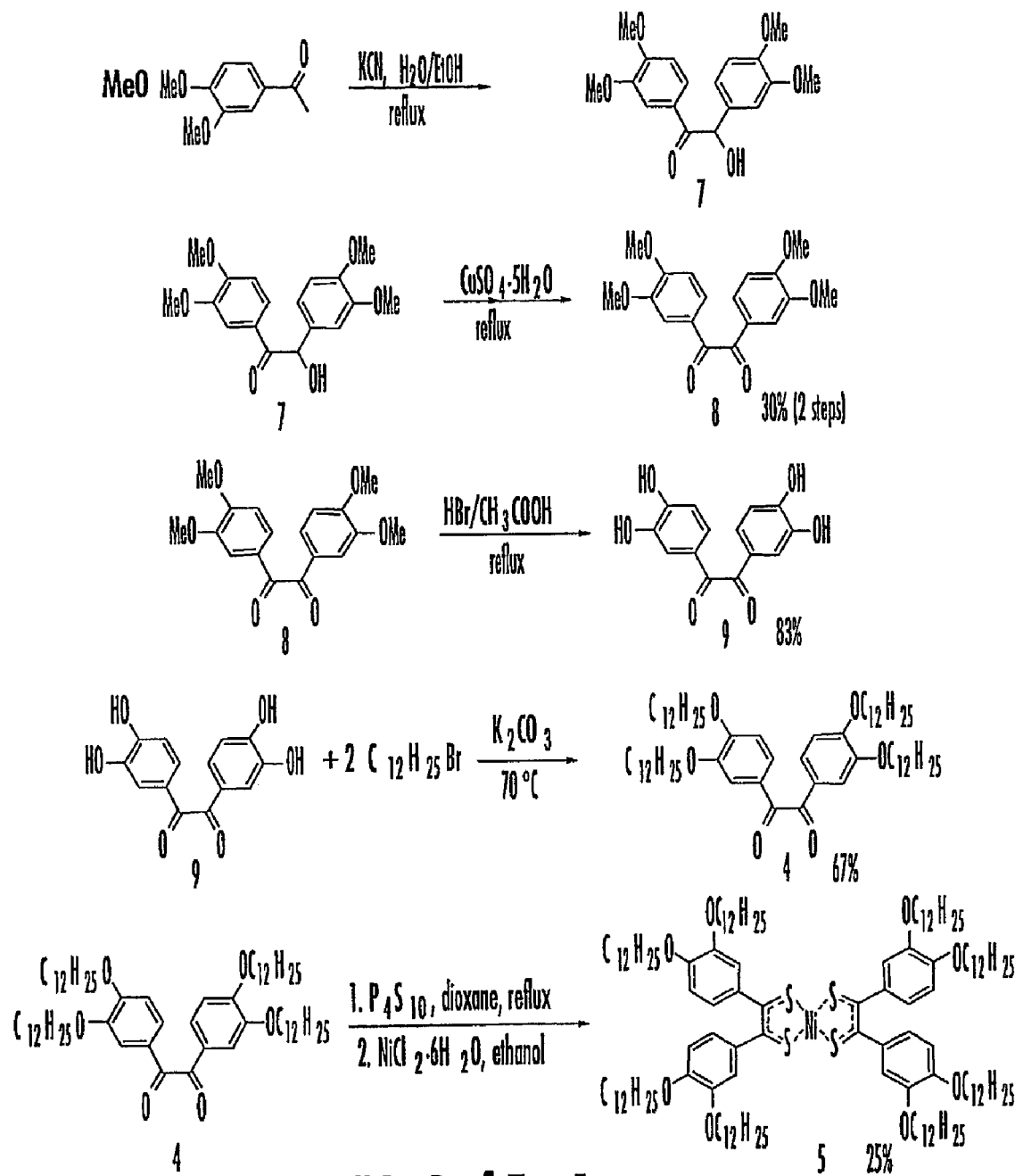
FIG. 2 of Ex. 1

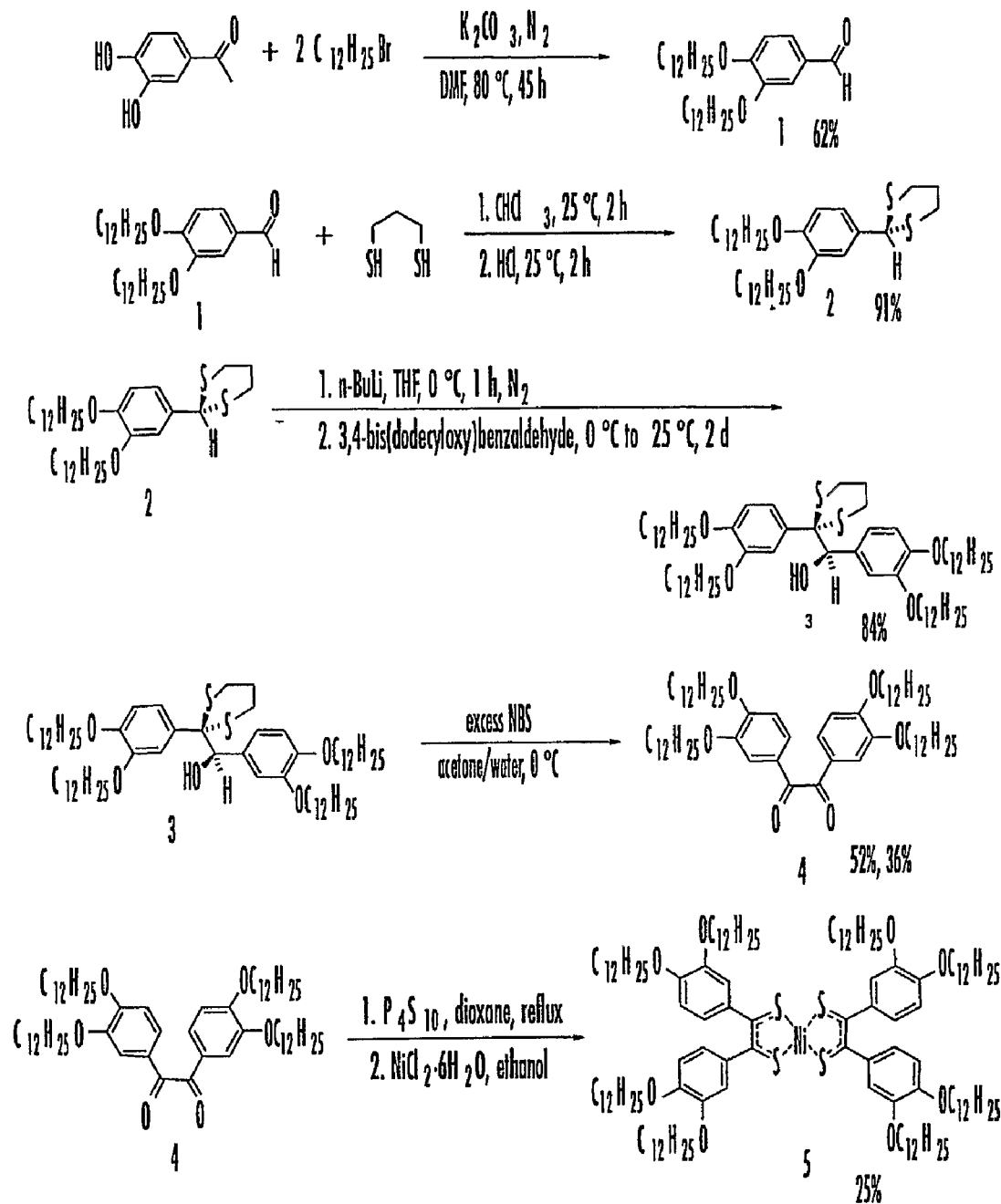
FIG. 3 of Ex. 1

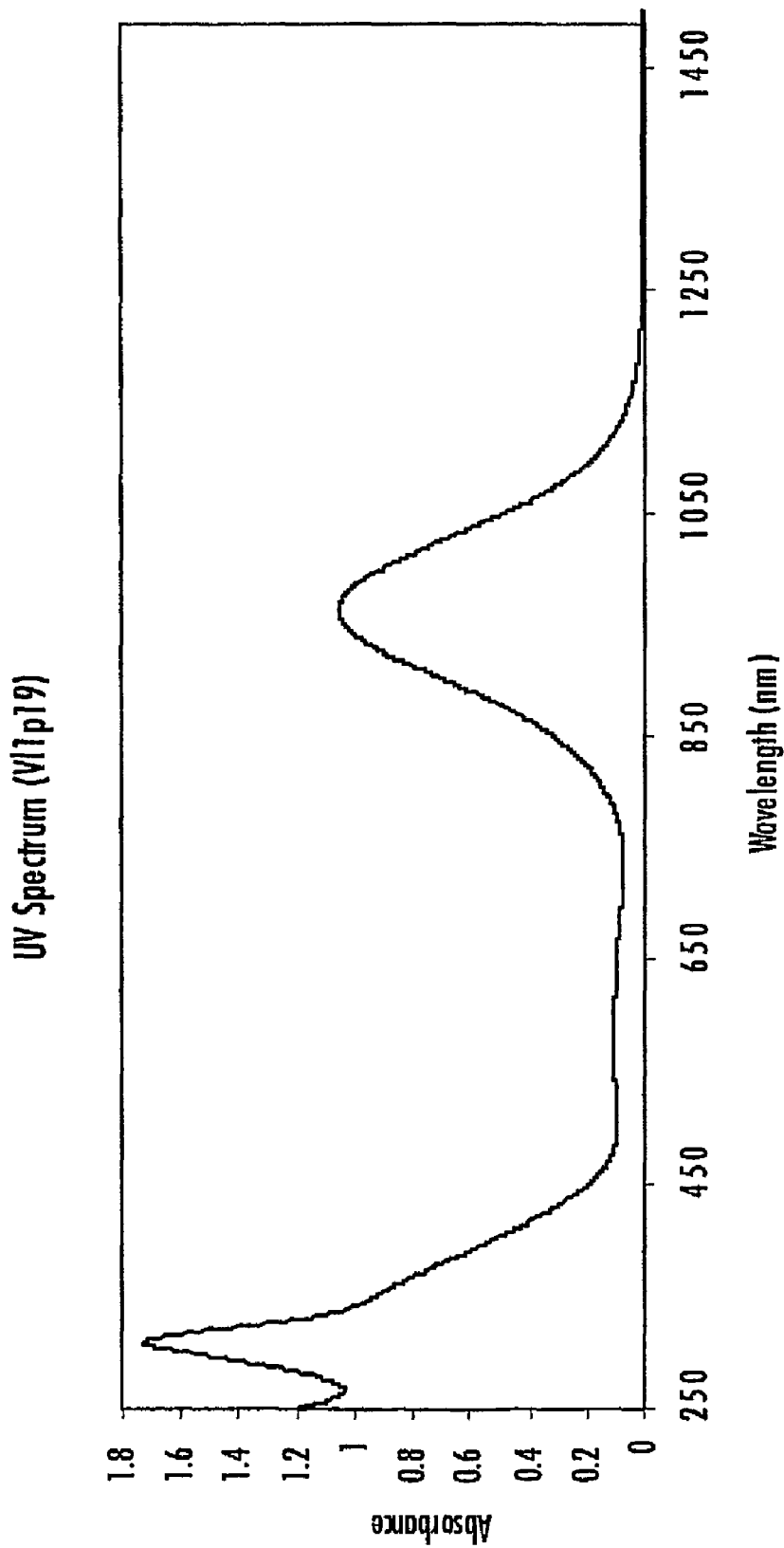
FIG. 4 of Ex. 1

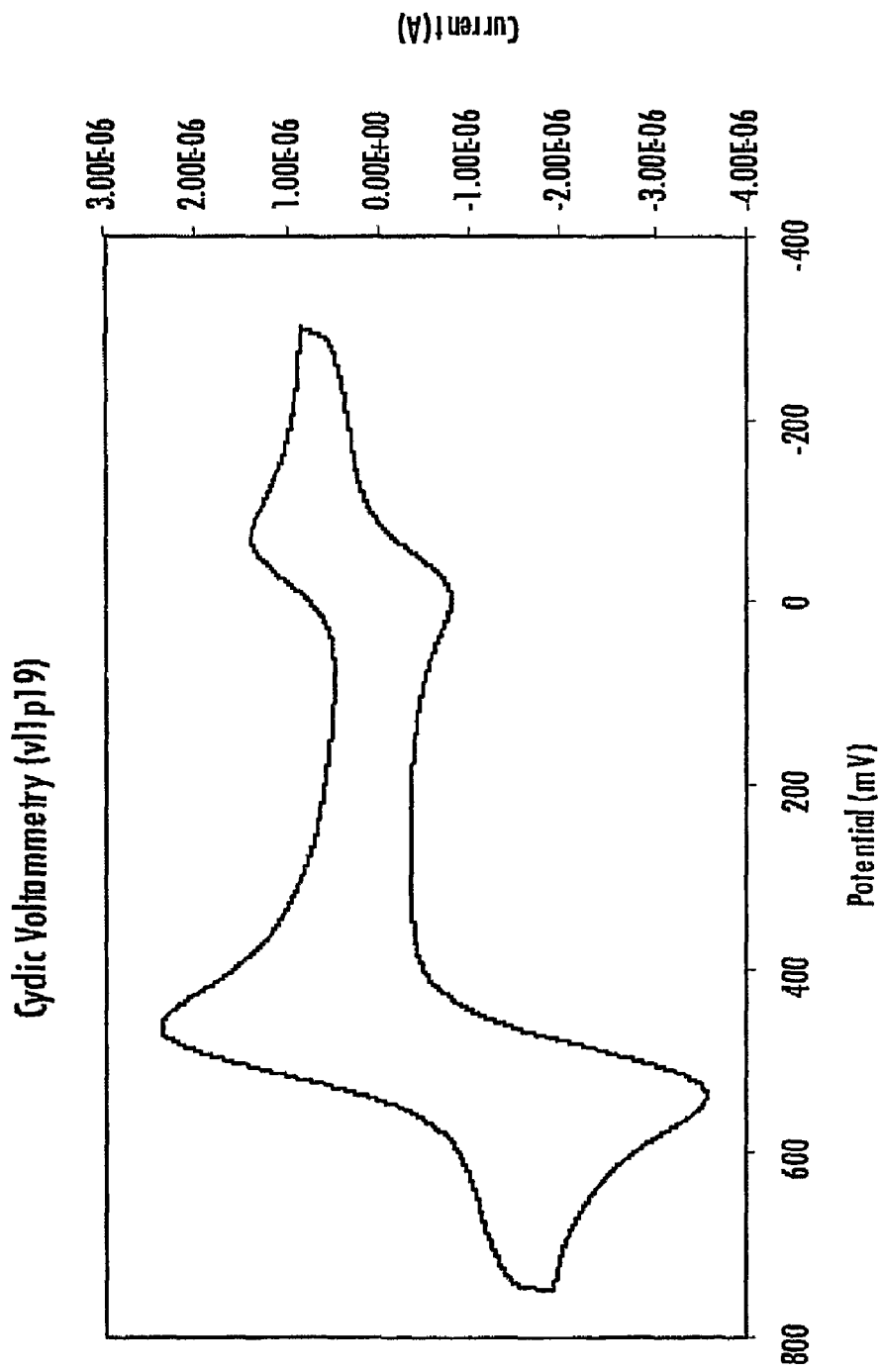
FIG. 5 of Ex. 1

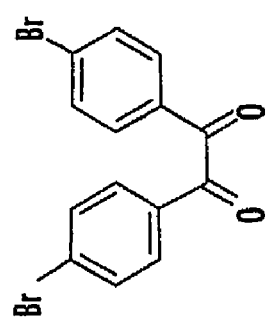
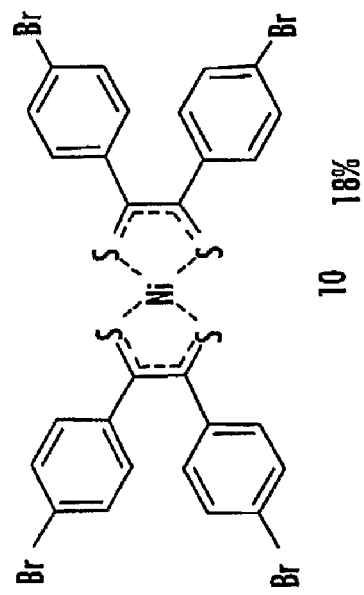
FIG. 6 of Ex. 1

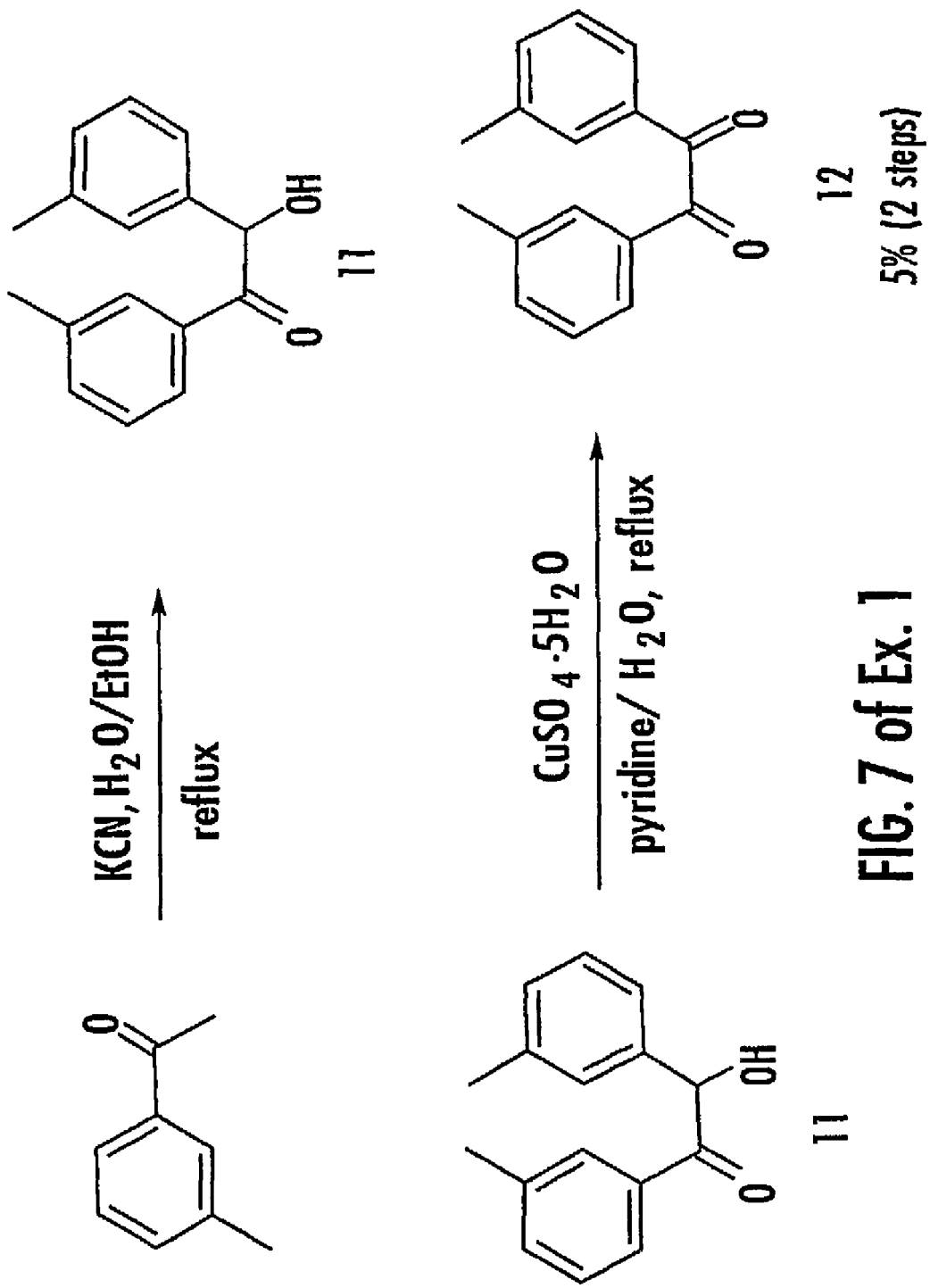
FIG. 7 of Ex. 1

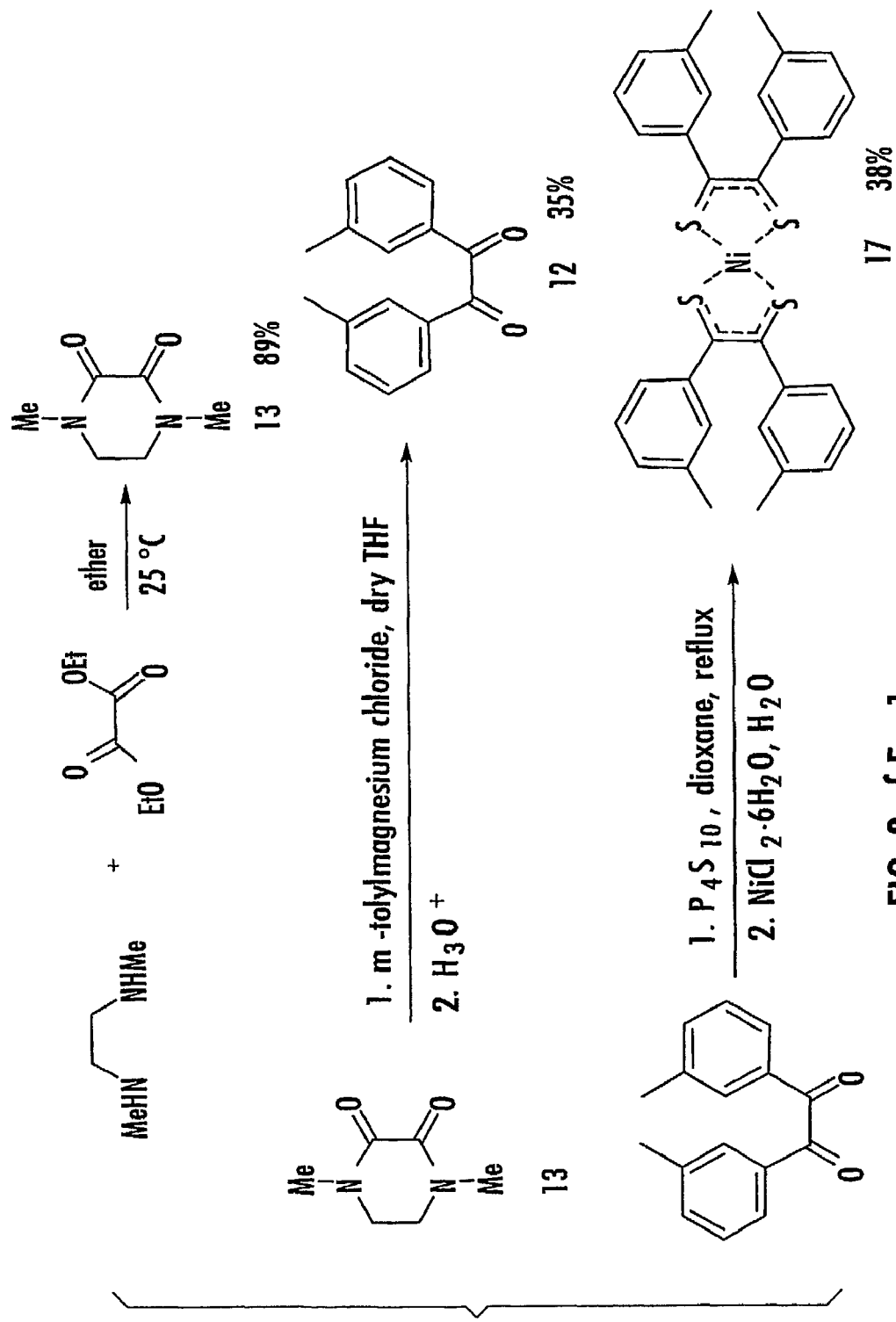
FIG. 8 of Ex. 1

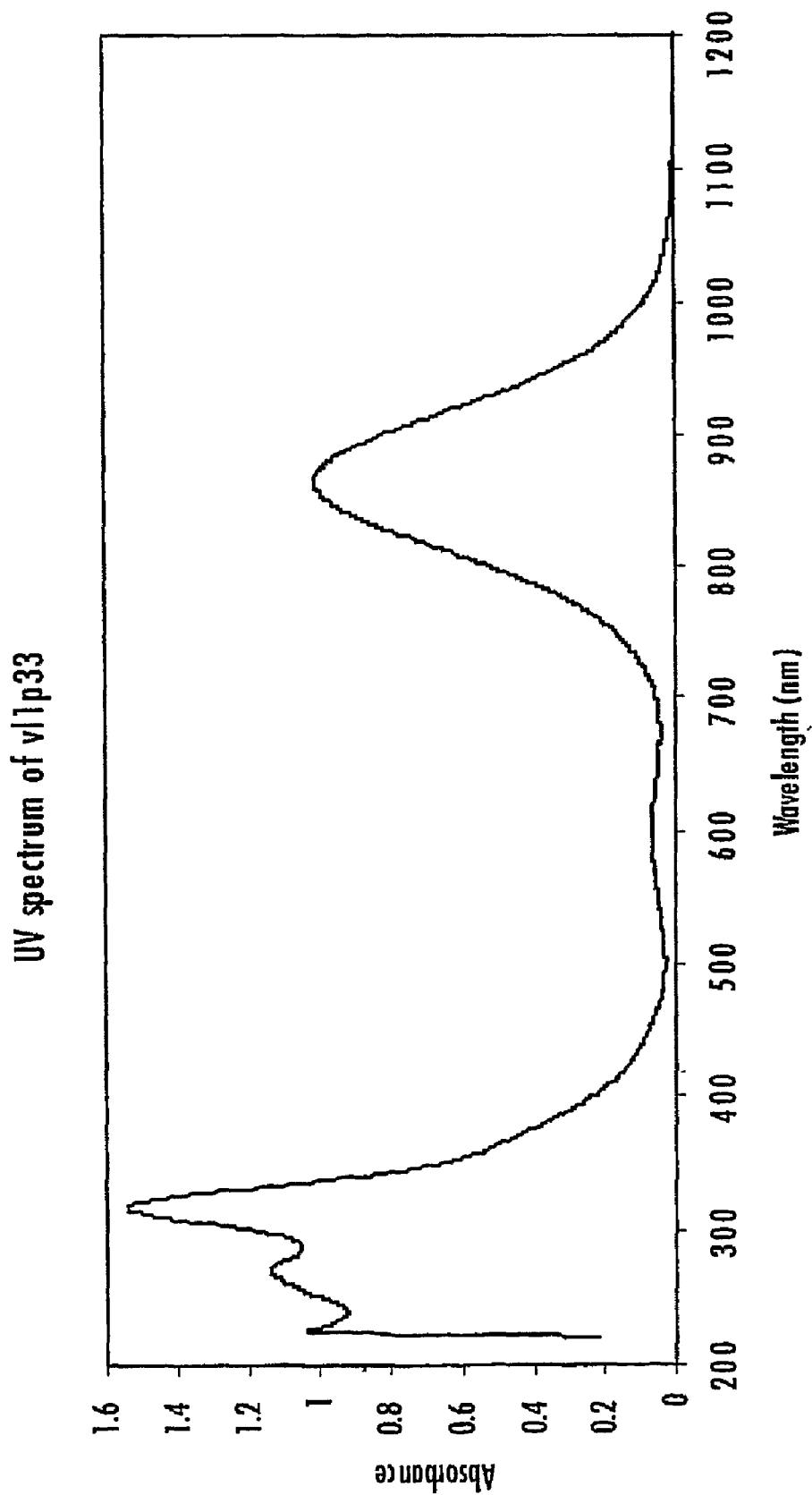
FIG. 9 of Ex. 1

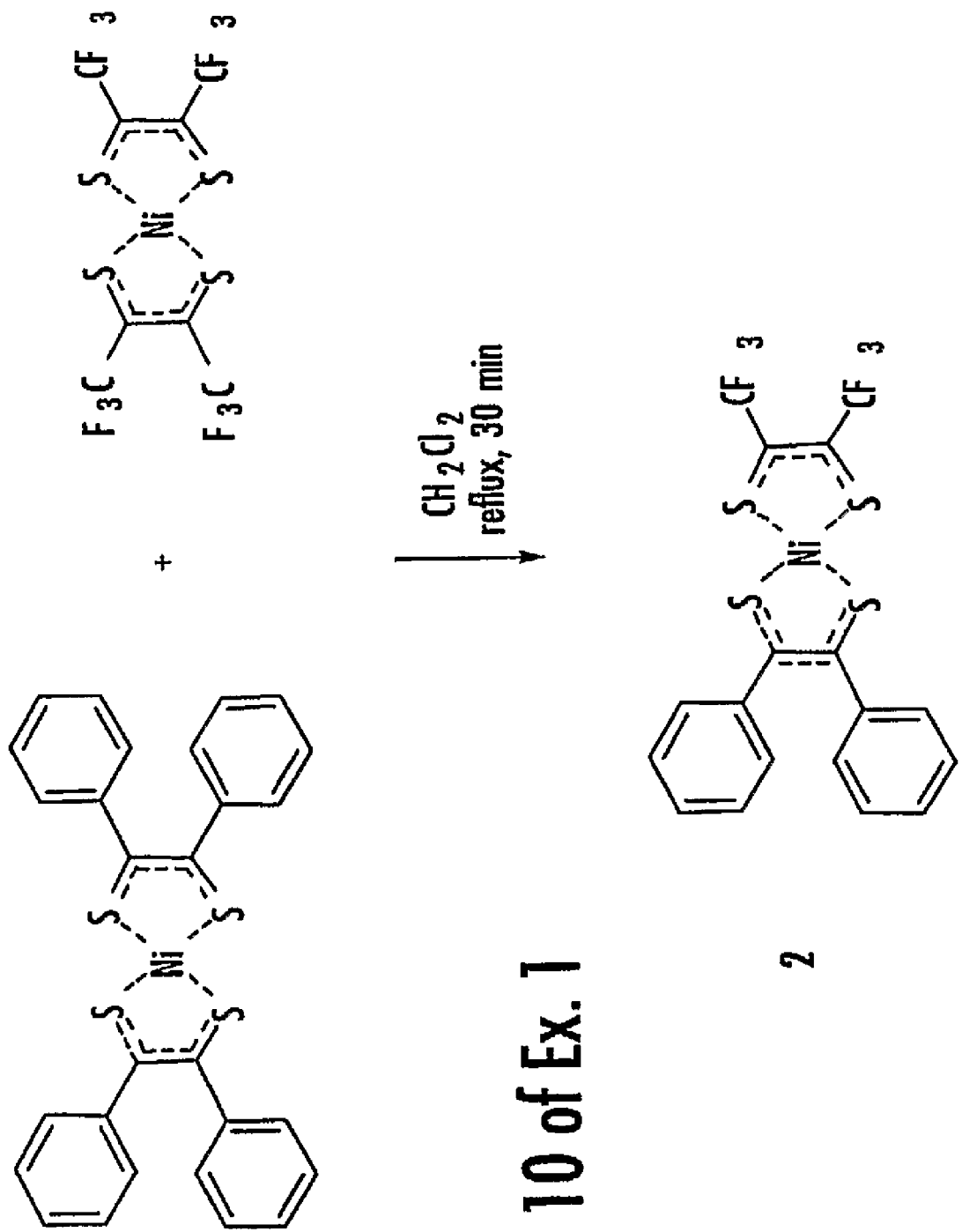
FIG. 10 of Ex. 1

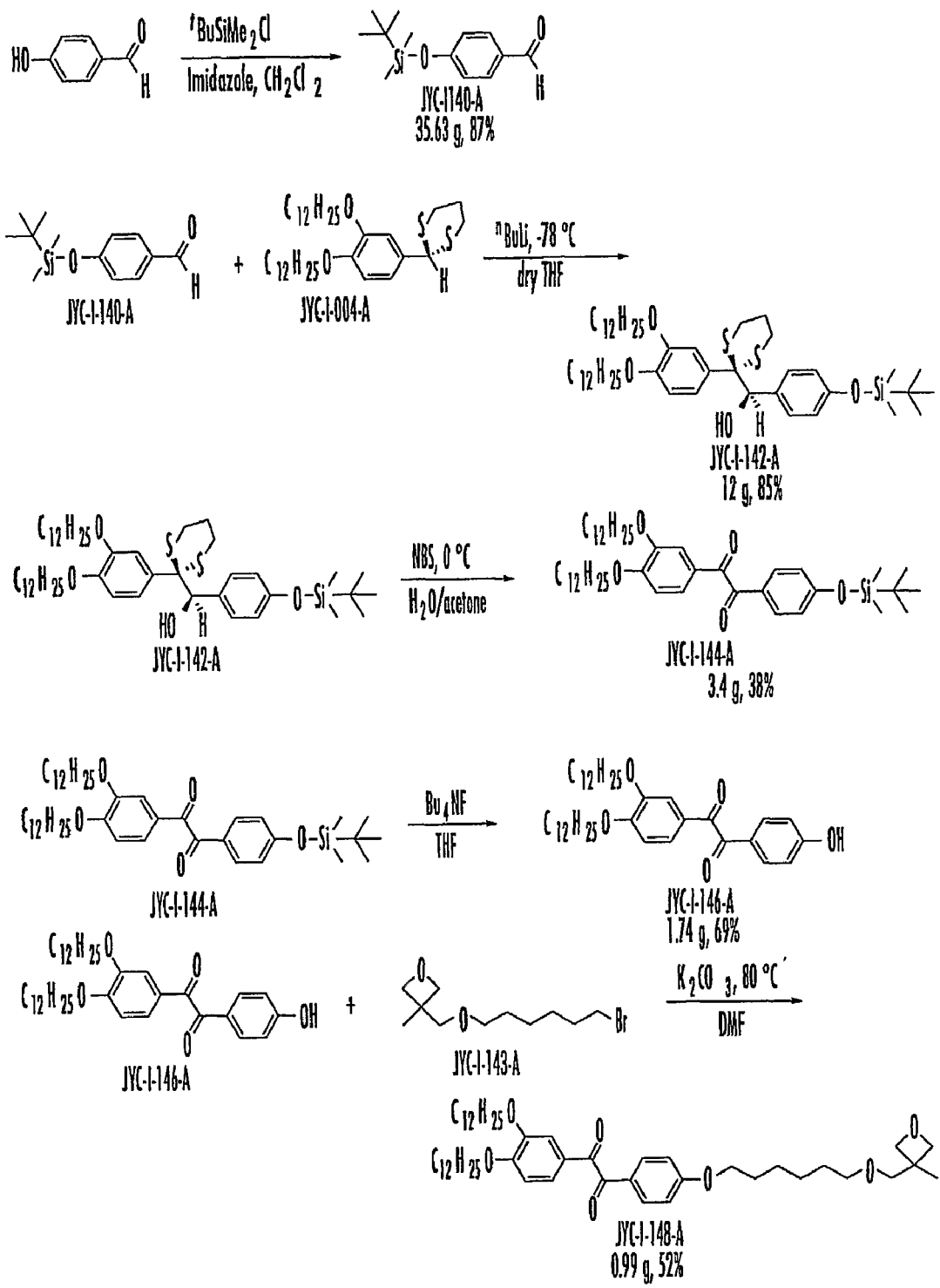
FIG. 1 of Ex. 2

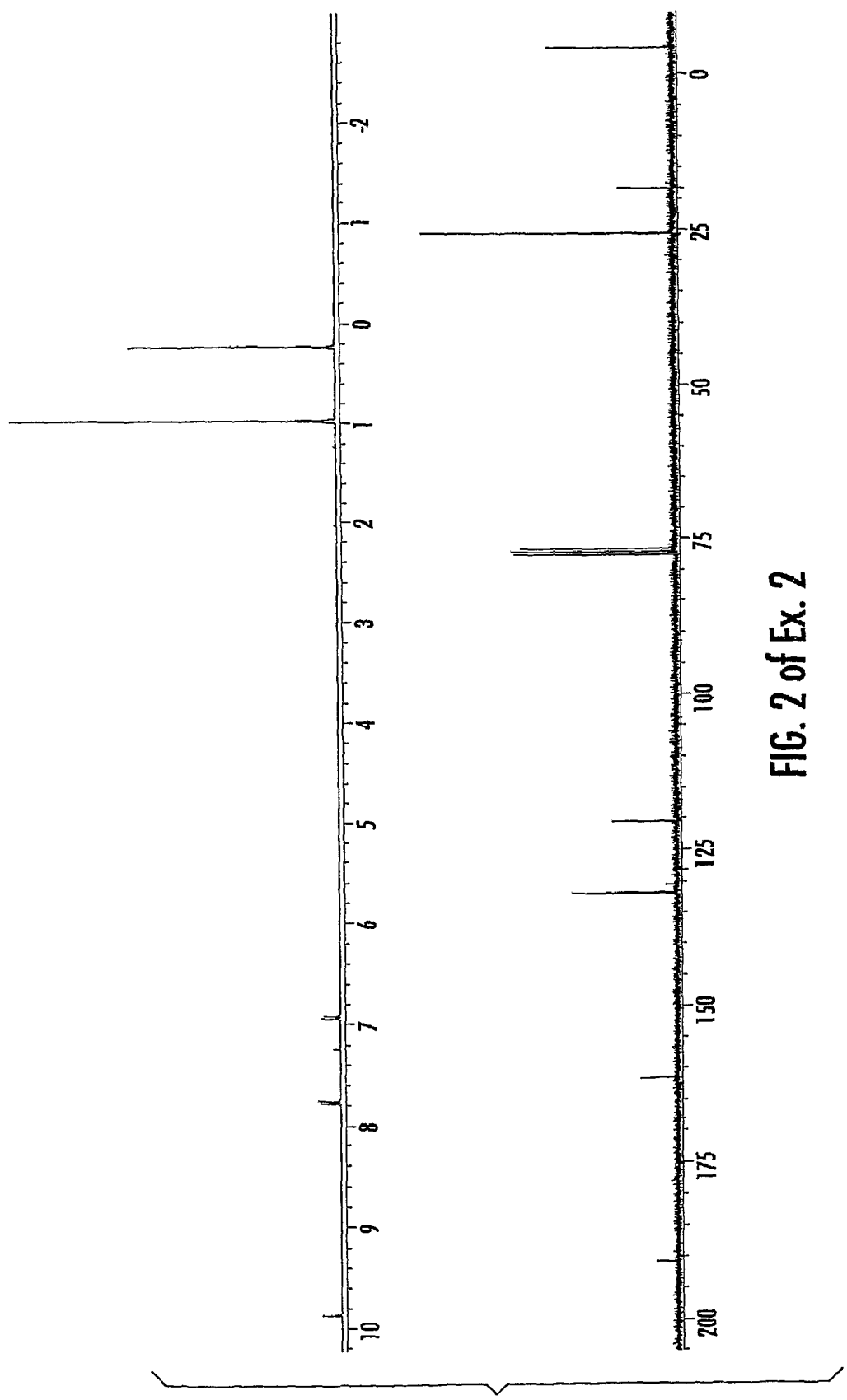
FIG. 2 of Ex. 2

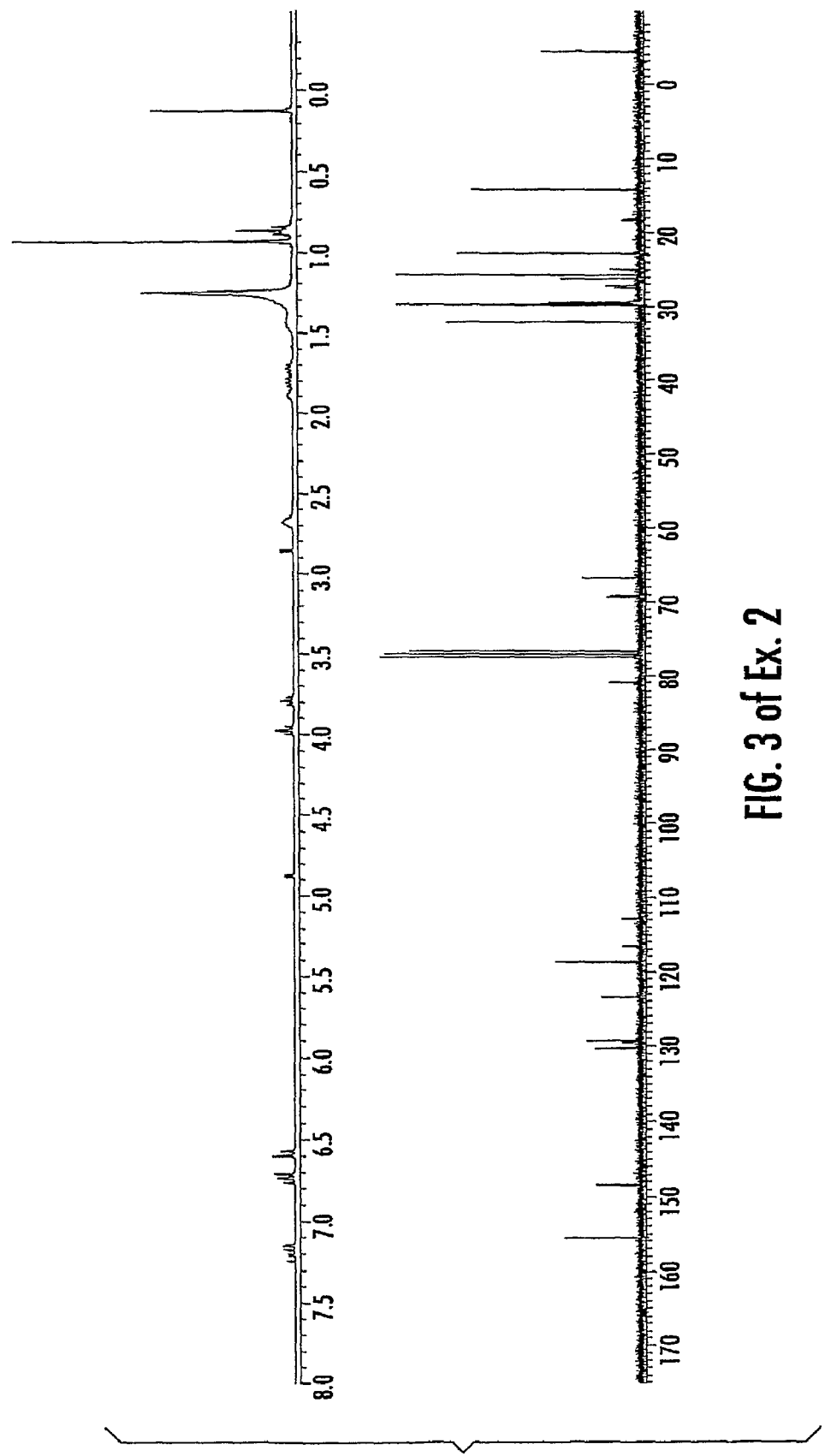
FIG. 3 of Ex. 2

FIG. 4 of Ex. 2

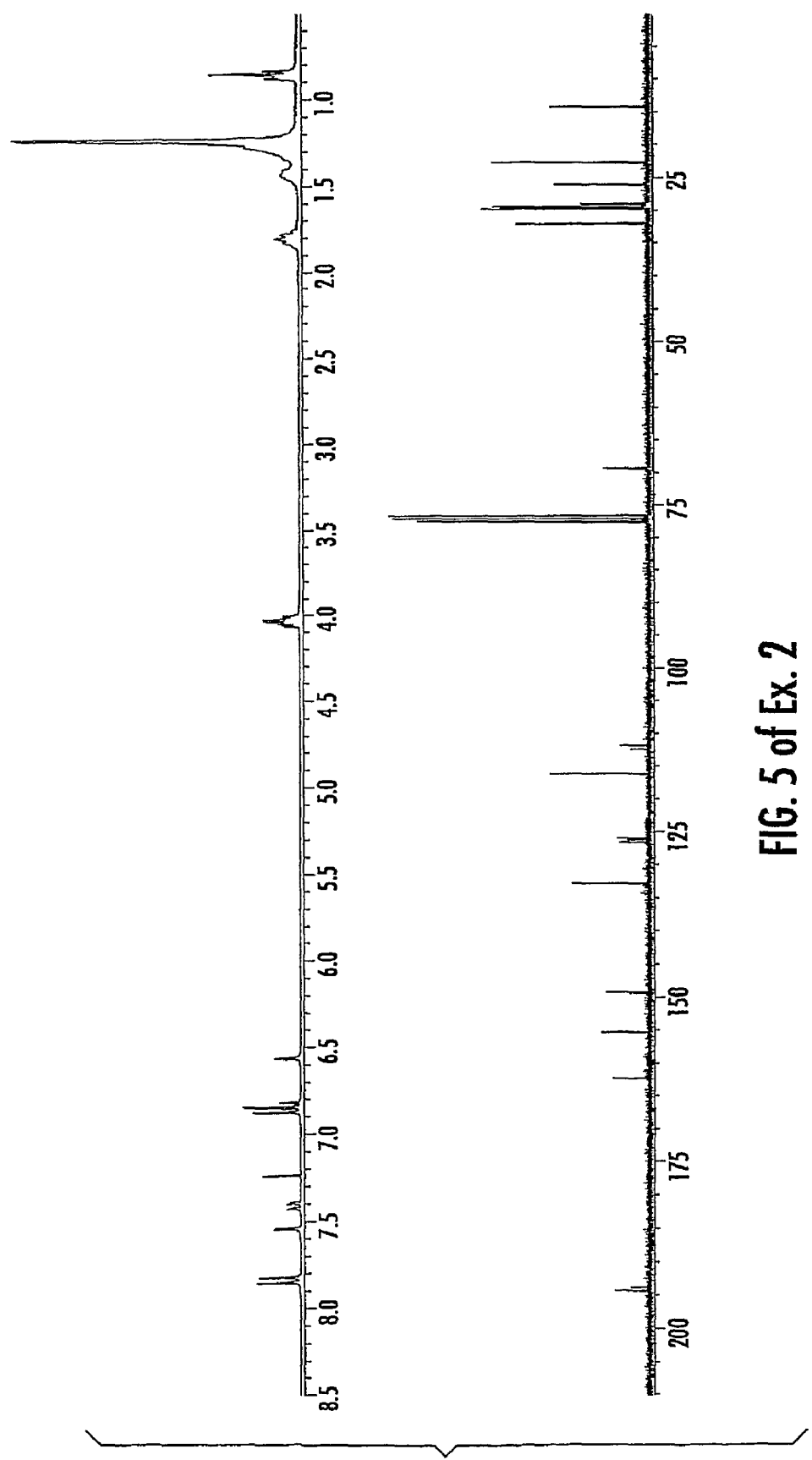
FIG. 5 of Ex. 2

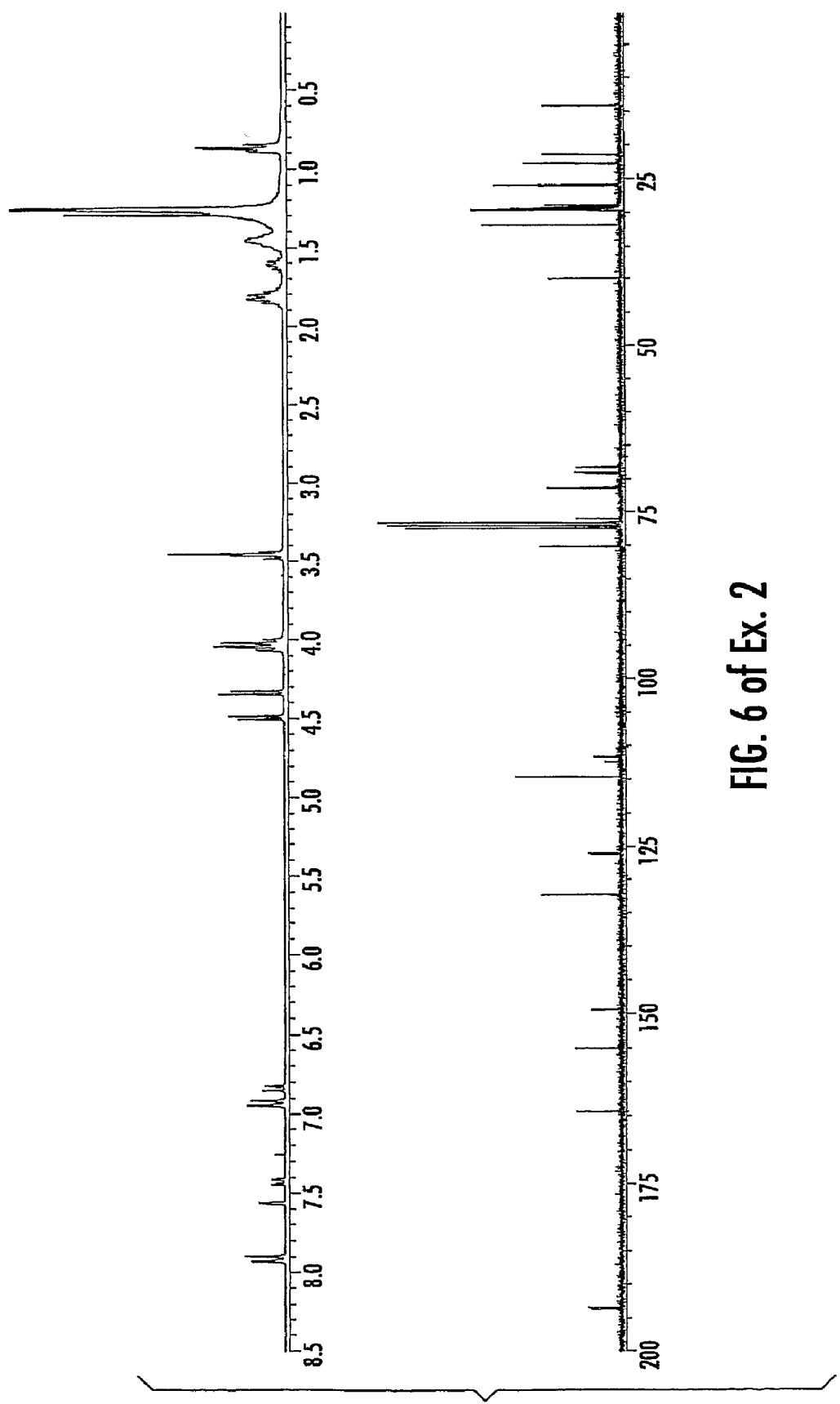
FIG. 6 of Ex. 2

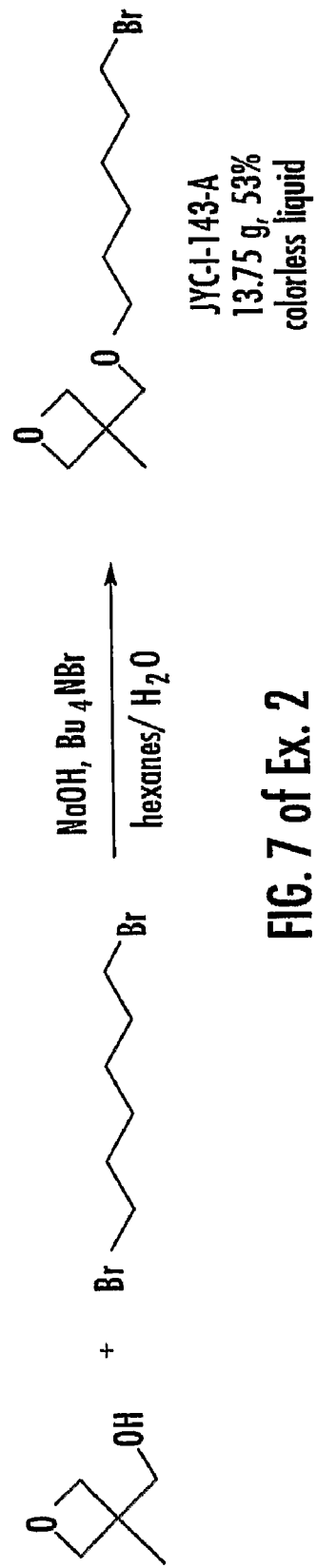
FIG. 7 of Ex. 2

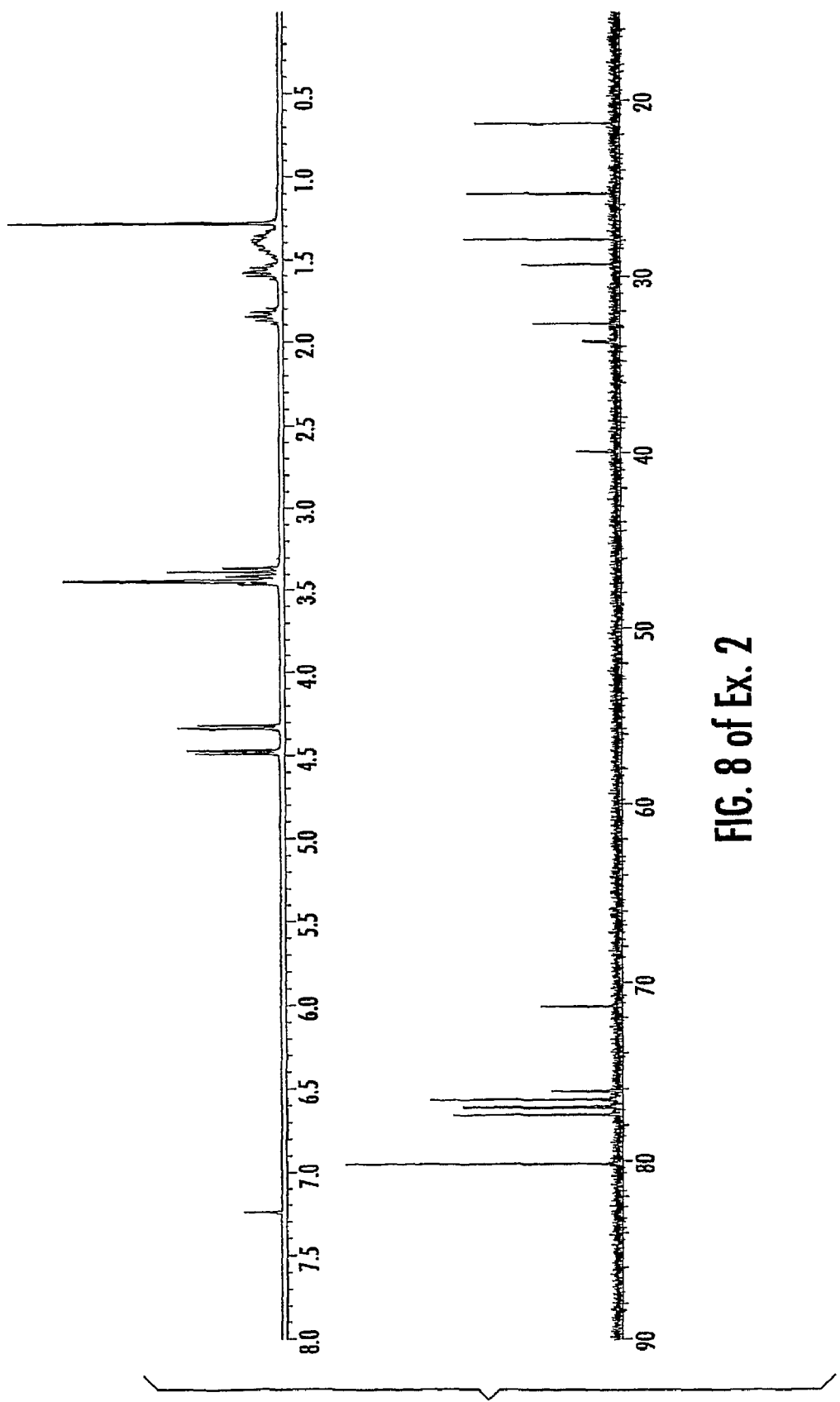
FIG. 8 of Ex. 2

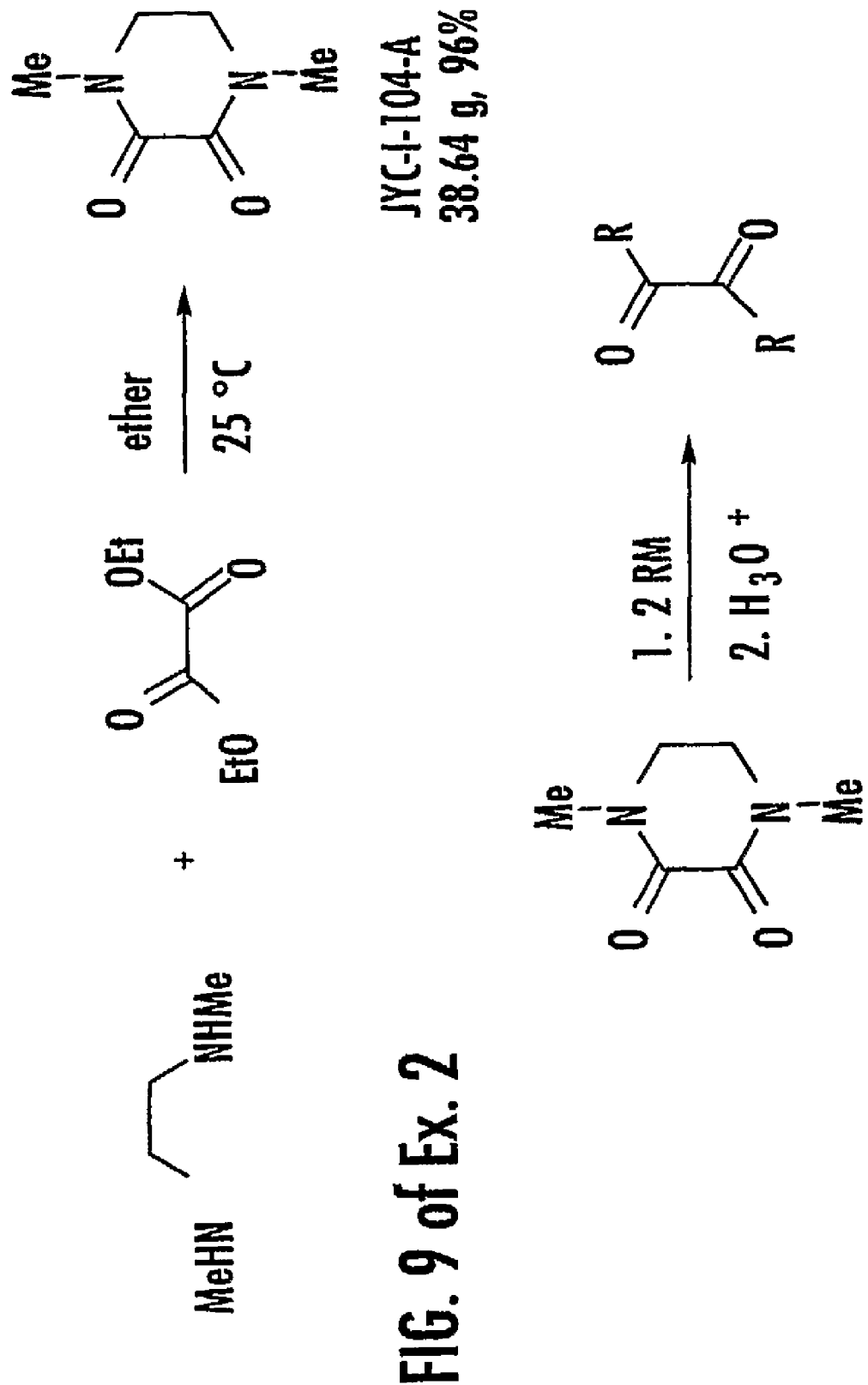
FIG. 9 of Ex. 2

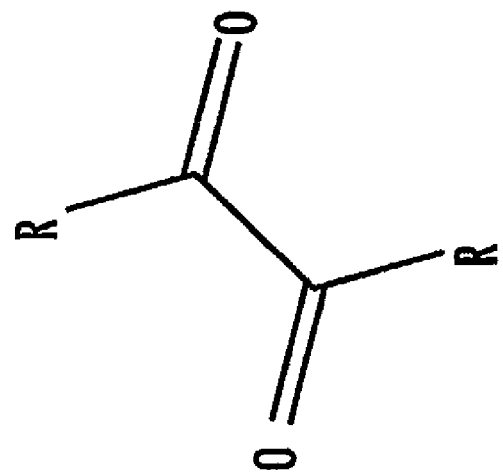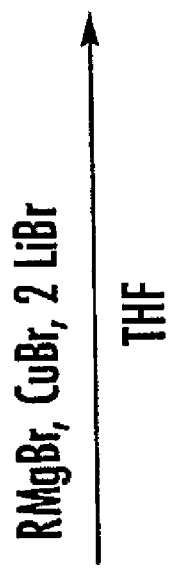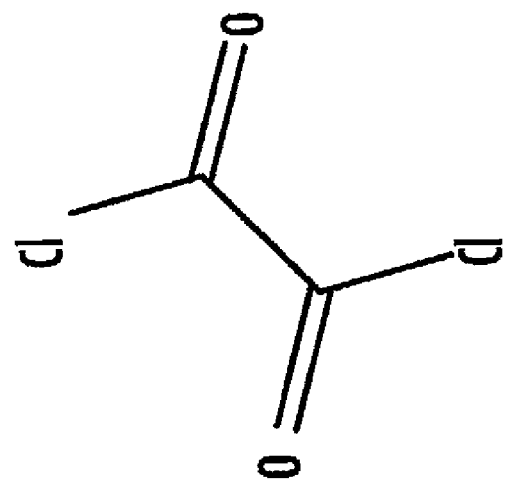
FIG. 10 of Ex. 2

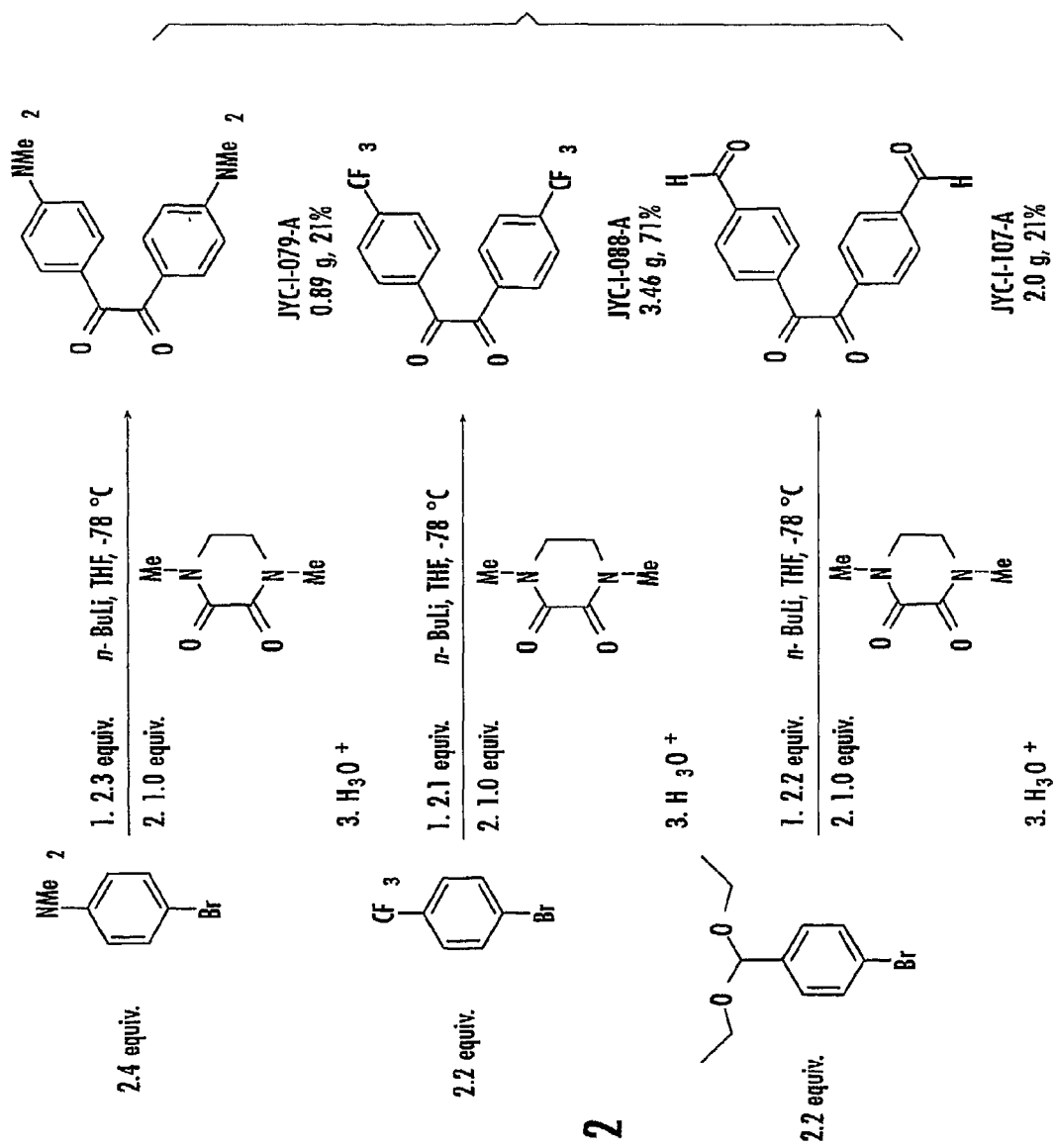
FIG. 11 of Ex. 2

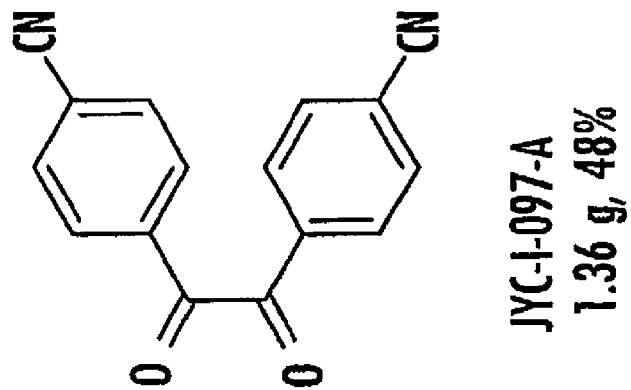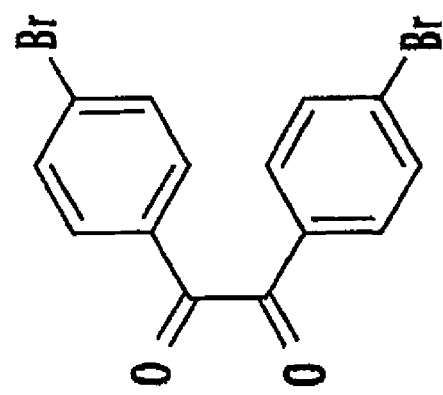
FIG. 12 of Ex. 2

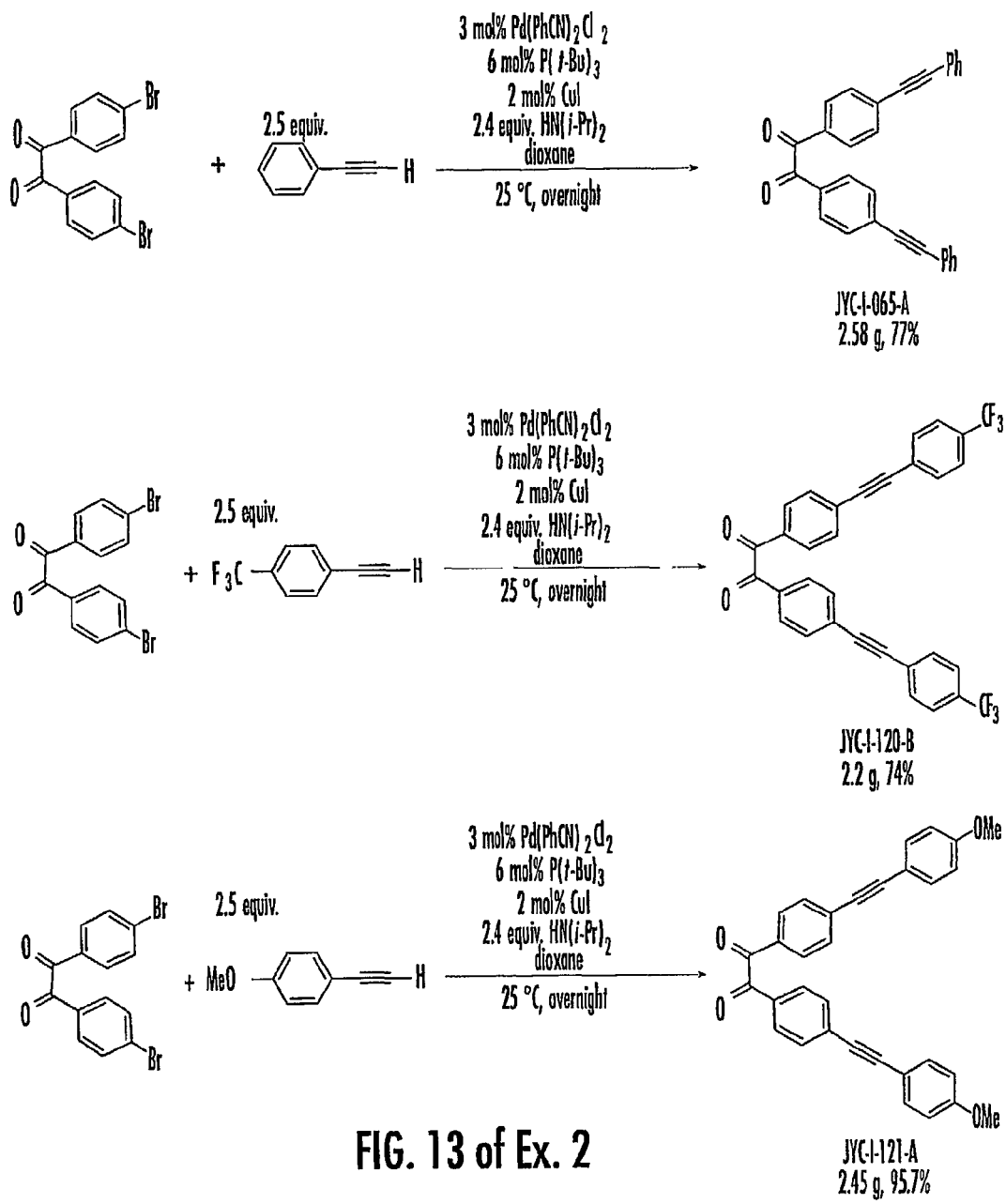
FIG. 13 of Ex. 2

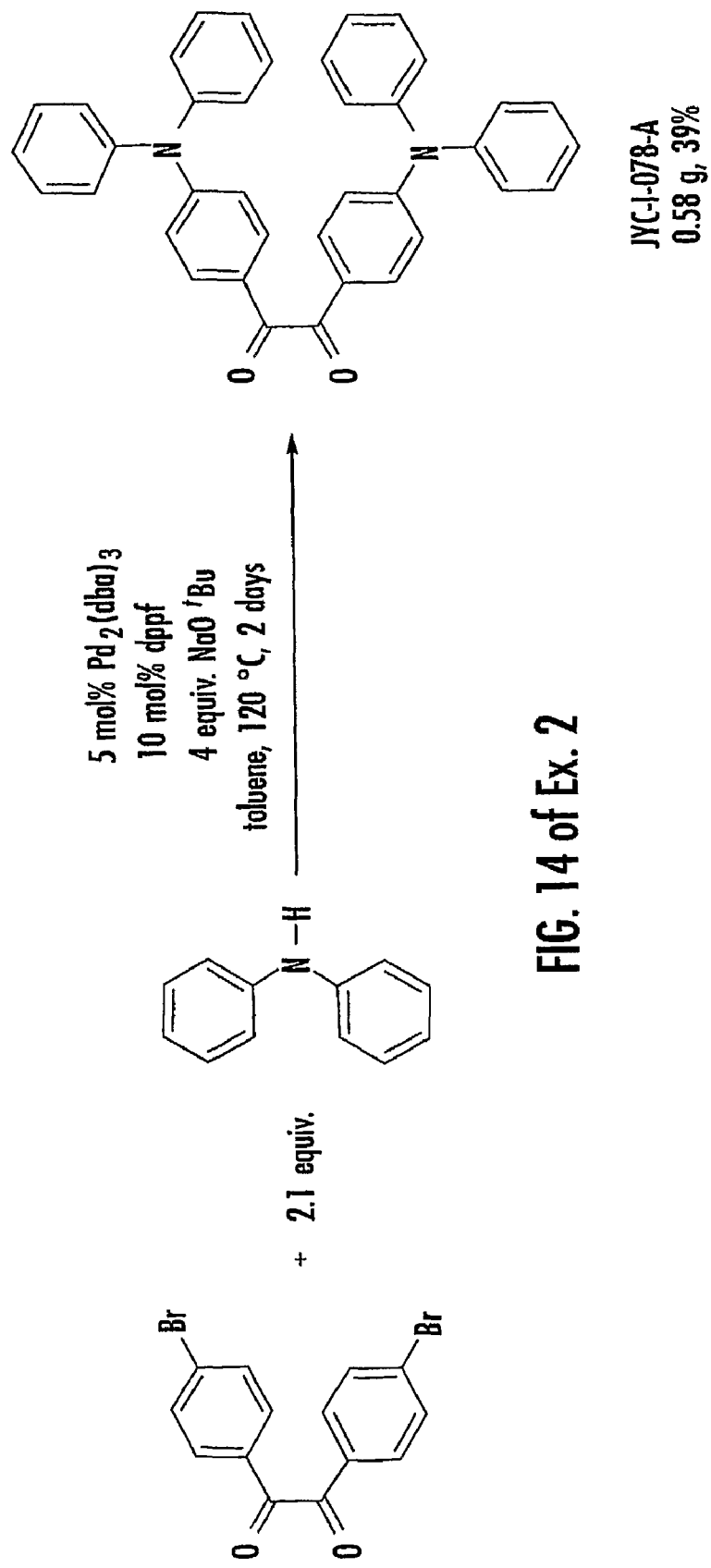
FIG. 14 of Ex. 2

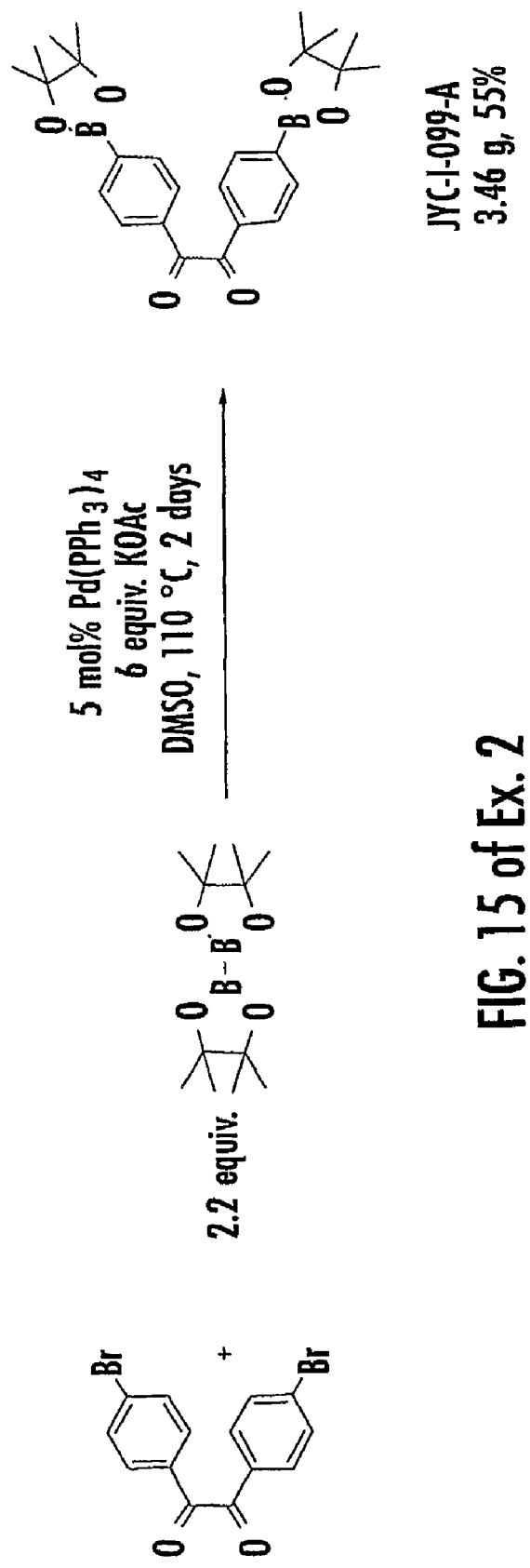
FIG. 15 of Ex. 2

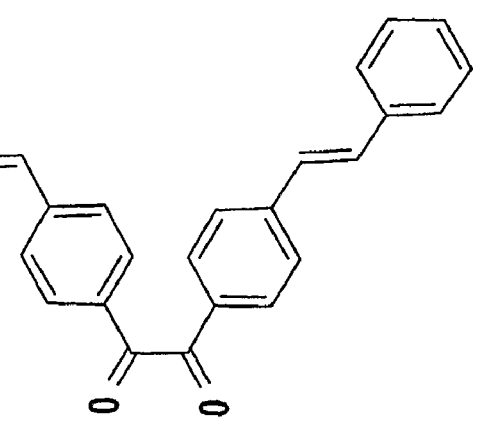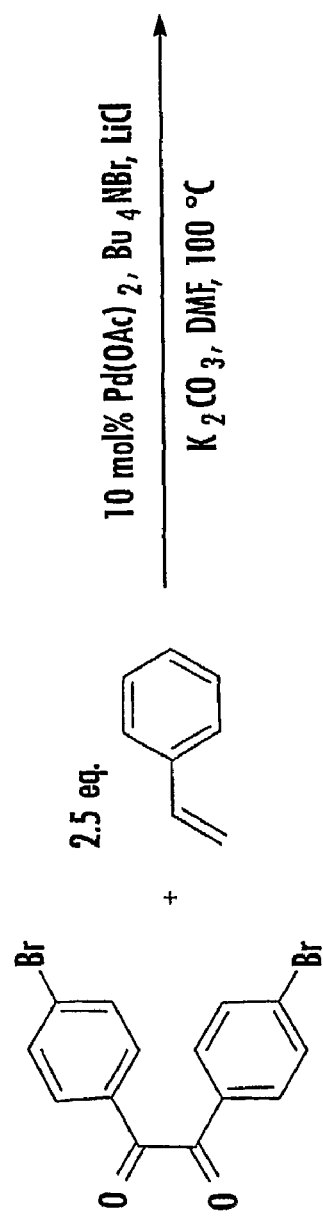
FIG. 16 of Ex. 2

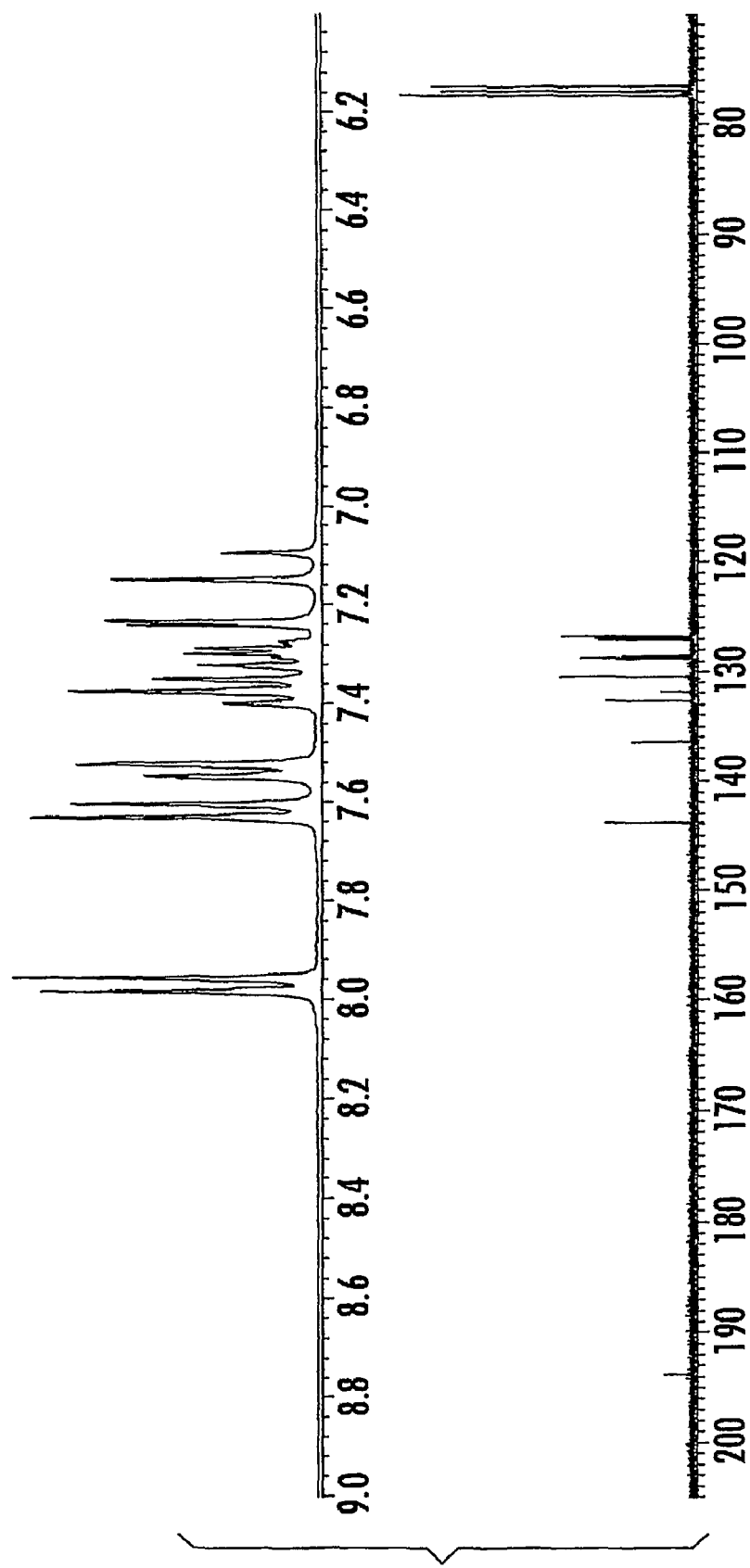
FIG. 17 of Ex. 2

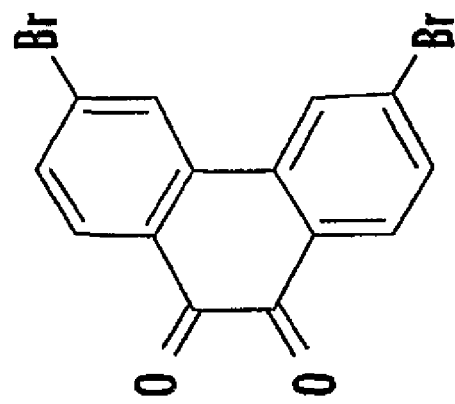
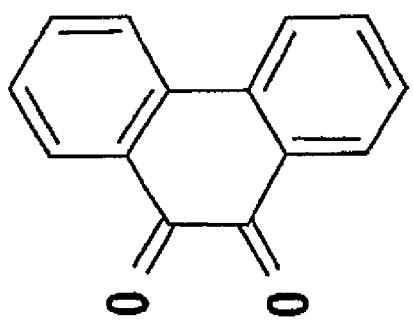
FIG. 18 of Ex. 2

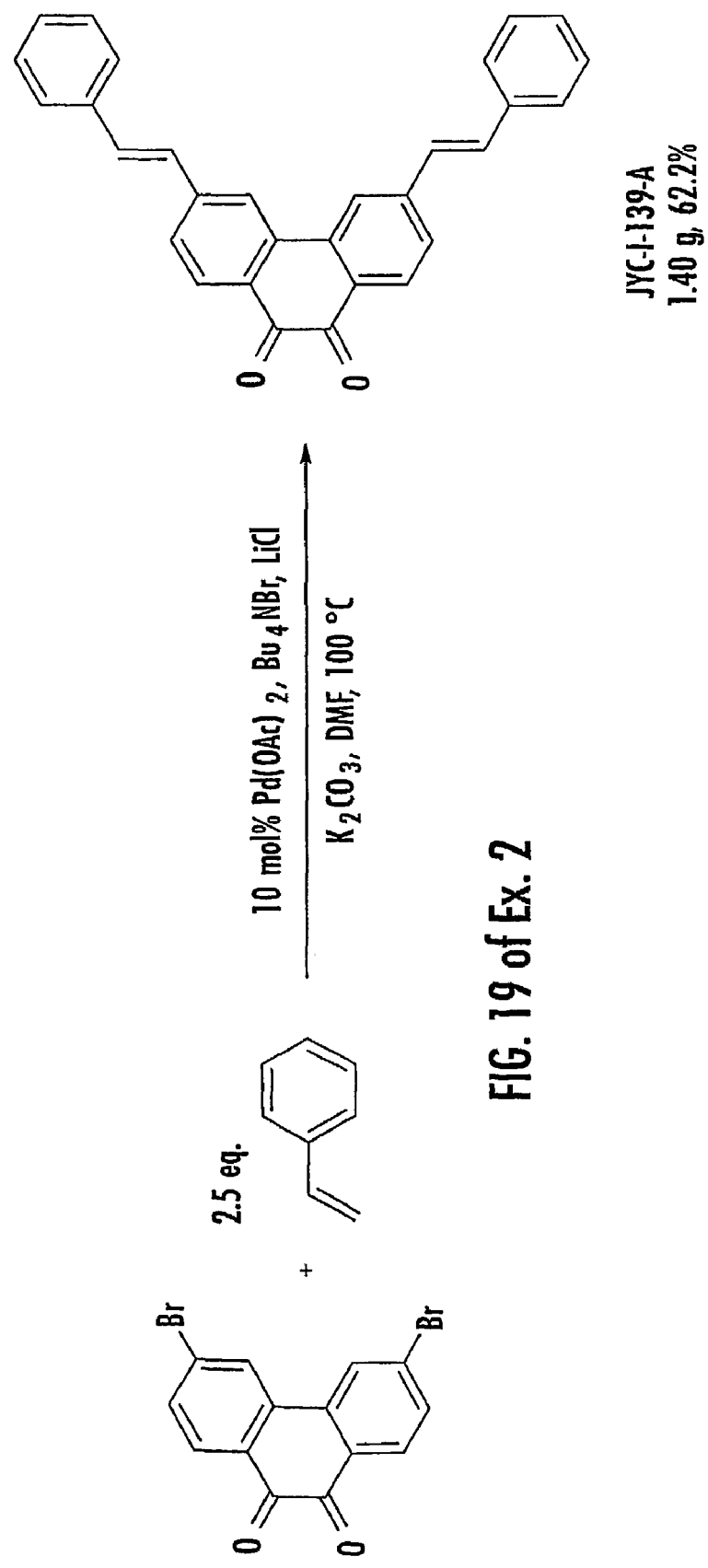
FIG. 19 of Ex. 2

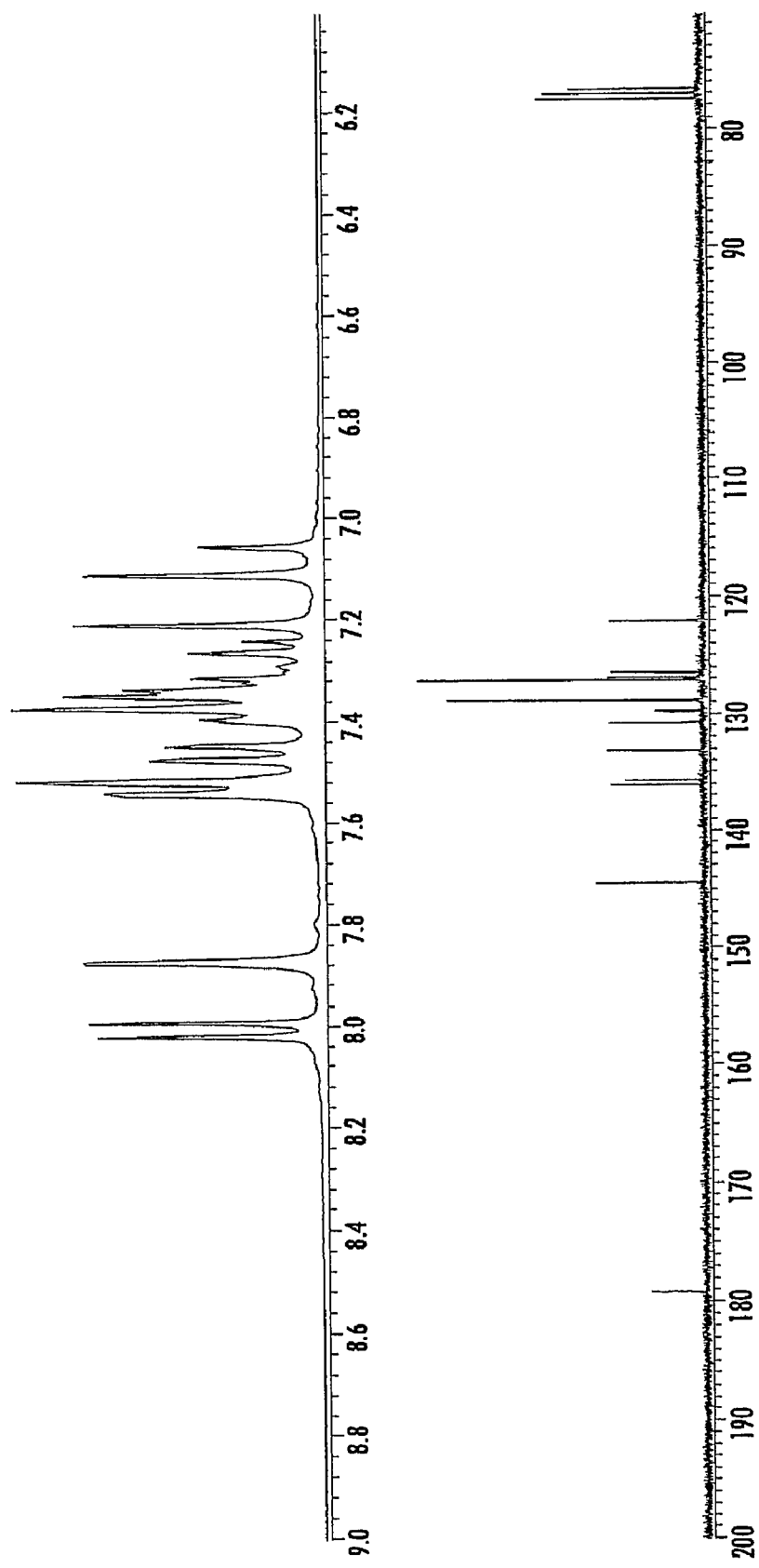
FIG. 20 of Ex. 2

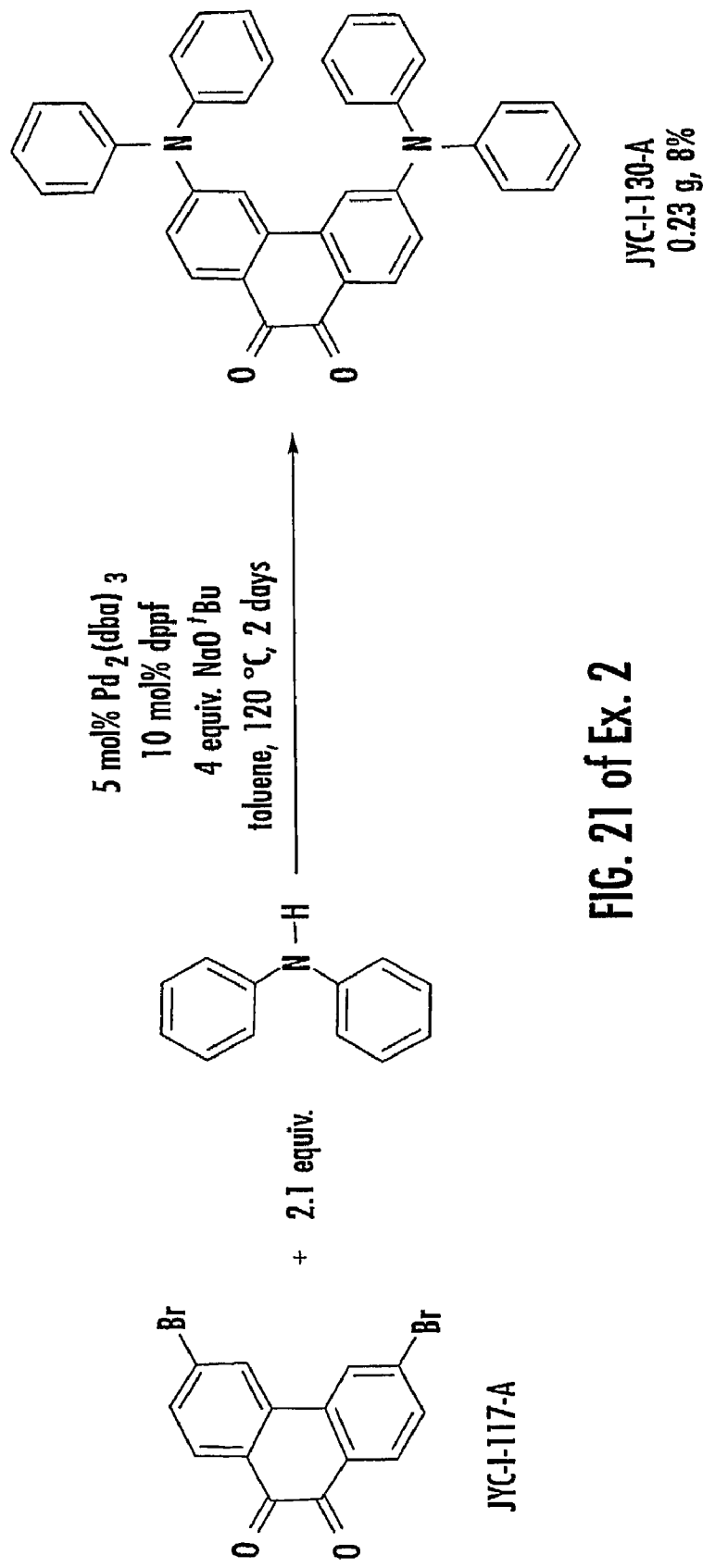
FIG. 21 of Ex. 2

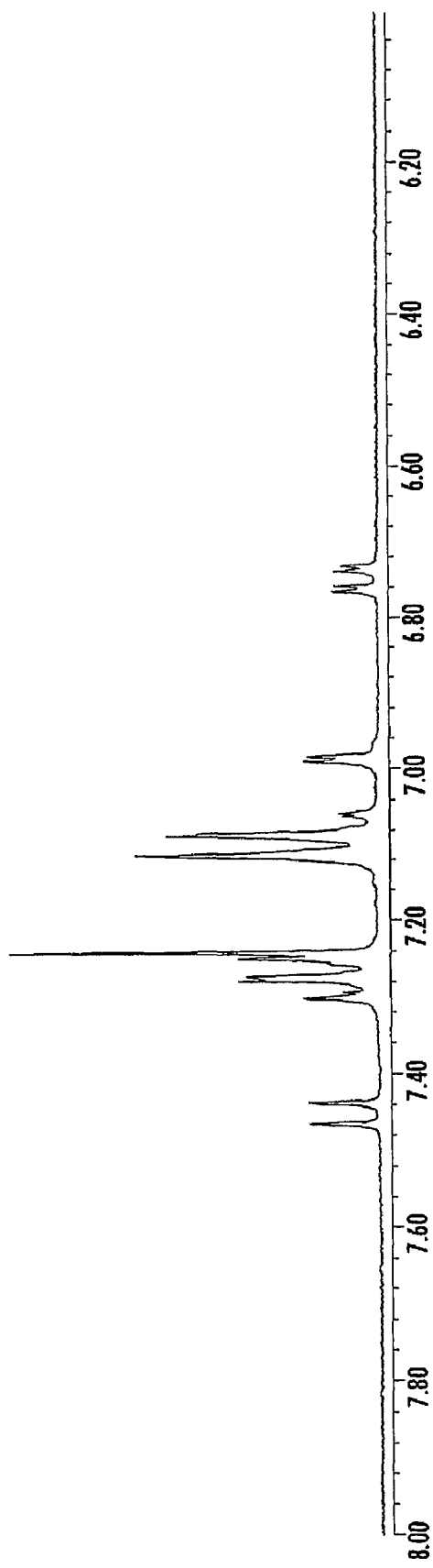
FIG. 22 of Ex. 2

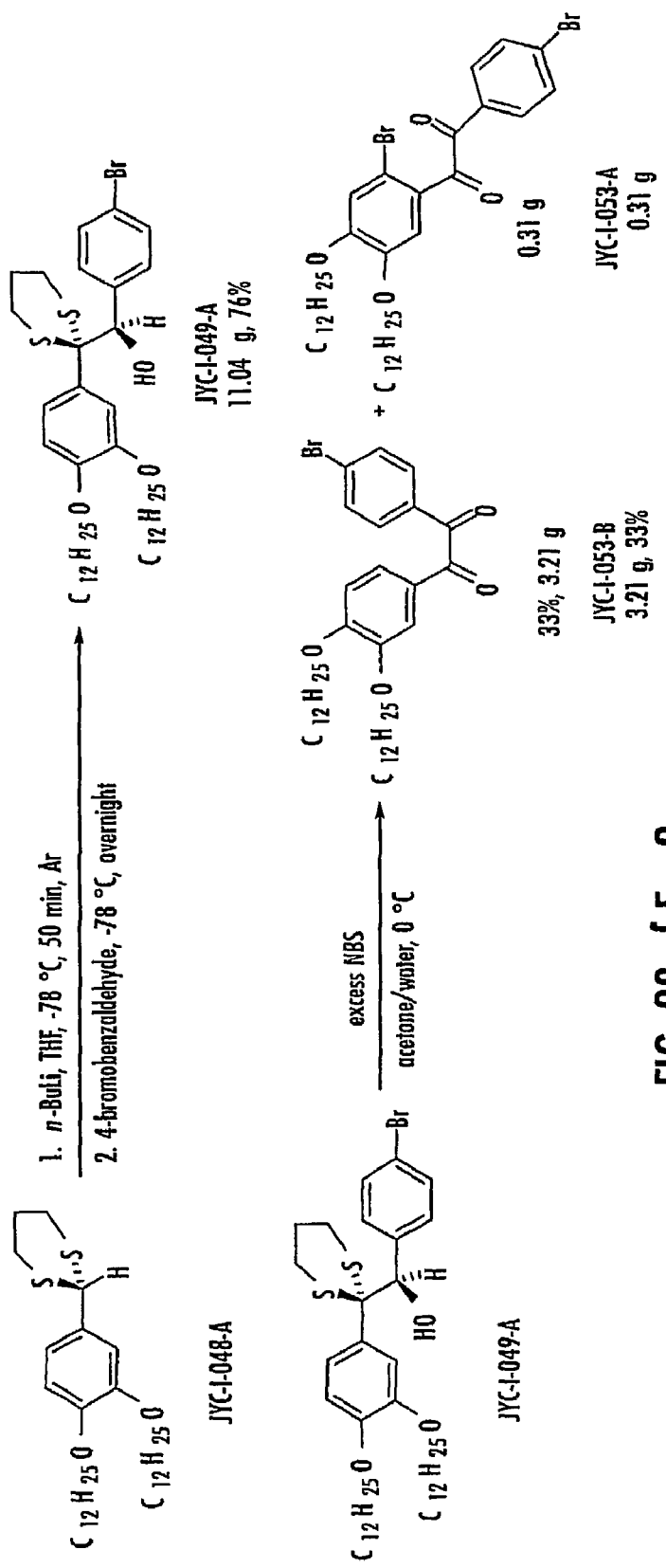
FIG. 23 of Ex. 2

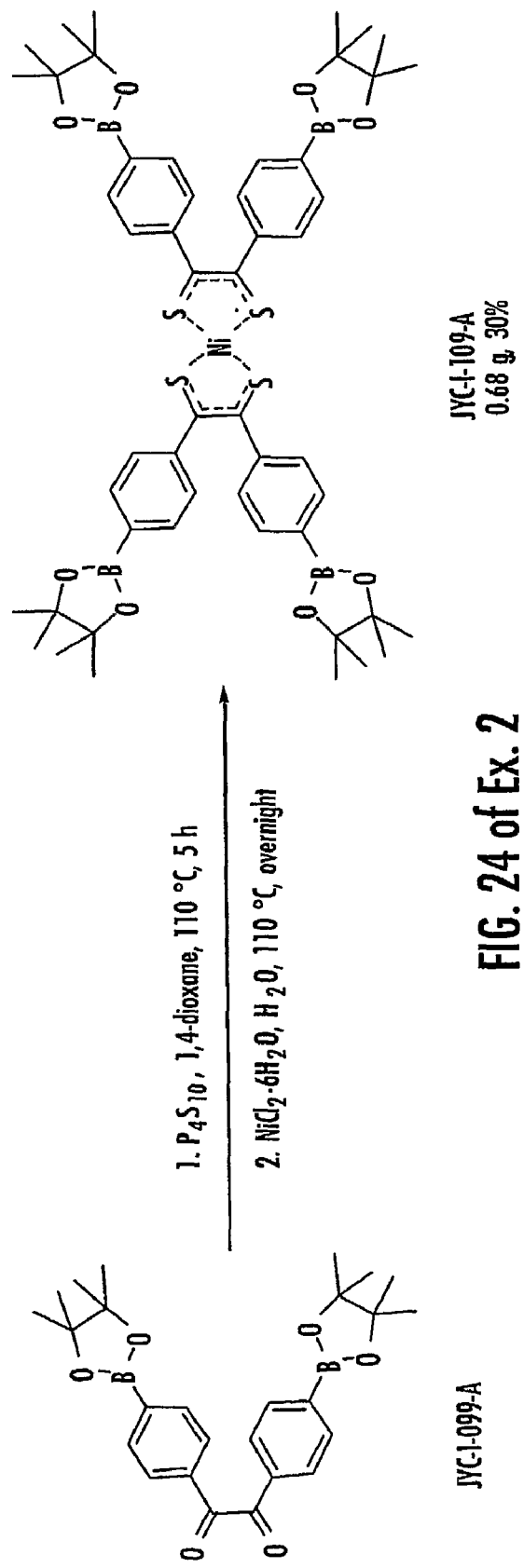
FIG. 24 of Ex. 2

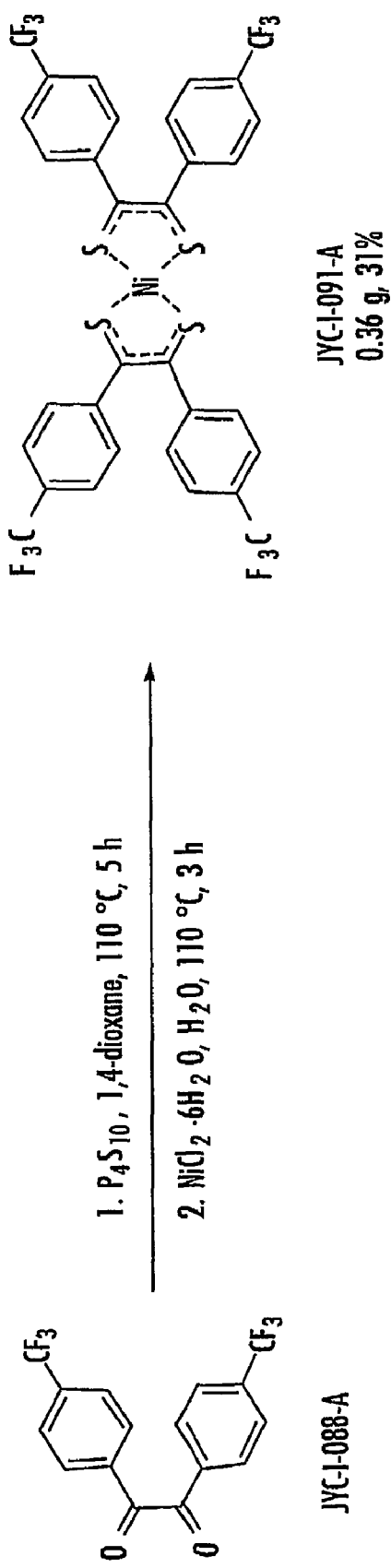
FIG. 25 of Ex. 2

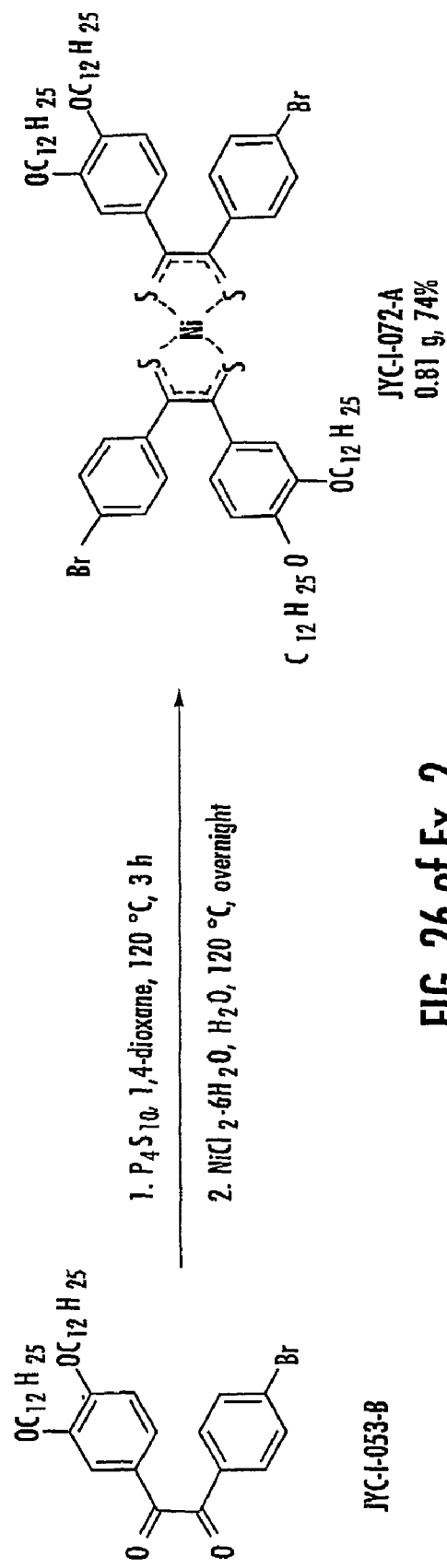
FIG. 26 of Ex. 2

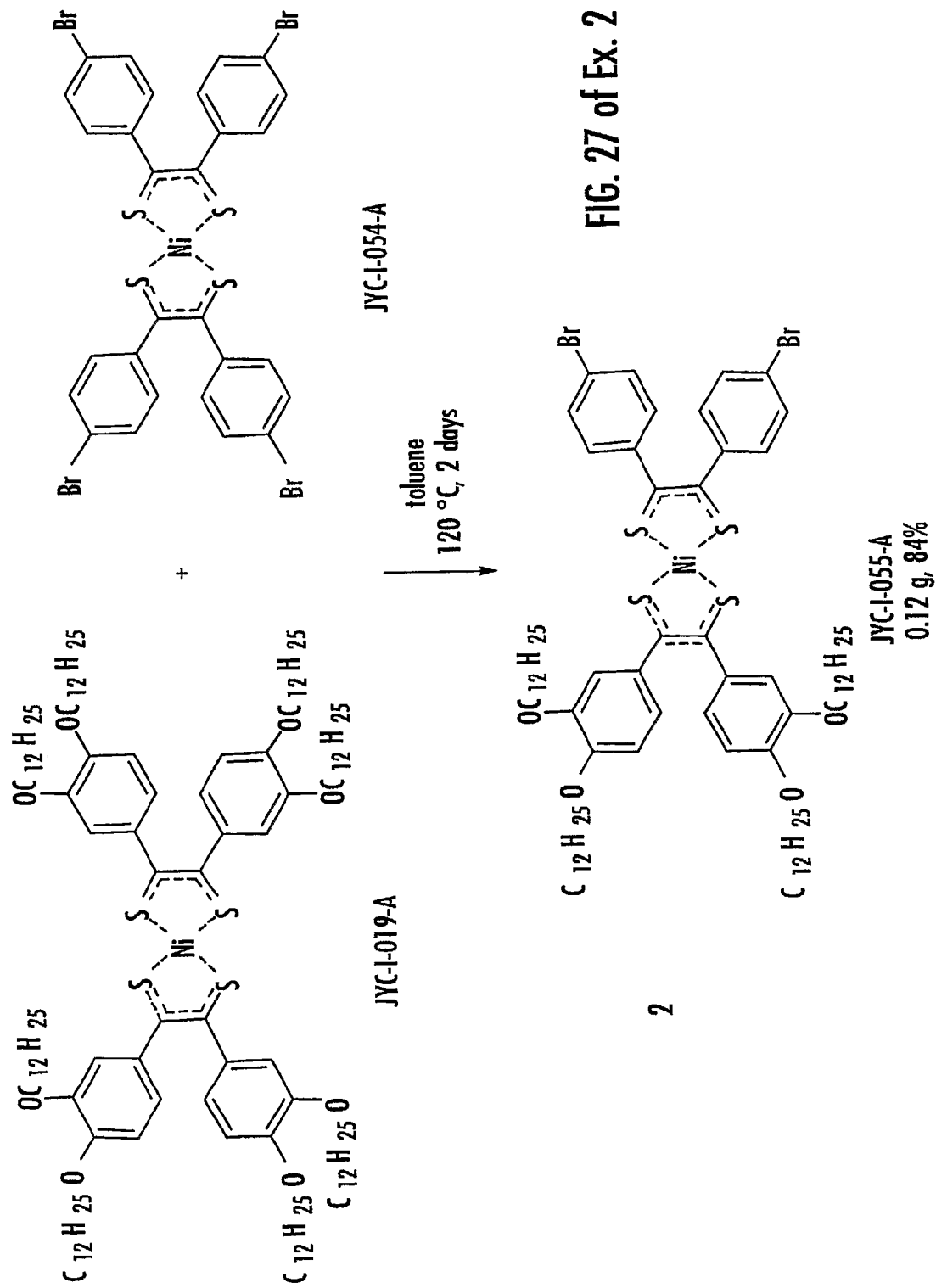
FIG. 27 of Ex. 2

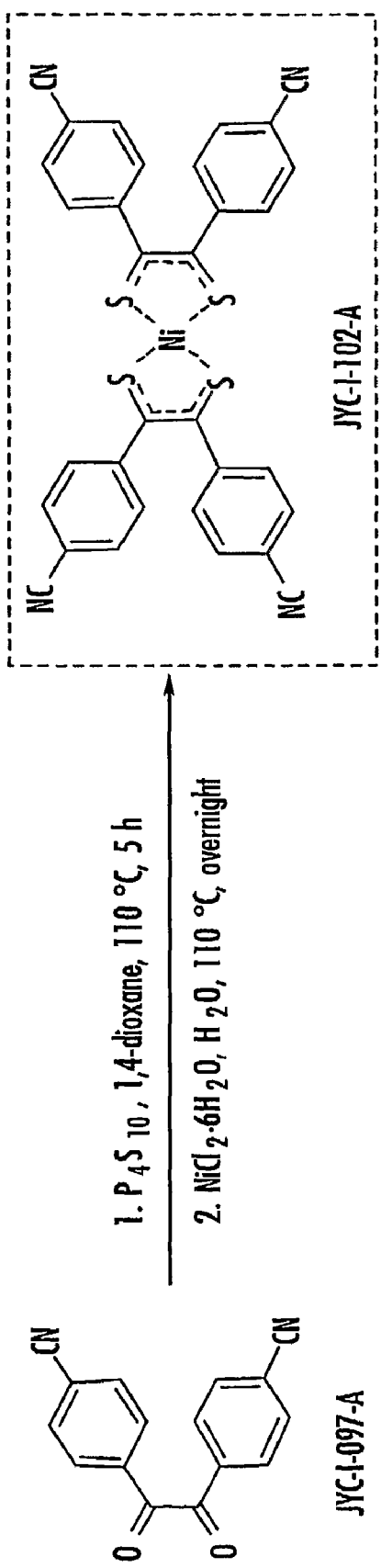
FIG. 28 of Ex. 2

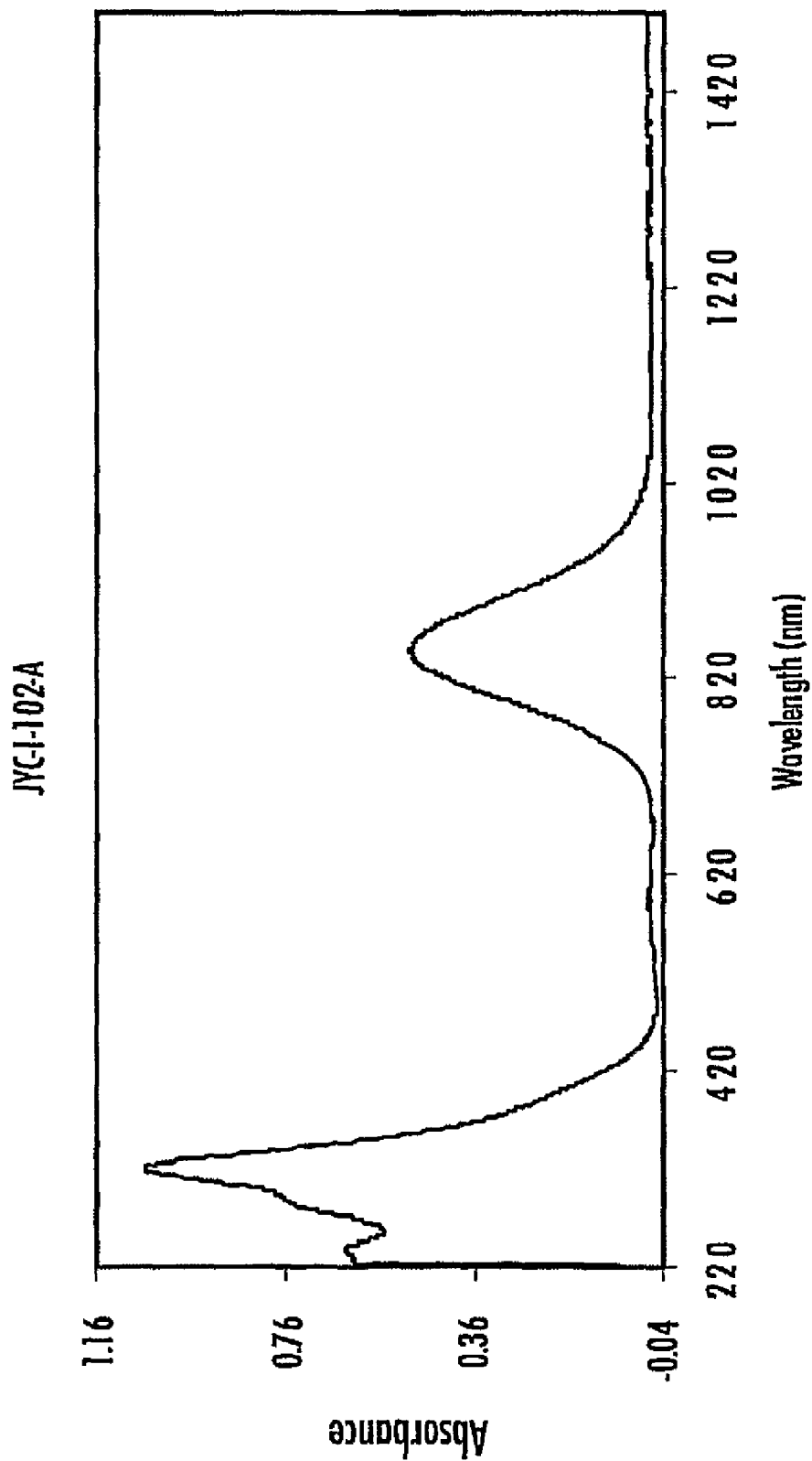
FIG. 29 of Ex. 2

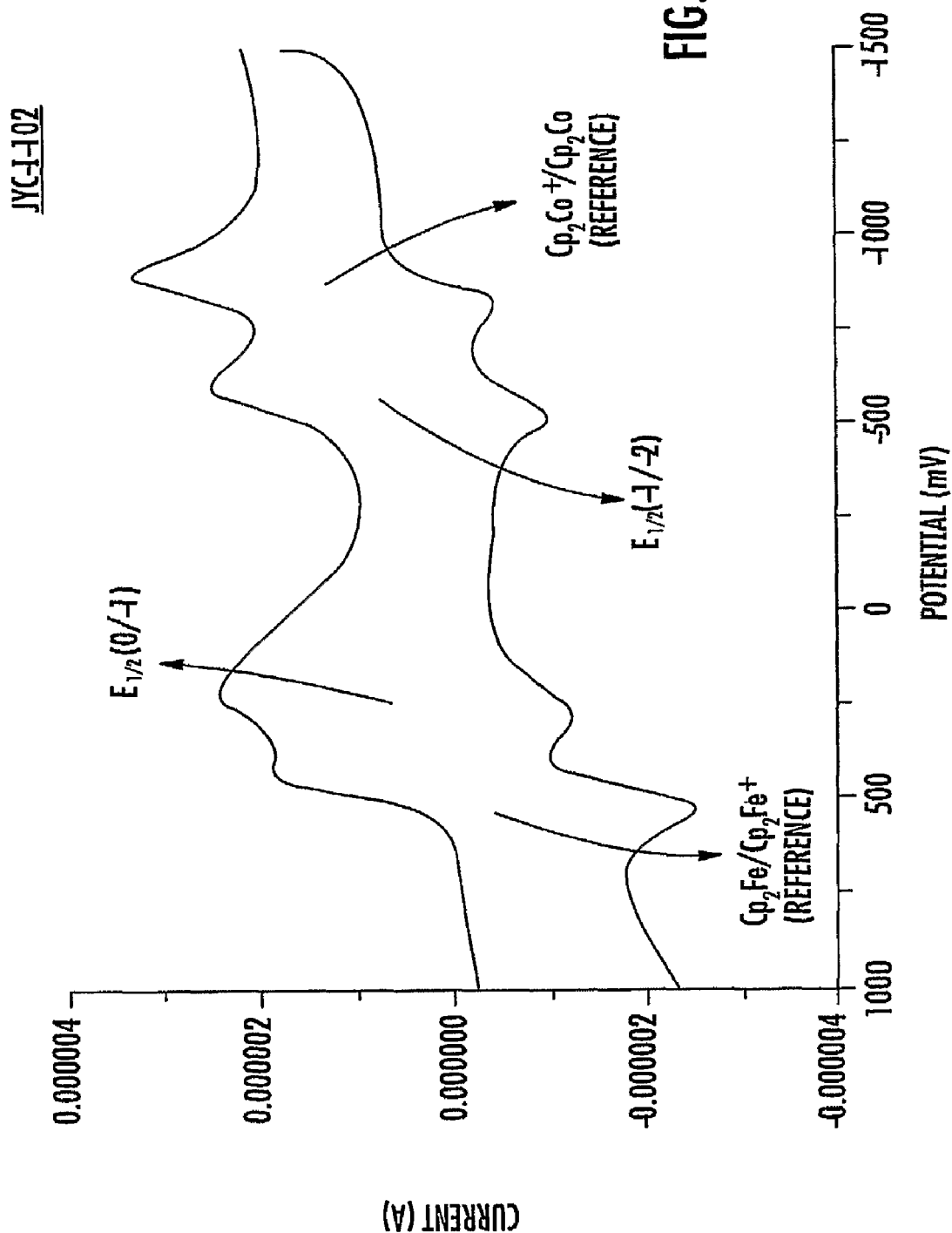
FIG. 30 of Ex. 2

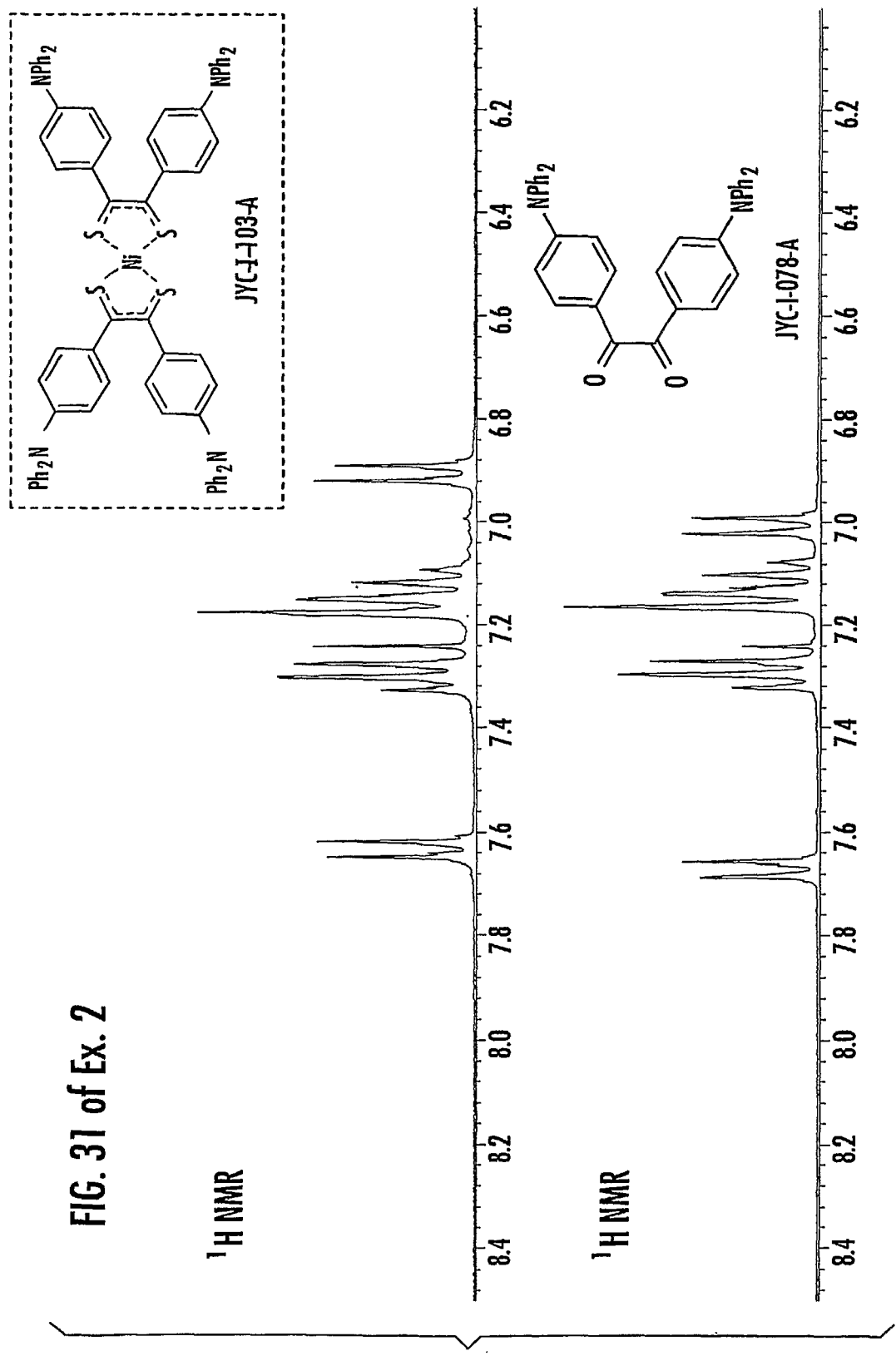
FIG. 31 of Ex. 2

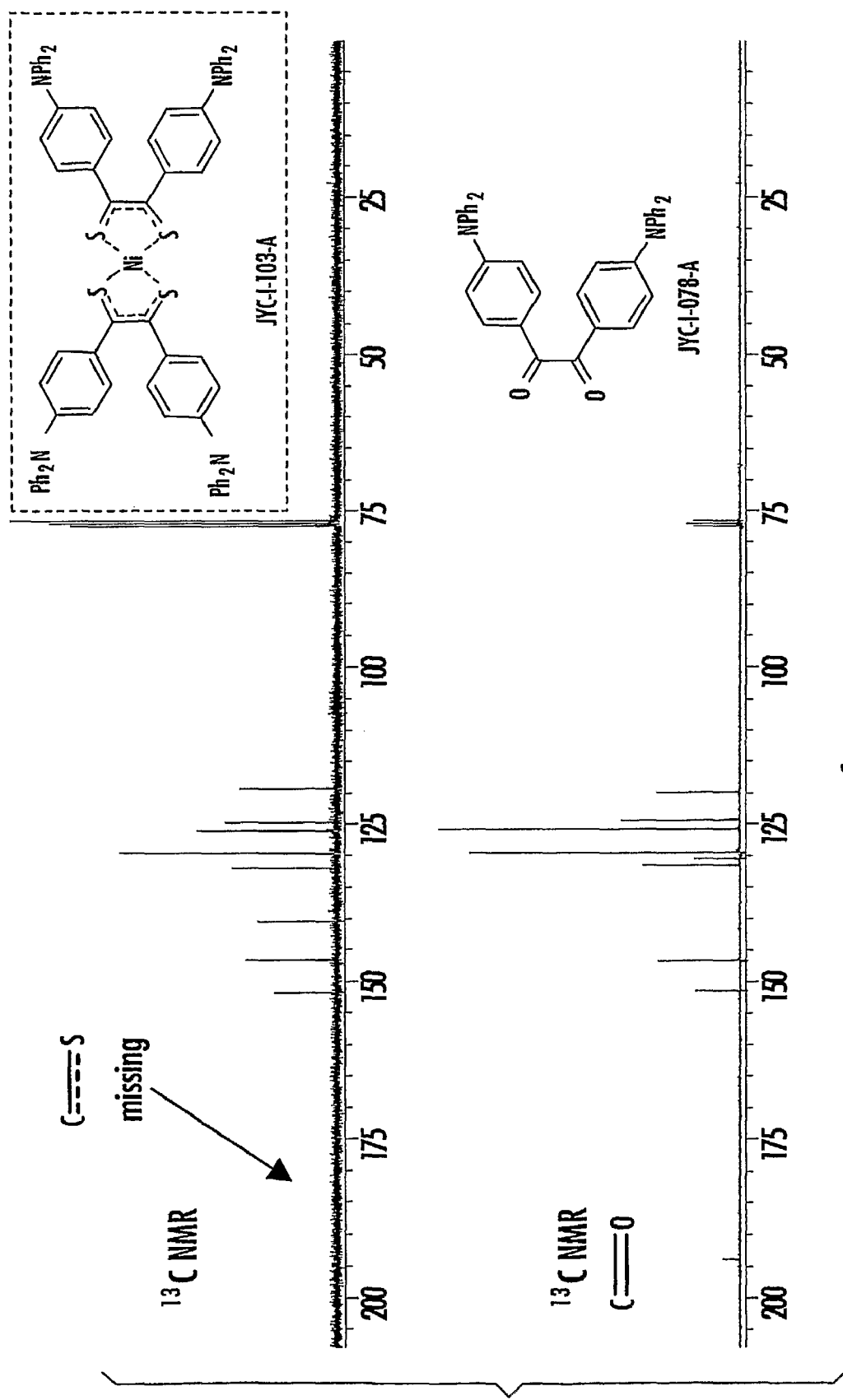
FIG. 32 of Ex. 2

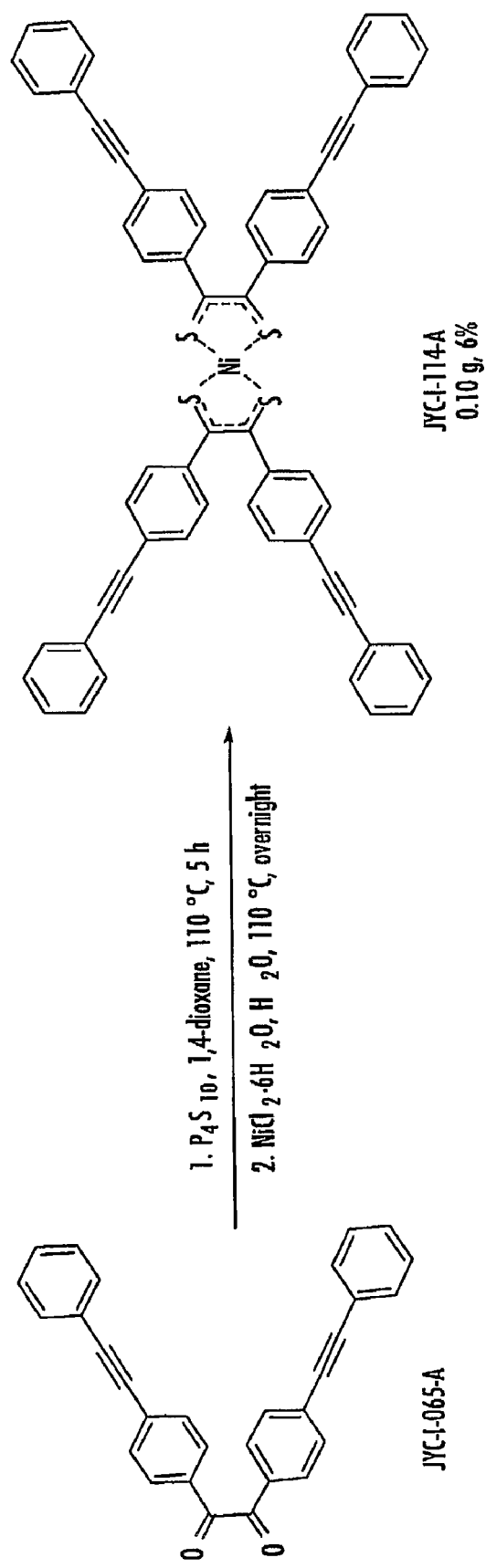
FIG. 33 of Ex. 2

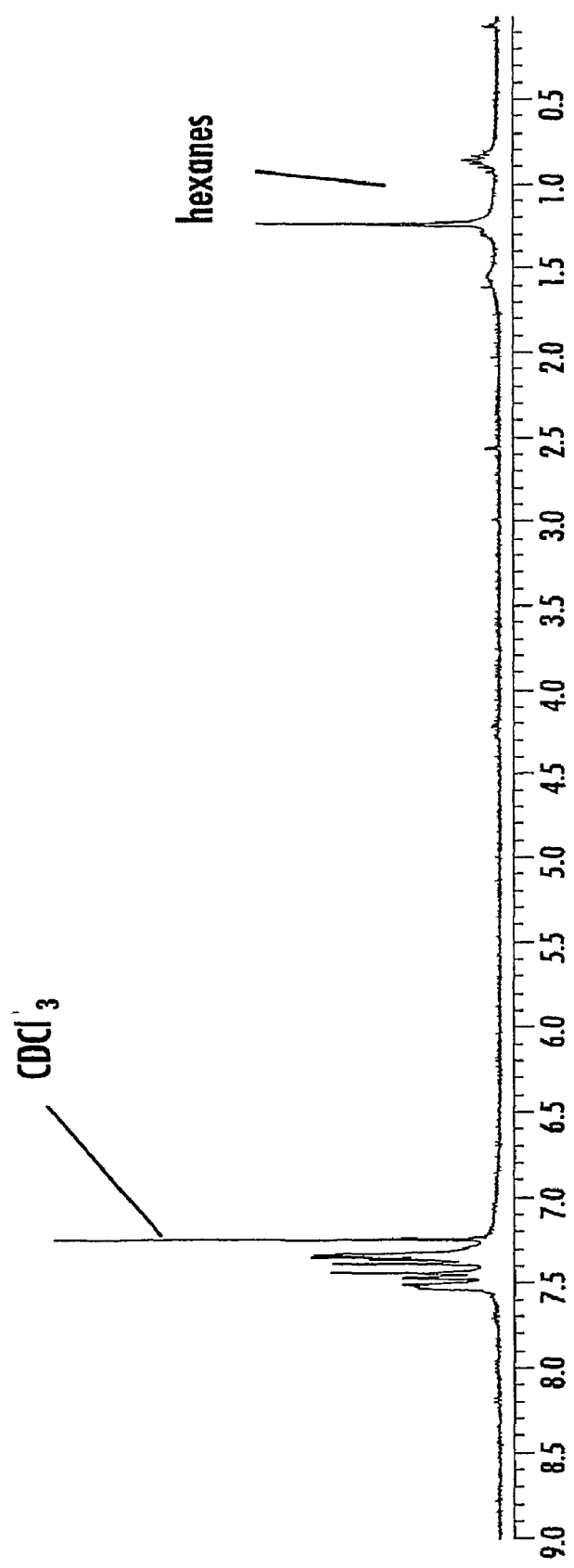
FIG. 34 of Ex. 2

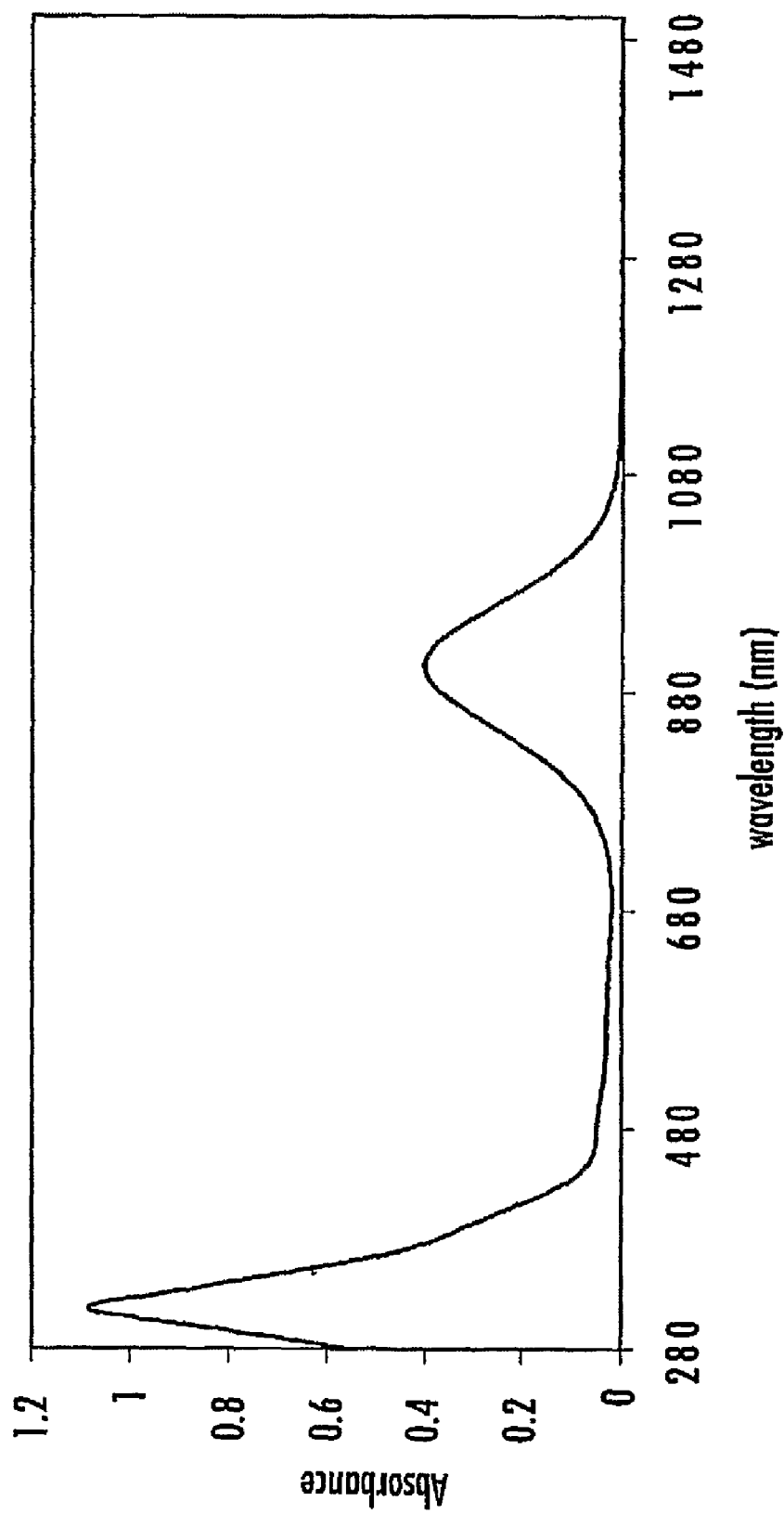
FIG. 35 of Ex. 2

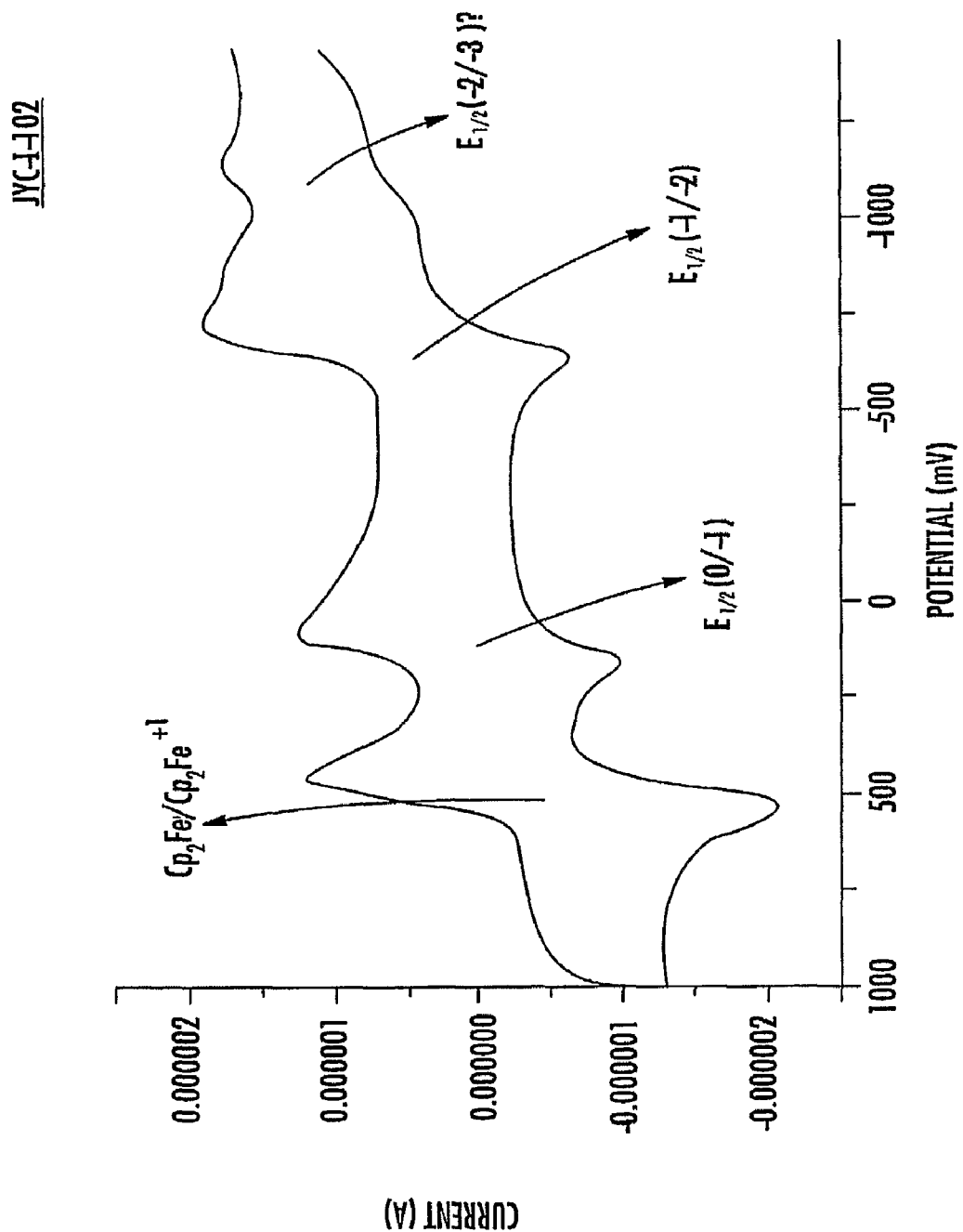
FIG. 36 of Ex. 2

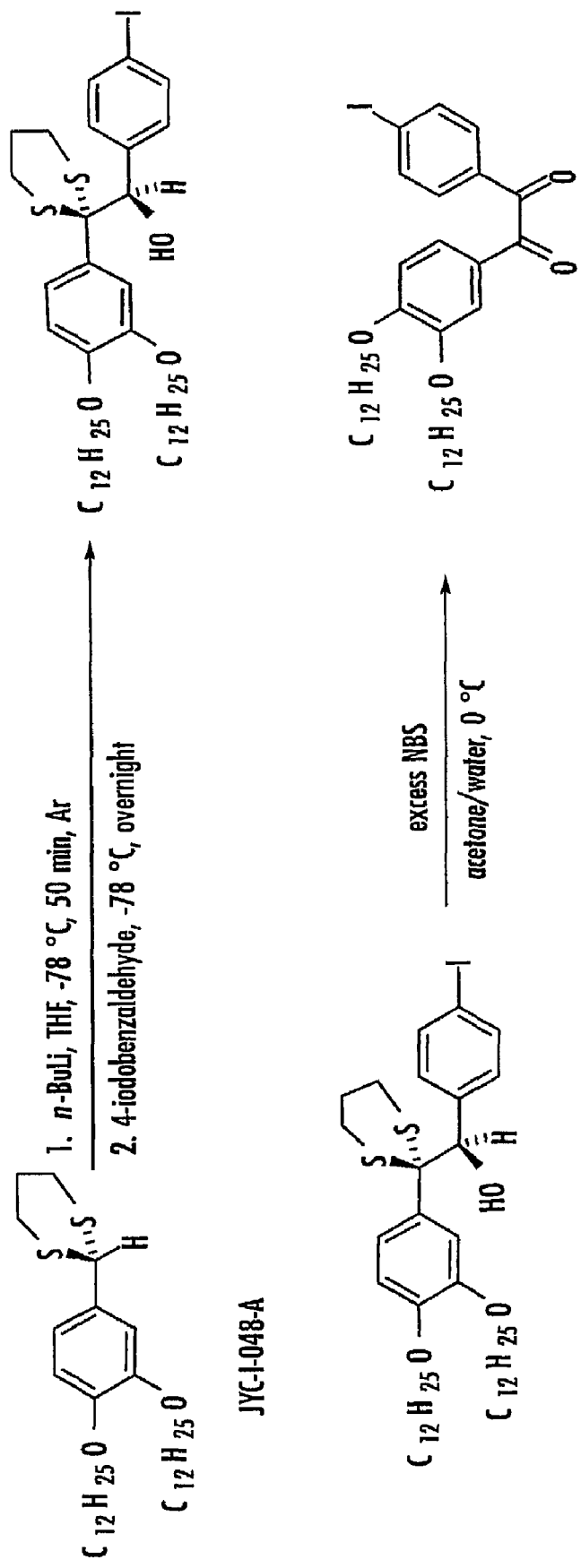
FIG. 37 of Ex. 2

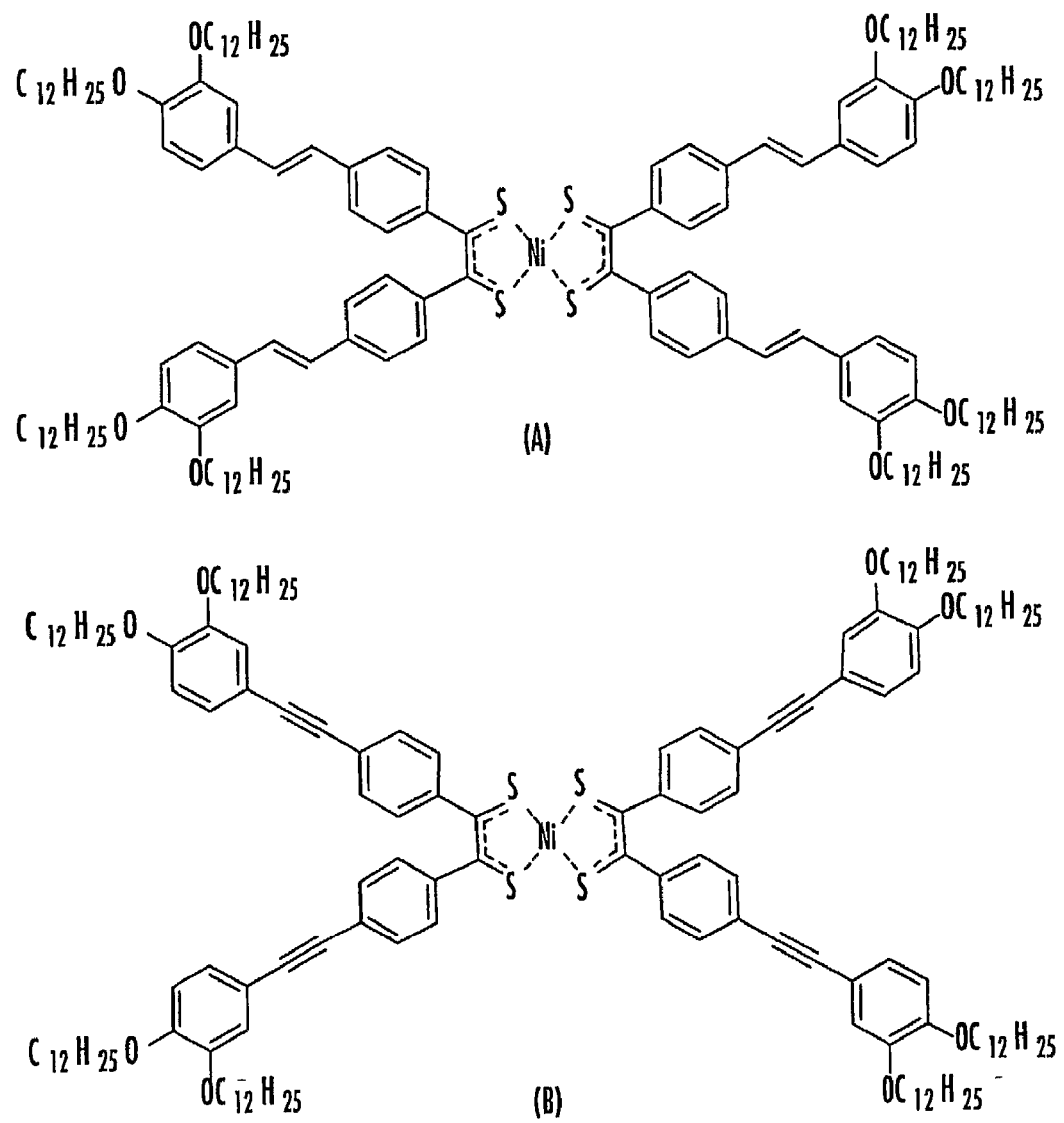
FIG. 1 of Ex. 3

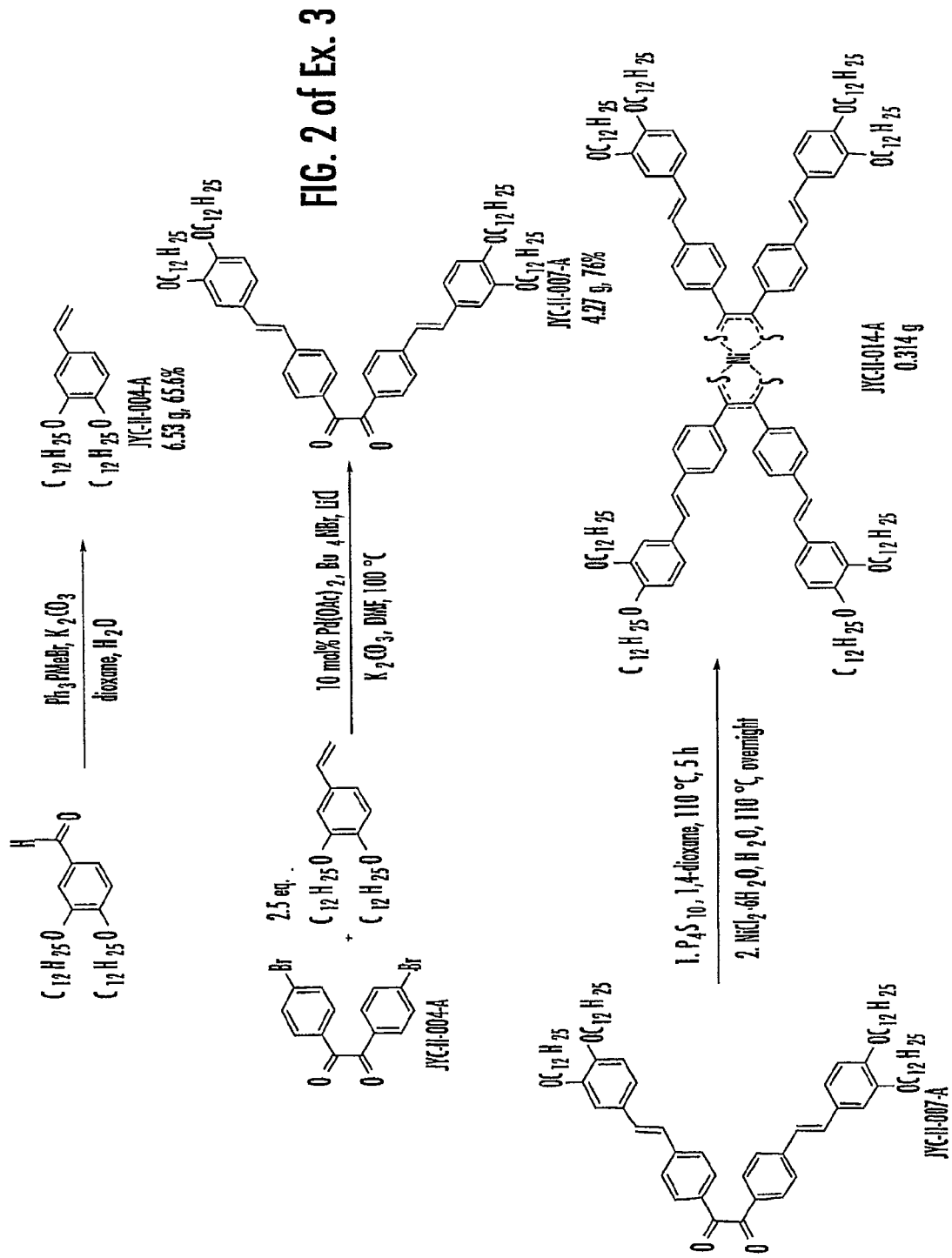
FIG. 2 of Ex. 3

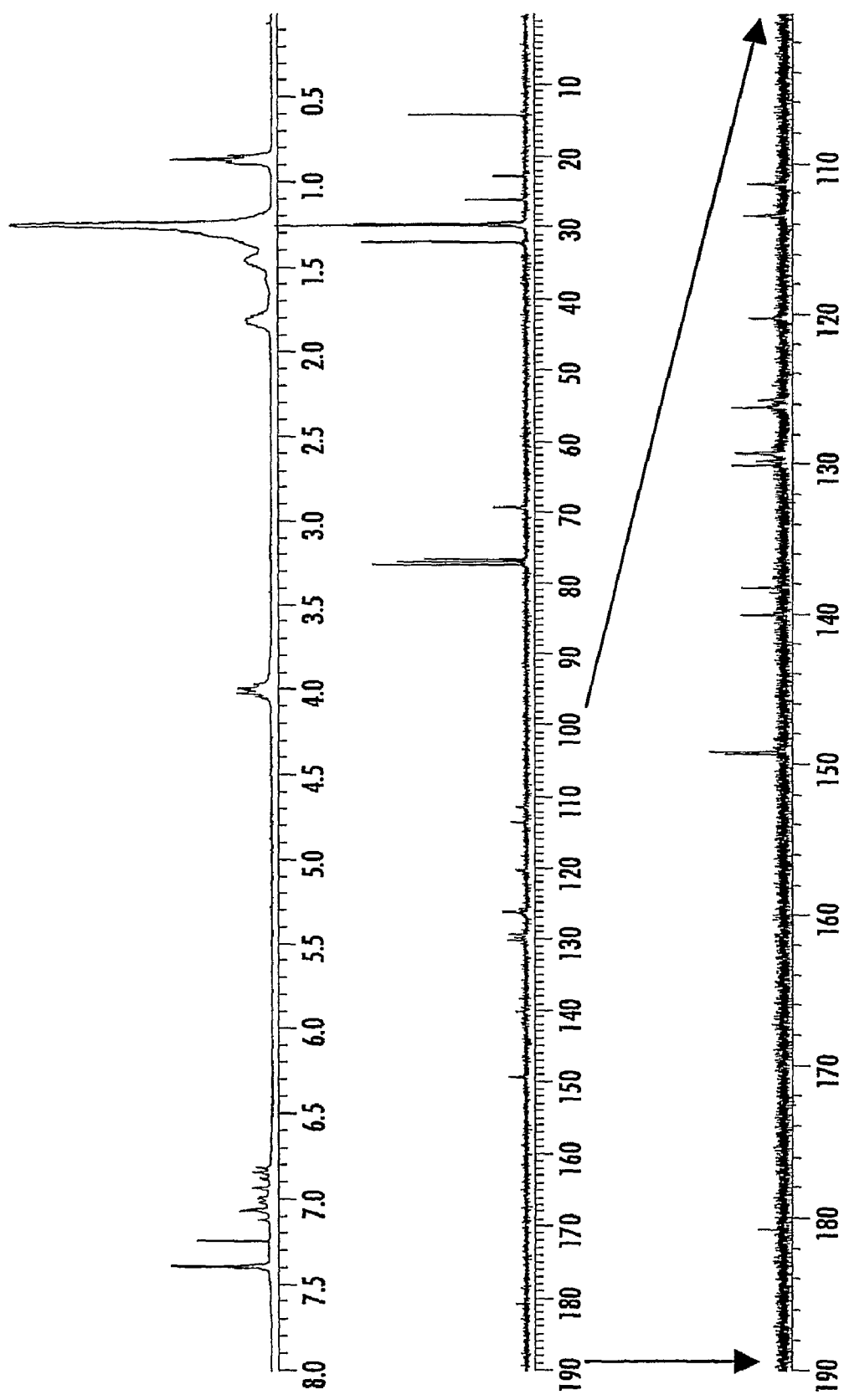
FIG. 3 of Ex. 3

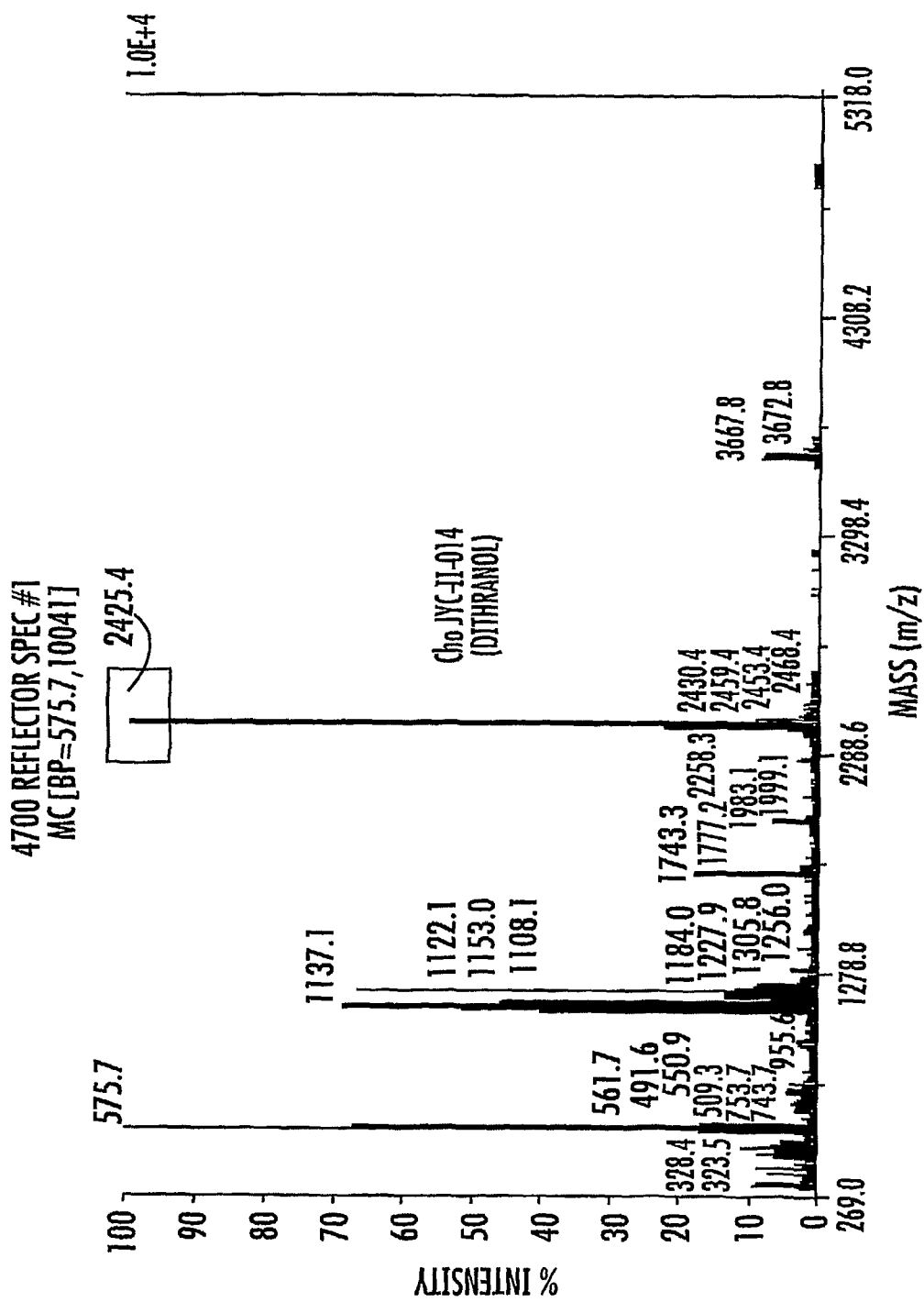
FIG. 4 of Ex. 3

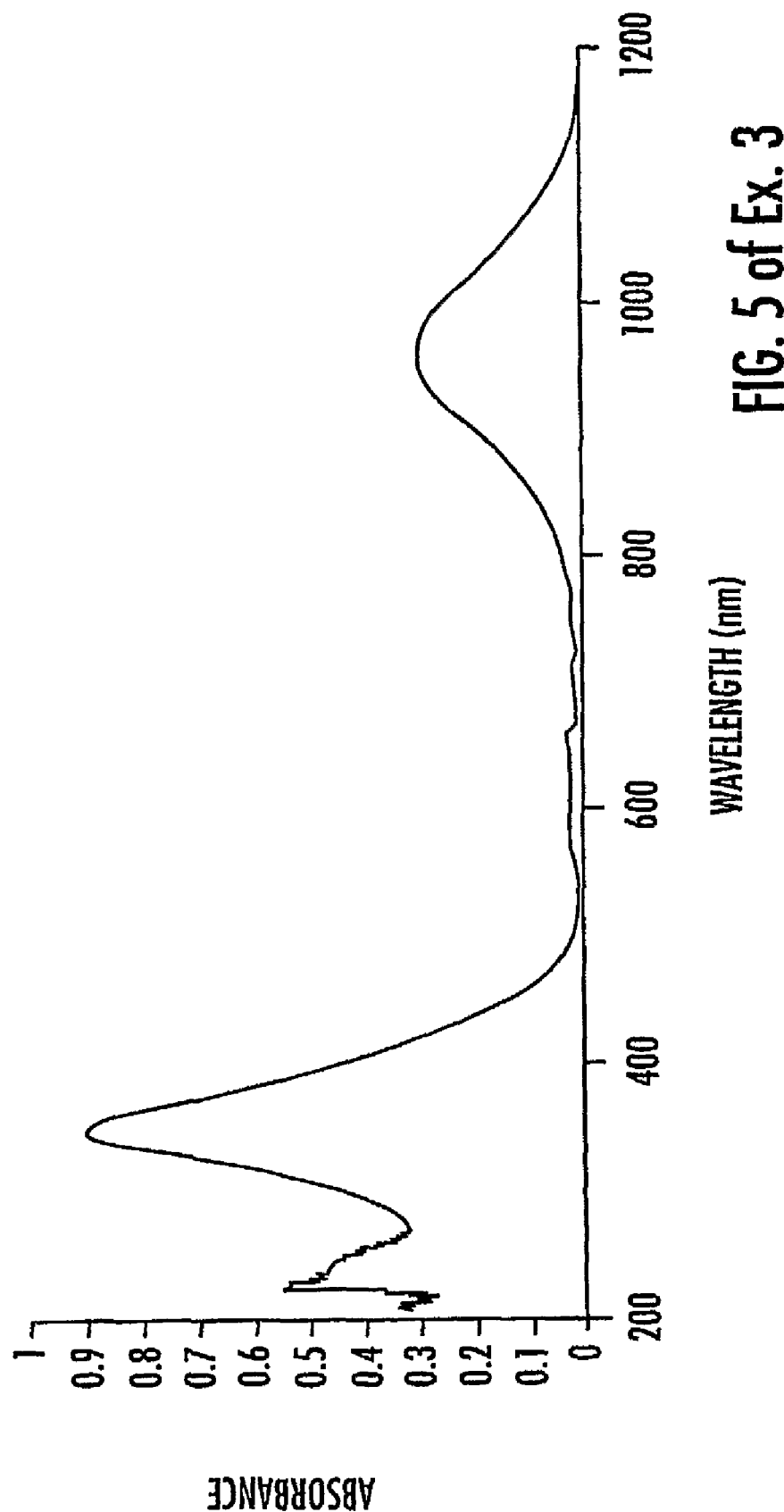
FIG. 5 of Ex. 3

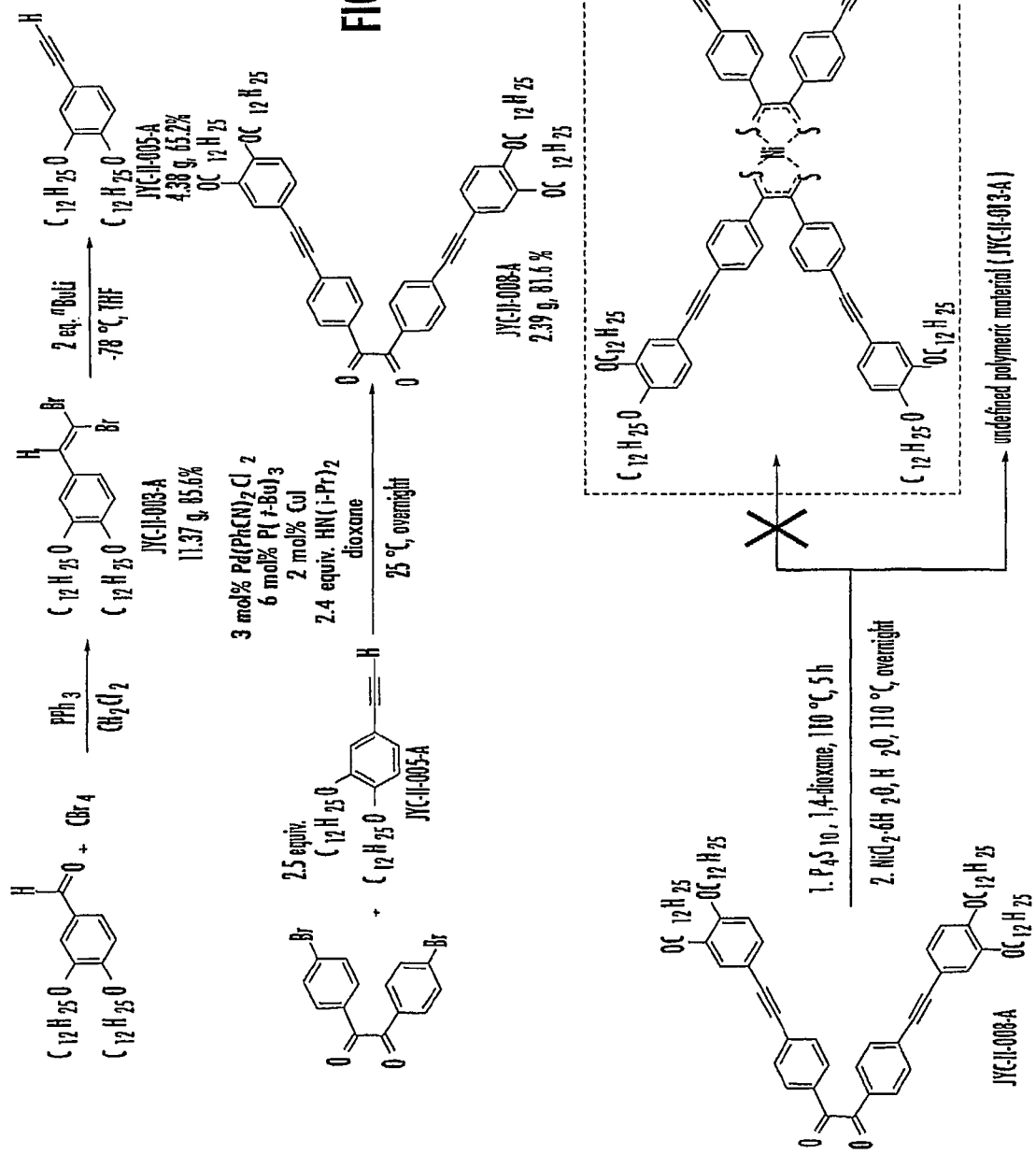
FIG. 6 of Ex. 3

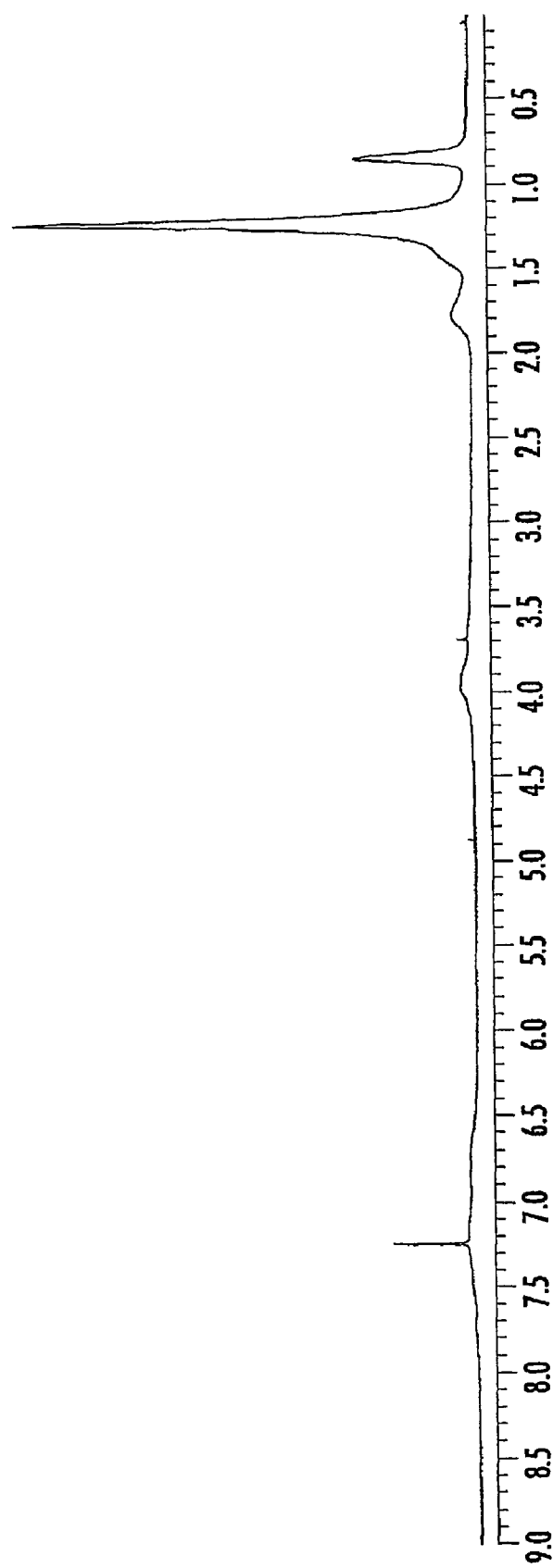
FIG. 7 of Ex. 3

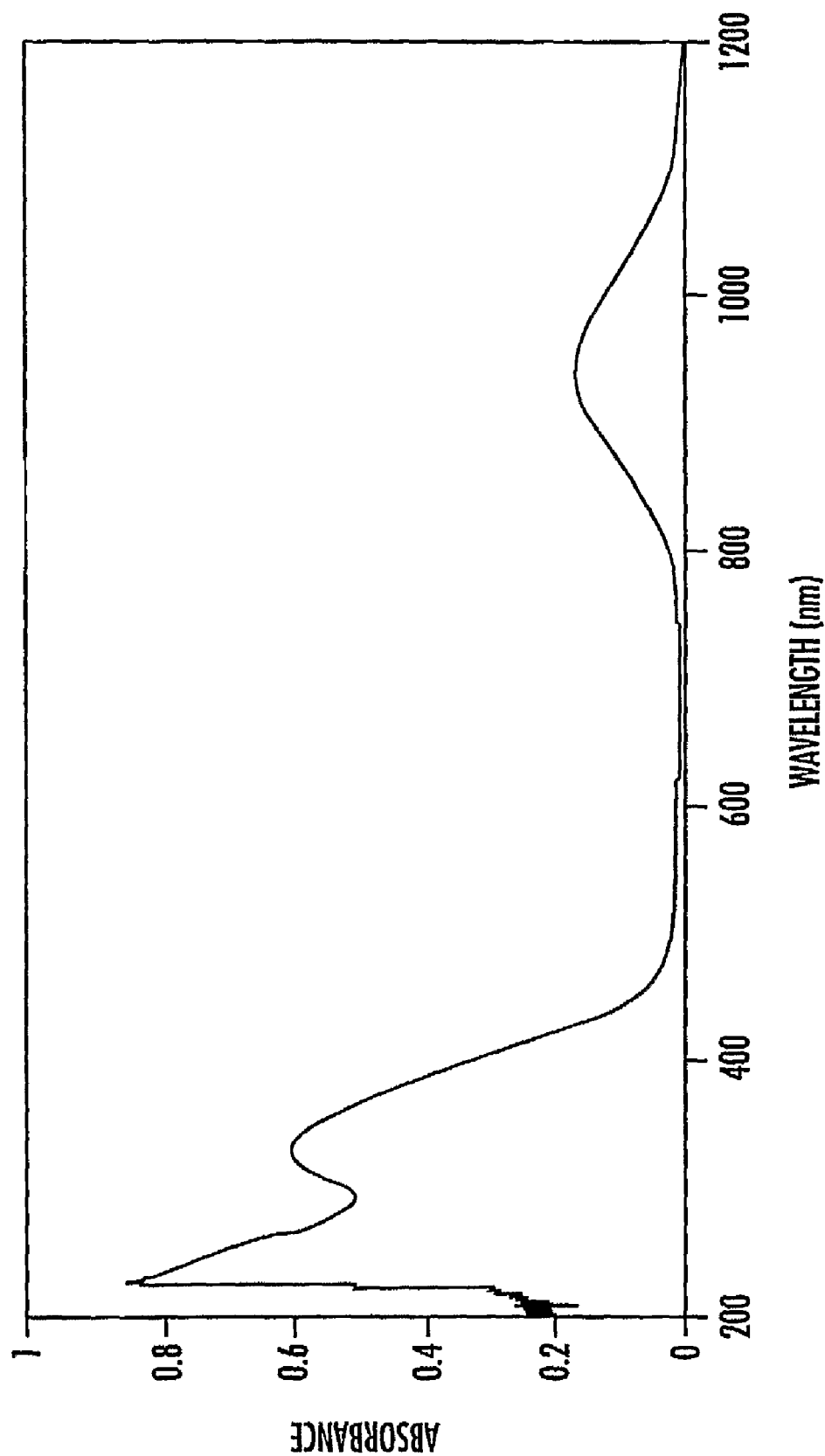
FIG. 8 of Ex. 3

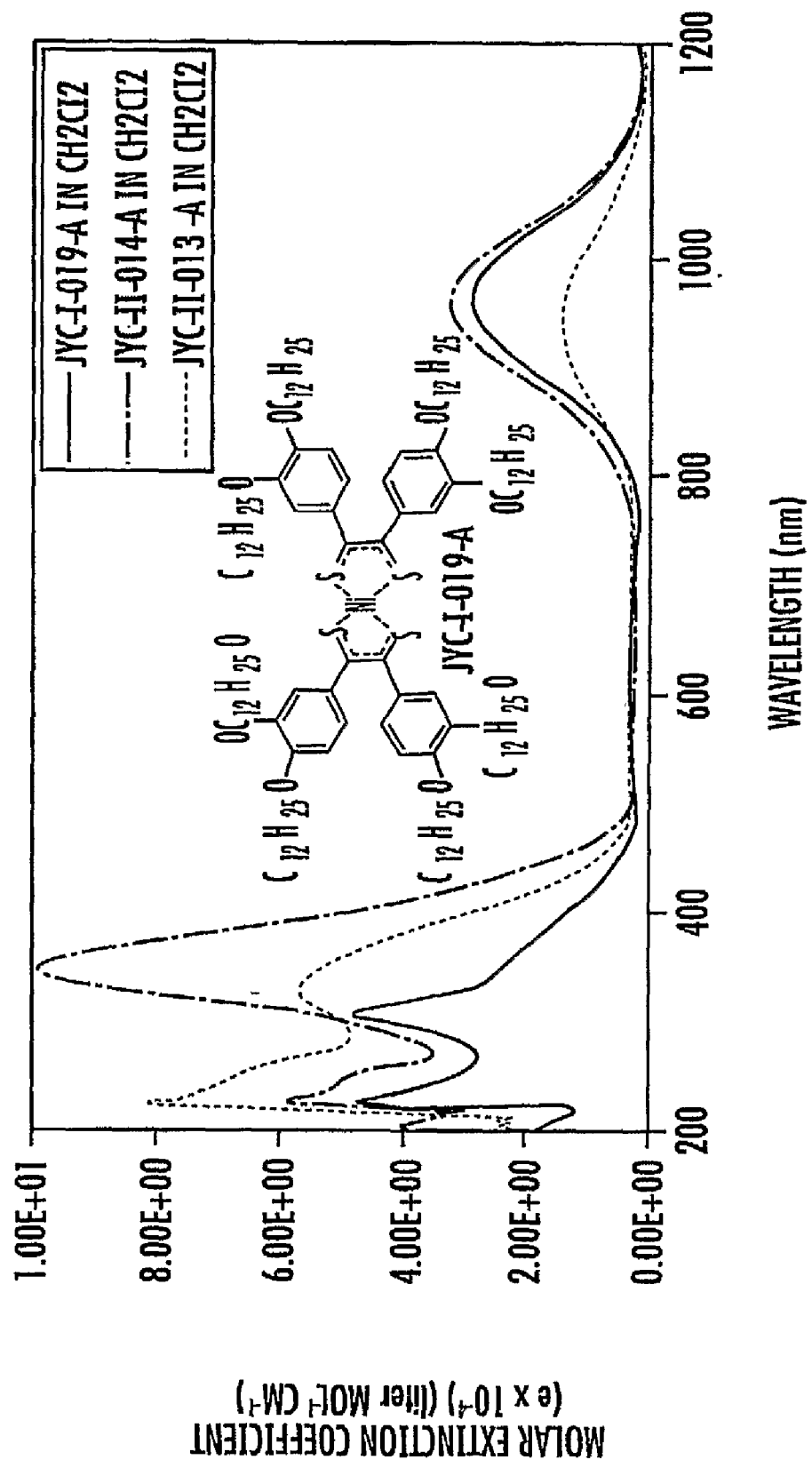
FIG. 9 of Ex. 3

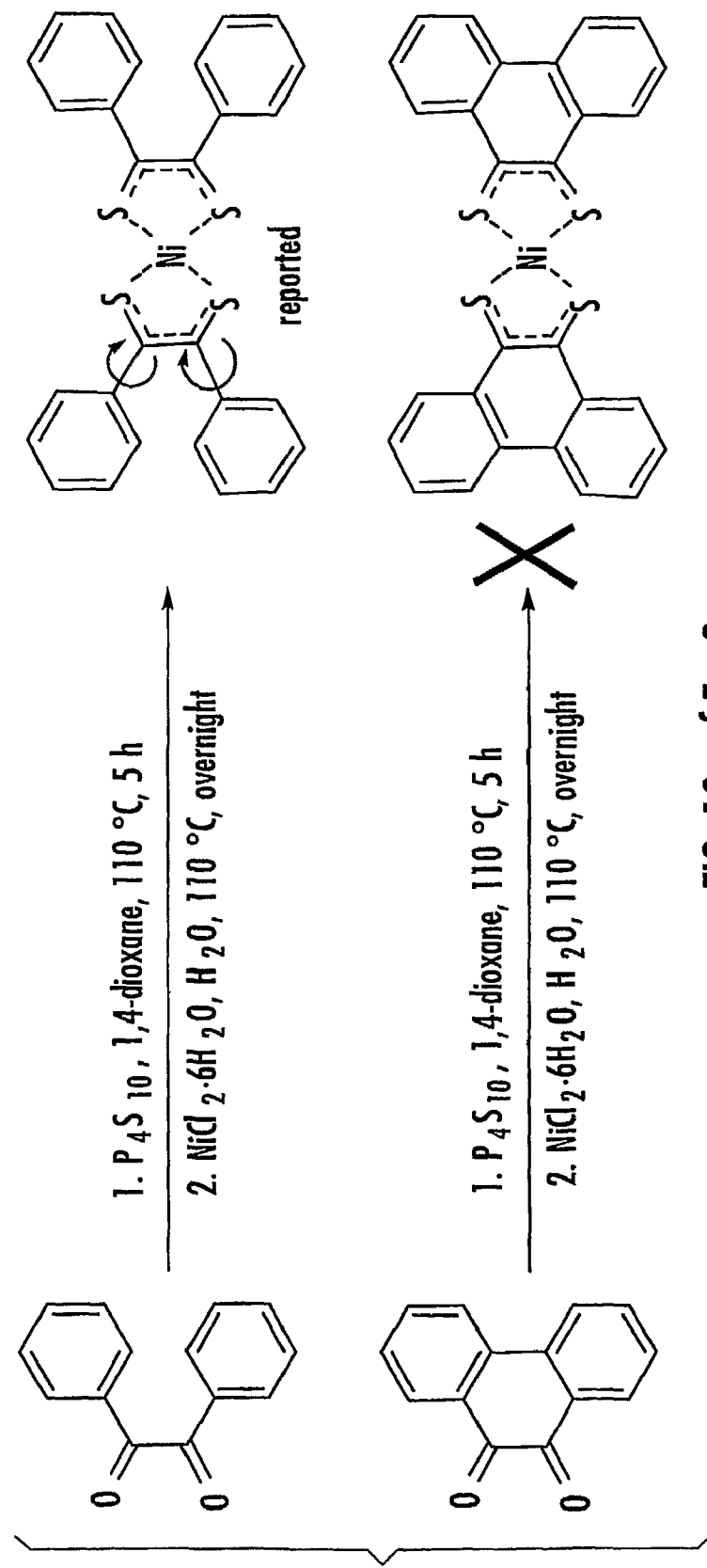
FIG. 10a of Ex. 3

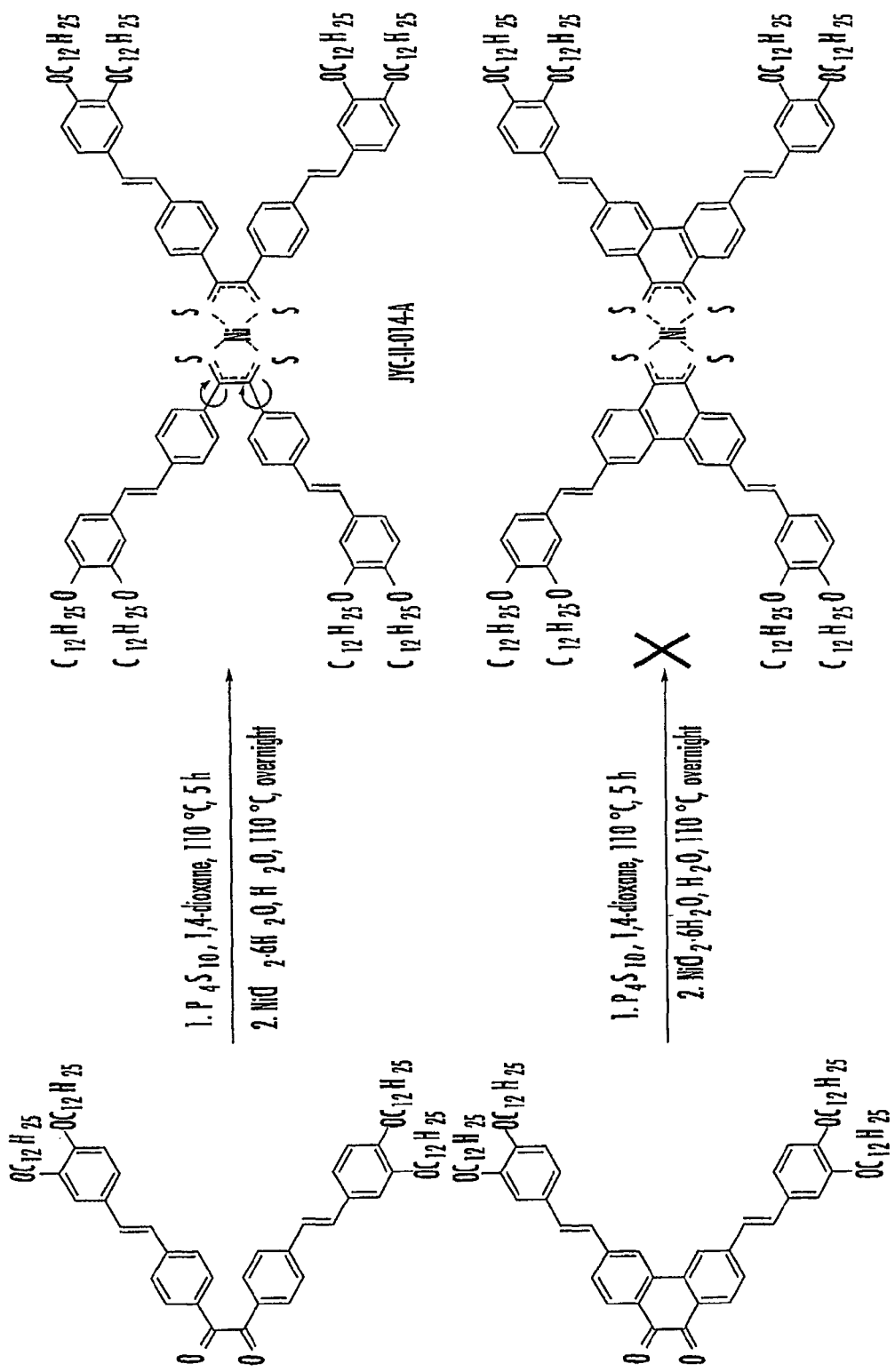
FIG. 10b of Ex. 3

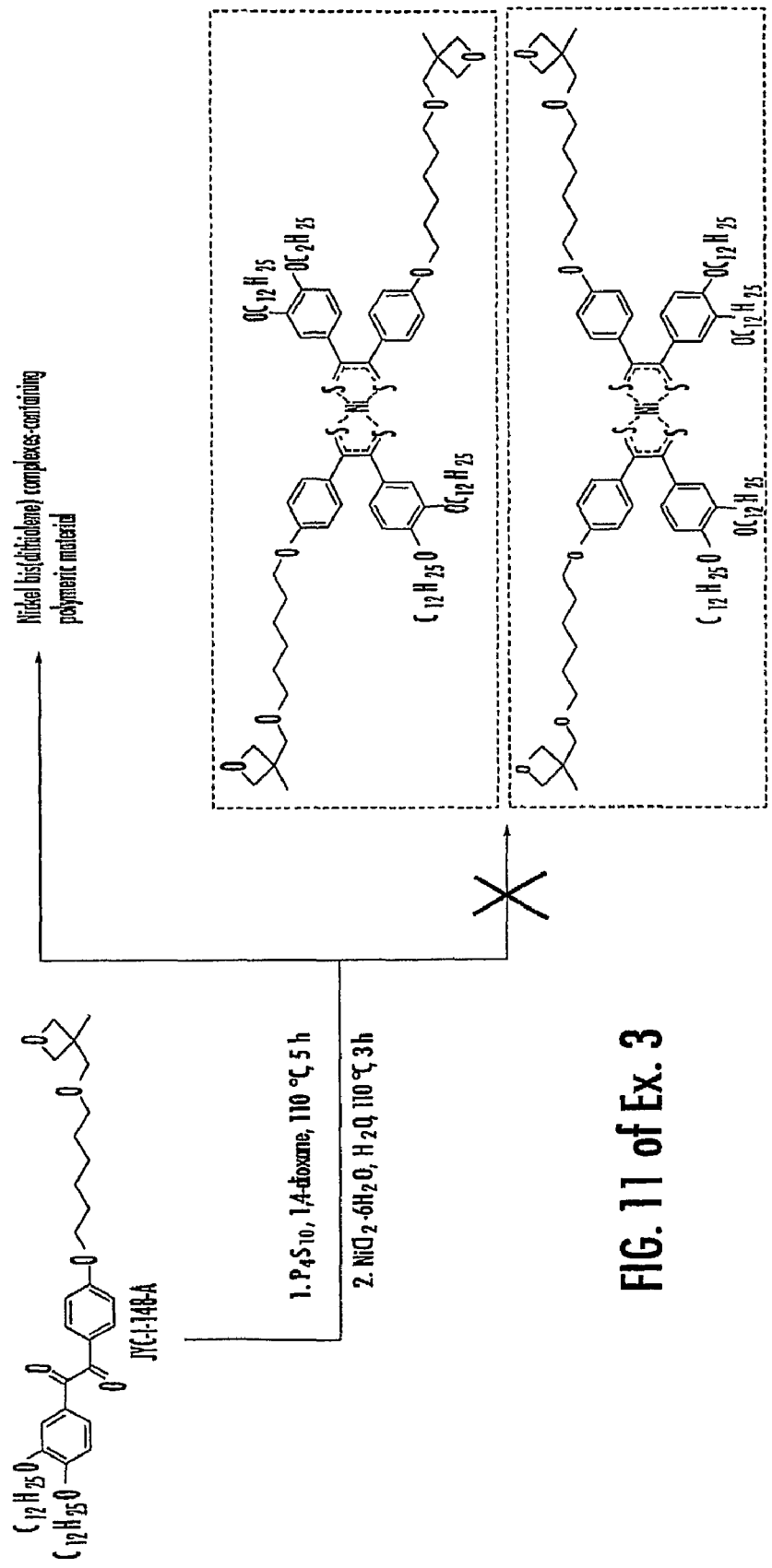
FIG. 11 of Ex. 3

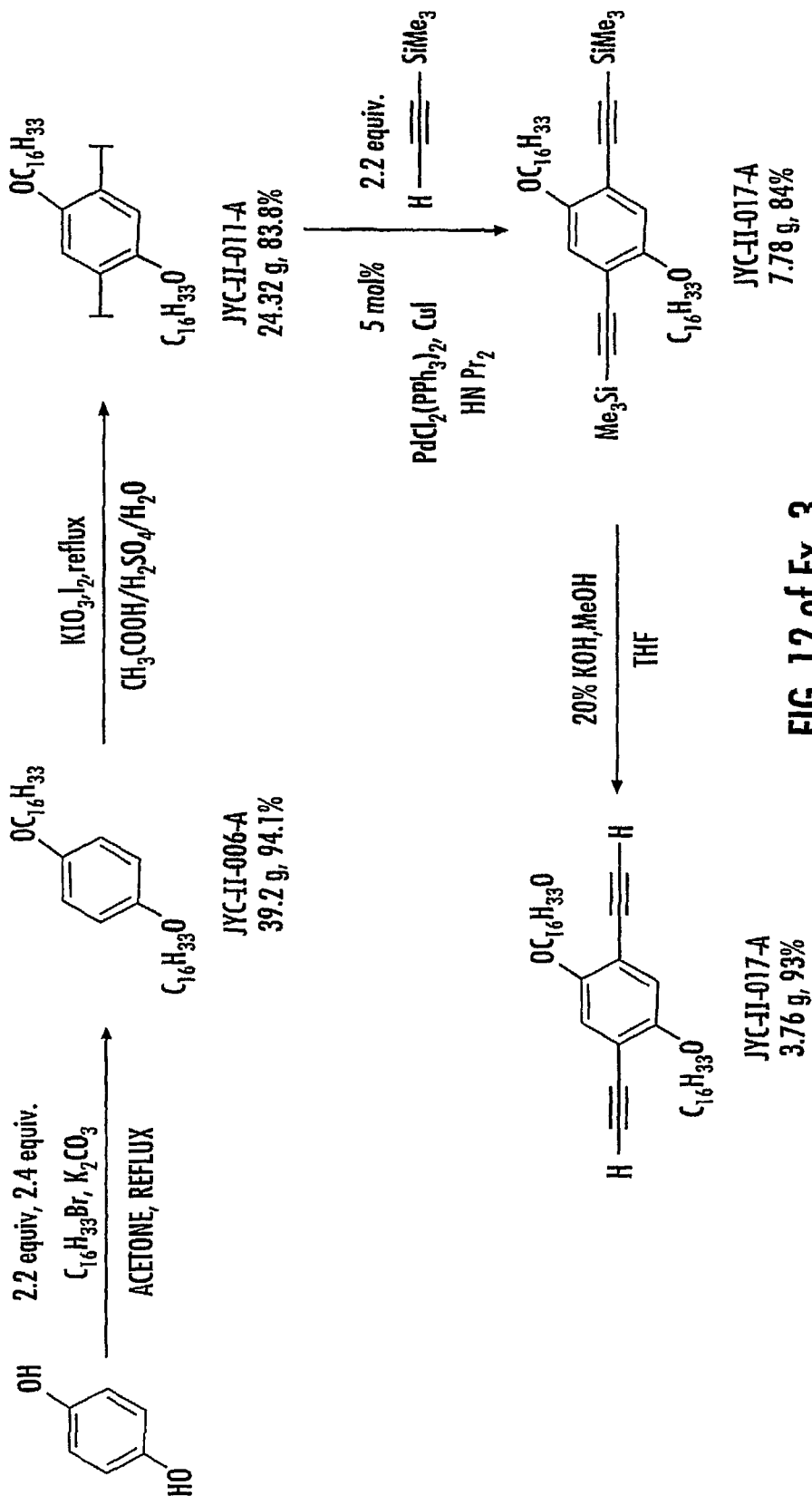
FIG. 12 of Ex. 3

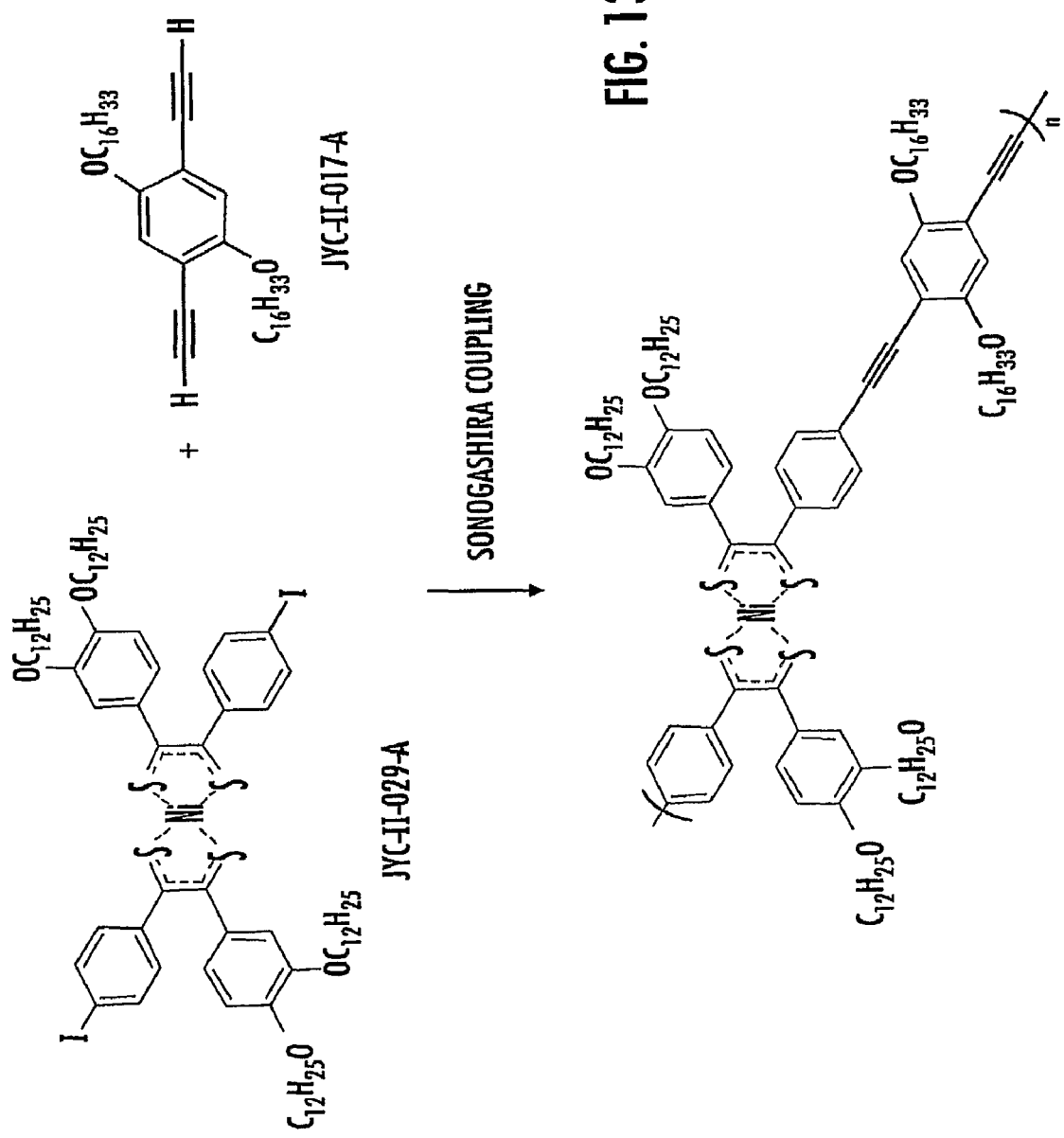
FIG. 13 of Ex. 3

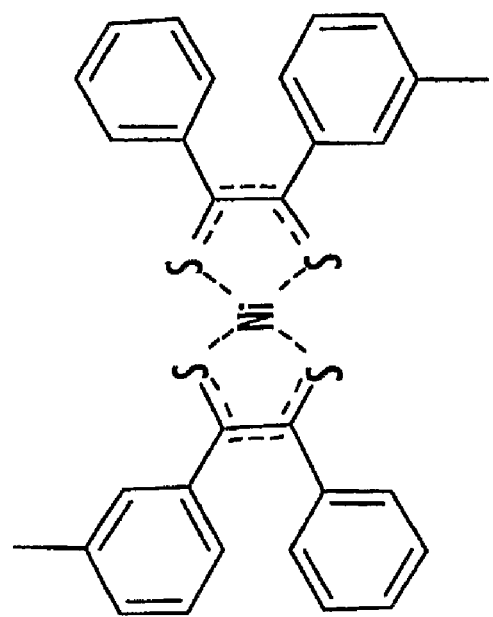
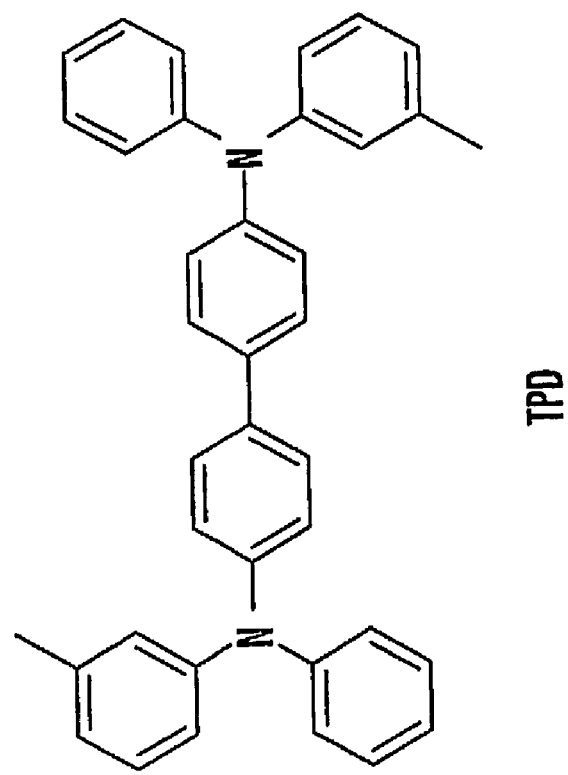
TPD
FIG. 14 of Ex. 3

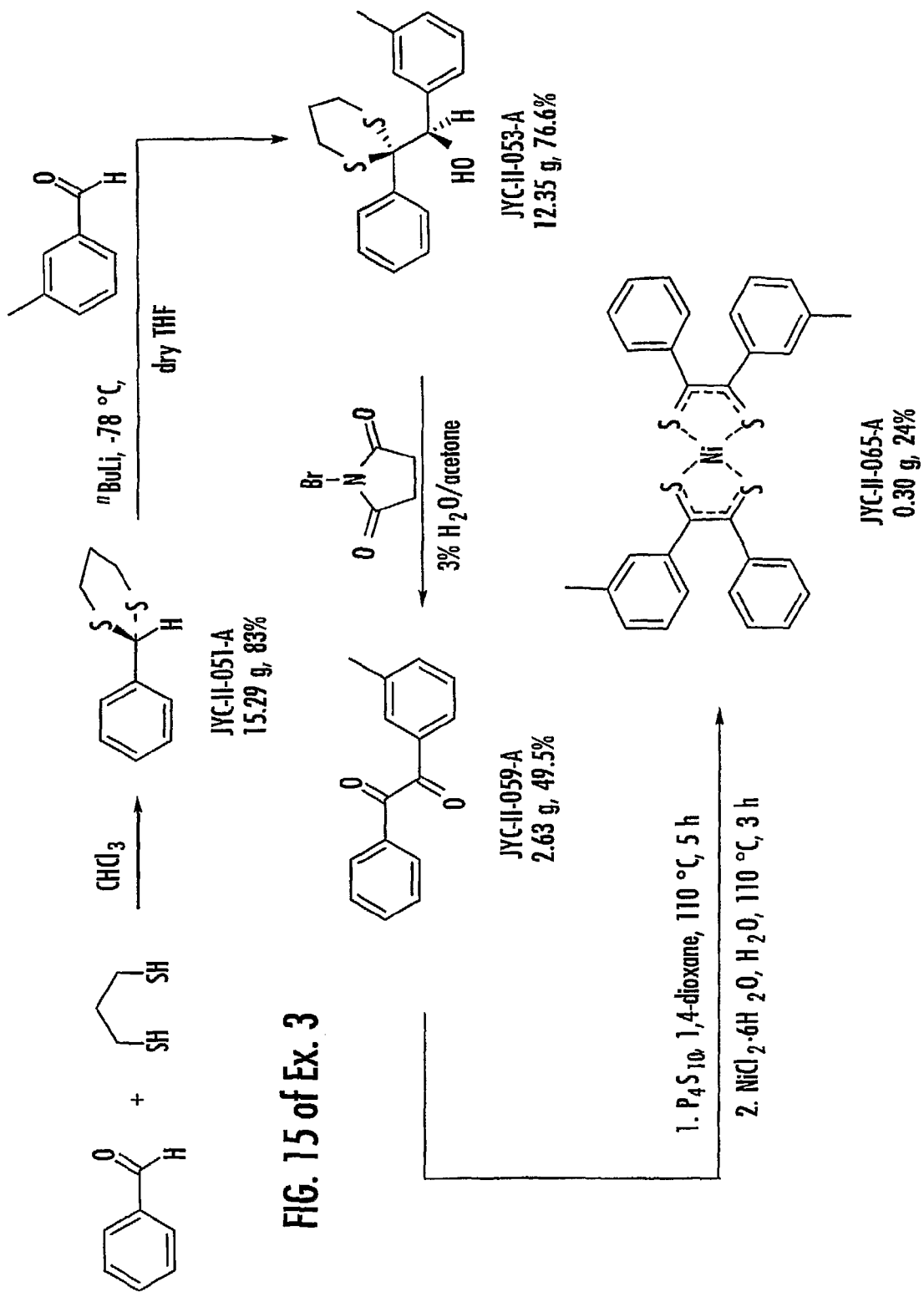
FIG. 15 of Ex. 3

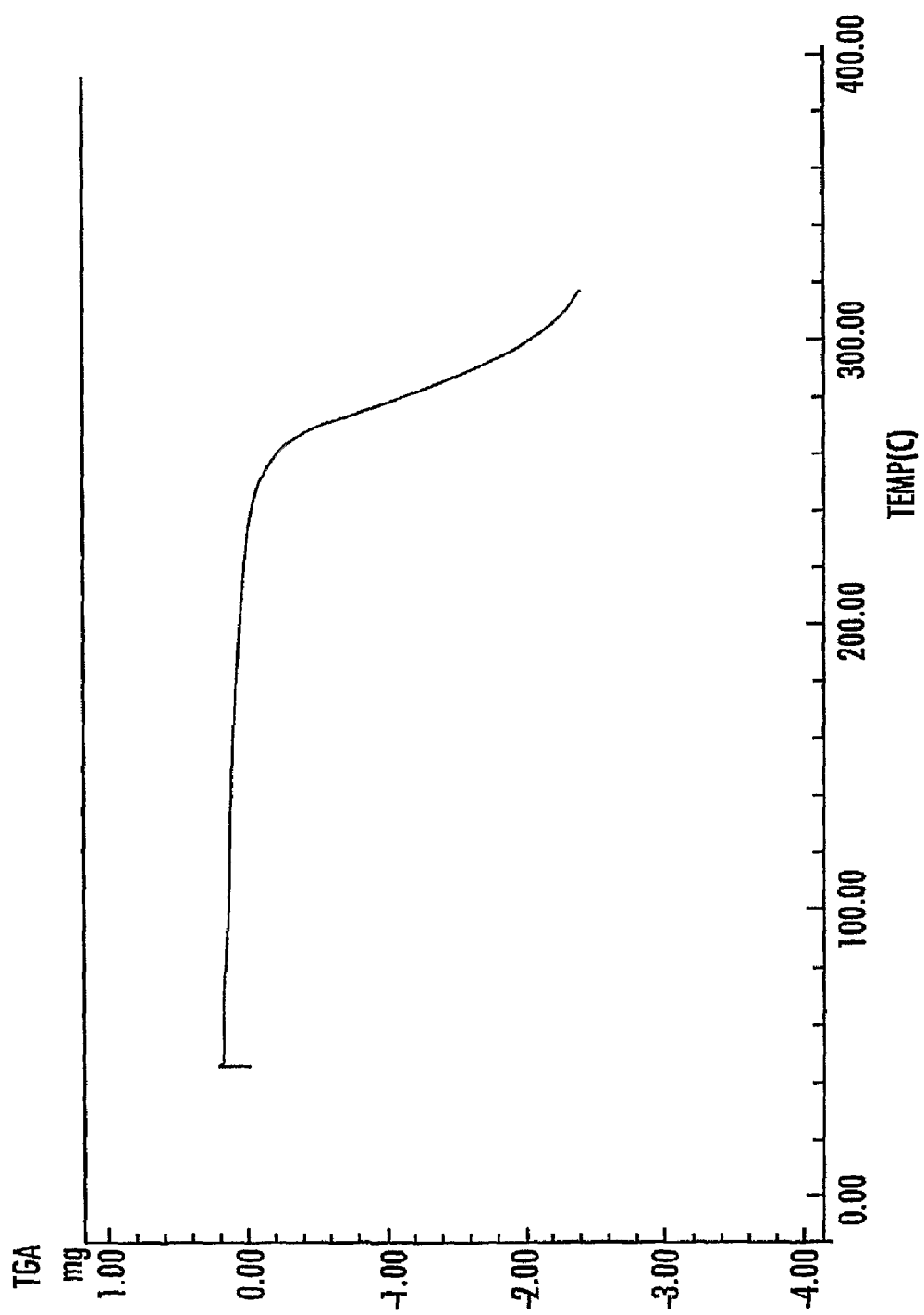
FIG. 16 of Ex. 3

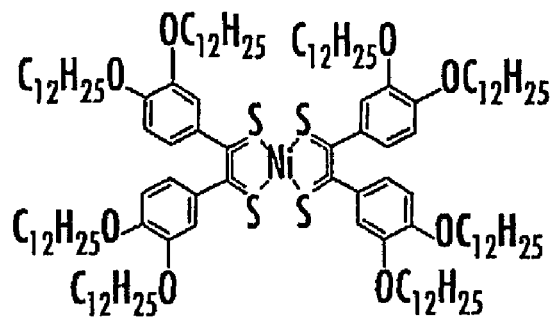
FIG. 1 of Ex. 4
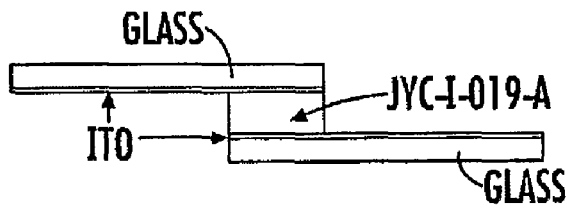
FIG. 2 of Ex. 4
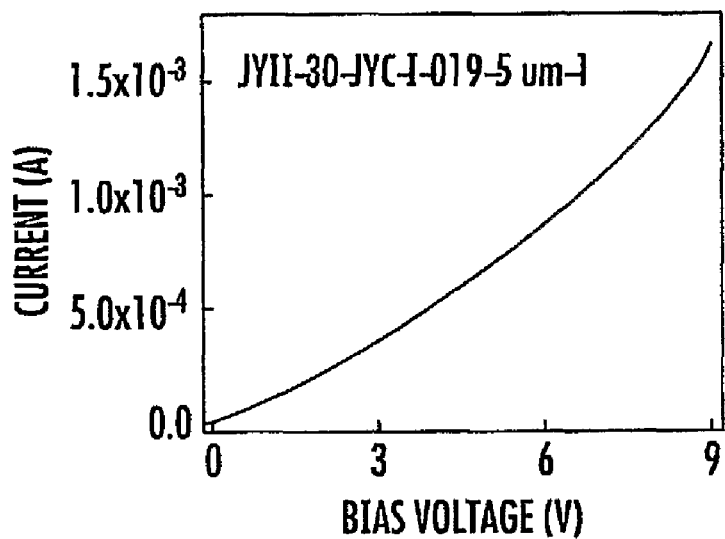
FIG. 3 of Ex. 4

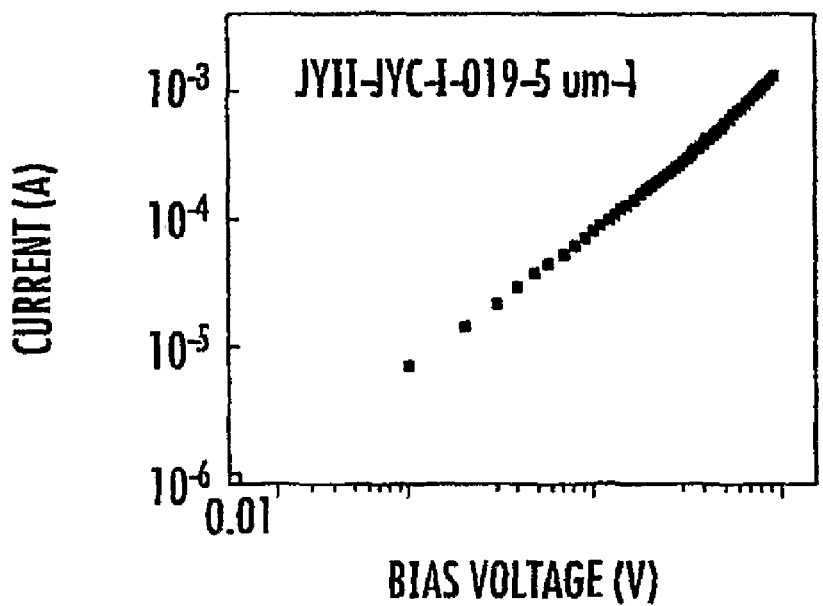
FIG. 4 of Ex. 4
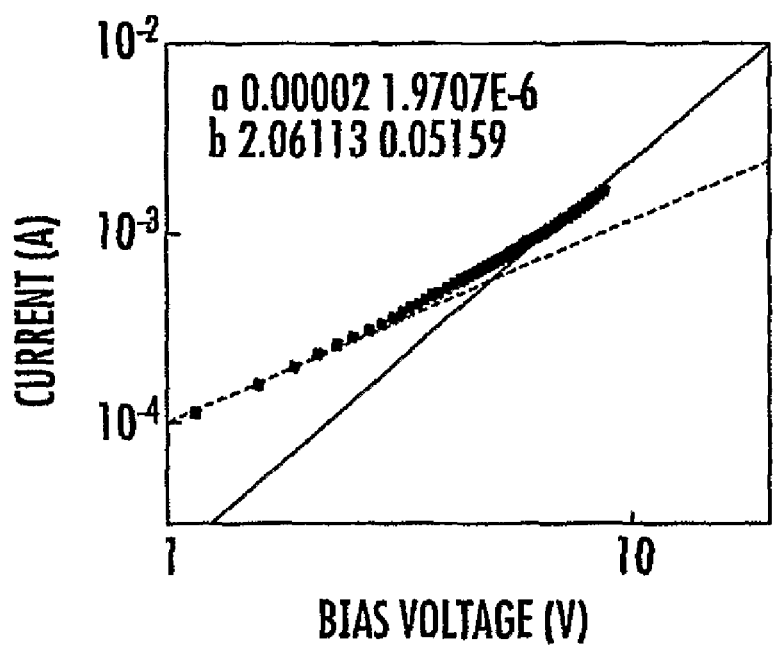
FIG. 5 of Ex. 4

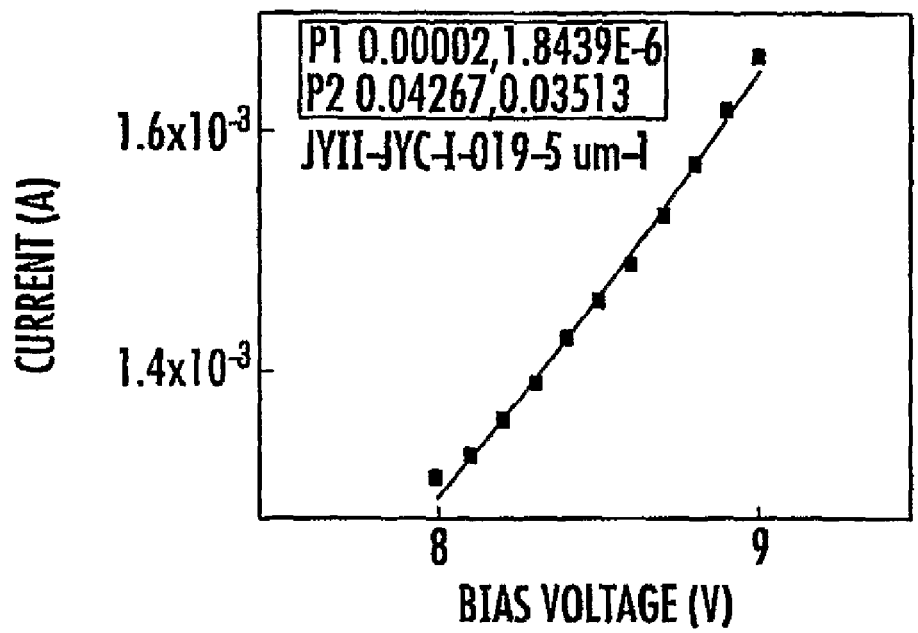
FIG. 6 of Ex. 4
$$I = \frac{9}{8}\mu_0 C \exp\left(0.84597 \frac{\gamma}{\sqrt{d}}\sqrt{V}\right)\frac{V^2}{d^2}$$
$$\Rightarrow y = (P1)*\exp\left[(P2)*x^{1/2}\right]*x^2$$
$$\mu(E=0) = \frac{8d^2(P1)}{9C}$$
$$\gamma = \frac{(P2)\sqrt{d}}{0.84597}$$
$$\mu(E=0) = 2.62\times 10^{-6}\,(m^2/Vs)$$
$$\gamma = 0.000112\,(m/V)^{1/2}$$
$$\mu = 2.62\times 10^{-6}\cdot\exp(1.12\times 10^{-4}\sqrt{E})$$
FIG. 7 of Ex. 4

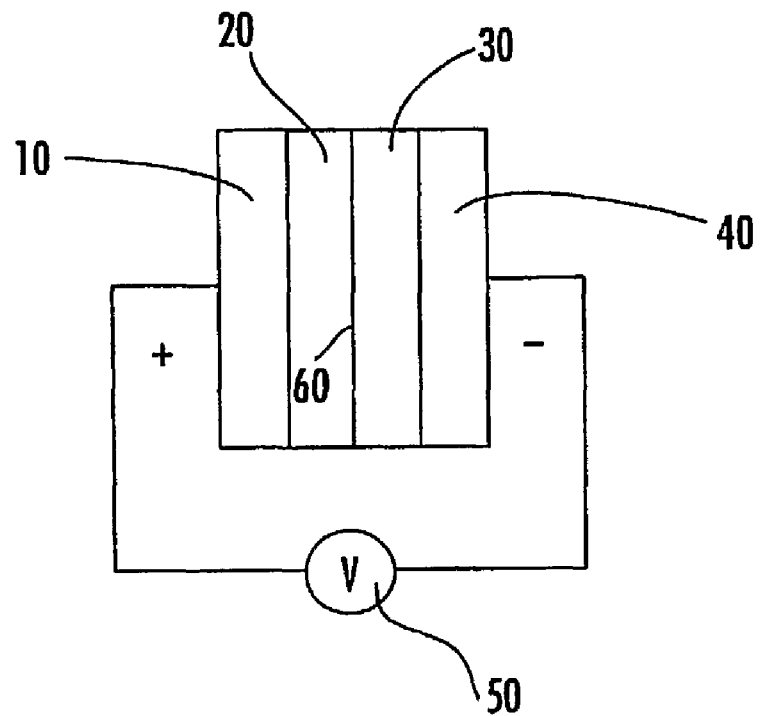
FIG. 1, Ex. 5
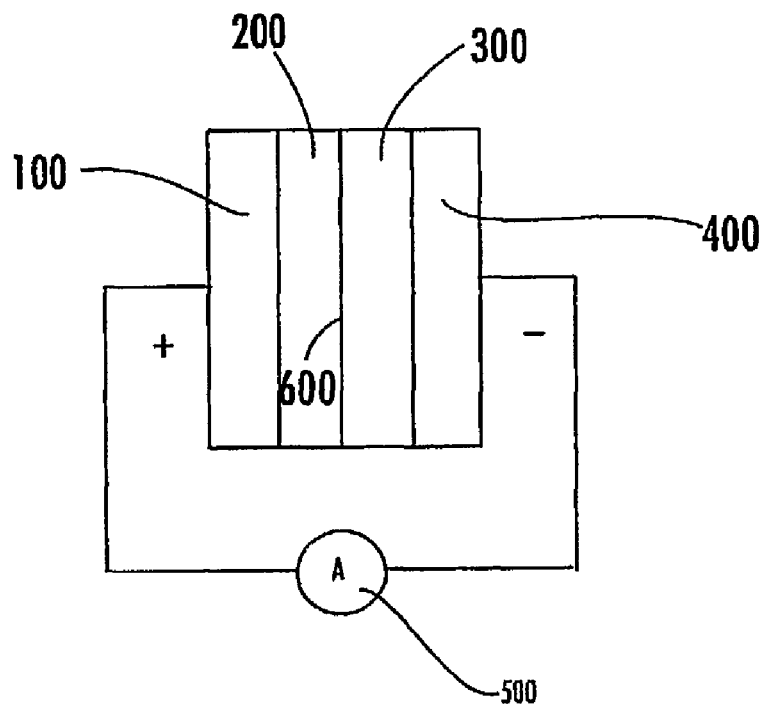
FIG. 2, Ex. 5

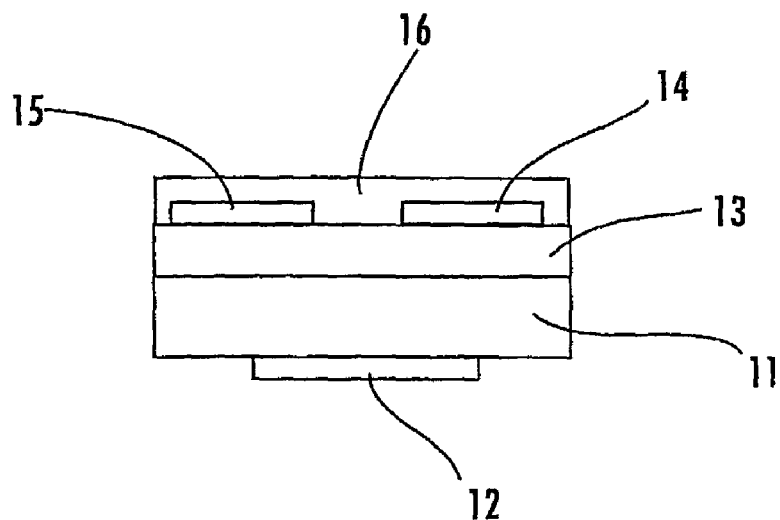
FIG. 3, Ex. 5
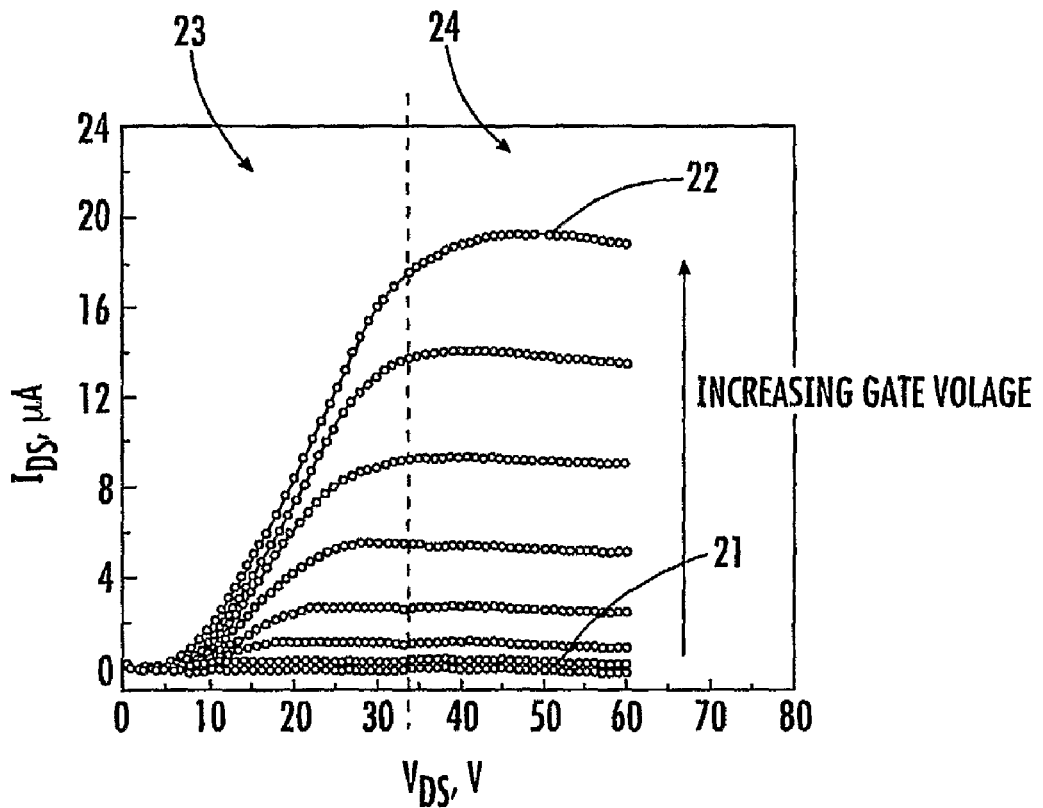
FIG. 4, Ex. 5

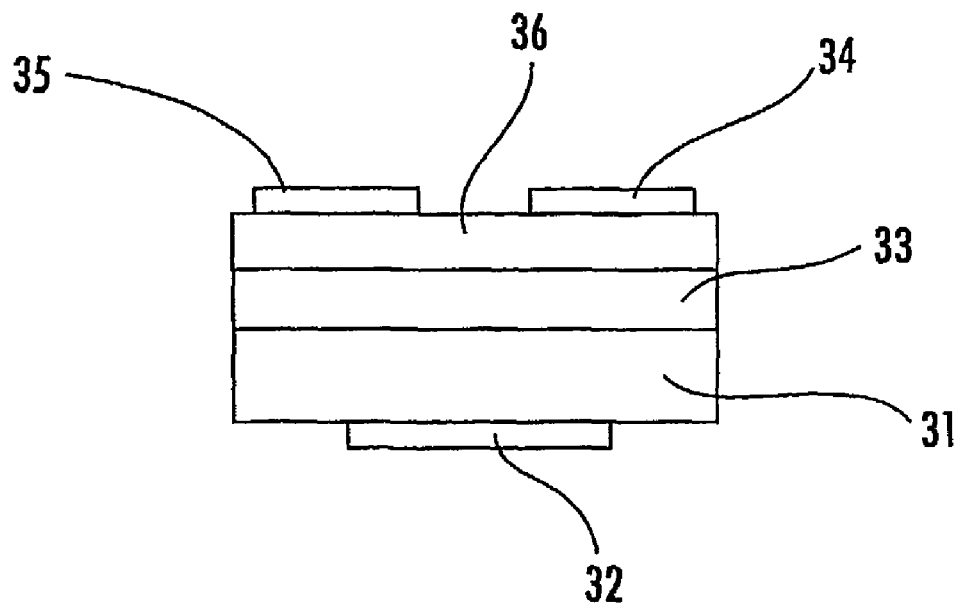
FIG. 5, Ex. 5
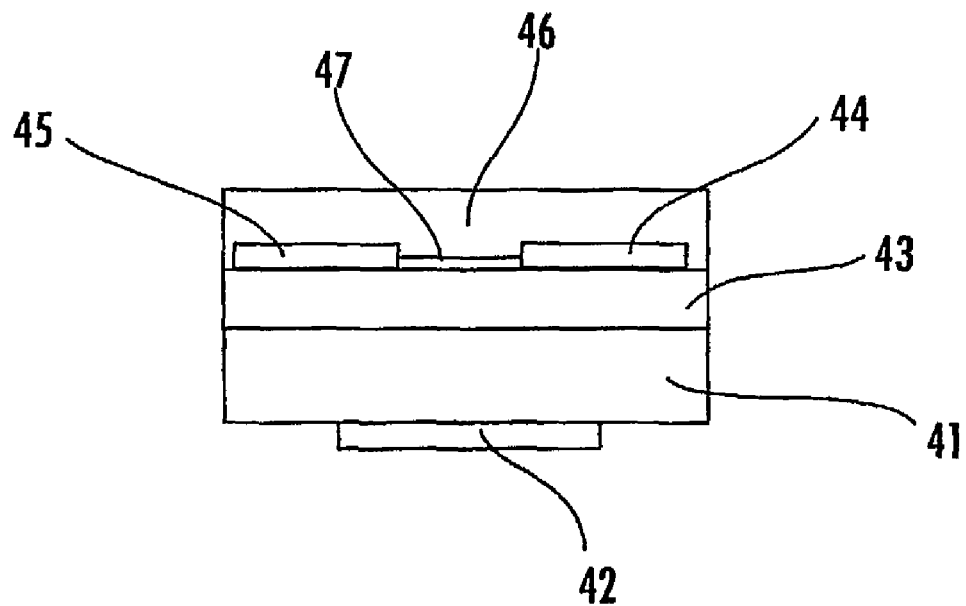
FIG. 6A, Ex. 5

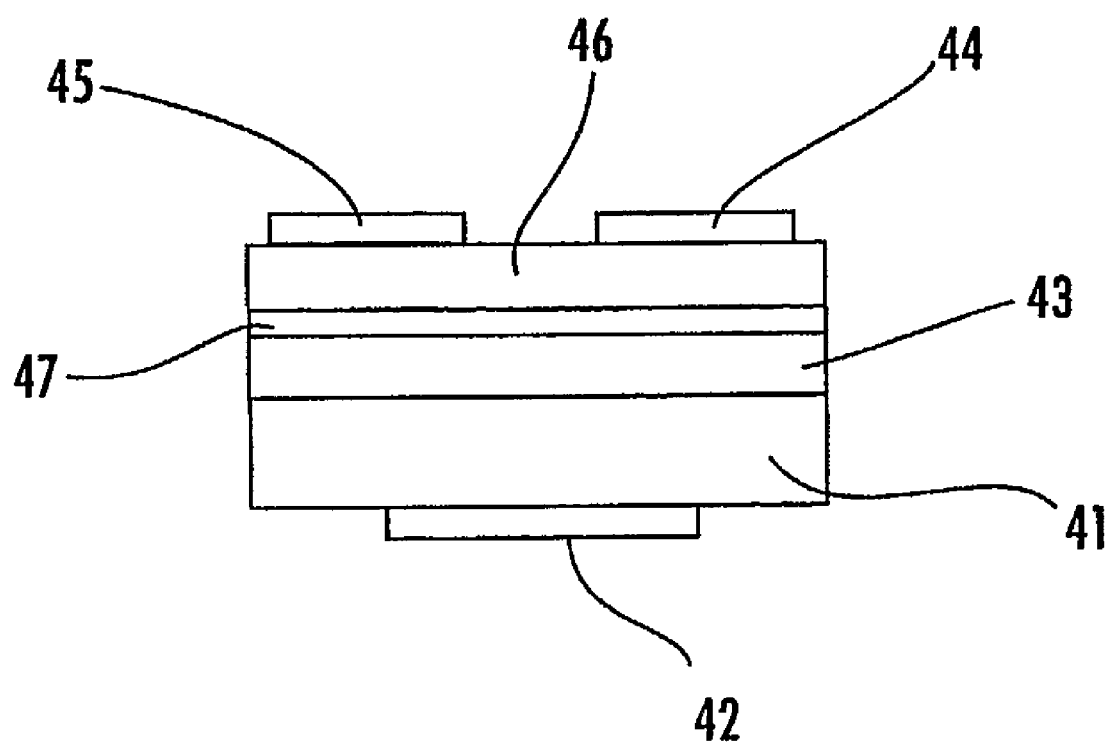
FIG. 6B, Ex. 5

TRANSITION-METAL CHARGE-TRANSPORT MATERIALS, METHODS OF FABRICATION THEREOF, AND METHODS OF USE THEREOF

CROSS-REFERENCE TO RELATED APPLICATION

This application claims priority to copending U.S. provisional patent application entitled "Metal Compounds For Use In Organic Electronics and OPTO-Electronics" filed on Jun. 14, 2004 and accorded Ser. No. 60/579,376, which is entirely incorporated herein by reference.

STATEMENT REGARDING FEDERALLY SPONSORED RESEARCH OR DEVELOPMENT

The U.S. government may have a paid-up license in embodiments of this disclosure and the right in limited circumstances to require the patent owner to license others on reasonable terms as provided for by the terms of grants awarded by the Office of Naval Research (grant #N00014-04-1-0120) and the National Science Foundation (grant #DMR 0120967 and grant #ECS-0309131) of the U.S. Government.

BACKGROUND

Charge-transport molecular and polymeric materials are semiconducting materials in which charges can migrate under the influence of an electric field. These charges may be present due to doping with oxidizing or reducing agents, so that some fraction of the transport molecules or polymer repeat units is present as radical cations or anions. More usually, charges are introduced by injection from another material under the influence of an electric field. Charge-transport materials may be classified into hole- and electron-transport materials. In a hole-transport material, electrons are removed, either by doping or injection, from a filled manifold of orbitals to give positively charged molecules or polymer repeat units. Transport takes place by electron-transfer between a molecule or polymer repeat unit and the corresponding radical cation; this can be regarded as movement of a positive charge (hole) in the opposite direction to this electronic motion. In an electron-transport material, extra electrons are added, either by doping or injection; here, the transport process includes electron-transfer from the radical anion of a molecule or polymer repeat unit to the corresponding neutral species. In addition, some material—ambi-polar materials—may transport both holes and electrons.

SUMMARY

Briefly described, embodiments of this disclosure include charge-transport materials; crystals, nanocrystals, liquid crystals, glasses, composites, polymers, co-polymers, and homopolymers including charge-transport materials; polymer layers including charge-transport materials, crystals, nanocrystals, liquid crystals, glasses, composites; and devices including charge-transport materials.

One exemplary charge-transport material, among others, includes a transition-metal charge-transport material monomer having a structure of Formula I:

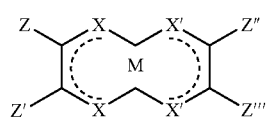

M is selected from one of the following: nickel (II), palladium (II), platinum (II), cobalt (I), iridium (I), rhodium (I), copper (II), copper (III), silver (III), and gold (III). L and L' can each be independently selected from one or more of the following groups: halogens, $NR_3$, $PR_3$, NCS, SCN, and CN; wherein R is selected from: linear or branched, unsubstituted alkyl groups with up to 25 carbons; linear or branched, substituted alkyl groups with up to 25 carbons; unsubstituted aryl groups; substituted aryl groups; and when L is $PR_3$, R can be an alkoxy group (R'O). X and X' can each be independently selected from one or more of the following: S, Se, O, NR', and a combination thereof. Z, Z', Z" and Z''', can each be independently selected from one or more of following groups: H; linear or branched, unsubstituted alkyl groups with up to 25 carbons; linear or branched, substituted alkyl groups with up to 25 carbons; donor groups; acceptor groups; unsubstituted aryl groups; substituted aryl groups; and polymerizable groups.

Another exemplary charge-transport material, among others, includes a transition-metal charge-transport material monomer having a structure of Formula II:

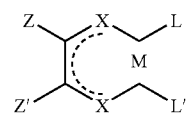

wherein M, L, L', Z, Z,' and X are defined above.

A polymer, co-polymer, or a homopolymer, among others, that can include one or more of a monomer such as, but not limited to, the Formula I monomer, the Formula II monomer, and combinations thereof.

A device, among others, that can include one or more of a monomer such as, but not limited to, the Formula I monomer, the Formula II monomer, and combinations thereof.

A polymer layer, among others, that can include one or more of a monomer such as, but not limited to, the Formula I monomer, the Formula II monomer, and combinations thereof.

A material, among others, that can include a mixture of components comprising a compound selected from: the Formula I of claim 1, the Formula II of claim 6, and combinations thereof. An amount of each compound present in the mixture is selected to control at least one property of the mixture. The property is selected from one of: volatility, solubility, crystallinity, melting point, phase transitions, shelf life, charge-transport ability, and combinations thereof.

A material, among others, that can include a mixture of components comprising a monomer, a polymer including the monomer, a co-polymer including the monomer, a homopolymer including the monomer, and combinations thereof. The monomer is selected from: the Formula I monomer of claim 1, the Formula II monomer of claim 6, and combinations thereof. An amount of each monomer present in the mixture is selected to control at least one property of the mixture. The property is selected from one of: volatility, solubility, crystallinity, melting point, phase transitions, shelf life, charge-transport ability, and combinations thereof.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Example 1 Figures

FIG. 1 of Example 1 illustrates the resonance hybrid of limiting structures of nickel dithiolene complexes.

FIG. 2 of Example 1 illustrates synthetic route (I) of bis[1,2-di(3',4'-di-n-dodecyloxyphenyl)ethane-1,2-dithiolene]nickel (5).

FIG. 3 of Example 1 illustrates synthetic route (II) of bis[1,2-di(3',4'-di-n-dodecyloxyphenyl)ethane-1,2-dithiolene]nickel (5).

FIG. 4 of Example 1 illustrates the UV spectrum of bis[1,2-di(3',4'-di-n-dodecyloxyphenyl)ethane-1,2-dithiolene]nickel (5).

FIG. 5 of Example 1 illustrates the cyclic voltammogram of bis[1,2-di(3',4'-di-n-dodecyloxyphenyl)ethane-1,2-dithiolene]nickel (5).

FIG. 6 of Example 1 illustrates the synthesis of $[Ni(S_2C_2(C_6H_4\text{-}p\text{-}Br)_2)_2]$ (10).

FIG. 7 of Example 1 illustrates the synthesis of 3,3'-dimethylbenzil (12) (Method 1).

FIG. 8 of Example 1 illustrates the synthesis of bis[1,2-di(3-methylphenyl)ethane-1,2-dithiolene]nickel (17).

FIG. 9 of Example 1 illustrates the absorption spectrum of complex 17.

FIG. 10 of Example 1 illustrates the synthesis of an unsymmetrical nickel dithiolene complex by Miller and Dance.

Example 2 Figures

FIG. 1 of Example 2 illustrates the synthesis of an unsymmetrical α-diketone containing oxetane group.

FIG. 2 of Example 2 illustrates the $^1H$ and $^{13}C$ NMR spectra of JYC-I-140-A.

FIG. 3 of Example 2 illustrates the $^1H$ and $^{13}C$ NMR spectra of JYC-I-142-A.

FIG. 4 of Example 2 illustrates the $^1H$ and $^{13}C$ NMR spectra of JYC-I-144-A.

FIG. 5 of Example 2 illustrates the $^1H$ and $^{13}C$ NMR spectra of JYC-I-146-A.

FIG. 6 of Example 2 illustrates the $^1H$ and $^{13}C$ NMR spectra of JYC-I-148-A.

FIG. 7 of Example 2 illustrates the synthesis of 3-(6-bromo-hexyloxymethyl)-3-methyloxetane (JYC-I-143-A).

FIG. 8 of Example 2 illustrates the $^1H$ and $^{13}C$ NMR spectra of JYC-I-143-A.

FIG. 9 of Example 2 illustrates the α-Diketone syntheses via 1,4-dimethylpiperazine-2,3-diones (JYC-I-104-A).

FIG. 10 of Example 2 illustrates the synthesis of α-diketones from oxalyl chloride.

FIG. 11 of Example 2 illustrates the syntheses of α-diketones JYC-I-079-A, JYC-I-088-A, and JYC-I-107-A via 1,4-dimethylpiperazine-2,3-diones FIG. 12 of Example 2 illustrates the synthesis of 4,4'-dicyanobenzil (JYC-I-097-A) from 4,4'-dibromobenzil and copper cyanide.

FIG. 13 of Example 2 illustrates the syntheses of JYC-I-065-A, JYC-I-120-B, and JYC-I-121-A via Sonogashira coupling reactions.

FIG. 14 of Example 2 illustrates the preparation of 4,4'-bis(N,N-diphenylamino)benzil (JYC-I-078-A) via Hartwig-Buchwald amination reaction.

FIG. 15 of Example 2 illustrates the synthesis of 4,4'-di(4,4,5,5-tetramethyl-1,3,2-dioxaborolyl)benzil (JYC-I-099-A) using Miyaura's protocol.

FIG. 16 of Example 2 illustrates the synthesis of 1,2-bis(4-styrylphenyl)ethane-1,2-dione (JYC-I-134-B) via Heck reaction.

FIG. 17 of Example 2 illustrates the $^1H$ and $^{13}C$ NMR spectra of JYC-I-134-B.

FIG. 18 of Example 2 illustrates the preparation of 3,6-dibromophenanthrenequinone (JYC-I-117-A).

FIG. 19 of Example 2 illustrates the preparation of 3,6-distyrylphenanthrene-9,10-dione (JYC-I-139-A) via Heck reaction.

FIG. 20 of Example 2 illustrates the $^1H$ and $^{13}C$ NMR spectra of JYC-I-139-A.

FIG. 21 of Example 2 illustrates the synthesis of 3,6-bis(diphenylamino)phenanthrene-9,10-dione (JYC-I-130-A) via amination reaction.

FIG. 22 of Example 2 illustrates the $^1H$ NMR spectrum of JYC-I-130-A.

FIG. 23 of Example 2 illustrates the synthesis of JYC-I-053-B.

FIG. 24 of Example 2 illustrates the synthesis of bis[1,2-di(4-(4,4,5,5-tetramethyl-1,3,2-dioxaborolyl)phenyl)-ethane-1,2-dithiolene]nickel (JYC-I-109-A).

FIG. 25 of Example 2 illustrates the synthesis of bis{1,2-di[(4-trifluoromethyl)phenyl]ethane-1,2-dithiolene}-nickel (JYC-I-091-A).

FIG. 26 of Example 2 illustrates the synthesis of bis{[1,2-[(4-bromophenyl)(3',4'-di-n-dodecyloxy-phenyl)]-ethane-1,2-dithiolene}nickel (JYC-I-072-A).

FIG. 27 of Example 2 illustrates the synthesis of {[1,2-di(4-bromophenyl)]ethane-1,2-dithiolene}{[1,2-di(3',4'-di-n-dodecyloxy-phenyl)]ethane-1,2-dithiolene]}nickel (JYC-I-055-A).

FIG. 28 of Example 2 illustrates the synthesis of bis{1,2-di[(4-cyano)phenyl]ethane-1,2-dithiolene}nickel (JYC-I-102-A).

FIG. 29 of Example 2 illustrates the absorption spectrum of impure bis{1,2-di[(4-cyano)phenyl]ethane-1,2-dithiolene}nickel (JYC-I-102-A).

FIG. 30 of Example 2 illustrates the cyclic voltammogram of the impure bis{1,2-di[(4-cyano)phenyl]ethane-1,2-dithiolene}nickel (JYC-I-102-A).

FIG. 31 of Example 2 illustrates the comparison of $^1H$ NMR spectra (in $CDCl_3$) of bis{1,2-di[(4-diphenylamino)phenyl]ethane-1,2-dithiolene}nickel (JYC-I-103-A) (top) and 4,4'-bis(N,N-diphenylamino)benzil (JYC-I-078-A) (bottom).

FIG. 32 of Example 2 illustrates the comparison of $^{13}C$ NMR spectra (in $CDCl_3$) of bis{1,2-di[(4-diphenylamino)phenyl]ethane-1,2-dithiolene}nickel (JYC-I-103-A) (top) and 4,4'-bis(N,N-diphenylamino)benzil (JYC-I-078-A) (bottom).

FIG. 33 of Example 2 illustrates the synthesis of bis{1,2-di[(4-phenylethynyl)phenyl]ethane-1,2-dithiolene}-nickel (JYC-I-114-A).

FIG. 34 of Example 2 illustrates the $^1H$ NMR spectrum of JYC-I-114-A after column chromatography.

FIG. 35 of Example 2 illustrates the absorption spectrum of impure JYC-I-114-A.

FIG. 36 of Example 2 illustrates the cyclic voltammogram of the impure JYC-I-114-A.

FIG. 37 of Example 2 illustrates the proposed synthesis of [2-(3,4-bis-dodecyloxy-phenyl)-[1,3]dithian-2-yl]-(4-iodo-phenyl)-methanol.

Example 3 Figures

FIG. 1 of Example 3 illustrates the structures of two targeted nickel bis(dithiolene) complexes (A) and (B).

FIG. 2 of Example 3 illustrates the synthesis of JYC-II-014-A.

FIG. 3 of Example 3 illustrates the $^1$H (top) and $^{13}$C{$^1$H} NMR spectra (middle and bottom) of JYC-II-014-A.

FIG. 4 of Example 3 illustrates the LRMS-MALDI data of JYC-II-014-A (LRMS-MALDI (m/z): [M]$^+$ calcd for $C_{156}H_{236}NiO_8S_4$, 2426.5; found, 2425.4).

FIG. 5 of Example 3 illustrates the absorption spectrum of JYC-II-014-A.

FIG. 6 of Example 3 illustrates the synthesis of JYC-II-013-A.

FIG. 7 of Example 3 illustrates the $^1$H NMR spectrum of JYC-II-013-A.

FIG. 8 of Example 3 illustrates the absorption spectrum of JYC-II-013-A.

FIG. 9 of Example 3 illustrates the comparison of the absorption spectra of JYC-I-019-A, JYC-II-014-A, and JYC-II-013-A.

FIG. 10 of Example 3 illustrates the comparison of reactivity in the preparation of nickel bis(dithiolene) complexes.

FIG. 11 of Example 3 illustrates the preparation of a nickel bis(dithiolene) complex from JYC-I-148-A.

FIG. 12 of Example 3 illustrates the preparation of JYC-II-017-A.

FIG. 13 of Example 3 illustrates the preparation of JYC-II-029-A.

FIG. 14 of Example 3 illustrates the a potential glassy material based on nickel bis(dithiolene) complex.

FIG. 15 of Example 3 illustrates the synthesis of bis[1,2-(m-tolyl)(phenyl)ethane-1,2-dithiolene]nickel (JYC-II-065-A).

FIG. 16 of Example 3 illustrates the thermogravimetric analysis of JYC-1H-065-A.

Example 4 Figures

FIG. 1 of Example 4 illustrates the structure of JYC-I-019-A.

FIG. 2 of Example 4 illustrates the simple electron-transport device based on JYC-I-019-A.

FIG. 3 of Example 4 illustrates the I-V curve of ITO/JYC-I-019-A (5 μm)/ITO device at room temperature.

FIG. 4 of Example 4 illustrates the log I-log V plot of ITO/JYC-I-019-A (5 μm)/ITO device.

FIG. 5 of Example 4 illustrates the Power fitting of I-V curve of ITO/JYC-I-019-A (5 μm)/ITO device.

FIG. 6 of Example 4 illustrates the experimental curve (dotted line) and numerical fitting using the modified SCLC equation (solid line).

FIG. 7 of Example 4 illustrates the modified SCLC equation.

Example 5 Figures

FIG. 1 is a schematic of an organic light-emitting diode.

FIG. 2 is a schematic of an organic photovoltaic cell.

FIG. 3 is a schematic of an organic field-effect transistor with bottom electrodes.

FIG. 4 is a schematic of the electrical output characteristic of an organic field-effect transistor. The curves show the current measured between source and drain electrodes as a function of the voltage between source and drain electrodes.

FIG. 5 is a schematic of an organic field-effect transistor with top electrodes.

FIG. 6A is a schematic of an organic field-effect transistor with a surface modifier and with bottom electrodes.

FIG. 6B is a schematic of an organic field-effect transistor with a surface modifier and top electrodes.

DETAILED DESCRIPTION

In accordance with the purpose(s) of the present disclosure, as embodied and broadly described herein, embodiments of the present disclosure, in one aspect, relate to transition-metal charge-transport materials, methods of making transition-metal charge-transport materials, and methods of using transition-metal charge-transport materials. In addition, embodiments of the present disclosure include charge-transport materials; crystals, nanocrystals, liquid crystals, glasses, composites, polymers, co-polymers, and homopolymers including charge-transport materials; and polymer layers including charge-transport materials, crystals, nanocrystals, liquid crystals, glasses, composites.

In particular, the transition-metal charge-transport materials include a transition-metal charge-transport core having side chains (groups or mesogens) attached to the core. In general, the transition-metal charge-transport materials have strong intermolecular overlap and low reorganization energies, coupled with the tunability of redox potentials, of glass-, crystal-, and liquid-crystal-forming abilities, of the delocalization of electronic structure, and of the degree of molecular and materials anisotropy. In particular, the side chains of the transition-metal charge-transport cores can be selected to provide charge-transport materials having various volatilities, solubilities, crystallinity, and charge-transport ability, as well as being a hole-transport material or an electron-transport material. In other words, the side chains can be selected to tune the characteristics of the transition-metal charge-transport materials as desired.

The transition-metal charge-transport materials described herein can be used in a wide variety of electronic applications that include, but are not limited to, active electronic components, passive electronic components, electroluminescent (EL) devices (e.g., organic light emitting devices (OLEDs)), photovoltaic cells, light-emitting diodes, field-effect transistors, phototransistors, radio-frequency ID tags, semiconductor devices, photoconductive diodes, metal-semiconductor junctions (e.g., Schottky barrier diodes), p-n junction diodes, p-n-p-n switching devices, photodetectors, optical sensors, phototransducers, bipolar junction transistors (BJTs), heterojunction bipolar translators, switching transistors, charge transfer devices, thin film transistors, organic radiation detectors, infra-red emitters, tunable microcavities for variable output wavelength, telecommunications devices and applications, optical computing devices, optical memory devices, chemical detectors, combinations thereof, and the like.

In addition, the transition-metal charge-transport materials can also be used to modify the surfaces of other material components with the aim of improving mechanical contact between materials and/or improving charge-transport from one material to another.

The transition-metal charge-transport materials can exist as or in crystals, mesoscopic phases, polymers, glasses, liquids, gases, and combinations thereof. The state of transition-metal charge-transport materials can be altered by processing the transition-metal charge-transport materials, mixing the transition-metal charge-transport materials with other materials, using different side chains in the transition-metal charge-transport materials relative to other transition-metal charge-transport materials, and the like. One skilled in the art could modify embodiments of the present disclosure to alter the state of the transition-metal charge-transport materials.

The transition-metal charge-transport material compounds can be processed to produce a highly ordered mesophase morphology. When the transition-metal charge-transport materials are used to form a layered thin film, the molecules have a preferential orientation in space. In particular, the transition-metal charge-transport materials can have a certain degree of long range orientational molecular order and long range translational molecular order. The mesophase ordering allows close packing of molecular pi-electron systems (e.g., closely packed conjugated aromatic rings, in which very close pi-pi stacking can occur). Pi-pi stacking allows intermolecular charge transport to occur more easily, leading to high charge carrier mobilities, which increases intermolecular charge transfer that occurs through a hopping mechanism between adjacent molecules. In particular, the transition-metal charge-transport material compounds can stack in the form of well-defined columns (e.g., the aromatic cores in one layer are substantially aligned with the aromatic cores in adjacent layers) forming one dimensional paths for charge transport along the stacked conjugated cores due to the good intermolecular overlap within the stacks.

This ordered, and oriented microstructure can be made substantially permanent by polymerizing the transition-metal charge-transport materials, which can also create a structure with long-range order, or a "monodomain." Formation of a monodomain also maximizes charge transfer by eliminating charge trap sites at grain boundaries, while the polymerization also improves the mechanical properties of the film. Further, by cross-linking the charge-transport material compounds, a highly stable structure results, which has an additional advantage of being substantially impervious to subsequent processing solvents during device fabrication, thus allowing a wider range of solvents to be used in deposition of the next layer of the device by solution techniques. In addition, the cross-linking may increase the density of the film, leading to smaller intermolecular distances and improved charge transport.

The transition-metal charge-transport materials can be in a liquid crystalline phase or can show liquid crystal phase behavior in mixtures with other compounds. In addition, when the compounds or materials, or the mixtures thereof, are polymerized, they can be in a liquid crystalline phase. As used herein, a "liquid crystalline phase" or "liquid crystal phase" includes a phase that is intermediate to a liquid phase and a crystalline phase. In the liquid crystalline phase, the orientations of a portion of the transition-metal charge-transport material compounds are correlated to each other (e.g., the orientation of each individual transition-metal charge-transport material compound is affected and is affecting the orientation of the neighboring transition-metal charge-transport material compound), and the correlation can extend to a large scale (e.g., equal to or larger than 1 micron, so that a substantial portion of the transition-metal charge-transport material compounds is orientated (e.g., the central aromatic cores are substantially aligned in subsequent layers to form a one dimensional column for charge transport). The orientation-correlation in the liquid crystals allows one to control the orientations of the transition-metal charge-transport material compounds with the aid of an electrical field, a magnetic field, or a pre-treated surface, so that one can switch the orientation or diminish the unwanted effect of the local environment (e.g., impurities). This is unlike an isotropic phase where the orientations of transition-metal charge-transport material compounds in solution are random.

The alignment of the molecules of the liquid crystals is conventionally regarded as being aligned with respect to a vector called the director. Unlike in the solid phase, in the crystalline state, the positions of the molecules in the liquid crystal phase do not have long-range order in at least one direction. For example, discotic liquid-crystalline mesophases include quasi-two-dimensional molecules, which include a rigid conjugated core and flexible side chains (e.g., transition-metal charge-transport molecules). The transition-metal charge-transport material compounds in the discotic liquid-crystalline mesophase can stack in the form of well defined columns forming one dimensional paths for charge transport along the stacked conjugated cores due to the good intermolecular overlap within the stacks.

Alignment of the liquid crystal material can be achieved for example by application of a magnetic and/or electric field (e.g., oscillating electro-magnetic radiation), by treatment of the substrate onto which the material is coated, by shearing the material during or after coating, by application of a magnetic and/or electric field (e.g., oscillating electro-magnetic radiation) to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75-77, and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement. (1981), pages 1-77.

The following structures illustrate embodiments of the transition-metal charge-transport materials having Formula I and Formula II:

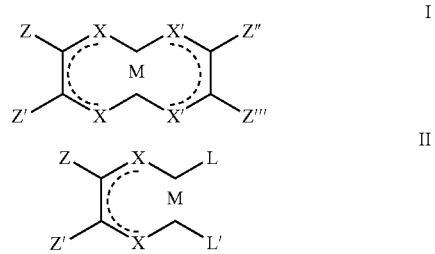

Embodiments of the transition-metal charge-transport materials compounds are represented by formula (I) and formula (II). In Formula I and Formula II, both structures have four atoms coordinated to the central metal atom in a square-planar fashion.

The transition-metal charge-transport materials having Formula I or Formula II are monomer units in a polymer of the charge-transport material, such as a homopolymer or a copolymer (e.g., block copolymers, random copolymers, alternating copolymers, periodic copolymers, and combinations thereof. The monomer units in embodiments of the copolymers can include transition-metal charge-transport materials having Formula I or Formula II, as well as other monomer units consistent with the purposes and characteristics of the charge-transport materials described herein.

Various groups (e.g., atoms and compounds) or mesogenic units can be bonded to the transition-metal charge-transport materials having Formula I or Formula II to form a variety of charge-transport materials. The type of group and/or the combinations of groups that can be bonded to the transition-metal charge-transport materials having Formula I or Formula II can be selected to tune the characteristics of volatility, solubility, crystallinity, and charge transport ability, of the charge-transport material. In addition, the type of group and/or the combinations of groups that can be bonded to the transition-metal charge-transport materials having Formula I or Formula II can be selected from a hole-transport material or an electron-transport material. Further, the transition metal, X, and X' can be selected to tune the volatility, solubility, crystallinity, and charge transport ability, of the charge-transport material.

In transition-metal charge-transport materials having Formula I or Formula II, an asterisk (*) in the structures shown below identifies the atom of attachment to a functional group and implies that the atom is missing one hydrogen that would normally be implied by the structure in the absence of the asterisk. Also note the following: "—" indicates a single bond between 2 atoms, "=" indicates a double bond between 2 atoms, and "≡" indicates a triple bond between 2 atoms.

In Formula I and Formula II, the groups can include from one type of group to multiple types of groups, depending on the particular charge-transport material. For example, Z, Z', Z" and Z''', could be the same type of group, two types of groups, three types of groups, or four types of groups. It should also be noted that the configuration (e.g., position on the molecule) of the groups on the molecules can vary, depending on the number of different groups bonded to the molecules to produce charge-transport materials having a particular characteristic.

M can include, but is not limited to, a metal that adopts a square-planar configuration. M can include, but is not limited to, transition metals. In particular, M can include, but is not limited to, nickel (II), palladium (II), platinum (II), cobalt (I), iridium (I), rhodium (I), copper(II), copper (III), silver (III), and gold (III).

Groups L and L' can each be independently selected from, but not limited to, one or more of the following groups: halogens, $NR_3$, $PR_3$, NCS, SCN, and CN. R can include, but is not limited to, linear or branched, unsubstituted alkyl groups with up to 25 carbons (e.g., 0, 1, 2, 3, 4, 5, 6, 7, 8, 9, 10, 11, 12, 13, 14, 15, 16, 17, 18, 19, 20, 21, 22, 23, 24, and 25 carbons in all isomer forms such as, normal, secondary, iso- and neo-isomers); linear or branched, substituted alkyl groups with up to 25 carbons (e.g., 0, 1, 2, 3, 4, 5, 6, 7, 8, 9, 10, 11, 12, 13, 14, 15, 16, 17, 18, 19, 20, 21, 22, 23, 24, and 25 carbons in all isomer forms, such as normal, secondary, iso- and neo-isomers); unsubstituted aryl groups (see discussion below); substituted aryl groups (see discussion below); and when L is $PR_3$, R can be an alkoxy group (R'O).

R' can be selected from, but is not limited to, linear or branched, alkyl groups with up to 25 carbons (e.g., 0, 1, 2, 3, 4, 5, 6, 7, 8, 9, 10, 11, 12, 13, 14, 15, 16, 17, 18, 19, 20, 21, 22, 23, 24, 25 carbons in all isomer forms, such as normal, secondary, iso- and neo-isomers); linear or branched, perfluorinated alkyl groups with up to 25 carbons (e.g., 0, 1, 2, 3, 4, 5, 6, 7, 8, 9, 10, 11, 12, 13, 14, 15, 16, 17, 18, 19, 20, 21, 22, 23, 24, 25 carbons in all isomer forms, such as normal, secondary, iso- and neo-isomers); aryl groups; fused aromatic rings; donor groups; acceptor groups; polymerizable groups; $-(CH_2CH_2O)_\alpha-(CH_2)_\beta CH_2OR_{a1}$; $-(CH_2CH_2O)_\alpha-(CH_2)_\beta CH_2NR_{a2}R_{a3}$; $-(CH_2CH_2O)_\alpha-(CH_2)_\beta CONR_{a2}R_{a3}$; $-(CH_2CH_2O)_\alpha-(CH_2)_\beta CH_2CN$; $-(CH_2CH_2O)_\gamma-(CH_2)_\delta CH_2F$; $-(CH_2CH_2O)_\gamma-(CH_2)_\delta CH_2NO_2$; $-(CH_2CH_2O)_\alpha-(CH_2)_\beta CH_2Cl$; $-(CH_2CH_2O)_\alpha-(CH_2)_\beta CH_2Br$; $-(CH_2CH_2O)_\alpha-(CH_2)_\beta CH_2I$; $-(CH_2CH_2O)_\alpha-(CH_2)_\beta$-Phenyl; $-CH_2-(CH_2)_\beta-(OCH_2CH_2)_\alpha R_{a1}$; $-CH_2-(CH_2)_\beta-(OCH_2CH_2)_\alpha NR_{a2}R_{a3}$; $-(CH_2)_\beta CH_2-(OCH_2CH_2)_\alpha CONR_{a2}R_{a3}$; $-CH_2-(CH_2)_\beta-(OCH_2CH_2)_\alpha CN$; $-CH_2-(CH_2)_\beta-(OCH_2CH_2)_\alpha F$; $-CH_2-(CH_2)_\beta-(OCH_2CH_2)_\alpha NO_2$; $-CH_2-(CH_2)_\beta-(OCH_2CH_2)_\alpha Cl$; $-CH_2-(CH_2)_\beta-(OCH_2CH_2)_\alpha Br$; $-CH_2-(CH_2)_\beta-(OCH_2CH_2)_\alpha I$; $-CH_2(CH_2)_\beta-(OCH_2CH_2)_\alpha$Phenyl; $-CF_2-(CF_2)_\beta OR_{a1}$; $-CF_2-(CF_2)_\beta CH_2NR_{a2}R_{a3}$; $-(CF_2)_\beta CF_3$; $-(CF_2)_\beta OR_{a1}$; $-CH_2CH_2(CF_2)_\beta OR_{a1}$; $-CH_2CH_2(CF_2)_\beta CH_2NR_{a2}R_{a3}$; $(CF_2)_\beta CH_2NR_{a2}R_{a3}$; $-CH_2CH_2(CF_2)_\beta CF_3$; $-CH_2-(CH_2)_\beta-(OCH_2CH_2)_\alpha$Phenyl; $-CF_2-(CF_2)_\beta-(OCH_2CH_2)_\alpha$Phenyl; $-CH_2-(CH_2)_\beta-(OCH_2CH_2)_\alpha$Aryl; $-CF_2-(CF_2)_\beta-(OCH_2CH_2)_\alpha$Aryl; $-CH_2CH_2-(OCH_2CH_2)_\alpha-O(CF_2)_\beta$Aryl; $CH_2CH_2-(OCH_2CH_2)_\alpha-O(CH_2)_\beta$Aryl; $-CH_2O(CH_2)_\beta$Aryl; and $-(CF_2)_\beta$Aryl; and combinations thereof.

In addition, groups R' can be selected from, but not limited to, one or more of the following groups $-(CH_2CH_2O)_\alpha-(CH_2)_\beta$-Phenyl; $-CH_2-(CH_2)_\beta-(OCH_2CH_2)_\alpha R_{a1}$; $-CH_2-(CH_2)_\beta-(OCH_2CH_2)_\alpha NR_{a2}R_{a3}$; $-(CH_2)_\beta CH_2-(OCH_2CH_2)_\alpha CONR_{a2}R_{a3}$; $-CH_2-(CH_2)_\beta-(OCH_2CH_2)_\alpha CN$; $-CH_2-(CH_2)_\beta-(OCH_2CH_2)_\alpha F$; $-CH_2-(CH_2)_\beta-(OCH_2CH_2)_\alpha NO_2$; $-CH_2-(CH_2)_\beta-(OCH_2CH_2)_\alpha Cl$; $-CH_2-(CH_2)_\beta-(OCH_2CH_2)_\alpha Br$; $-CH_2-(CH_2)_\beta-(OCH_2CH_2)_{a1}I$; $-CH_2(CH_2)_\beta-(OCH_2CH_2)_\alpha$Phenyl; $-CF_2-(CF_2)_\beta OR_{a1}$; $-CF_2-(CF_2)_\beta CH_2NR_{a2}R_{a3}$; $-(CF_2)_\beta CF_3$; $-(CF_2)_\beta OR_{a1}$; $-CH_2CH_2(CF_2)_\beta OR_{a1}$; $-CH_2CH_2(CF_2)_\beta CH_2NR_{a2}R_{a3}$; $(CF_2)_\beta CH_2NR_{a2}R_{a3}$; $-CH_2CH_2(CF_2)_\beta CF_3$; $-CH_2-(CH_2)_\beta-(OCH_2CH_2)_\alpha$Phenyl; $-CF_2-(CF_2)_\beta-(OCH_2CH_2)_\alpha$Phenyl; $-CH_2-(CH_2)_\beta-(OCH_2CH_2)_\alpha$Aryl; $-CF_2-(CF_2)_\beta-(OCH_2CH_2)_\alpha$Aryl (see discussion below); $-CH_2CH_2-(OCH_2CH_2)_\alpha-O(CF_2)_\beta$Aryl (see discussion below); $CH_2CH_2-(OCH_2CH_2)_\alpha-O(CH_2)_\beta$Aryl (see discussion below); $-CH_2O(CH_2)_\beta$Aryl (see discussion below); and $-(CF_2)_\beta$Aryl (see discussion below).

$R_{a1}$, $R_{a2}$, and $R_{a3}$ can each be independently selected from, but not limited to, one or more of the following groups: H, linear or branched, alkyl groups with up to 25 carbons (e.g., 0, 1, 2, 3, 4, 5, 6, 7, 8, 9, 10, 11, 12, 13, 14, 15, 16, 17, 18, 19, 20, 21, 22, 23, 24, 25 carbons in all isomer forms such as normal, secondary, iso- and neo-isomers), and a functional group derived from amino acids, nucleic acids, biotin, ferrocene, ruthenocene, cyanuric chloride, methacryloyl chloride, and derivatives thereof. Subscript $\alpha$ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25). Subscript $\beta$ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25).

X and X' can each independently include, but are not limited to, S, Se, O, NR', and a combination thereof. In another embodiment X and X" can each independently include S.

Groups Z, Z', Z" and Z''', can each be independently selected from, but not limited to, the one or more of following groups: H, linear or branched, unsubstituted alkyl groups with up to 25 carbons (e.g., 0, 1, 2, 3, 4, 5, 6, 7, 8, 9, 10, 11, 12, 13, 14, 15, 16, 17, 18, 19, 20, 21, 22, 23, 24, and 25 carbons in all isomer forms such as normal, secondary, iso- and neo-isomers); linear or branched, substituted alkyl groups with up to 25 carbons (e.g., 0, 1, 2, 3, 4, 5, 6, 7, 8, 9, 10, 11, 12, 13, 14, 15, 16, 17, 18, 19, 20, 21, 22, 23, 24, and 25 carbons in all isomer forms such as normal, secondary, iso- and neo-isomers); donor groups (e.g., those having low ionization potentials, see discussion below); acceptor groups (e.g., those having high electron affinity, see discussion below); unsubstituted aryl groups (see discussion below); substituted aryl groups (see discussion below); and polymerizable groups (see discussion below).

The aryl group can include aromatic ring systems having up to 20 carbons in the aromatic ring framework (e.g., 0, 1, 2, 3, 4, 5, 6, 7, 8, 9, 10, 11, 12, 13, 14, 15, 16, 17, 18, 19, and 20 carbons in all isomer forms), (e.g., does not include carbons on the substituents). The aryl group can include, but is not limited to the following structures:

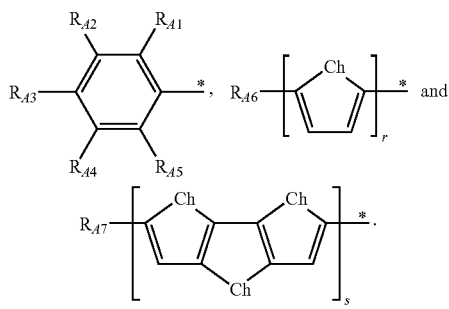

It should be noted that Ch can be an atom such as, but not limited to, Se, S, O, and a combination thereof when more than one Ch is present in the aryl ring system. $R_{A1}$, $R_{A2}$, $R_{A3}$, $R_{A4}$, $R_{A5}$, $R_{A6}$, and $R_{A7}$, can each be independently selected from, but not limited to, the following groups: H; a linear or branched alkyl group with up to 25 carbons (e.g., 0, 1, 2, 3, 4, 5, 6, 7, 8, 9, 10, 11, 12, 13, 14, 15, 16, 17, 18, 19, 20, 21, 22, 23, 24, and 25 carbons in all isomer forms such as normal, secondary, iso- and neo-isomers); —(CH$_2$CH$_2$O)$_\gamma$—(CH$_2$)$_\delta$OCH$_3$;  —(CH$_2$CH$_2$O)$_\gamma$—(CH$_2$)$_\delta$N(CH$_3$)$_2$; —(CH$_2$CH$_2$O)$_\gamma$—(CH$_2$)$_\delta$CON(CH$_3$)$_2$;  —(CH$_2$CH$_2$O)$_\gamma$—(CH$_2$)$_\delta$CN; —(CH$_2$CH$_2$O)$_\gamma$—(CH$_2$)$_\delta$CH$_2$F —(CH$_2$CH$_2$O)$_\gamma$—(CH$_2$)$_\delta$NO$_2$—(CH$_2$CH$_2$O)$_\gamma$—(CH$_2$)$_\delta$CH$_2$Cl; —(CH$_2$CH$_2$O)$_\gamma$—(CH$_2$)$_\delta$CH$_2$Br;  —(CH$_2$CH$_2$O)$_\gamma$(CH$_2$)$_\delta$CH$_2$I;  —(CH$_2$CH$_2$O)$_\gamma$—(CH$_2$)$_\delta$-Phenyl;  —(CH$_2$)$_\delta$—(OCH$_2$CH$_2$)$_\gamma$CH$_3$;  —(CH$_2$)$_\delta$—(OCH$_2$CH$_2$)$_\gamma$CH$_2$N(CH$_3$)$_2$; —(CH$_2$)$_\delta$—(OCH$_2$CH$_2$)$_\gamma$CON(CH$_3$)$_2$;  —(CH$_2$)$_\delta$—(OCH$_2$CH$_2$)$_\gamma$CN;  —(CH$_2$)$_\delta$—(OCH$_2$CH$_2$)$_\gamma$CH$_2$F; —(CH$_2$)$_\delta$—(OCH$_2$CH$_2$)$_\alpha$NO$_2$;  —(CH$_2$)$_\delta$—(OCH$_2$CH$_2$)$_\gamma$CH$_2$Cl;  —(CH$_2$)$_\delta$—(OCH$_2$CH$_2$)$_\alpha$CH$_2$Br;  —(CH$_2$)$_\delta$—(OCH$_2$CH$_2$)$_\gamma$I;  —(CH$_2$)$_\delta$—(OCH$_2$CH$_2$)$_\gamma$Phenyl; —(CF$_2$)$_\beta$OCH$_3$;  —(CF$_2$)$_\beta$CH$_2$N(CH$_3$)$_2$;  —(CF$_2$)$_\beta$CF$_3$; —O(CF$_2$)$_\beta$OCH$_3$; —OCH$_2$CH$_2$(CF$_2$)$_\beta$OCH$_3$; —OCH$_2$CH$_2$(CF$_2$)$_\beta$CH$_2$N(CH$_3$)$_2$; —O(CF$_2$)$_\beta$CH$_2$N(CH$_3$)$_2$; —OCH$_2$CH$_2$(CF$_2$)$_\beta$CF$_3$;  —(CH$_2$)$_\beta$—(OCH$_2$CH$_2$)$_\alpha$Phenyl; and —(CF$_2$)$_\beta$—(OCH$_2$CH$_2$)$_\alpha$Phenyl.

The subscript γ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25). The subscript δ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25). The subscript r is an integer number from 0 to 6 (e.g., 0, 1, 2, 3, 4, 5, and 6). The subscript s is an integer number from 0 to 3 (e.g., 0, 1, 2, and 3).

The polymerizable group (functionalities) can include, but is not limited to, vinyl, allyl, 4-styryl, acroyl, epoxide, oxetane, cyclic-carbonate, methacroyl, and acrylonitrile, each of which may be polymerized by either a radical, cationic, atom transfer, or anionic polymerization process.

In addition, the polymerizable group can include, but is not limited to, isocyanate, isothiocyanate, and epoxides, such that they can be copolymerized with difunctional amines or alcohols such as HO(CH$_2$)$_\chi$OH, H$_2$N(CH$_2$)$_\chi$NH$_2$, where χ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25).

Also the polymerizable group can include, but is not limited to, strained ring olefins such as, but not limited to, dicyclopentadienyl, norbornenyl, and cyclobutenyl. Such monomers can be polymerized via ring opening metathesis polymerization using an appropriate metal catalyst as would be known to those skilled in the art.

Further, the polymerizable group can include, but is not limited to, (—CH$_2$)$_\eta$SiCl$_3$, (—CH$_2$)$_\eta$Si(OCH$_2$CH$_3$)$_3$, or (—CH$_2$)$_\eta$Si(OCH$_3$)$_3$, where the monomers can be reacted with water under conditions known to those skilled in the art to form either thin film or monolithic organically modified sol-gel glasses, or modified silicated surfaces, where η is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25).

Furthermore, the polymerizable group can include, but is not limited to, polymerizable groups that can be photochemically dimerized or polymerized, and these include the following structures:

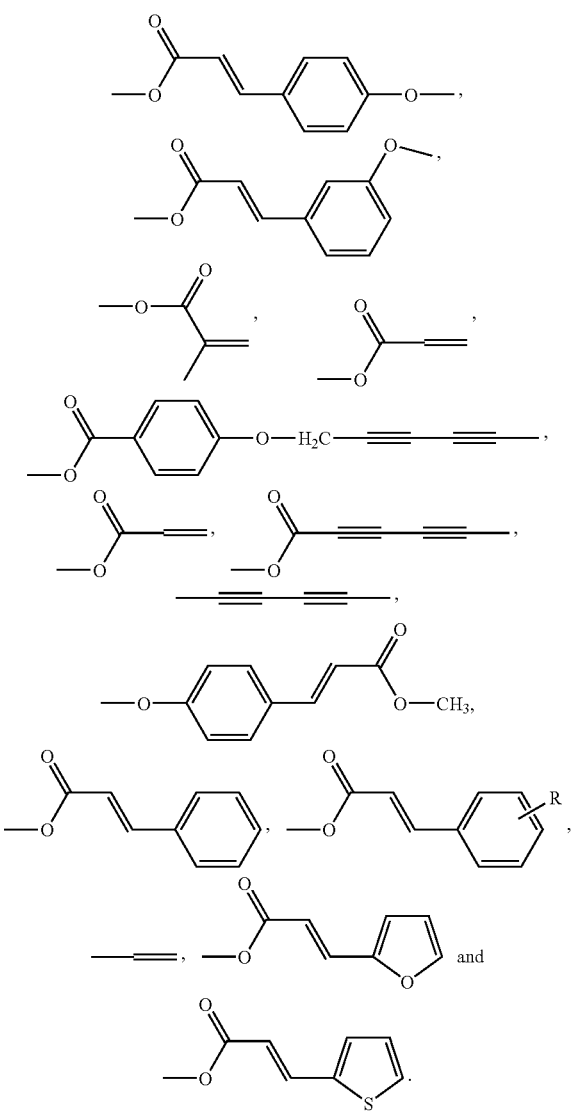

The donors can include structures such as, but not limited to, the following:
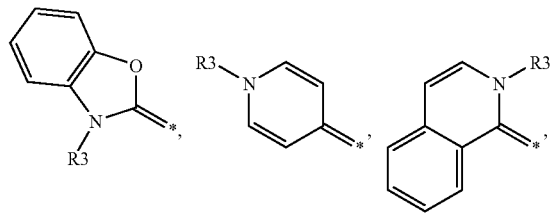
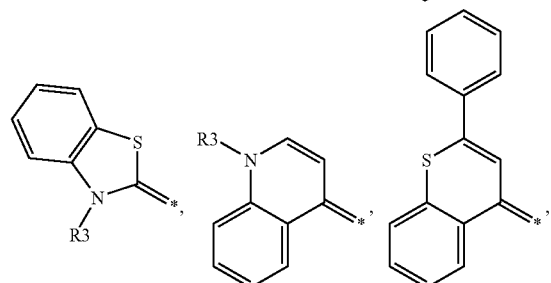
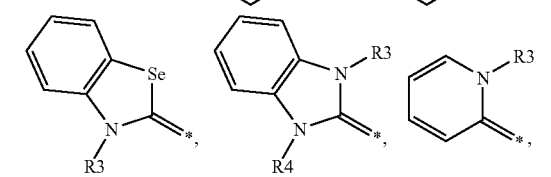
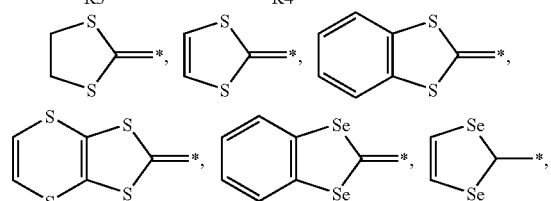
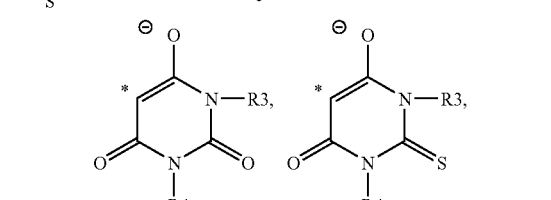
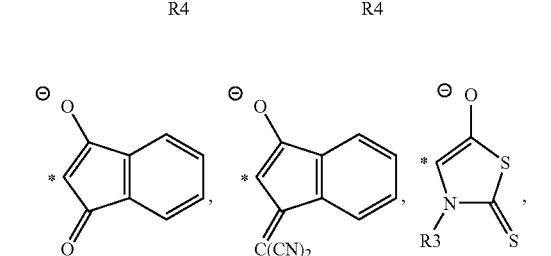
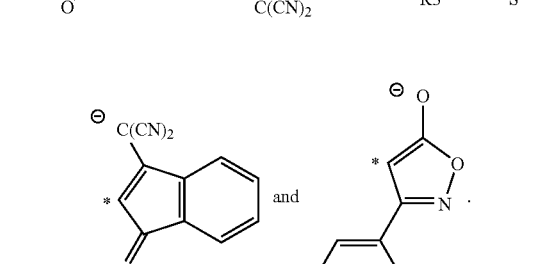
 and .
The acceptors can include structures such as, but not limited to, the following:
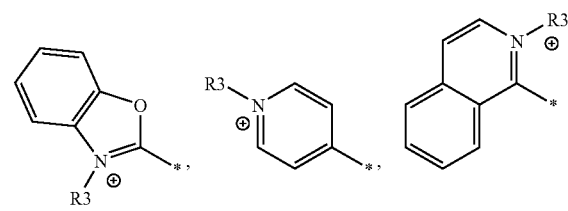
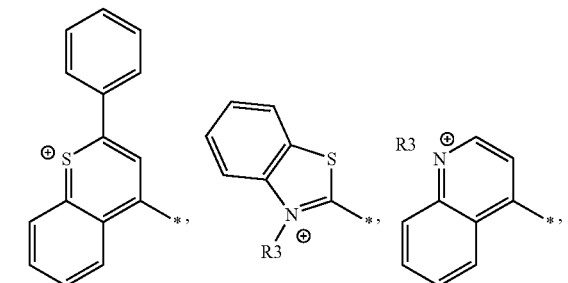
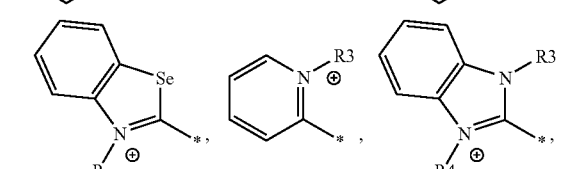
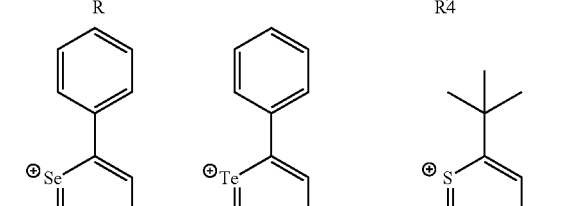
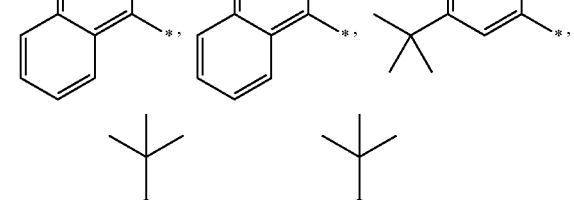
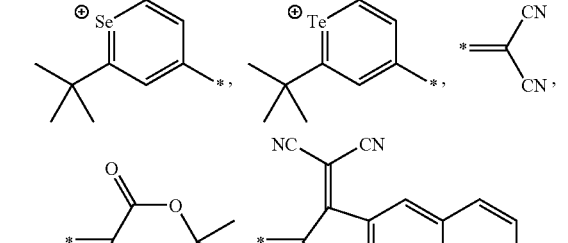
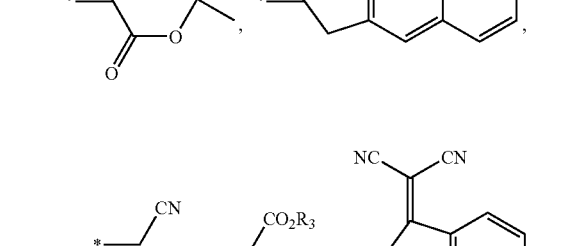
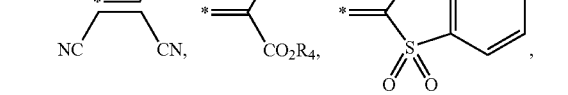

-continued

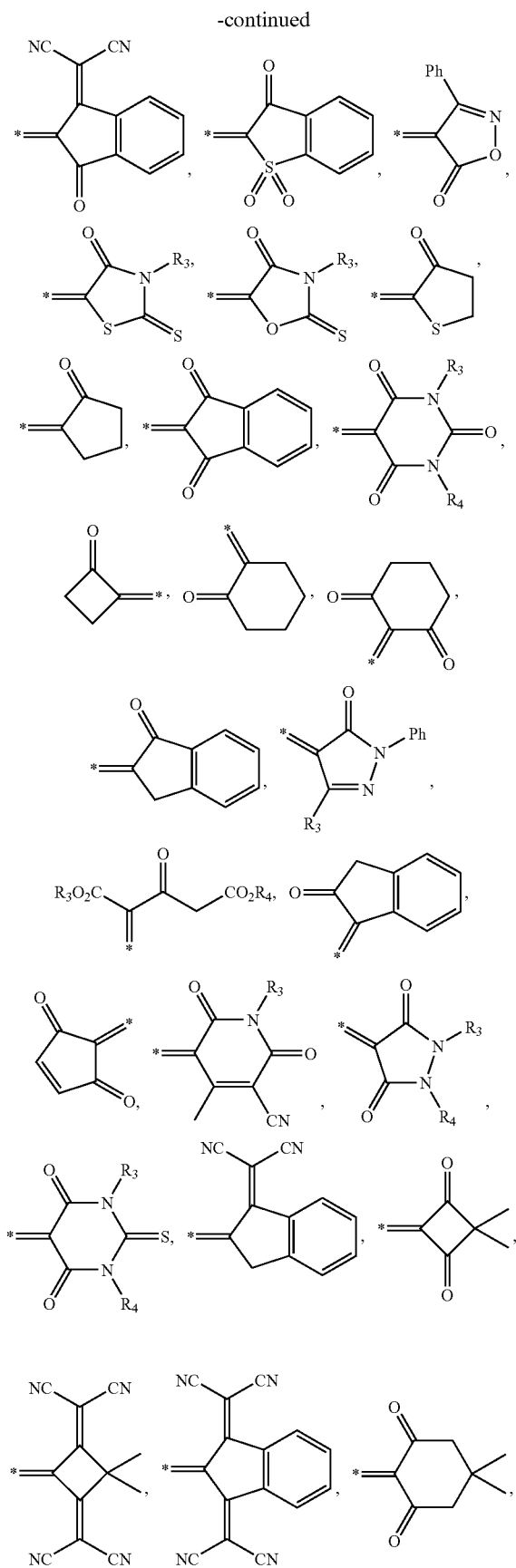

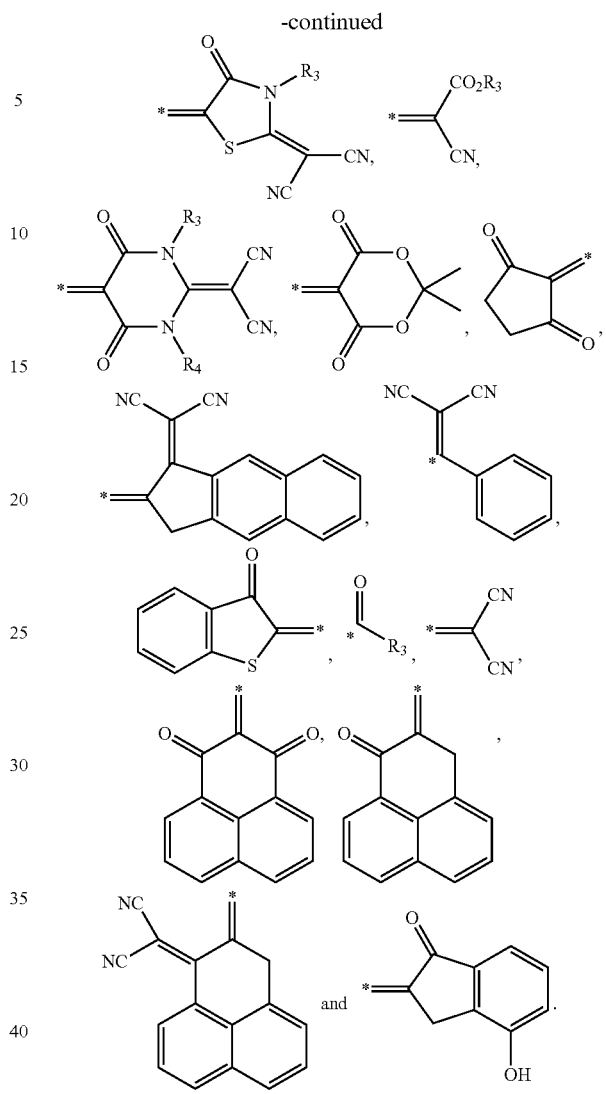

In particular, Z, Z', Z" and Z'", can each be independently selected from, but not limited to, one or more of the following groups: substituted or unsubstituted alkyl, aryl (including aromatic and heteroaromatic groups, which are explained in J. March, "Advanced Organic Chemistry: Reactions, Mechanisms and Structure", Fourth edition, Wiley-Interscience, New York, 1992, Chapter 2, which is incorporated herein by reference in its entirety), cycloalkyl, or heterocyclic groups which are bonded to the carbon atom either directly or via a linking group. Also, Z, Z', Z" and Z'", can each be independently selected from, but not limited to, one or more of the following groups: donors and/or acceptors such as those described herein and in U.S. Pat. No. 6,267,913, which is incorporated herein by reference in its entirety. Further, Z, Z', Z" and Z'", can each be independently selected from, but not limited to, the following groups: any of the groups described above linked through a pi-conjugated linking group as described in U.S. Pat. No. 6,267,913. In addition, a combination of Z, Z', Z" and Z'" can include another square planar metal complex, either directly or indirectly linked. Thus, the compound may be dinuclear, trinuclear, oligomeric, or polymeric.

Exemplary embodiments of the transition-metal charge-transport materials having Formula I or Formula II include, but are not limited to, compounds having the following formula:

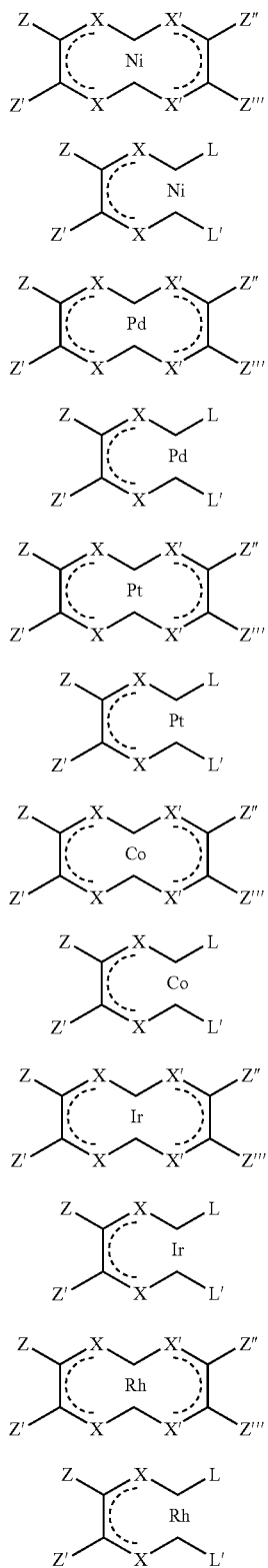

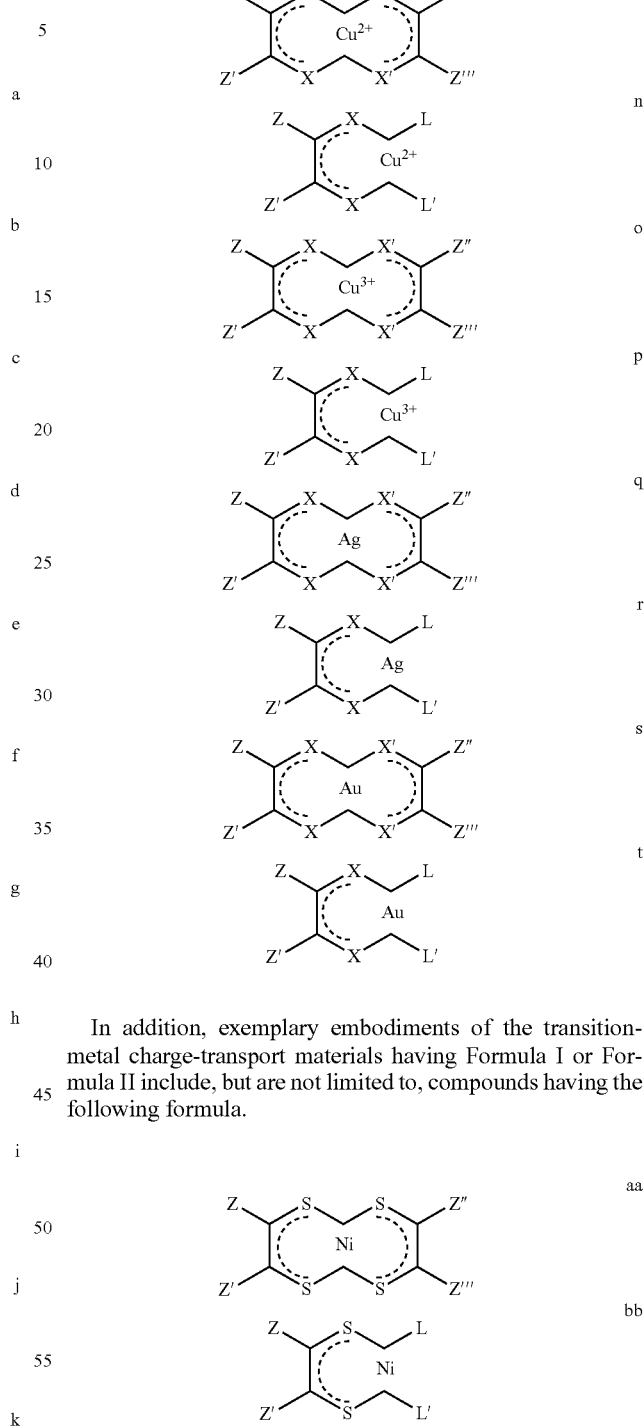

In addition, exemplary embodiments of the transition-metal charge-transport materials having Formula I or Formula II include, but are not limited to, compounds having the following formula.

The transition-metal charge-transport materials have a room temperature, zero field electron mobility of at least about $10^{-6}$ to $10^2$ cm²/Vs, $10^{-4}$ to $10^2$ cm²/Vs, and $10^{-2}$ to $10^2$ cm²/Vs.

The distance between adjacent molecules in adjacent layers is about 4.0 Å and 3.1 Å.

In an embodiment, a polymer layer of the transition-metal charge-transport material can be formed by disposing a layer of a polymerizable material, including monomers, oligomers, and/or polymers of the transition-metal charge-transport material, onto a surface. The molecules of the transition-metal charge-transport material can be optionally aligned into a substantially uniform orientation or a patterned orientation such that in each pattern, the orientation is substantially uniform. Then, a polymerization reaction is initiated and the monomers, oligomers, and/or polymers of the transition-metal charge-transport material form a layer of polymerized charge-transport material. The polymerization process can be repeated to produce a plurality of layers. In addition, cross-linking processes can also be performed to cross-link the molecules in adjacent layers. One skilled in the art could perform a polymerization process in a manner different than described here and obtain the polymer layer of the transition-metal charge-transport material, and such processes are intended to be included herein.

A plurality of layers of transition-metal charge-transport material can be produced to form a charge-transport layer that can have a thickness of about 0.01 to 1000 µm, 0.05 to 100 µm, or 0.05 to 10 µm. The length and width of the charge-transport layer can vary depending on the application, but in general, the length can be about 0.01 µm to 1000 cm, and the width can be about 0.01 µm to 1000 cm.

It should be noted that in some embodiments is it advantageous to have the aromatic core aligned parallel to the substrate materials (e.g., in photovoltaic cells and other devices where a perpendicular alignment may be more preferable (e.g., transistor configurations)).

It should also be noted that the transition-metal charge-transport material could be used as mixtures with other electron-transport materials including those described herein, as well as others. Likewise the transition-metal charge-transport material could be used in combination with other hole-transport materials, sensitizers, emitters, chromophores, and the like, to add other functionality to devices.

The polymerization and cross-linking of the transition-metal charge-transport material molecules can be performed using methods understood by those skilled in the art. In general, polymerization may take place by exposure to heat or actinic radiation in the presence of an initiator. In general, cross-linking may occur due to internal reactions and/or by the addition of a cross-linking additive. Additional details regarding preparation of the transition-metal charge-transport materials are described in Examples 1-4.

Actinic radiation means irradiation with radiation (e.g., UV light, IR light or visible light, irradiation with X-rays or gamma rays or irradiation with high-energy particles, such as ions or electrons). In an embodiment, a polymerization initiator can be used that decomposes when heated to produce free radicals or ions that start the polymerization. In another embodiment, the polymerization can be carried out in the presence of an initiator absorbing at the wavelength of the actinic radiation. For example, when polymerizing using UV light, an UV initiator can be used that decomposes under TV irradiation to produce free radicals or ions that start the polymerization reaction.

The UV initiator can include chemicals such as, but not limited to, a free radical initiator, a cationic initiator, or combinations thereof. The free-radical initiator includes compounds that produce a free radical on exposure to UV radiation. The free-radical is capable of initiating a polymerization reaction among the monomers and/or oligomers present.

Examples of free-radical initiators include, but are not limited to, benzophenones (e.g., benzophenone, methyl benzophenone, Michler's ketone, and xanthones), acylphosphine oxide type free radical initiators (e.g., 2,4,6-trimethylbenzoyldiphenyl phosphine oxide (TMPO), 2,4,6-trimethylbenzoylethoxyphenyl phosphine oxide (TEPO), and bisacylphosphine oxides (BAPO's)), azo compounds (e.g., AIBN), benzoins, and benzoin alkyl ethers (e.g., benzoin, benzoin methyl ether and benzoin isopropyl ether).

In addition, the free radical photoinitiator can include, but is not limited to: acyloin; a derivative of acyloin, such as benzoin ethyl ether, benzoin isobutyl ether, desyl bromide, and α-methylbenzoin; a diketone, such as benzil and diacetyl; an organic sulfide, such as diphenyl monosulfide, diphenyl disulfide, desyl phenyl sulfide, and tetramethylthiuram monosulfide; a thioxanthone; an S-acyl dithiocarbamate, such as S-benzoyl-N,N-dimethyldithiocarbamate and S-(p-chlorobenzoyl)-N,N-dimethyldithiocarbamate; a phenone, such as acetophenone, α-α-α-tribromoacetophenone, o-nitro-α-α-α-tribromoacetophenone, benzophenone, and p,p'-tetramethyldiaminobenzophenone; a quinone; a triazole; a sulfonyl halide, such as p-toluenesulfonyl chloride; a phosphorus-containing photoinitiator, such as an acylphosphine oxide; an acrylated amine; or mixtures thereof.

The free-radical initiator can be used alone or in combination with a co-initiator. Co-initiators are used with initiators that need a second molecule to produce a radical that is active in UV-systems. For example, benzophenone uses a second molecule, such as an amine, to produce a reactive radical. A preferred class of co-initiators are alkanolamines such as, but not limited to, triethylamine, methyldiethanolamine, and triethanolamine Suitable cationic initiators include, but are not limited to, compounds that form aprotic acids or Brønsted acids upon exposure to UV light sufficient to initiate polymerization. The cationic initiator used may be a single compound, a mixture of two or more active compounds, or a combination of two or more different compounds (e.g., co-initiators).

The cationic photoinitiator can include, but is not limited to, onium salt, such as a sulfonium salt, an iodonium salt, or mixtures thereof. In addition, the cationic photoinitiator can include, but is not limited to, an aryldiazonium salt, a bis-diaryliodonium salt, a diaryliodonium salt of sulfonic acid, a triarylsulfonium salt of sulfonic acid, a diaryliodonium salt of boric acid, a diaryliodonium salt of boronic acid, a triarylsulfonium salt of boric acid, a triarylsulfonium salt of boronic acid, or mixtures thereof. Examples of cationic photoinitiators include, but are not limited to, diaryliodonium hexafluoroantimonate, aryl sulfonium hexafluorophosphate, aryl sulfonium hexafluoroantimonate, bis(dodecyl phenyl) iodonium hexafluoroarsenate, tolyl-cumyliodonium tetrakis(pentafluorophenyl) borate, bis(dodecylphenyl) iodonium hexafluoroantimonate, dialkylphenyl iodonium hexafluoroantimonate, diaryliodonium salts of perfluoroalkylsulfonic acids (such as diaryliodonium salts of perfluorobutanesulfonic acid, perfluoroethanesulfonic acid, perfluorooctanesulfonic acid, and trifluoromethane sulfonic acid), diaryliodonium salts of aryl sulfonic acids (such as diaryliodonium salts of para-toluene sulfonic acid, dodecylbenzene sulfonic acid, benzene sulfonic acid, and 3-nitrobenzene sulfonic acid), triarylsulfonium salts of perfluoroalkylsulfonic acids (such as triarylsulfonium salts of perfluorobutanesulfonic acid, perfluoroethanesulfonic acid, perfluorooctanesulfonic acid, and trifluoromethane sulfonic acid), triarylsulfonium salts of aryl sulfonic acids (such as triarylsulfonium salts of para-toluene sulfonic acid, dodecylbenzene sulfonic acid, benzene sulfonic acid, and 3-nitrobenzene sulfonic acid), diaryliodonium salts of perhaloarylboronic acids, triarylsulfonium salts of perhaloarylboronic acid, or mixtures thereof.

The visible radiation initiator can include, but is not limited to, diketones (e.g., camphorquinone, 1,2-acenaphthylenedione, 1H-indole-2,3-dione, 5H-dibenzo[a,d]cycloheptene-10, and 11-dione), phenoxazine dyes (e.g., Resazurin, Resorufin), acylphosphine oxides, (e.g., diphenyl (2,4,6-trimethylbenzoyl) phosphine oxide), and the like.

In an embodiment, the polymerization of the transition-metal charge-transport materials can be carried out as in-situ polymerization of a coated layer of the material, possibly during fabrication of the device of interest that includes the transition-metal charge-transport material. In case of liquid crystal materials, these are preferably aligned in their liquid crystal state into homeotropic orientation prior to polymerization, where the conjugated pi-electron systems are orthogonal to the direction of charge transport. This ensures that the intermolecular distances are minimized and hence then energy required to transport charge between molecules is minimized. The molecules are then polymerized and/or cross-linked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45-66.

The polymers including the transition-metal charge-transport material can have a molecular weight from about 3000 to 300,000 daltons, and about 2000 to 200,0000 daltons.

It should be emphasized that the embodiments of the present disclosure and Examples 1-5 below are merely possible examples of implementations, and are merely set forth for a clear understanding of the principles of this disclosure. Many variations and modifications may be made to the embodiment(s) of the disclosure and Examples 1-5 without departing substantially from the spirit and principles of the disclosure. All such modifications and variations are intended to be included herein within the scope of this disclosure and protected by the claims.

EXAMPLE 1

Design and Synthesis of Nickel Dithiolene Complexes for Opto-Electronic Applications Transition-metal dithiolene complexes possess unusual chemical properties including the ability to undergo a sequence of reversible electron-transfer reactions and intensive absorbance in the visible and near-infrared region. They have attracted much attention for their potential applications in the field of new molecular materials. For example, they have been used for optical recording materials, Q switch dyes for near-infrared lasers (such as Neodymium lasers, which operate at 1064 nm),[1] light compensation filters for near-infrared radiation, and singlet oxygen quenchers such as light stabilizer and photo-deterioration inhibitors of organic dyes. They have also been studied as materials for molecular magnets, conductors, and superconductors.[2] A qualitative description of the bonding in neutral square-planar nickel dithiolene complexes involves a resonance hybrid of limiting structures with formal oxidation states of nickel as 0, +2, and +4. The ligands work as neutral dithioketones (A), dithioketone-dithiolate (B), and dithiolates (C) as shown in FIG. 1.

The high degree of electron-delocalization of nickel bis-dithiolene complexes is responsible for an intensive electronic transition at low energy ($\lambda_{max}$>700 nm), assigned to a π→π* transition between the HOMO and LUMO,[3] which makes these complexes suitable to be used as near-infrared dyes.

Some bisdithiolene nickel complexes exhibit mesogenic behavior. Since those complexes potentially have good intermolecular electronic coupling and isotropic overlap, they may provide some advantages over traditional organic charge-transport agents in transport material applications. In 1989, Ohta[4] and co-workers reported the octasubstituted bis (diphenylethane-1,2-dithiolato) nickel complex with hexagonal discotic columnar liquid crystal phase between 84-112° C. The claim was supported by X-ray scattering data, which gave lines representing hexagonal symmetry. According to Ohta and co-workers' report (FIG. 2),[5] 3,4-dimethoxybenzaldehyde was used as a starting material. First, the reaction between 3,4-dimethoxybenzaldehyde and potassium cyanide yielded 3,3',4,4'-tetramethoxybenzoin (7). Compound 7 was then oxidized to 3,3',4,4'-tetramethoxybenzil (8) with copper sulfate pentahydrate in pyridine and water mixture under reflux. Acidification of compound 8 generated 3,3',4,4'-tetrahydroxybenzil (9). Alkylation of compound 9 with 4 equivalents of 1-bromododecane yielded 3,3',4,4'-tetra-n-dodecyloxybenzil (4).

First, alkylation of 3,4-dihydroxybenzaldehyde with 1-bromododecane afforded 3,4-bis(dodecyloxy)benzaldehyde. 3,3',4,4'-tetra-n-dodecyloxybenzil (4) was efficiently produced in two steps by the reaction of aldehyde with the anion derived from 2-substituted dithiane, followed by treatment of the resulting alcohol with N-bromosuccinimide (NBS) in aqueous acetone.[6]

Two different synthetic routes for the preparation of bis[1, 2-di(3',4'-di-n-dodecyloxyphenyl)ethane-1,2-dithiolene] nickel (5) are compared and shown in FIGS. 2 and 3. The overall yield of the synthetic route (1) is 4.2% (5 steps) (FIG. 2) and the overall yield of the synthetic route (II) is 6.2% (5 steps) (FIG. 3). It should be noted that 3,3',4,4'-tetra-n-dodecyloxybenzil (4) can be prepared in a different route as shown in FIG. 3.

The absorption spectrum of complex 5 is shown in FIG. 4. It shows one broad band around 962 nm, which is in the near infrared region. From the cyclic voltammogram of complex 5 (FIG. 5), the half wave potential for the reduction of complex 5 (0/−1 couple) is −0.54 V versus ferrocene in dichloromethane.

One of the advantages of the route (II) provides a convenient way to prepare unsymmetrical 1,2-diketones. One idea is to prepare 3',4'-bis(dodecyloxy)-4-bromobenzil and synthesize the corresponding nickel dithiolene complex. Presently, 2-{1-hydroxy[4-bromobenzyl]}-2-[3',4'-bis(dodecyloxy)phenyl]-1,3-dithiane has been successfully prepared by deprotonation of [3,4-bis(dodecyloxy)phenyl]-1,3-dithiane with 1 equivalent of n-BuLi at −78° C., followed by reaction with 4-bromobenzaldehyde. [Ni($S_2C_2(C_6H_4$-p-Br$)_2)_2$] (10) was prepared from the reaction between 4,4'-dibromobenzil and phosphorus pentasulfide in 1,4-dioxane, followed by the reaction with NiCl$_2$.6H$_2$O (FIG. 6). The compound has been reported to be obtained in higher yield (~60%). Only ~20% yield of the product was isolated. This specific compound potentially can be used as a core to construct larger nickel dithiolene complexes and even dendrimeric structure for electro-optical applications.

Below are ways to construct the larger nickel dithiolene complexes based on [Ni($S_2C_2(C_6H_4$-p-Br$)_2)_2$] (10) as a starting material. Various coupling reactions have been developed in the past two decades and such processes are routinely used in fields ranging from materials science to natural product synthesis. The Suzuki cross-coupling is among the most powerful carbon-carbon bond-forming transformation available to synthetic organic chemists.[8] For the utilization of Suzuki cross-coupling reactions, there are two approaches. One is to couple [Ni($S_2C_2(C_6H_4$-p-Br$)_2)_2$] (10) with various aryl boronic acids to form new carbon-carbon bonds.

In order to obtain a potentially glassy material for application as hole-transport layer, [Ni(S$_2$C$_2$(C$_6$H$_4$-m-Me)$_2$)$_2$] was targeted and synthesized. The first method involves the reaction between potassium cyanide and m-tolualdehyde to yield 3,3'-dimethylbenzoin (11), which was then oxidized to 3,3'-dimethylbenzil (12) (FIG. 7). However, the yield was very slow via this synthetic route due to the difficulties in the isolation process.

Mueller-Westerhoff[9] and co-workers reported a simple, high-yield two-step synthesis of symmetrically substituted α-diones. The first step involves the preparation of 1,4-dimethylpiperazine-2,3-dione (13). Compound 13 was prepared in high yield from the reaction between N,N'-dimethylethylenediamine and diethyl oxalate in anhydrous diethyl ether at room temperature overnight. Second, compound 13 reacts with 2 equivalents of organolithium or Grignard compounds to form symmetrically-substituted α-diones after hydrolysis. 3,3'-Dimethylbenzil was prepared from the reaction between compound 13 and 2 equivalents of m-tolylmagnesium chloride in dry THF, followed by acidic workup in 35% yield (not optimized). Bis[1,2-di(3-methylphenyl)ethane-1,2-dithiolene]nickel (17) was then prepared by Schrauzer and Mayweg procedure as shown in FIG. 8.[10]

The absorption spectrum of complex 17 is shown in FIG. 9. It shows one broad band around 864 nm, which is in the near infrared region. From the cyclic voltammogram of complex 17, the half wave potential for the reduction of complex 17 are −0.48 V (for 0/−1 couple) and −1.3 V (for −1/−2 couple) versus ferrocene in dichloromethane.

An interesting nickel dithiolene complex, bis[1,2-di(4-vinylphenyl)ethane-1,2-dithiolene]nickel, with a vinyl group at the 4 position of each benzene ring, is a target compound to synthesize. The compound can be used as a core to construct an extended structure. 4-Formylstyrene[11] (14) was prepared cleanly from the reaction between 4-vinylphenyl magnesium chloride, generated in situ from 4-chlorostyrene and magnesium turnings, and DMF in dry THF in 77% yield. 4,4'-Divinylbenzoin (15) was prepared from the reaction between potassium cyanide and 4-formylstyrene in a mixture of water and ethanol in 91%. 4,4'-Divinylbenzoin was then converted to 4,4'-divinylbenzil (16) in 68% yield via neutral, room temperature oxidation with copper sulfate and hexamethylphosphoric triamide. It was reported[12] that hexamethylphosphoric triamide compared to pyridine has higher efficiency probably due to the enhanced solubility of copper sulfate in hexamethylphosphoric triamide relative to pyridine.

Miller and Dance have reported the synthesis of [Ni(S$_2$C$_2$(C$_6$H$_5$)$_2$)(S$_2$C$_2$(CF$_3$)$_2$)][13] by mixing a molar ratio 1:1 mixture of [Ni(S$_2$C$_2$(C$_6$H$_5$)$_2$)$_2$] and [Ni(S$_2$C$_2$(CF$_3$)$_2$)$_2$] in dichloromethane under reflux (FIG. 10).

Reference, which are incorporated herein by reference.

[1] Mueller-Westerhoff, U. T.; Vance, B.; Yoon, D. I. *Tetrahedron* 1991, 47, 909.

[2] (a) Cassoux, P.; Valade, L.; Kobayashi, H.; Kobayashi, A.; Clark, R. A.; Underhill, A. E. *Coord. Chem. Rev.* 1991, 110, 115. (b) Miller, J. S.; Epstein, A. J. *Angew. Chem. Int. Ed. Engl.* 1994, 3, 385.

[3] Herman, Z. S.; Kirchner, R. F., Loew, G. H.; Mueller-Westerhoff, U. T., Nazal, A.; Zerner, M. C. *Inorg. Chem.* 1982, 21, 46.

[4] Ohta, K.; Hasebe, H,; Ema, H.; Fujimoto, T.;Yamamoto, I. *J. Chem. Soc., Chem. Commun.* 1989, 1610.

[5] Ohta, K; Hasebe, H.; Ema, H.; Moriya, M.; Fujimoto, T.; Yamamoto, I. *Mol. Cryst. Liq. Cryst.* 1991, 208, 21-32.

[6] Page, P. C. B.; Graham A. E.; Park, B. K. *Tetrahedron* 1992, 48, 7265-7274.

[7] Sung, K.-M.; Holm, R. H. *J. Am. Chem. Soc.* 2002, 124, 4312-4320.

[8] (a) Miyaura, N.; Suzuki, A. *Chem. Rev.* 1995, 95, 2457-2483. (b) Suzuki, A. *J. Organomet. Chem.* 1999, 576, 147-168.

[9] Mueller-Westerhoff U. T.; Zhou, M. *J. Org. Chem.* 1994, 59, 4988-4992.

[10] Schrauzer, G. N.; Wayweg, V. P. *J. Am. Chem. Soc.* 1965, 87, 1483.

[11] Ishizone, T.; Sugiyama, K.; Hirao, A.; Nakahama, S. *Macromolecules* 1993, 26, 3009-3018.

[12] Macaione, D. P.; Wentworth, S. E. *Synthesis* 1974, 10, 716.

[13] Miller, T. R.; Dance, I. G. *J. Am. Chem. Soc.* 1973, 95, 6970.

EXAMPLE 2

(I) Synthesis of Side-Chain Liquid Crystalline Polymers Containing Nickel Dithiolene Complexes The liquid crystal state (known as a mesophase) represents a discrete state of matter existing between the solid and liquid states. It exhibits fluidity, order, and anisotropic physical properties. Liquid crystals based on metal complexes (metallomesogens) have been known since early 20$^{th}$ century. However, the renaissance of the subject is often ascribed to a publication by Giroud-Godquin and Mueller-Westerhoff in 1977.[1] They reported the synthesis and liquid crystal properties of some nickel dithiolene complexes. Since then, the subject has grown rapidly and has been the subject of many reviews.[2] Side-chain liquid crystalline polymers are of theoretical and practical interest because they combine the anisotropic properties of liquid crystals with polymeric properties.[3] In earlier reports, the backbones of the side-chain liquid crystalline polymers were prepared by radical polymerization of methacrylate[4] and by the hydrosilation of poly(methylhydrosiloxane).[5] In recent years, a variety of methods including living cationic polymerization,[6] ring-opening polymerization,[7] and living ring-opening metathesis polymerization[8] have been used to synthesize new well-defined side-chain liquid crystalline polymers. In 1991, Kawakami and co-workers reported the first example of side-chain liquid crystalline polyoxetanes by cationic ring-opening polymerization.[5b,9] Polyoxetane as the backbone is thought to be flexible due to the quality of ethereal oxygen bonds and its low glass transition temperature. In addition, these side-chain liquid crystalline polyoxetanes, prepared by cationic ring-opening polymerization, show narrow PDI. Several nickel dithiolene complexes have been prepared to evaluate their performance in photovoltaic applications. The incorporation of nickel dithiolene complexes into a polymer affords a material exhibiting the interesting properties of the metal complex and concurrently retaining useful polymeric properties of processability and mechanical durability in the device processing. Bis[1,2-di(3',4'-di-n-dodecyloxy-phenyl)ethane-1,2-dithiolene]nickel (JYC-I-019-A) was previously prepared and it exhibits hexagonal discotic columnar liquid crystal mesophase between 72° C. and 108° C.[10] To maintain the liquid crystal mesophase and to possibly permanently lock in the stacking of the molecules using a polymerizable side chain, the synthesis of side-chain liquid crystalline polyoxetanes containing nickel dithiolene complexes is contemplated by the present disclosure.

Results and Discussions

An α-diketone containing oxetane group, 1-(3,4-bis-dodecyloxy-phenyl)-2-{4-[6-(3-methyloxetan-3-ylmethoxy)hexyloxy]phenyl}ethane-1,2-dione (JYC-I-148-A), was prepared in a multi-step process shown in FIG. 1.

The first step involved the protection of 4-hydroxybenzaldehyde with tBuSiMe$_2$Cl to form 1-[4(tert-butyldimethylsilanyloxy)phenyl]-ethanone (JYC-I-140-A) in 87% yield. The $^1$H and $^{13}$C NMR spectra of JYC-I-140-A are shown in FIG. 2.

JYC-I-140-A was then reacted with the lithium salt of JYC-I-004-A to afford [2-(3,4-bis-dodecyloxy-phenyl)-[1,3]dithian-2-yl][4-(tert-butyldimethylsilanyloxy)phenyl]methanol (JYC-I-142-A) in 85% yield. The $^1$H and $^{13}$C NMR spectra of JYC-I-142-A The reaction of JYC-I-142-A with NBS in acetone/H$_2$O at 0° C. resulted in the formation of 1-(3,4-bis-dodecyloxy-phenyl)-2-[4-(tert-butyldimethylsilanyloxy)pheny]-ethane-1,2-dione (JYC-I-144-A) in 38% yield. The $^1$H and $^{13}$C NMR spectra of JYC-I-144-A are shown in FIG. 4.

The deprotection reaction of JYC-I-144-A with tetrabutylammonium fluoride in THF yielded 1-(3,4-bis-dodecyloxy-phenyl)-2-(4-hydroxyphenyl)ethane-1,2-dione (JYC-I-146-A) in 69% yield. The $^1$H and $^{13}$C NMR spectra of JYC-I-146-A are shown in FIG. 5.

JYC-I-146-A was then reacted with 3-(6-bromo-hexyloxymethyl)-3-methyloxetane (JYC-I-143-A) to generate 1-(3,4-bis-dodecyloxy-phenyl)-2-{4-[6-(3-methyloxetan-3-ylmethoxy)hexyloxy]phenyl}ethane-1,2-dione (JYC-I-148-A) in 52% yield. The $^1$H and $^{13}$C NMR spectra of JYC-I-148-A are shown in FIG. 6.

3-(6-Bromo-hexyloxymethyl)-3-methyloxetane was re-prepared in 53% yield (13.75 g) (JYC-I-143-A) after vacuum distillation (b.p. 90-92° C., 0.1 mmHg). The synthesis of JYC-I-143-A is shown in FIG. 7 and the $^1$H and $^{13}$C NMR spectra of JYC-I-143-A are shown in FIG. 8.

Presently one of the proposed unsymmetrical diketone ligands, 1-(3,4-bis-dodecyloxy-phenyl)-2-{4-[6-(3-methyloxetan-3-ylmethoxy)hexyloxy]phenyl}-ethane-1,2-dione (JYC-I-148-A) has been synthesized.

(II) Synthesis of α-Diketones Via Pd-Catalyzed Cross-Coupling Reactions

α-Diketones have a great deal of interests in organic synthesis as versatile intermediates with useful functional groups which undergo various chemical transformations. Over the past twenty years, several synthetic approaches have been elaborated for their synthesis. In 1993, Mueller-Westerhoff and Zhou[11] reported a simple two-step synthesis of symmetrically substituted α-diones (FIG. 9). The first step involves the preparation of 1,4-dimethylpiperazine-2,3-dione (JYC-I-104-A), which can be prepared in high yield from the reaction between N,N'-dimethylethylenediamine and diethyl oxalate in anhydrous diethyl ether at room temperature overnight. 1,4-Dimethylpiperazine-2,3-dione is able to react with two equivalents of organolithium or Grignard compounds to form symmetrically substituted α-diones after hydrolysis.

Marchese[12] and co-workers reported α-diketones synthesis from oxalyl chloride. They showed that cross-coupling reactions of oxalyl chloride with organocopper reagents, derived from Grignard reagents, cuprous bromide, and lithium bromide, provide a simple and straightforward method for the synthesis of symmetrical α-diketones in relatively good yield. The scheme of the reaction is shown in FIG. 10.

However, some α-diketones are not easily accessible through traditional synthetic methods. Therefore, new approaches based on various metal-catalyzed coupling reactions have been examined. A variety of coupling reactions have been rapidly developed in the past two decades and those processes are routinely used in the fields ranging from materials science to natural product synthesis.

Results and Discussions 4,4'-Bis(N,N-dimethylamino)benzil (JYC-I-079-A), 4,4'-bis(trifluoromethyl)-benzil (JYC-I-088-A), and 4,4'-oxalyldibenzaldehyde (JYC-I-107-A) were successfully prepared following Mueller-Westerhoff and Zhou's method.[11] The scheme of the reaction is shown in FIG. 11. The reaction between 1,4-dimethylpiperazine-2,3-dione and 2 equivalents of lithium reagents, which were generated iii situ from corresponding bromo compounds and n-BuLi reagent at −78° C., gave 4,4'-bis(N,N-dimethylamino)benzil (JYC-I-079-A), 4,4'-bis(trifluoromethyl)benzil (JYC-I-088-A) in 21% and 71% yields respectively. An important experimental observation is that the reactions need to be carried out at −78° C. instead of 0° C. or room temperature. The reactions performed at 0° C. gave little amount of desired product. For the synthesis of 4,4'-oxalyldibenzaldehyde, 4-bromobenzaldehyde diethyl acetal was first lithiated by reacting with n-BuLi at −78° C. The resulting lithium reagent was then reacted with 1,4-dimethylpiperazine-2,3-dione (DMPD), followed by acidic work-up and column chromatography to yield 4,4'-oxalyldibenzaldehyde (JYC-I-107-A) in 21% yield.

Here we have discovered that the compound can be easily synthesized from commercially available 4,4'-dibromobenzil. The reaction between 4,4'-dibromobenzil and copper cyanide in DMF at 165° C. yielded 4,4'-dicyanobenzil (JYC-I-097-A) as a yellow solid (1.36 g, 48%) after column chromatography. The scheme of the reaction is shown in FIG. 12.

The Sonogashira coupling reaction of terminal acetylenes with aryl and vinyl halides provides a powerful method for synthesizing conjugated alkynes, an important class of molecules that have found applications in material science. Bis [4-(phenylethynyl)phenyl]ethanedione (JYC-I-065-A) was prepared from the reaction between 4,4'-dibromobenzil and phenylacetylene catalyzed by 3 mol % Pd(PhCN)$_2$Cl$_2$/6 mol % P(t-Bu)$_3$ in the presence of 2 mol % CuI and 2.4 equiv. HN(i-Pr)$_2$ in dioxane at room temperature.[13] 1,2-Bis[4-(4-trifluoromethylphenylethynyl)phenyl]ethane-1,2-dione (JYC-I-120-B) and 1,2-bis[4-(4-methoxyphenylethynyl)phenyl]ethane-1,2-dione (JYC-I-121-A) were also prepared in a similar manner from the reaction between 4,4'-dibromobenzil and 4-ethynyl-α,α,α-trifluorotoluene and 4-ethynylanisole, respectively. The scheme of the reactions is shown in FIG. 13.

Recent research by Hartwig's and Buchwald's groups led to a highly efficient synthesis of tertiary aromatic amines from primary or secondary amines and aryl bromides or chlorides. 4,4'-Bis(N,N-diphenylamino)benzil (JYC-I-078-A) was prepared in 39% yield from the reaction between 4,4'-dibromobenzil and diphenylamine catalyzed by 5 mol % Pd$_2$(dba)$_3$ and 10 mol % dppf in the presence of 4 equivalents of NaOtBu. The reaction was monitored by TLC and was stopped after 2 days at 120° C. with an indication of no further conversion. The product was isolated by column chromatography to give a yellow solid (0.58 g, 39%). The scheme of the reaction is shown in FIG. 14.

The arylboronic ester of 4,4'-dibromobenzil was prepared according to Miyaura's protocol. The reaction between 4,4'-dibromobenzil and pinacol diboron catalyzed by 5 mol %

Pd(PPh$_3$)$_4$ in the presence of excess KOAc gave 4,4'-di(4,4,5,5-tetramethyl-1,3,2-dioxaborolyl)benzil (JYC-I-099-A) in 55% yield after column chromatography. The reaction scheme for the preparation of JYC-I-099-A is shown in FIG. 15.

1,2-Bis(4-styrylphenyl)ethane-1,2-dione (JYC-I-134-B) was prepared from the Heck reaction between 4,4'-dibromobenzil and styrene (FIG. 16). The reaction was catalyzed by 10 mol % Pd(OAc)$_2$ in the presence Bu$_4$NBr, LiCl, and K$_2$CO$_3$ in DMF at 100° C. and the product was isolated in 69% yield. From the $^1$H NMR spectra of JYC-I-134-B (FIG. 17), the isolated product is a trans isomer based on the coupling constants of the two vinyl protons in the compound JYC-I-134-B (J$_{HH}$=16.6 Hz).

α-Diketones based on the molecule with a rigid backbone, phenanthrenequinone, were synthesized. In order to functionalize the backbone of phenanthrenequinone, the compound was first converted to 3,6-dibromophenanthrenequinone (JYC-I-117-A) via a bromonation reaction under irradiation of a tungsten light at ~60° C. using the method reported by Bhatt.[14] The reaction yielded orange brown crystals (7.84 g, 90%) after recrystallization from nitrobenzene. The scheme of the reaction is shown in FIG. 18.

The Heck reaction between 3,6-dibromophenanthrenequinone (JYC-I-117-A) and styrene gave 3,6-distyrylphenanthrene-9,10-dione (JYC-I-139-A) as an orange solid in 62% yield. The scheme of the reaction is shown in FIG. 19.

From the $^1$H NMR spectra of (JYC-I-139-A) (FIG. 20), the isolated compound is also a trans isomer based on the coupling constants of the two vinyl protons in the compound JYC-I-139-A (J$_{HH}$=16.5 Hz).

Due to the rigidity of the backbone of 3,6-distyrylphenanthrene-9,10-dione (JYC-I-139-A), the phenyl rings are coplanar and the compound is more conjugated than 1,2-bis(4-styrylphenyl)ethane-1,2-dione (JYC-I-134-B).

3,6-Bis(diphenylamino)phenanthrene-9,10-dione (JYC-I-130-A) was prepared via amination reaction between 3,6-dibromophenanthrenequinone (JYC-I-117-A) and diphenylamine catalyzed by 5 mol % Pd$_2$(dba)$_3$ and 10 mol % dppf as shown in FIG. 21 and was isolated as an orange solid in 8% yield. The $^1$H NMR of JYC-I-130-A is shown in FIG. 22.

Bulman Page[15] and co-workers reported a convenient preparation of symmetrical and unsymmetrical α-diketones. They can be efficiently produced in a two-step process by reaction of aldehydes with anions derived from 2-substituted dithianes followed by treatment of the resulting alcohols with excess NBS in aqueous acetone. One of unsymmetrical α-diketone ligands used for the synthesis of an unsymmetrical nickel dithiolene complex was prepared by this method. 1-(3,4-Bis-dodecyloxy-phenyl)-2-(4-bromo-phenyl)-ethane-1,2-dione (JYC-I-053-B) was successfully prepared by reacting [2-(3,4-bis-dodecyloxy-phenyl)-[1,3]dithian-2-yl]-(4-bromo-phenyl)-methanol (JYC-I-049-A) with excess N-bromosuccinimide (NBS). The reaction gave a mixture of 1-(3,4-bis-dodecyloxy-phenyl)-2-(4-bromo-phenyl)-ethane-1,2-dione (JYC-I-053-B) and 1-(2-bromo-4,5-bis-dodecyloxy-phenyl)-2-(4-bromo-phenyl)-ethane-1,2-dione (JYC-I-053-A) after recrystallization from hexanes. The two compounds can be separated by column chromatography (silica gel, hexanes:dichloromethane=1:1 (v/v)). The synthesis of JYC-I-053-B is shown in FIG. 23.

(III) Synthesis of Nickel Dithiolene Complexes

Transition-metal dithiolene complexes possess unusual chemical properties including the ability to undergo a sequence of reversible electron-transfer reactions and intensive absorbance in the visible and near-infrared region. They have attracted much attention for their potential applications in the field of new molecular materials. The high degree of electron-delocalization of nickel dithiolene complexes is responsible for an intensive electronic transition at low energy ($\lambda_{max}$>700 nm), assigned to a π→π* transition between orbitals that are delocalized over NiS$_4$C$_4$ core of the complex, which makes these complexes suitable to be used as near-infrared dyes.

Results and Discussions

The nickel dithiolene complex, bis[1,2-di(4-(4,4,5,5-tetramethyl-1,3,2-dioxaborolyl)phenyl)ethane-1,2-dithiolene] nickel (JYC-I-109-A) was successfully prepared by refluxing 4,4'-di(4,4,5,5-tetramethyl-1,3,2-dioxaborolyl)benzil (JYC-I-099-A) with excess phosphorous pentasulfide in 1,4-dioxane followed by the reaction with NiCl$_2$.6H$_2$O (FIG. 24). Compound JYC-I-109-A was isolated as a green solid. The compound has similar absorption spectrum and electrochemical properties as [Ni(S$_2$C$_2$(C$_6$H$_4$-p-Br)$_2$)$_2$] (JYC-I-054-A). In addition, the solubility of JYC-I-109-A in organic solvent is higher than that of JYC-I-054-A, which makes JYC-I-109-A a better candidate in material science application.

The synthesis of bis{1,2-di[(4-trifluoromethyl)phenyl]ethane-1,2-dithiolene}-nickel (JYC-I-091-A) was carried out in 1,4-dioxane. The reaction resulted in the precipitation of a blue solid. The crude product was further purified by column chromatography (silica gel, hexanes:dichloromethane=2:1 (v/v)) to give a grayish blue solid (0.36 g, 31%). The reaction scheme is shown in FIG. 25. Since the solid has very poor solubility in the eluting solvent mixture, serious tailing occurs during column chromatography.

There are two different types of unsymmetrical nickel dithiolene complexes: One is a complex with an A^A and a B^B type ligands and the other one is a complex with two A^B type ligands. Both examples of complexes have been synthesized. One of them is bis{[1,2-[(4-bromophenyl)(3',4'-di-n-dodecyloxy-phenyl)]ethane-1,2-dithiolene}nickel (JYC-I-072-A), with two A^B type ligands, which was prepared in a traditional method with a higher yield in 1,4-dioxane than in 1,3-dimethyl-2-imidazolidinone. The product was isolated as a green solid and the scheme of the reaction is shown in FIG. 26.

{[1,2-Di(4-bromophenyl)]ethane-1,2-dithiolene}{[1,2-di(3',4'-di-n-dodecyloxy-phenyl)]ethane-1,2-dithiolene]} nickel (JYC-I-055-A), a complex with an A^A and a B^B type ligands, was prepared from a molar ratio 1:1 mixture of bis [1,2-di(3',4'-di-n-dodecyloxy-phenyl)ethane-1,2-dithiolene] nickel (JYC-I-019-A) and [Ni(S$_2$C$_2$(C$_6$H$_4$-p-Br)$_2$)$_2$] (JYC-I-054-A) in chloroform solvent under reflux. Miller and Dance have reported the synthesis of [Ni(S$_2$C$_2$(C$_6$H$_5$)$_2$)(S$_2$C$_2$(CF$_3$)$_2$)][16] using this approach in 1973. Through ligand exchange the desired product, JYC-I-055-A, was isolated as a green sticky solid in 84% yield after column chromatography (FIG. 27).

Bis[1,2-di(3',4'-di-n-dodecyloxy-phenyl)ethane-1,2-dithiolene]nickel (JYC-I-019-A), bis[1,2-di(4-bromophenyl) ethane-1,2-dithiolene]nickel (JYC-I-054-A), bis[1,2-(4-bromophenyl)(3',4'-di-in-dodecyloxy-phenyl)ethane-1,2-dithiolene]nickel (JYC-I-072-A), and {[1,2-di(4-bromophenyl)]ethane-1,2-dithiolene}{[1,2-di(3',4'-di-n-dodecyloxy-phenyl)]ethane-1,2-dithiolene]}nickel (JYC-I-055-A) have been isolated. The comparison of these four complexes is listed in Table 1.

TABLE 1

The comparison of JYC-I-019-A, JYC-I-054-A, JYC-I-072-A, and JYC-I-055 A in their absorption spectra and electrochemistry.

| Complex | UV ($\lambda_{max}$, nm ($\epsilon$)) | CV (vs. ferrocene in $CH_2Cl_2$) |
|---|---|---|
| JYC-I-019-A | 310 (57450)<br>348 (sh, 31395)<br>572 (3680)<br>638 (sh, 3360)<br>962 (35210) | $E_{1/2}$ (0/−1) = −0.54 V<br>$E_{1/2}$ (−1/−2) = −1.30 V |
| JYC-I-054-A | 278 (56050)<br>321 (64720)<br>604 (2550)<br>864 (40950) | $E_{1/2}$ (0/−1) = −0.35 V<br>$E_{1/2}$ (−1/−2) = −1.15 V |
| JYC-I-072-A | 314 (58370)<br>604 (2740)<br>920 (34950) | $E_{1/2}$ (0/−1) = 0.45 V<br>$E_{1/2}$ (−1/−2) = −1.22 V |
| JYC-I-055-A | 314 (54980)<br>596 (2870)<br>925 (33710) | $E_{1/2}$ (0/−1) = −0.46 V<br>$E_{1/2}$ (−1/−2) = −1.27 V |

This is the first time that four different types of nickel dithiolene complexes with two A^A ligands, two B^B ligands, two A^B ligands, or one A^A ligand and one B^B ligand, were synthesized and compared. By comparing electronic absorption spectra of these complexes, it is shown that the substituents of dithiolene ligands have effects on the absorbance in near-infrared region, which corresponds to the π→π* transition between orbitals that are delocalized over $NiS_4C_4$ core of the complex. The complex with all electron-donating groups (alkoxy groups), JYC-I-019-A, has a lower energy near-IR absorption band. On the contrary, the complex with all electron-withdrawing groups (Br groups), JYC-I-054-A, has a higher energy near-IR absorption band. For the two unsymmetrical nickel dithiolene complexes, JYC-I-055-A and JYC-I-072-A, containing both electron-donating groups (alkoxy groups) and electron-withdrawing groups (Br groups), their near-IR absorption band are between those of JYC-I-019-A and JYC-I-054-A in terms of energy. According to the results from electrochemistry, JYC-I-054-A containing electron-withdrawing groups is more easily reduced from neutral form to anion and from anion to dianion than JYC-I-019-A containing electron-donating groups. The oxidizing power of nickel dithiolene complexes depends on substituents in the backbone of complexes but is independent of the symmetry of complexes.

The nickel dithiolene complex, bis{1,2-di[(4-cyano)phenyl]ethane-1,2-dithiolene}nickel (JYC-I-102-A), was synthesized from the reaction between 4,4'-dicyanobenzil and excess phosphorus pentasulfide in 1,4-dioxane at 110° C. for 5 h, followed by the reaction with $NiCl_2.6H_2O$ (FIG. 28). The crude product was isolated as a black solid, which has very poor solubility, so no purification by column chromatography was carried out. The $^1H$ NMR of the black solid in DMSO-$d_6$ shows broad peaks in the aromatic region. The compound has very poor solubility in $CH_2Cl_2$ and acetonitrile. The absorption spectrum and cyclic voltammogram of the crude black solid were obtained even though the compound is not completely pure. UV ($CH_2Cl_2$) $\lambda_{max}$, nm: 848, 597, 321 (FIG. 29). Cyclic voltammetry: $E_{1/2}(0/-1)=-0.23$ V; $E_{1/2}(-1/-2)=-1.04$ V (versus ferrocene in dichloromethane) (FIG. 30). Since the product was not pure, no extinction coefficients were reported.

The nickel dithiolene complex, bis{1,2-di[(4-phenylethynyl)phenyl]ethane-1,2-dithiolene}nickel (JYC-I-114-A), was synthesized from the reaction between bis[4-(phenylethynyl)phenyl]ethanedione and excess phosphorus pentasulfide in 1,4-dioxane under reflux, followed by the reaction with $NiCl_2.6H_2O$ (FIG. 33).

The crude product was purified by column chromatography (silica gel, hexanes:dichloromethane=1:1 (v/v)) to give a greenish brown solid. The isolated greenish brown solid is the desired product based on the evidence of HRMS-MALDI and a $^1H$ NMR spectrum (FIG. 34). The HRMS-MALDI data strongly supports the isolation of JYC-I-114-A ([M]$^+$ calcd for $C_{60}H_{36}S_4Ni$, 942.1060; found, 942.1031). From the cyclic voltammogram of isolated material JYC-I-114-A, $E_{1/2}$ (0/−1)=−0.38 V and $E_{1/2}(-1/-2)=-1.17$ V (versus ferrocene in dichloromethane) were extracted (FIG. 36).

(IV) Synthesis of Polymers Containing Transition Metals

Polymers containing transition metals in the backbone have attracted considerable attention since these polymers offer properties distinct from their individual inorganic or organic components. However, synthetic difficulties and solubility problems have hampered the progress in the field. Recent reports show that metal-containing polymers may be useful in catalysis,[17] for responsive and conducting materials,[18] for their use as the active medium in optical, electronic, optoelectronic, and chemical sensing devices.[19]

Over the past decade, significant progress has been made toward the synthesis of hybrid metal/polymer materials with useful and novel properties.[20] These synthetic tools include supramolecular self assembly, ring-opening polymerization, and metal-catalyzed polycondensation. Since metal-containing polymers are emerging as interesting and useful materials, further synthetic breakthroughs are still needed.

Results and Discussions

Applying transition metal-catalyzed cross-coupling reactions to construct supramolecular structures based on a nickel dithiolene core and to synthesize nickel dithiolene complexes-containing polymers has been investigated. The synthesis of the ligand is proposed in FIG. 18 in which bromo groups are changed to iodo groups since iodo-carbon bond is weaker and more reactive.

In another embodiment, alkoxy substituents are attached to the phenyl ring of the coupling partner to increase the solubility of the resulting supramolecules and polymers. The synthesis of 1,4-diethynyl-2,5-dihexadecyloxybenzene (B) can be prepared according to the report by Swager[21] and co-workers. The synthesis of (C) can utilize Sonogashira cross-coupling to generate nickel dithiolene complexes-containing polymer. The overlap of the metal dπ-orbitals with the alkyne pπ*-orbitals in the complex should give rise to a partially delocalized π system along the polymer chain, the extent of which depends on the degree of orbital overlap. Furthermore, the attachment of flexible chains to the polymer backbone makes it likely to have liquid crystalline properties.

Syntheses

1-[4(tert-Butyldimethylsilanyloxy)phenyl]ethanone (JYC-I-140-A). To a stirred solution of 4-hydroxybenzaldehyde (20.0 g, 0.16 mol) in 200 mL of $CH_2Cl_2$ at 0° C., imidazole (24.5 g, 0.36 mol) and $^tBuSiMe_2Cl$ (27.2 g, 0.18 mol) were added. The reaction mixture was stirred at 25° C. for 1 h. The reaction mixture was diluted with $H_2O$ and extracted with $CH_2Cl_2$. The organic phase was dried over anhydrous $MgSO_4$ and the solvent was removed under reduced pressure. The crude product was purified by column chromatography (silica gel, hexanes:ethyl acetate=50:1 (v/v)) to give colorless oil (35.63 g, 86.9%). $^1H$ NMR (300 MHz, CDCl$_3$, δ): 9.86 (s, 2H), 7.77 (d, J=8.8 Hz, 2H), 6.92 (d, J=8.8 Hz, 2H), 0.97 (s, 9H), 0.23 (s, 6H). $^{13}C\{^1H\}$ NMR (75 MHz, CDCl$_3$, δ): 190.76, 161.49, 131.87, 130.50, 120.47, 25.55, 18.25, −4.37. HRMS-FAB (m/z): [M+H]$^+$ calcd for $C_{14}H_{23}O_2Si$, 251.1467; found, 251.1469.

[2-(3,4-Bis-dodecyloxy-phenyl)-[1,3]dithian-2-yl][4-(tert-butyldimethylsilanyloxy)phenyl]methanol (JYC-I-142-A). JYC-I-004-A (10.0 g, 17.7 mmol) was dissolved in 80 mL of dry THF and cooled down to −78° C. nBuLi (7.8 mL of 2.5 M solution in hexanes, 19.5 mmol) was added dropwise under argon counterflow and the reaction mixture was stirred at 0° C. for 30 min. A solution of JYC-I-140-A (4.43 g, 17.7 mmol) in dry THF was added at −78° C. The reaction mixture was stirred at 0° C. for an additional 30 min and warmed up to room temperature over 1 h. The reaction was quenched with a saturated NH$_4$Cl aqueous solution. The organic phase was washed with H$_2$O and a saturated NaCl aqueous solution and dried over anhydrous MgSO$_4$. The solvent was removed under reduced pressure to give thick brown oil. The crude product was purified by column chromatography (silica gel, dichloromethane:hexanes=5:1 (v/v)) to give yellow oil (12 g, 85%).$^1H$ NMR (300 MHz, CDCl$_3$, δ): 7.19 (dd, J=8.3 Hz, 2.4 Hz, 1H), 7.14 (d, J=2.0 Hz, 1H), 6.75 (d, J=8.3 Hz, 1H), 6.72 (d, J=8.3 Hz, 2H), 6.58 (d, J=8.3 Hz, 2H), 4.87 (d, J=3.9 Hz, 1H), 3.97 (t, J=6.8 Hz, 2H), 3.79 (t, J=6.8 Hz, 2H), 2.85 (d, 3.9 Hz, 1H), 2.67 (m, 4H), 1.88 (m, 2H), 1.67-1.85 (m, 4H), 1.20-1.52 (m, 36H), 0.93 (s, 9H), 0.86 (t, J=6.3 Hz, 6H), 0.12 (s, 6H). $^{13}C\{^1H\}$ NMR (75 MHz, CDCl$_3$, δ): 155.46, 148.45, 130.18, 129.50, 129.26, 123.37, 118.619, 116.48, 112.74, 80.83, 69.29, 69.09, 66.66, 31.91, 29.71, 29.69, 29.63, 29.49, 29.47, 29.36, 29.29, 27.35, 27.02, 26.06, 25.64, 24.86, 22.67, 18.15, 14.08, −4.46, −4.48. HRMS-FAB (m/z): [M+H−H$_2$]$^+$ calcd for C$_{47}$H$_{79}$O$_4$S$_i$S$_2$, 799.5189; found, 799.5183. Anal. Calcd for C$_{47}$H$_{80}$O$_4$S$_i$S$_2$: C, 70.44; H, 10.06; S, 8.00. Found: C, 70.55; H, 10.07; S, 8.07.

3-(6-Bromo-hexyloxymethyl)-3-methyloxetane (JYC-I-143-A). A two phase system composed of 1,6-dibromohexane (74.06 g, 0.30 mmol) in hexanes (100 mL) and 3-methyl-3-oxetanemethanol (10.0 g, 0.10 mmol), NaOH (65.02 g, 1.63 mol), and Bu$_4$NBr (0.5 g, 1.55 mmol) in H$_2$O (100 mL) was stirred at 0° C. in an ice bath for 30 min. The reaction mixture was warmed up to room temperature and stirred at room temperature for 1 day. It was then heated at 100° C. for additional 2 h. The reaction mixture was allowed to cool down to room temperature and H$_2$O was added. The mixture was extracted with hexanes three times. The combined organic phase was dried over anhydrous MgSO$_4$ and the solvent was removed under reduced pressure. The crude product was distilled under vacuum to give colorless liquid (b.p. 90-92° C., 0.1 mmHg) (13.75 g, 53%). $^1$H NMR (300 MHz, CDCl$_3$, δ): 4.48 (d, J=5.5 Hz, 2H), 4.33 (d, J=5.9 Hz, 1H), 3.45 (s, 2H), 3.44 (t, J=6.4 Hz, 2H), 3.39 (t, J=6.8 Hz, 2H), 1.85 (m, 2H), 1.58 (m, 2H), 1.30-1.50 (m, 4H), 1.28 (s, 3H). $^{13}$C{$^1$H} NMR (75 MHz, CDCl$_3$, δ): 80.17, 76.12, 71.34, 39.94, 33.71, 32.70, 29.34, 27.93, 25.34, 21.35. HRMS-FAB (m/z): [M+H]$^+$ calcd for C$_{11}$H$_{22}$BrO$_2$, 265.0803; found, 265.0802.

1-(3,4-Bis-dodecyloxy-phenyl)-2-[4-(tert-butyldimethyl-silanyloxy)phenyl]-ethane-1,2-dione (JYC-I-144A). A solution of JYC-I-142-A (10.0 g, 12.5 mmol) in 200 mL of acetone was added dropwise to a solution of NBS (38.65 g, 217.1 mmol) in 600 mL of solvent mixture (3% H$_2$O/acetone (v/v)) at 0° C. in an ice bath. The reaction mixture was stirred at 0° C. and gradually warmed up to room temperature over 30 min. The reaction mixture was poured into a saturated Na$_2$SO$_3$ aqueous solution (300 mL) and CH$_2$Cl$_2$ (800 mL). The resulting mixture was stirred at room temperature for additional 10 min. The organic phase was washed with H$_2$O and dried over anhydrous MgSO$_4$. The solvent was removed under reduced pressure to give brown oil. The crude product was purified by column chromatography (silica gel, dichloromethane:hexanes=2:3 (v/v)) to give yellow oil (3.4 g, 38.4%). $^1$H NMR (300 MHz, CDCl$_3$, δ): 7.86 (d, J=8.8 Hz, 2H), 7.55 (d, J=2.4 Hz, 1H), 7.42 (dd, J=8.8 Hz, 2.0 Hz, 1H), 6.88 (d, J=8.8 Hz, 2H), 6.83 (d, J=8.8 Hz, 1H), 4.03 (t, J=6.8 Hz, 4H), 1.82 (m, 4H), 1.20-1.50 (m, 36H), 0.96 (s, 9H), 0.86 (t, J=6.3 Hz, 6H), 0.22 (s, 6H). $^{13}$C{$^1$H} NMR (75 MHz, CDCl$_3$, δ): 193.55, 193.72, 161.75, 155.04, 149.33, 134.20, 132.25, 126.88, 126.08, 120.33, 112.32, 111.62, 69.23, 69.10, 31.90, 29.64, 29.60, 29.57, 29.34, 29.05, 28.91, 25.97, 25.90, 25.51, 22.66, 18.22, 14.08, −4.38. HRMS-FAB (m/z): [M+H]$^+$ calcd for C$_{44}$H$_{73}$O$_5$S$_i$, 709.5227; found, 709.5218.

1-(3,4-Bis-dodecyloxy-phenyl)-2-(4-hydroxyphenyl)ethane-1,2-dione (JYC-I-146-A). To a solution of JYC-I-144-A in anhydrous THF (25 mL) was added Bu$_4$NF (4.2 mL of 1M solution in THF, 4.2 mmol). The resulting orange solution was stirred at room temperature for 45 min. The reaction mixture was poured into H$_2$O and extracted with ethyl acetate. The organic phase was dried over anhydrous MgSO$_4$ and the solvent was removed under reduced pressure. The crude product was purified by column chromatography (silica gel, hexanes:ethyl acetate=3:1 (v/v)) to give a yellow solid (1.74 g, 69%). $^1$H NMR (300 MHz, CDCl$_3$, δ): 7.84 (d, J=8.8 Hz, 2H), 7.54 (d, J=2.0 Hz, 1H), 7.42 (dd, J=8.3 Hz, 2.0 Hz, 1H), 6.86 (d, J=8.8 Hz, 2H), 6.83 (d, J=8.3 Hz, 1H), 6.56 (s, 1H), 4.04 (t, J=6.8 Hz, 2H), 4.03 (t, J=6.3 Hz, 2H), 1.81 (m, 4H), 1.20-1.50 (m, 36H), 0.86 (t, J=6.3 Hz, 6H). $^{13}$C{$^1$H} NMR (75 MHz, CDCl$_3$, δ): 194.20, 193.75, 162.14, 155.24, 149.27, 132.71, 126.44, 126.04, 125.88, 116.01, 112.34, 111.68, 69.35, 69.21, 31.89, 29.67, 29.64, 29.59, 29.56, 29.34, 28.99, 28.85, 25.95, 25.88, 22.65, 14.07. HRMS-FAB (m/z): [M+H]$^+$ calcd for C$_{38}$H$_{59}$O$_5$, 595.4363; found, 595.4340.

1-(3,4-Bis-dodecyloxy-phenyl)-2-{4-[6-(3-methyloxetan-3-ylmethoxy)hexyloxy]phenyl}ethane-1,2-dione (JYC-I-148-A). A mixture of JYC-I-146-A (1.46 g, 2.5 mmol), JYC-I-43-A (0.72 g, 2.7 mmol), and K$_2$CO$_3$ (0.68 g, 4.9 mmol) in 30 mL of DMF was refluxed at 80° C. overnight and then heated at 150° C. for additional 3 h. The reaction mixture was quenched with a saturated NH$_4$Cl aqueous solution and extracted with CH$_2$Cl$_2$. The organic phase was washed with H$_2$O and dried over anhydrous MgSO$_4$. The solvent was removed under reduced pressure to give brown oil. The crude product was purified by column chromatography (silica gel, hexanes:ethyl acetate=6:1 (v/v)) to give a yellow solid (0.99 g, 52%). $^1$H NMR (300 MHz, CDCl$_3$, δ): 7.89 (d, J=8.8 Hz, 2H), 7.54 (d, J=2.0 Hz, 1H), 7.41 (dd, J=8.3 Hz, 2.0 Hz, 1H), 6.91 (d, J=9.3 Hz, 2H), 6.82 (d, J=8.8 Hz, 1H), 4.47 (d, J=5.9 Hz, 2H), 4.32 (d, J=5.9 Hz, 2H), 3.98-4.05 (m, 6H), 3.443 (t, J=6.3 Hz, 2H), 3.437 (s, 2H), 1.80 (m, 6H), 1.59 (m, 2H), 1.27 (s, 3H), 1.20-1.50 (m, 40H), 0.85 (t, J=6.6 Hz, 6H). $^{13}$C {$^1$H} NMR (75 MHz, CDCl$_3$, δ): 193.73, 193.45, 164.35, 154.99, 149.30, 132.28, 126.19, 126.08, 126.03, 114.61, 112.31, 111.60, 80.13, 76.04, 71.36, 69.20, 69.07, 68.26, 39.88, 31.86, 29.65, 29.61, 29.57, 29.54, 29.41, 29.30, 29.03, 28.93, 28.88, 25.94, 25.87, 25.74, 22.63, 21.32, 14.05. HRMS-FAB (m/z): [M]$^+$ calcd for C$_{49}$H$_7$O$_7$, 778.5748; found, 778.5740. Anal. Calcd for C$_{49}$H$_{78}$O$_7$: C, 75.54; H, 10.09. Found: C, 75.44; H, 10.20.

4-[6-(3-Methyloxetan-3-ylmethoxy)hexyloxy]benzaldehyde (JYC-I-141-A). A mixture of JYC-I-143-A (5 g, 18.9 mmol), 4-hydroxybenzaldehyde (2.53 g, 20.7 mmol), and K$_2$CO$_3$ (5.21 g, 37.7 mmol) in 50 mL of DMF was heated at 150° C. for 5 h. The reaction mixture was allowed to cool down to room temperature and poured into a separatory funnel containing H$_2$O. The mixture was extracted with CH$_2$Cl$_2$ and the organic phase was washed with H$_2$O and a saturated NaCl aqueous solution. The organic phase was dried over anhydrous MgSO$_4$. The solvent was removed under reduced pressure to give brown oil. The crude product was purified by column chromatography (silica gel, hexanes:ethyl acetate:=4:1 (v/v)) to give light yellow liquid (4.75 g, 82%). $^1$H NMR (300 MHz, CDCl$_3$, δ): 9.84 (s, 1H), 7.79 (d, J=8.8 Hz, 2H), 6.95 (d, J=8.8 Hz, 2H), 4.47 (d, J=5.5 Hz, 2H), 4.32 (d, J=5.5 Hz, 2H), 4.01 (t, J=6.4 Hz, 2H), 3.45 (t, J=6.4 Hz, 2H), 3.44 (s, 2H), 1.80 (m, 2H), 1.60 (m, 2H), 1.44 (m, 4H), 1.27 (s, 3H). $^{13}$C{$^1$H} NMR (75 MHz, CDCl$_3$, δ): 190.66, 164.13, 131.88, 129.72, 114.66, 80.09, 76.00, 71.33, 68.20, 39.85, 29.38, 28.94, 25.85, 25.73, 21.30. HRMS-FAB (m/z): [M+H]$^+$ calcd for C$_{18}$H$_{27}$O$_4$, 307.1909; found, 307.1905.

1,4-Dimethylpiperazine-2,3-dione (JYC-I-104-A). To a stirred solution of N,N'-dimethylethylenediamine (25.0 g, 0.28 mol) in 150 mL of dry diethyl ether was added diethyl oxalate (38.5 mL, 0.28 mol) in one portion. After a few minutes white crystals started to precipitate. The reaction mixture was stirred at room temperature overnight. The product was filtered and washed with dry diethyl ether. The product was dried under vacuum at 47° C. overnight to give colorless crystals (38.64 g, 96%). $^1$H NMR (200 MHz, CDCl$_3$, δ): 3.50 (s, 4H), 2.99 (s, 6H). $^{13}$C{$^1$H} NMR (200 MHz, CDCl$_3$, δ): 157.35, 45.91, 34.74.

4,4'-Bis(N,N-dimethylamino)benzil (JYC-I-079-A). To a solution of 4-bromo-N,N-dimethylaniline (6.76 g, 33.7 mmol) in 40 mL of dry THF was added 13 mL of n-BuLi (2.5 M in hexanes, 32.5 mmol) by a syringe at −78° C. After stirring at −78° C. for 1 h, the mixture was transferred to a suspension of 1,4-dimethylpiperazine-2,3-dione (DMPD) (2.0 g, 14.1 mmol) in 40 mL of dry THF dropwise via a cannula under an argon counterflow. The reaction mixture was gradually warmed up to room temperature and stirred at room temperature for additional 2 h. The mixture was then hydrolyzed with 100 mL of 10% HCl and extracted with $CH_2Cl_2$. The organic layer was dried over anhydrous $MgSO_4$ and the solvent was removed under reduced pressure. The product was purified by column chromatography (silica gel, dichloromethane:hexanes=2:1 (v/v), and then ethyl acetate:hexanes=1:1 (v/v)) to give a bright yellow solid (0.89 g, 21%). $^1$H NMR (300 MHz, $CDCl_3$, δ): 7.82 (d, J=9.3 Hz, 4H), 6.60 (d, J=9.3 Hz, 4H), 3.03 (s, 12H). $^{13}C\{^1H\}$ NMR (75 MHz, $CDCl_3$, δ): 193.89, 154.11, 132.12, 121.42, 110.74, 39.96. IR ($cm^{-1}$): 2915, 1643, 1588, 1545, 1378, 1161. HRMS-FAB (m/z): $[M+H]^+$ calcd for $C_{18}H_{21}N_2O_2$, 297.1603; found, 297.1602. Anal. Calcd for $C_{18}H_{20}N_2O_2$: C, 72.95; H, 6.80; N, 9.45. Found: C, 72.61; H, 6.79; N, 9.39.

4,4'-Bis(trifluoromethyl)benzil (JYC-I-088-A). To a solution of 4-bromobenzotrifluoride (6.96 g, 30.9 mmol) in 30 mL of dry THF was added 11.8 mL of n-BuLi (2.5 M in hexanes, 29.5 mmol) by a syringe at −78° C. After stirring at −78° C. for 1 h, the mixture was transferred to a suspension of 1,4-dimethylpiperazine-2,3-dione (DMPD) (2.0 g, 14.1 mmol) in 30 mL of dry THF dropwise via a cannula under an argon counterflow. The reaction mixture was gradually warmed up to room temperature and stirred at room temperature for an additional 2 h. The mixture was then hydrolyzed with 100 mL of 10% HCl and extracted with $CH_2Cl_2$. The organic layer was dried over anhydrous $MgSO_4$ and the solvent was removed under reduced pressure. The product was purified by column chromatography (silica gel, dichloromethane:hexanes=1:5 (v/v)) to give a yellow solid (3.46 g, 71%). $^1$H NMR (300 MHz, $CDCl_3$, δ): 8.10 (d, J=7.8 Hz, 4H), 7.78 (d, J=8.3 Hz, 4H). $^{13}C\{^1H\}$ NMR (75 MHz, $CDCl_3$, δ): 191.89 (C=O, 2C), 136.17 (q, $^2J_{CF}$=32.9 Hz, 2C), 135.18 (s, 2C), 130.34 (s, 4C), 126.15 (q, $^3J_{CF}$=3.7 Hz, 4C), 123.25 (q, $^1J_{CF}$=273.1 Hz, 2C). HRMS-EI (m/z): [M] calcd for $C_{16}H_8F_6O_2$, 346.0428; found, 346.0432. Calcd for $C_{16}H_8F_6O_2$: C, 55.50; H, 2.33; F, 32.92. Found: C, 55.46; H, 2.33; N, 33.04.

4,4'-Oxalyldibenzaldehyde (JYC-I-107-A). To a solution of 4-bromobenzaldehyde diethyl acetal (20.05 g, 77.4 mmol) in 80 mL of dry THF was added 31 mL of n-BuLi (2.5 M in hexanes, 77.4 mmol) by a syringe at −78° C. After stirring at −78° C. for 1 h, the mixture was transferred to a suspension of 1,4-dimethylpiperazine-2,3-dione (DMPD) (5.0 g, 35.0 mmol) in 80 mL of dry THF dropwise via a cannula under an argon counterflow. The reaction mixture was gradually warmed up to room temperature and stirred at room temperature for an additional 2 h. The mixture was then hydrolyzed with 10% HCl and extracted with $CH_2Cl_2$. The organic layer was dried over anhydrous $MgSO_4$ and the solvent was removed under reduced pressure. The product was purified by column chromatography (silica gel, dichloromethane:hexanes=4:1 (v/v)) to give a yellow solid (2.00 g, 21%j. $^1$H NMR (300 MHz, $CDCl_3$, δ): 10.13 (s, 2H), 8.14 (d, J=8.1 Hz, 4H), 8.02 (d, J=8.8 Hz, 4H). $^{13}C\{^1H\}$ NMR (75 MHz, $CDCl_3$, δ): 192.41, 191.24, 140.22, 136.60, 130.54, 130.04. HRMS-EI (m/z): $[M]^+$ calcd for $C_{16}H_{10}O_4$, 266.0579; found, 266.0584. Anal. Calcd for $C_{16}H_8N_2O_2$: C, 72.18; H, 3.79. Found: C, 72.03; H, 3.74.

4,4'-Dicyanobenzil (JYC-I-097-A). A mixture of copper cyanide (2.53 g, 28.3 mmol) and 4,4'-dibromobenzil (4.0 g, 10.9 mmol) in 60 mL of DMF was refluxed at 165° C. for 1 day. The reaction mixture was quenched with a saturated NaCl aqueous solution and extracted with diethyl ether. The combined organic layer was dried over anhydrous $MgSO_4$ and the solvent was removed under reduced pressure. The product was purified by column chromatography (silica gel, dichloromethane:hexanes=5:1 (v/v) and dried under vacuum at 47° C. overnight to give a yellow solid (1.36 g, 48%). $^1$H NMR (300 MHz, $CDCl_3$, δ): 8.09 (d, J=8.3 Hz, 4H), 7.83 (d, J=8.8 Hz, 4H). $^{13}C\{^1H\}$ NMR (75 MHz, $CDCl_3$, δ): 190.76, 135.27, 132.85, 130.36, 118.36, 117.40. HRMS-EI (m/z): $[M]^+$ calcd for $C_{16}H_8N_2O_2$, 260.0586; found, 260.0580. Anal. Calcd for $C_{16}H_8N_2O_2$: C, 73.84; H, 3.10; N, 10.76. Found: C, 73.79; H, 2.99; N, 10.75.

Bis[4-(phenylethynyl)phenyl]ethanedione (JYC-I-065-A). In a glove box, a schlenk tube was charged with $Pd(PhCN)_2Cl_2$ (94 mg, 0.25 mmol) and CuI (31 mg, 0.16 mmol). Under argon counterflow, anhydrous dioxane (60 mL), $P(t-Bu)_3$ (4 mL of 0.123 M solution in toluene, 0.49 mmol), $HN(i-Pr)_2$ (2.7 mL, 19.3 mmol), 4,4'-dibromobenzil (3.0 g, 8.2 mmol), and phenylacetylene (2.2 mL, 20 mmol) were added to the schlenk tube sequentially. After stirring at room temperature overnight, the reaction mixture was diluted with ethyl acetate and filtered through a pad of celite with EtOAc rinsing. The solvent was removed under reduced pressure and the product was purified by column chromatography (silica gel, hexanes:dichloromethane=1:1 (v/v)) to give light yellow crystals (2.58 g, 77%). $^1$H NMR (200 MHz, $CDCl_3$, δ): 7.96 (d, J=8.3 Hz, 8H), 7.64 (d, J=8.3 Hz, 8H), 7.50-7.57 (m, 8H), 7.33-7.38 (m, 12H). $^{13}C\{^1H\}$ NMR (50 MHz, $CDCl_3$, δ): 193.20, 182.81, 132.04, 131.83, 130.22, 129.85, 129.06, 128.47, 122.37, 94.19, 88.45.

1,2-Bis[4-(4-trifluoromethylphenylethynyl)phenyl]ethane-1,2-dione (JYC-I-120-B). In a glove box, a schlenk tube was charged with $Pd(PhCN)_2Cl_2$ (63 mg, 0.16 mmol) and CuI (21 mg, 0.11 mmol). Under argon counterflow, anhydrous dioxane (50 mL), $P(t-Bu)_3$ (2.7 mL of 0.123 M solution in toluene, 0.33 mmol), $HN(i-Pr)_2$ (1.8 mL, 13 mmol), 4,4'-dibromobenzil (2.0 g, 5.4 mmol), and 4-ethynyl-α,α,α-trifluorotoluene (2.31 g, 13.6 mmol) were added to the schlenk tube sequentially. After stirring at room temperature overnight, the reaction mixture was diluted with ethyl acetate and filtered through a pad of celite with EtOAc rinsing. The solvent was removed under reduced pressure and the product was purified by column chromatography (silica gel, hexanes:dichloromethane=3:1 (v/v), then hexanes:dichloromethane=1:1 (v/v)) to give light yellow needles (2.20 g, 74%). $^1$H NMR (300 MHz, $CDCl_3$, δ): 7.98 (d, J=8.3 Hz, 4H), 7.64 (d, J=8.3 Hz, 2H), 7.64-7.60 (m, 8H). HRMS-FAB (m/z): $[M+H]^+$ calcd for $C_{32}H_{17}O_2F_6$, 547.1133; found, 547.1146. Anal. Calcd for $C_{32}H_{16}F_6O_2$: C, 70.33; H, 2.95; F, 20.86. Found: C, 70.07; H, 2.81; F, 20.71.

1,2-Bis[4-(4-methoxyphenylethynyl)phenyl]ethane-1,2-dione (JYC-I-121-A). In a glove box, a schlenk tube was charged with $Pd(PhCN)_2Cl_2$ (63 mg, 0.16 mmol) and CuI (21 mg, 0.11 mmol). Under argon counterflow, anhydrous dioxane (50 mL), $P(t-Bu)_3$ (2.7 mL of 0.123 M solution in toluene, 0.33 mmol), $HN(i-Pr)_2$ (1.8 mL, 13 mmol), 4,4'-dibromobenzil (2.0 g, 5.4 mmol), and 4-ethynylanisole (1.80 g, 13.6 mmol) were added to the schlenk tube sequentially. After stirring at room temperature overnight, the reaction mixture was diluted with ethyl acetate and filtered through a pad of celite with EtOAc rinsing. The solvent was removed under reduced pressure and the product was purified by column chromatography (silica gel, hexanes:dichloromethane=2:3 (v/v)) to give bright yellow solid (2.45 g, 96%). $^1$H NMR (300 MHz, $CDCl_3$, δ): 7.93 (d, J=8.8 Hz, 4H), 7.60 (d, J=8.3 Hz, 4H), 7.48 (d, J=9.3 Hz, 4H), 6.88 (d, J=8.8 Hz, 4H), 3.82 (s, 6H). $^{13}C\{^1H\}$ NMR (75 MHz, $CDCl_3$, δ): 193.31, 160.25, 133.41, 131.79, 131.59, 130.64, 129.84, 114.42, 114.14, 94.56, 87.49, 55.33. HRMS-FAB (m/z): $[M+H]^+$ calcd for $C_{32}H_{23}O_4$, 471.1596; found, 471.1595. Anal. Calcd for $C_{32}H_{22}O_4$: C, 81.69; H, 4.71. Found: C, 81.37; H, 4.58.

4,4'-Bis(N,N-diphenylamino)benzil (JYC-I-078-A). A schlenk tube was charged with diphenylamine (0.97 g, 5.7 mmol), 4,4'-dibromobenzil (1.0 g, 2.7 mmol), $Pd_2(dba)_3$ (0.12 g, 0.13 mmol), dppf (0.15 g, 0.27 mmol), and NaOtBu (1.04 g, 11 mmol) in 50 mL of dry toluene. The reaction mixture was refluxed at 120° C. for 2 days under an argon atmosphere. The reaction mixture was then poured into a saturated NH$_4$Cl aqueous solution and extracted with CH$_2$Cl$_2$. The combined organic layer was dried over anhydrous MgSO$_4$ and the solvent was removed under reduced pressure. The product was purified by column chromatography (silica gel, dichloromethane:hexanes=2:1 (v/v)) to give a yellow solid (0.58 g, 39%). $^1$H NMR (300 MHz, CDCl$_3$, δ): 7.67 (d, J=8.8 Hz, 4H), 7.07-7.33 (m, 20H), 7.01 (d, J=8.8 Hz). $^{13}$C{$^1$H} NMR (75 MHz, CDCl$_3$, δ): 193.82, 151.32, 146.62, 131.54, 130.50, 129.50, 125.72, 124.31, 119.87. IR (cm$^{-1}$): 3059, 3055, 1646, 1636, 1585, 1489, 1311, 1278, 1172. Anal. Calcd for C$_{38}$H$_{28}$N$_2$O$_2$: C, 83.80; H, 5.18; N, 5.14. Found: C, 84.12; H, 5.44; N, 5.02.

4,4'-Di(4,4,5,5-tetramethyl-1,3,2-dioxaborolyl)benzil (JYC-I-099-A). In a glove box, a schlenk tube was charged with Pd(PPh$_3$)$_4$ (0.79 g, 0.7 mmol), KOAc (8.0 g, 81.5 mmol), pinacol diboron (7.59 g, 29.9 mmol), and 4,4'-dibromobenzil (5 g, 13.6 mmol). Under an argon atmosphere, dry DMSO (50 mL) was added to the reaction mixture. After stirring at 110° C. for 2 days, the reaction mixture was cooled down to room temperature, extracted with benzene, washed with water, and dried over anhydrous MgSO$_4$. The solvent was removed under reduced pressure. The product was purified by column chromatography (silica gel, ethyl acetate:hexanes=1:9 (v/v), and then ethyl acetate:hexanes=1:2 (v/v)) to give a yellow solid (3.46 g, 55%). $^1$H NMR (300 MHz, CDCl$_3$, δ): 7.91 (s, 8H), 1.33 (s, 24H). $^{13}$C{$^1$H} NMR (75 MHz, CDCl$_3$, δ): 194.75, 135.16, 134.70, 128.76, 84.35, 24.83. $^{11}$B NMR (96 MHz, CDCl$_3$) δ 31.1. IR (cm$^{-1}$): 2979, 1677, 1508, 1401, 1359, 1142, 1091. HRMS-FAB (m/z): [M+H]$^+$ calcd for C$_{26}$H$_{33}$B$_2$O$_6$, 463.2473; found, 463.2452. Anal. Calcd for C$_{26}$H$_{32}$B$_2$O$_6$: C, 67.57; H, 6.98. Found: C, 67.63; H, 6.98.

1,2-Bis(4-styrylphenyl)ethane-1,2-dione (JYC-I-134-B). A schlenk tube was charged with 4,4'-dibromobenzil (2.0 g, 5.4 mmol), K$_2$CO$_3$ (3.75 g, 27.2 mmol), Bu$_4$NBr (1.75 g, 5.4 mmol), LiCl (0.23 g, 5.4 mmol), Pd(OAc)$_2$ (0.12 g, 0.54 mmol), styrene (1.6 mL, 13.6 mmol), and 50 mL of dry DMF. The reaction mixture was heated at 100° C. for 14 h. The reaction mixture was allowed to cool down to room temperature and extracted with CH$_2$Cl$_2$. The organic phase was washed with H$_2$O and dried over anhydrous MgSO$_4$. The solvent was removed under reduced pressure. The crude product was purified by column chromatography (silica gel, dichloromethane:hexanes=1:2 (v/v), then dichloromethane:hexanes=1:1 (v/v)) to give a light yellow solid (1.56 g, 69.3%). $^1$H NMR (300 MHz, CDCl$_3$, δ): 7.97 (d, J=8.3 Hz, 4H), 7.62 (d, J=8.8 Hz, 4H), 7.53 (d, J=6.8 Hz, 4H), 7.27-7.40 (m, 6H), 7.26 (d, J=16.6 Hz, 2H), 7.12 (d, J=16.6 Hz, 2H). $^{13}$C{$^1$H} NMR (75 MHz, CDCl$_3$, δ): 193.82, 143.82, 136.45, 132.63, 131.83, 130.48, 128.83, 128.60, 127.17, 126.96, 126.84. HRMS-FAB (m/z): [M+H]$^+$ calcd for C$_{30}$H$_{23}$O$_2$, 415.1698; found, 415.1699. Anal. Calcd for C$_{30}$H$_{22}$O$_2$: C, 86.93; H, 5.35. Found: C, 86.90; H, 5.26.

3,6-Dibromophenanthrenequinone (JYC-I-117-A). A mixture of phenanthrenequinone (5.0 g, 24 mmol), Br$_2$ (2.6 mL, 50.4 mmol), nitrobenzene (45 mL), and benzoyl peroxide (0.25 g, 1 mmol) was exposed to a tungsten lamp and heated at 60° C. for 17 h. The reaction mixture was allowed to cool down to room temperature. The light brown crystals were collected by filtration and washed with ethanol. A second of the crop of crystals were obtained after cooling in ice. The crystals were dried under vacuum at 60° C. overnight to give light brown crystals (7.84 g, 90%). The product was recrystallized from nitrobenzene to give orange brown crystals. $^1$H NMR (300 MHz, CDCl$_3$, δ): 8.10 (d, J=2.0 Hz, 2H), 8.05 (d, J=8.3 Hz, 2H), 7.65 (dd, J=8.3 Hz, 2.0 Hz, 2H). $^{13}$C{$^1$H} NMR (75 MHz, CDCl$_3$, δ): 178.87, 135.97, 133.43, 132.08, 129.92, 127.40. HRMS-FAB (m/z): [M+H]$^+$ calcd for C$_{14}$H$_7$O$_2$Br$_2$, 364.8813; found, 364.8813. Anal. Calcd for C$_{14}$H$_6$Br$_2$O$_2$: C, 45.94; H, 1.64; Br, 43.66. Found: C, 45.95; H, 1.57; Br, 43.71.

3,6-Distyrylphenanthrene-9,10-dione (JYC-I-139-A). A schlenk tube was charged with JYC-I-117-A (2.0 g, 5.5 mmol), K$_2$CO$_3$ (3.78 g, 27.3 mmol), Bu$_4$NBr (1.76 g, 5.5 mmol), LiCl (0.23 g, 5.5 mmol), Pd(OAc)$_2$ (0.12 g, 0.55 mmol), styrene (1.6 mL, 13.7 mmol), and 50 mL of dry DMF. The reaction mixture was heated at 100° C. overnight. The reaction mixture was allowed to cool down to room temperature and extracted with CH$_2$Cl$_2$. The organic phase was washed with H$_2$O and dried over anhydrous MgSO$_4$. The solvent was removed under reduced pressure. The crude product was purified by column chromatography (silica gel, ethyl acetate:hexanes=1:3 (v/v)) to give an orange solid (1.40 g, 62.2%): $^1$H NMR (300 MHz, CDCl$_3$, δ): 8.00 (d, J=8.1 Hz, 2H), 7.87 (s, 2H), 7.29-7.54 (m, 12H), 7.23 (d, J=16.5 Hz, 2H), 7.08 (d, J=16.5 Hz, 2H). $^{13}$C{$^1$H} NMR (75 MHz, CDCl$_3$, δ): 179.21, 144.49, 136.09, 135.70, 133.14, 130.77, 129.80, 128.83, 127.06, 126.90, 126.43, 122.08. HRMS-FAB (m/z): [M+H]$^+$ calcd for C$_{30}$H$_{21}$O$_2$, 413.1542; found, 413.1545.

3,6-Bis(diphenylamino)phenanthrene-9,10-dione (JYC-I-130-A). A schlenk tube was charged with JYC-I-117-A (2.0 g, 5.5 mmol), diphenylamine (2.03 g, 12 mol), Pd$_2$(dba)$_3$ (0.25 g, 0.27 mmol), dppf (0.3 g, 0.55 mmol), NaO$^t$Bu (2.1 g, 22 mmol), and 40 mL of dry toluene. The reaction mixture was refluxed at 120° C. for 2 days. The reaction mixture was allowed to cool down to room temperature and the solvent was removed under reduced pressure. The crude product was purified by column chromatography (silica gel, dichloromethane:hexanes=4:1 (v/v)) to give an orange solid (0.23 g, 8%). $^1$H NMR (300 MHz, CDCl$_3$, δ): 7.45 (d, J=8.3 Hz, 2H), 7.24-7.30 (m, 8H), 7.06-7.11 (m, 12H), 6.99 (d, J=2.0 Hz, 2H), 6.75 (dd, J=7.8 Hz, 2.0 Hz, 2H). $^{13}$C{$^1$H} NMR (75 MHz, CDCl$_3$, δ): 190.86, 153.40, 146.71, 145.21, 129.56, 128.49, 125.58, 125.12, 124.37, 121.28, 113.32. HRMS-FAB (m/z): [M+H]$^+$ calcd for C$_{18}$H$_{27}$O$_4$, 307.1909; found, 307.1905.

2-(3,4-Bis-dodecyloxy-phenyl)-[1,3]dithiane (JYC-I-048-A). 1,3-propanedithiol (4.7 mL, 46.8 mmol) was added to a solution of 3,4-bis(dodecyloxy)benzaldehyde (20.0 g, 42.1 mmol) in 100 mL of chloroform. The reaction mixture was stirred at room temperature for 2 h. Concentrated hydrochloric acid (1.5 mL) was added to the mixture and the mixture was stirred at room temperature for additional 2 h. The mixture was washed with water and a saturated aqueous NaCl solution several times. The organic phase was dried over anhydrous MgSO$_4$. The solvent was removed under reduced pressure and the product was further dried under vacuum at 47° C. overnight to give an off-white solid (22.7 g, 95%). mp 73-75° C. $^1$H NMR (200 MHz, CDCl$_3$, δ): 6.91-7.00 (m, 2H), 6.78 (d, J=7.8 Hz, 1H), 5.08 (s, 1H), 3.96 (q, J=6.2 Hz, 4H), 2.80-3.12 (m, 4H), 1.89-2.21 (m, 2H), 1.78 (m, 4H), 1.42 (m, 4H), 1.24 (s, 32H), 0.86 (t, J=6.2 Hz, 6H). $^{13}$C{$^1$H} NMR (50 MHz, CDCl$_3$, δ): 149.12, 131.56, 120.02, 113.52, 113.14, 69.12, 51.19, 32.15, 31.86, 29.57, 29.36, 29.30, 29.20, 25.97, 25.04, 22.63, 14.05. IR (cm$^{-1}$): 2916, 2847, 1586, 1517, 1466, 1269, 1137. HRMS-FAB (m/z): [M+H]$^+$ calcd for C$_{34}$H$_{61}$O$_2$S$_2$, 565.4113; found, 565.4087. Anal. Calcd for C$_{34}$H$_{60}$O$_2$S$_2$: C, 72.28; H, 10.70. Found: C, 72.47; H, 10.78.

[2-(3,4-Bis-dodecyloxy-phenyl)-[1,3]dithian-2-yl]-(4-bromo-phenyl)-methanol (JYC-I-049-A). A solution of 2-(3,4-bis-dodecyloxy-phenyl)-[1,3]dithiane (JYC-I-048-A, 12.0 g, 21 mmol) in 120 mL of dry THF in a schlenk tube was cooled down to −78° C. n-BuLi (8.5 mL of 2.5 M in hexanes, 21 mmol) was added dropwise to the solution via a syringe. The solution was stirred at 0° C. for 1 h. At −78° C., 4-bromobenzaldehyde (3.57 g, 19 mmol) in 100 mL of dry THF was added dropwise to the reaction mixture via a cannula. The mixture was allowed to warm up to room temperature and stir at room temperature overnight under an argon atmosphere. The mixture was quenched with water and THF was removed under reduced pressure. The resulting slurry was extracted with dichloromethane. The organic layer was washed with water and a saturated aqueous NaCl solution several times and dried over anhydrous MgSO$_4$. The solvent was removed under reduced pressure. The product was purified by column chromatography (silica gel, hexanes:dichloromethane=1:1 (v/v)) to give light yellowish viscous liquid (11.04 g, 76%). $^1$H NMR (200 MHz, CDCl$_3$, δ): 7.20-7.26 (m, 3H), 7.04-7.06 (m, 1H), 6.72-6.80 (m, 3H), 4.86 (d, J=3.6 Hz, 1H), 3.98 (t, J=13.2 Hz, 2H), 3.75 (t, J=13.2 Hz, 2H), 3.02 (d, J=3.6 Hz, 1H), 2.70 (m, 4H), 1.25-1.90 (m, 42H), 0.87 (t, J=6.4 Hz, 6H). $^{13}$C{$^1$H} NMR (300 MHz, CDCl$_3$, δ): 148.61, 148.51, 136.41, 130.02, 129.88, 129.12, 123.07, 122.01, 116.17, 112.71, 80.46, 69.32, 69.06, 66.35, 31.90, 29.62, 29.44, 29.35, 29.25, 29.20, 27.33, 26.93, 26.01, 24.72, 22.66, 14.09. IR (cm$^{-1}$): 3482, 2923, 2853, 1593, 1506, 1468, 1259, 1134. HRMS-FAB (m/z): [MH−H$_2$O]$^+$ calcd for C$_{41}$H$_{64}$BrO$_2$S$_2$, 531.3518; found, 531.3565. Anal. Calcd for C$_{41}$H$_{65}$BrO$_3$S$_2$: C, 65.66; H, 8.74. Found: C, 65.87; H, 8.77.

1-(3,4Bis-dodecyloxy-phenyl)-2-(4-bromo-phenyl)-ethane-1,2-dione (JYC-I-053-B). A solution of [2-(3,4-bis-dodecyloxy-phenyl)-[1,3]dithian-2-yl]-(4-bromo-phenyl)-methanol (JYC-I-049-A). (10.99 g, 0.015 mol) in 400 mL of acetone was added dropwise to a solution of N-bromosuccinimide (NBS) (45.4 g, 0.255 mol) in 300 mL of 3% water/acetone (v/v) at 0° C. in an ice bath. The reaction mixture was stirred at 0° C. and gradually warmed up to room temperature over 30 min. The mixture was then poured into a saturated aqueous NaSO$_3$ solution (400 mL) and dichloromethane (400 mL). The mixture was stirred for an additional 10 min. The organic layer was washed with water several times and dried over anhydrous MgSO$_4$. The solvent was removed under reduced pressure to give a pale yellow solid. Purification was carried out by first recrystallization from hexanes, followed by column chromatography (silica gel, hexanes:dichloromethane=1:1 (v/v)) to afford two products. The major product, 1-(3,4-bis-dodecyloxy-phenyl)-2-(4-bromo-phenyl)-ethane-1,2-dione (JYC-I-053-B), was isolated as a yellow solid. (3.21 g, 33%). $^1$H NMR (200 MHz, CDCl$_3$, δ): 7.81 (d, J=8.7 Hz, 2H), 7.62 (d, J=8.7 Hz, 2H), 7.54 (d, J=2.0 Hz, 1H), 7.39 (dd, J=2.0 Hz, 8.4 Hz, 1H), 6.83 (d, J=8.4 Hz, 1H), 4.04 (t, J=6.6 Hz, 2H), 4.03 (t, J=6.6 Hz, 2H), 1.82 (m, 4H), 1.20-1.52 (m, 40H), 0.85 (t, J=6.2 Hz, 6H). $^{13}$C{(H} NMR (50 MHz, CDCl$_3$, δ): 193.60, 192.64, 155.37, 149.46, 132.30, 132.08, 131.24, 130.17, 126.22, 125.60, 112.13, 111.58, 69.23, 69.15, 31.91, 29.61, 29.36, 29.03, 28.88, 25.97, 25.90, 22.68, 14.10. HRMS-FAB (m/z): [M+H]$^+$ calcd for C$_{38}$H$_{58}$BrO$_4$, 657.3518; found, 657.3515. Anal. Calcd for C$_{39}$H$_{57}$BrO$_4$: C, 69.39; H, 8.73. Found: C, 69.27; H, 8.71. The minor product, 1-(2-bromo-4,5-bis-dodecyloxy-phenyl)-2-(4-bromo-phenyl)-ethane-1,2-dione (JYC-I-053-A), was isolated as a white solid (0.31 g). $^1$H NMR (200 MHz, CDCl$_3$, δ): 7.85 (d, J=8.6 Hz, 2H), 7.65 (d, J=8.6 Hz, 2H), 7.39 (s, 1H), 6.98 (s, 1H), 4.02 (t, J=6.6 Hz, 2H), 4.01 (t, J=6.6 Hz, 2H), 1.82 (m, 4H), 1.20-1.52 (m, 36H), 0.86 (t, J=6.4 Hz, 6H). HRMS-FAB (m/z): [M+H]$^+$ calcd for C$_{38}$H$_{57}$Br$_2$O$_4$, 735.2624; found, 735.2638.

[Ni(S$_2$C$_2$(C$_6$H$_4$-p-Br)$_2$)$_2$] (JYC-I-054-A). A mixture of 4,4'-dibromobenzil (5.0 g, 14 mmol), phosphorus pentasulfide (9.06 g, 41 mmol), and 50 mL of 1,3-dimethyl-2-imidazolidinone was refluxed at 120° C. for 2 h under an argon atmosphere. The reaction mixture was cooled down to ~50° C. and NiCl$_2$.6H$_2$O (1.62 g, 7 mmol) in 10 mL of H$_2$O was added. The reaction mixture was refluxed at 120° C. for additional 3 h. The mixture was allowed to cool down to room temperature and poured into 200 mL of ethanol. The precipitate was collected by filtration and washed with ethanol and water. The crude product was purified by column chromatography (silica gel, hexanes:dichloromethane=1:1 (v/v)) to give a dark green crystalline solid (2.5 g, 43%). $^1$H NMR (300 MHz, CDCl$_3$, δ): 7.44 (d, J=8.3 Hz, 8H), 7.22 (d, J=8.3 Hz, 8H). HRMS-MALDI (m/z): [M]$^+$ calcd for C$_{28}$H$_{16}$Br$_4$NiS$_4$, 857.6179; found, 857.6234.

Bis[1,2-di(4-(4,4,5,5-tetramethyl-1,3,2-dioxaborolyl) phenyl)ethane-1,2-dithiolene]nickel (JYC-I-109-A). A mixture of 4,4'-di(4,4,5,5-tetramethyl-1,3,2-dioxaborolyl)benzil (2.0 g, 4.3 mmol), phosphorus pentasulfide (2.89 g, 6.5 mmol), and 15 mL of 1,4-dioxane was refluxed at 110° C. for 5 h under an argon atmosphere. The reaction mixture was allowed to cool down to room temperature and filtered to remove an insoluble pale yellow solid under argon couterflow. A solution of NiCl$_2$.6H$_2$O (0.52 g, 2.2 mmol) in 1.5 mL of H$_2$O was added to the filtrate. The reaction mixture was refluxed at 110° C. overnight. After cooling down to room temperature, a green solid was precipitated. The solid was collected by filtration and washed with ethanol, warm water, hot ethyl acetate, and hexanes to give a green solid (0.68 g, 30%). $^1$H NMR (300 MHz, CDCl$_3$, δ): 7.68 (d, J=7.8 Hz, 8H), 7.35 (d, J=8.3 Hz, 8H), 1.34 (s, 48H). $^{13}$C{$^1$H} NMR (75 MHz, CDCl$_3$, δ): 181.79, 143.51, 134.74, 128.14, 83.98, 24.89. $^{13}$C{$^1$H} NMR (75 MHz, CDCl$_2$, δ): 182.37, 143.83, 134.93, 128.51, 84.39, 25.04. UV (CH$_2$Cl$_2$) λ$_{max}$, nm (ε, Lmol$^{-1}$cm$^{-1}$): 862 (36920), 599 (2260), 319 (65220), 280 (51200). Cyclic voltammetry: E$_{1/2}$(0/−1)=−0.38 V; E$_{1/2}$(−1/−2)=−1.17 V (versus ferrocene in dichloromethane). HRMS-FAB (m/z): [M]$^+$ calcd for C$_{52}$H$_{64}$B$_4$O$_8$S$_4$Ni, 1046.3242. found, 1046.3246. Anal. Calcd for C$_{52}$H$_{64}$B$_4$O$_8$S$_4$Ni: C, 59.64; H, 6.16; S, 12.25. Found: C, 59.50; H, 6.14; S, 12.42.

Bis{1,2-di[(4-trifluoromethyl)phenyl]ethane-1,2-dithiolene}nickel (JYC-I-091-A). A mixture of 4,4'-bis(trifluoromethyl)benzil (1.0 g, 2.9 mmol), phosphorus pentasulfide (1.93 g, 4.3 mmol), and 15 mL of 1,4-dioxane was refluxed at 110° C. for 5 h under an argon atmosphere. The reaction mixture was allowed to cool down to room temperature and filtered to remove an insoluble pale yellow solid under argon counterflow. A solution of NiCl$_2$.6H$_2$O (0.34 g, 1.44 mmol) in 1.5 mL of H$_2$O was added to the filtrate. The reaction mixture was refluxed at 110° C. for additional 3 h. After cooling down to room temperature, a grayish blue solid was precipitated. The solid was collected by filtration and washed with ethanol and warn water. The product was purified by column chromatography (silica gel, hexanes:dichloromethane=2:1 (v/v)) to give a grayish blue solid (0.36 g, 31%). $^1$H NMR (300 MHz, CDCl$_3$, δ): 7.61 (d, J=8.3 Hz, 8H), 7.52 (d, J=8.3 Hz, 8H). UV (CH$_2$Cl$_2$) λ$_{max}$, nm (ε, Lmol$^{-1}$cm$^{-1}$): 829 (42470), 592 (2770), 314 (79160), 273 (52450). Cyclic voltammetry: E$_{1/2}$(0/−1)=−0.28 V; E$_{1/2}$(−1/−2)=−1.10 V (versus ferrocene in dichloromethane). HRMS-MALDI (m/z): [M]$^+$ calcd for C$_{32}$H$_{16}$F$_{12}$NiS$_4$, 813.9298; found, 813.9272. Anal. Calcd for C$_{32}$H$_{16}$F$_{12}$NiS$_4$: C, 47.14; H, 1.98; F, 27.96; S, 15.73. Found: C, 47.14; H, 2.13; F, 28.09; S, 15.66.

Bis[1,2-(4-bromophenyl)(3',4'-di-n-dodecyloxy-phenyl) ethane-1,2-dithiolene]nickel (JYC-I-072-A). A mixture of 1-(3,4-bis-dodecyloxy-phenyl)-2-(4-bromo-phenyl)-ethane-1,2-dione (JYC-I-053-B) (1.0 g, 1.52 mmol), phosphorus pentasulfide (1.01 g, 2.28 mmol), and 15 mL of dioxane was refluxed at 120° C. for 3 h under an argon atmosphere. The reaction mixture was cooled down to 60° C. and $NiCl_2.6H_2O$ (0.181 g, 0.76 mmol) in 3 mL of $H_2O$ was added. The reaction mixture was refluxed at 120° C. overnight. The mixture was allowed to cool down to room temperature and poured into 200 mL of 2-propanol. The precipitate was collected by filtration and washed with 2-propanol and water. The crude product was purified by column chromatography (silica gel, hexanes:dichloromethane=2:1 (v/v)) to give a sticky green semi-solid (0.81 g, 74%). $^1$H NMR (300 MHz, $CDCl_3$, δ): 7.38 (d, J=8.8 Hz, 2H), 7.21 (d, J=8.3 Hz, 2H), 6.99 (dd, J=2.0 Hz, 8.3 Hz, 1H), 6.75 (d, J=8.8 Hz, 1H), 6.72 (d, J=2.0 Hz, 1H), 3.99 (t, J=6.6 Hz, 2H), 3.71 (t, J=6.6 Hz, 2H), 1.82 (m, 2H), 1.67 (m, 2H), 1.20-1.52 (m, 36H), 0.87 (t, J=7.3 Hz, 6H). $^{13}$C{$^1$H} NMR (50 MHz, $CDCl_3$, δ): 181.56, 178.44, 150.23, 148.36, 140.50, 133.44, 131.55, 130.35, 123.17, 122.26, 114.17, 112.62, 69.04, 68.94, 31.91, 29.69, 29.65, 29.62, 29.43, 29.36, 29.16, 28.95, 26.01, 25.95, 22.68, 14.12. UV ($CH_2Cl_2$) $\lambda_{max}$, nm (ε, $Lmol^{-1}cm^{-1}$): 920 (34950), 604 (2740), 314 (58370). Cyclic voltammetry: $E_{1/2}(0/-1)$=−0.45 V; $E_{1/2}(-1/-2)$=−1.22 V (versus ferrocene in dichloromethane). HRMS-FAB (m/z): [M]$^+$ calcd for $C_{76}H_{114}O_4Br_2S_4Ni$, 1434.5320. found, 1434.5287. Anal. Calcd for $C_{76}H_{114}O_4Br_2S_4Ni$: C, 63.46; H, 7.99; S, 8.92. Found: C, 63.70; H, 8.14; S, 9.10.

{[1,2-di(4-bromophenyl)]ethane-1,2-dithiolene}{[1,2-di(3',4'-di-n-dodecyloxy-phenyl)]ethane-1,2-dithiolene]} nickel (JYC-I-055-A). A mixture of compound (JYC-I-019-A) (0.1 g, 4.96×10$^{-5}$ mol) and compound (JYC-I-054-A), and 80 mL of dry toluene was refluxed at 120° C. for 2 days under an argon atmosphere. The solvent was removed under reduced pressure. The product was purified by column chromatography (silica gel, hexanes:dichloromethane=3:1 (v/v)) to give a green sticky semi-solid (0.12 g, 84%). $^1$H NMR (300 MHz, $CDCl_3$, δ): 7.39 (d, J=8.3 Hz, 2H), 7.18 (d, J=8.3 Hz, 2H), 7.00 (dd, J=2.0 Hz, 8.3 Hz, 1H), 6.84 (d, J=2.0 Hz, 1H), 6.74 (d, J=8.3 Hz, 1H), 3.97 (t, J=6.6 Hz, 2H), 3.75 (t, J=6.6 Hz, 2H), 1.81 (m, 2H), 1.68 (m, 2H), 1.20-1.52 (m, 36H), 0.86 (t, J=7.8 Hz, 6H). $^{13}$C{$^1$H} NMR (200 MHz, $CDCl_3$, δ): 185.16, 175.05, 150.44, 148.61, 139.75, 134.35, 131.61, 130.62, 123.19, 121.87, 113.88, 112.68, 69.11, 69.03, 31.92, 29.75, 29.69, 29.67, 29.65, 29.45, 29.39, 29.37, 29.16, 29.01, 26.02, 25.99, 22.69, 14.12. UV ($CH_2Cl_2$) $\lambda_{max}$, nm (ε, $Lmol^{-1}cm^{-1}$): 925 (33710), 596 (2870), 314 (54980). Cyclic voltammetry: $E_{1/2}(0/-1)$=−0.46 V; $E_{1/2}(-1/-2)$=−1.27 V (versus ferrocene in dichloromethane).

Synthesis of bis{1,2-di[(4-cyano)phenyl]ethane-1,2-dithiolene}nickel (JYC-I-102-A). A mixture of 4,4'-dicyanobenzil (1.0 g, 3.8 mmol), phosphorus pentasulfide (2.56 g, 5.8 mmol), and 15 mL of 1,4-dioxane was refluxed at 110° C. for 5 h under an argon atmosphere. The reaction mixture was allowed to cool down to room temperature and filtered to remove an insoluble pale yellow solid under argon counterflow. A solution of $NiCl_2.6H_2O$ (0.46 g, 1.9 mmol) in 1.5 mL of $H_2O$ was added to the filtrate. The reaction mixture was refluxed at 110° C. overnight. After cooling down to room temperature, the precipitate was collected by filtration and washed with ethanol and warm water. The crude product was washed with hexanes and dried under vacuum to give a black solid. The $^1$H NMR of the black solid in DMSO-$d_6$ shows broad peaks in the aromatic region. The absorption spectrum and cyclic voltammogram of the black solid were obtained. UV ($CH_2Cl_2$) $\lambda_{max}$, nm: 848, 597, 321. Cyclic voltammetry: $E_{1/2}(0/-1)$=0.23 V; $E_{1/2}(-1/-2)$=−1.04 V (versus ferrocene in dichloromethane).

Synthesis of bis{1,2-di[(4-diphenylamino)phenyl]ethane-1,2-dithiolene}nickel (JYC-I-103-A). A mixture of 4,4'-bis(N,N-diphenylamino)benzil (0.89 g, 1.6 mmol), phosphorus pentasulfide (1.09 g, 2.5 mmol), and 15 mL of 1,4-dioxane was refluxed at 110° C. for 5 h under an argon atmosphere. The reaction mixture was allowed to cool down to room temperature and filtered to remove an insoluble pale yellow solid under argon counterflow. A solution of $NiCl_2.6H_2O$ (0.20 g, 0.82 mmol) in 1.5 mL of $H_2O$ was added to the filtrate. The reaction mixture was refluxed at 110° C. overnight. After cooling down to room temperature, the precipitate was collected by filtration and washed with ethanol and warm water. The crude product reacted with silica gel during column chromatography (first time). A green brown solid was collected (second time). The data for the green brown solid: $^1$H NMR (300 MHz, $C_6D_6$, δ): 7.79 (d, J=8.8 Hz, 8H), 7.00-7.04 (m, 32H), 6.85-6.89 (m, 8H), 6.83 (d, J=8.3 Hz, 8H). $^{13}$C{$^1$H} NMR (75 MHz, $C_6D_6$, δ): 151.50, 147.07, 141.31, 132.17, 129.80, 126.04, 124.50, 120.05.

Synthesis of bis{1,2-di[(4-phenylethynyl)phenyl]ethane-1,2-dithiolene}nickel (JYC-I-114-A). A mixture of bis[4-(phenylethynyl)phenyl]ethane-1,2-dione (1.50 g, 3.7 mmol), phosphorus pentasulfide (2.44 g, 5.5 mmol), and 15 mL of 1,4-dioxane was refluxed at 110° C. for 5 h under an argon atmosphere. The reaction mixture was allowed to cool down to room temperature and filtered to remove an insoluble pale yellow solid under argon counterflow. A solution of $NiCl_2.6H_2O$ (0.44 g, 1.8 mmol) in 1.5 mL of $H_2O$ was added to the filtrate. The reaction mixture was refluxed at 110° C. overnight. After cooling down to room temperature, a brown solid was collected by filtration and washed with ethanol and warm water. The crude product was purified by column chromatography (silica gel, hexanes:dichloromethane=1:1 (v/v)) to give a dark brown solid (0.10 g, 6%). The isolated brown solid is the desired product based on the evidence of $^1$H NMR spectrum and HRMS-MALDI data. $^1$H NMR (300 MHz, $CDCl_3$, δ): 7.32-7.54 (m, 36H). HRMS-MALDI (m/z): [M]$^+$ calcd for $C_{60}H_{36}S_4Ni$, 942.1060; found, 942.1031. The absorption spectrum and cyclic voltammogram of the greenish brown solid were obtained. UV ($CH_2Cl_2$) $\lambda_{max}$, nm: 904, 316. Cyclic voltammetry: $E_{1/2}(0/-1)$=−0.38 V; $E_{1/2}(-1/-2)$=−1.17 V (versus ferrocene in dichloromethane).

Synthesis of bis{1,2-di-[4-(4-trifluoromethylphenylethynyl)phenyl]ethane-1,2-dithiolene}nickel (JYC-I-122-A). A mixture of 1,2-bis[4-(4-trifluoromethylphenylethynyl)phenyl]ethane-1,2-dione (JYC-I-120-B) (1.0 g, 1.8 mmol), phosphorus pentasulfide (1.22 g, 2.7 mmol), and 15 mL of 1,4-dioxane was refluxed at 110° C. for 5 h under an argon atmosphere. The reaction mixture was allowed to cool down to room temperature and filtered to remove an insoluble pale yellow solid under argon counterflow. A solution of $NiCl_2.6H_2O$ (0.22 g, 0.9 mmol) in 1.5 mL of $H_2O$ was added to the filtrate. The reaction mixture was refluxed at 110° C. overnight. After cooling down to room temperature, a green solid was collected by filtration and washed with ethanol and warm water. The crude product was purified by column chromatography (silica gel, hexanes:dichloromethane=4:1 (v/v)) to give a green solid.

$^1$H NMR (300 MHz, $CDCl_3$, δ): 7.59 (m, 8H), 7.46 (d, J=8.3 Hz, 4H), 7.38 (d, J=8.8 Hz, 4H).

Synthesis of 1,2-bis(4-[1,3]dioxolan-2-yl-phenyl)ethane-1,2-dione (JYC-I-118-A). A mixture of 4,4'-oxalyldibenzaldehyde (JYC-I-113-A) (0.2 g, 0.75 mmol), dry ethylene glycol (0.19 g, 3 mmol), activated $Al_2O_3$, and 10 mL of $CCl_4$ was refluxed at 75° C. for 42 h. The resulting yellow solid was collected by filtration. The crude product was dissolved in $CH_2Cl_2$ and filtered to remove $Al_2O_3$. The filtrate was concentrated under reduced pressure to give a yellow solid (0.16 g). $^1$H NMR and TLC of the yellow solid indicate it is the starting material, 4,4'-oxalyldibenzaldehyde.

Coupling reaction between bis[1,2-(4-bromophenyl)(3',4'-di-n-dodecyloxy-phenyl)ethane-1,2-dithiolene]nickel and 4-ethynylanisole. In a glovebox, a schlenk tube was charged with Pd(PhCN)$_2$Cl$_2$ (5 mg, 0.013 mmol) and CuI (2 mg, 0.009 mmol). Anhydrous dioxane (50 mL), P(t-Bu)$_3$ (0.21 mL of 0.123 M solution in toluene, 0.026 mmol), HN(i-Pr)$_2$ (0.15 mL, 1.05 mmol), bis[1,2-(4-bromophenyl)(3',4'-di-n-dodecyloxy-phenyl)ethane-1,2-dithiolene]nickel (0.63 g, 0.44 mmol), and 4-ethynylanisole (0.15 g, 1.1 mmol) were added to the schlenk tube sequentially under an argon counterflow. After stirring at room temperature overnight, the reaction mixture was diluted with ethyl acetate and filtered through a pad of celite with EtOAc rinsing.

References, which are incorporated herein by reference.
[1] Giroud-Godquin, A. M.; Mueller-Westehoff, U. T. *Mol. Cryst. Liq. Cryst.* 1977, 41, 11.
[2] (a) Date, R. W.; Iglesias, E. F.; Rowe, K. E.; Elliott, J. M.; Bruce, D. W. *J. Chem. Soc., Dalton Trans.* 2003, 10, 1914-1931. (b) Donnio, B.; Bruce, D. W. *Struct. Bonding (Berlin)* 1999, 95, 193-247. (c) Giroud-Godquin, A. M. *Coord. Chem. Rev.* 1998, 178-180, 1485-1499. (d) Giroud-Godquin, A. M. *Handbook of Liquid Crystals* 1998, 2B, 901-932.
[3] (a) Floudas, G.; Mierzwa, M.; Schonhals, A. *Physical Review E: Statistical, Nonlinear, and Soft Matter Physics* 2003, 67, 031705/1-031705/8. (b) Lee, K. M.; Han, C. D. *Macromolecules* 2002, 35, 6263-6273. (c) Zeng, E.; Jacob, K. I.; Polk, M. B. *Polymer* 2002, 43, 2169-2178. (d) Kim, W.-S; Lee, J.-W.; Kwak, Y.-W.; Lee, J.-K.; Park, Y.-T.; Yoh, S.-D. *Polymer Journal* 2001, 33, 643-646. (e) Peeler, A. M.; Mahadevan, S.; Hoyle, C. E.; Creed, D. *Polymer Preprints* 1999, 40, 540-541. (f) Cho, I.; Jo, S.-Y. *Macromolecules* 1999, 32, 521-523. (g) Kawatsuki, N.; Ono, H.; Takatsuka, H.; Yamamoto, T.; Sangen, O. *Macromolecules* 1997, 30, 6680-6682.
[4] (a) Scherowski, G., Beer, A.; Coles, H. J. *Liq. Cryst.* 1991, 10, 809. (b) Suzuki, T.; Okawa, T. *Makromol. Chem., Rapid Commun.* 1988, 9, 755. (c) Shibaev, V. P.; Kozlovsky, M. V.; Beresnev, L. A.; Blinov, L. M.; Platé, N. A. *Polym. Bull.* 1984, 12, 299.
[5] (a) Hsu, C. S.; Percec, V. *J Polym Sci, Part A: Polym Chem* 1987, 25, 2909-23. (b) Moment, A.; Miranda, R.; Hammond; P. T. *Macromol Rapid Commun* 1998, 19, 573-579. (c) Moment, A. J.; Hammond, P. T. *Polymer Preprints* 1998, 39, 1022-1023.
[6] Percec, V.; Tomazos, D. *Adv. Mater.* 1992, 4, 549.
[7] (a) Tuan, P. A.; Kostromin, S. G.; Shibaev, V. P. *Polym. Bull.* 1992, 29, 49. (b) Kawakami, Y.; Takahashi, K.; Nishiguchi, S.; Toida, K. *Polym. Int.* 1993, 31, 35.
[8] (a) Kim, S. H.; Lee, H. J.; Jin, S. H.; Cho, H. N.; Choi, S. K. *Macromolecules* 1993, 26, 846. (b) Komiya, Z.; Schrock, R. R. *Macromolecules* 1993, 26, 1387. (c) Komiya, Z.; Schrock, R. R. *Macromolecules* 1993, 26, 1393.
[9] (a) Kawakami, Y.; Takahashi, K.; Hibino, H. *Macromolecules* 1991, 24, 4531. (b) Kawakami, Y.; Takahashi, K. *Polym. Bull.* 1991, 25, 439.
[10] Ohta, K; Hasebe, H.; Ema, H.; Moriya, M.; Fujimoto, T.; Yamamoto, I. *Mol. Cryst. Liq. Cryst.* 1991, 208, 33-41.
[11] (a) Mueller-Westerhoff, U. T.; Zhou, M. *Tetrahedron Lett.* 1993, 34, 571-574. (b) Mueller-Westerhoff, U. T.; Zhou, M. *J. Org. Chem.* 1994, 59, 4988-4992.
[12] Babudri, F.; Fiandanese, V.; Marchese, G.; Punzi, A. *Tetrahedron Lett.* 1995, 36, 7305-7308.
[13] Hundertmark, T.; Littke, A. F.; Buchwald, S. L.; Fu, G. C. *Org. Lett.* 2000, 2, 1729-1731.
[14] Bhatt, M. V. *Tetrahedron* 1964, 20, 803-821.
[15] Bulman Page, P. C.; Graham, A. E.; Park, B. K. *Tetrahedron* 1992, 48, 7265-7274.
[16] Miller, T. R.; Dance, I. G. *J. Am. Chem. Soc.* 1973, 95, 6970.
[17] (a) Králik, M.; Kratky, V.; De Rosso, M.; Tonelli, M.; Lora, S.; Corain, B. *Chem.-Eur. J.* 2003, 9, 209. (b) Chandrasekhar, V.; Athimoolan, A. *Org. Lett.* 2002, 4, 2113-2116.
[18] (a) Vöegtle, F.; Plevoets, M.; Nieger, M.; Azzellini, G. C.; Credi, A.; De Cola, L.; De Marchis, V.; Venturi, M.; Balzani, V. *J. Am. Chem. Soc.* 1999, 121, 6290. (b) Newkome, G. R.; He, E.; Moorefield, C. N. *Chem. Rev.* 1999, 99, 1689.
[19] (a) *Handbook of Conducting Polymers*, ed. Skotheim, T. A.; Elsenbaumer, R. L.; Reynolds, J. R.; Marcel Dekker, New York, 2nd edn. 1998. (b) Bassler, H.; Rothberg, L. J. *Chem. Phys.* 1998, 227, 1. (c) Kraft, A.; Grimsdale, A. C.; Holmes, A. B. *Angew. Chem., Int. Ed. Engl.* 1998, 37, 402 (d) Schlüter, A. D.; Wegner, G. *Acta Polym.* 1993, 44, 59. (e) Tour, J. M. *Chem. Rev.* 1996, 96, 537. (f) Jones, L. R.; Schumm, J. S.; Tour, J. M. *J. Org. Chem.* 1997, 62, 1388 (g) Moore, J. S. *Acc. Chem. Res.* 1997, 30, 402. (h) Moroni, M.; LeMoigne, J.; Luzzati, S. *Macromolecules* 1994, 27, 562. (i) Ziener, U.; Godt, A. *J. Org. Chem.* 1997, 62, 6137. (j) Kukula, H.; Veit, S.; Godt, A. *Eur. J. Org. Chem.* 1999, 277.
[20] (a) Manners, I. *Angew. Chem. Int. Ed. Engl.* 1996, 35, 1602. (b) Archer, R. D. *Inorganic and organometallic polymers* (Wiley-VCH, Weinheim, 2001). (c) Manners, I. *Science* 2001, 294, 1664-1666.
[21] Swager, T. M.; Gil, C. J.; Wrighton, M. S. *J. Phys. Chem.* 1995, 99, 4886-4893.

EXAMPLE 3

(A) Synthesis of Nickel Bis(dithiolene) Complexes with Longer Conjugated Chains

Charge-transport in materials can be regarded as a series of electron-transfer reactions between a charge-carrying and a neutral molecule, which is analogous to solution self exchange. According to Marcus theory, the barrier for an electron self-exchange reaction, $\Delta G^{\ddagger}$, depends on the reorganization energy, $\lambda$, and the electronic coupling, V. High-mobility materials can be achieved by minimizing the reorganization energy and maximizing the intermolecular electronic coupling.

Nickel bis(dithiolene) complexes exhibiting mesogenic behavior have been reported. In 1989, Ohta[1] and co-workers reported the synthesis of octasubstituted bis(diphenylethene-1,2-dithiolato) nickel complexes with hexagonal discotic columnar liquid crystal phase. Their claim has been supported by X-ray scattering data, which gave lines representing hexagonal symmetry.

These complexes potentially have good intermolecular electronic coupling since orbital overlap along the column of molecules is maximized. In addition, the frontier orbitals are widely delocalized, so they most likely have small reorganization energy. These two factors might provide advantages over traditional organic charge-transport materials in transport material applications. In 2001, Warman[2] and co-workers reported the core-size effect on the mobility of charge in discotic liquid crystalline organic materials. They showed that the mobility does in fact increase with core size. The reasons are as follows: a) by increasing the orbital overlap (intermolecular electronic coupling) between the p-orbitals of adjacent macrocycles, and b) by increasing the cohesive forces between macrocycles via van der Waals and electrostatic interactions. The latter effect should result in a reduction in the magnitude of lateral and rotational displacements and hence a decrease in the structural disorder within the columns. The general tendency of an increase with increasing core size of the temperature up to which the $D_h$ phase is stable with respect to formation of the isotropic liquid was also shown in their paper. To potentially broaden the temperature range over which the mesophases are stable and to have better stacking of the molecules to maximize intermolecular electronic coupling, we synthesized nickel bis(dithiolene) complexes that have larger cores and retain hexagonal discotic columnar liquid crystal phase through conjugation strategy.

Results and Discussions

Two targeted complexes are shown in FIG. 1.

1,2-Bis-dodecyloxy-4-vinyl-benzene (JYC-II-004-A) was synthesized in 66% yield according to a simplified Wittig reaction procedure reported by Gaset and co-workers.[3] The Pd-catalyzed Heck coupling reaction between 4,4'-dibromobenzil and 1,2-bis-dodecyloxy-4-vinyl-benzene gave 1,2-bis-{4-[2-(3,4-bis-dodecyloxy-phenyl)-vinyl]-phenyl}-ethane-1,2-dione (JYC-II-007-A) in 76% yield as a bright yellow solid. Bis{1,2-di-{4-[2-(3,4-bis-dodecyloxy-phenyl)-vinyl]-phenyl}-ethane-1,2-dithiolene}nickel (JYC-II-014-A) was prepared from the reaction between JYC-II-007-A and excess phosphorus pentasulfide in 1,4-dioxane at 110° C. for 5 h, followed by the reaction with $NiCl_2.6H_2O$. The product was isolated as a dark green solid. The synthesis of JYC-II-014-A is shown in FIG. 2.

However, purification of JYC-II-014-A by repeated column chromatography and recrystallization failed to give an analytically pure material. There is always one spot having a very similar $R_f$ value under a long wavelength UV light irradiation as that of the desired product under a short wavelength UV light irradiation in a TLC plate. The separation of these two spots was unsuccessful. The $^1H$ and $^{13}C\{^1H\}$ NMR data (FIG. 3) and LRMS-MALDI data (FIG. 4) of JYC-II-014-A confirmed the formation of the desired product. In addition, the absorption spectrum (FIG. 5) showed a characteristic intensive absorbance in the near-infrared region (960 nm), which corresponds to $\pi \to \pi^*$ transition between orbitals that are delocalized over $NiS_4C_4$ core of the complex.

4-(2,2-Dibromo-vinyl)-1,2-bis-dodecyloxy-benzene[4] (JYC-II-003-A) was prepared from the reaction between 3,4-bis-dodecyloxy-benzaldehyde and $CBr_4$ in the presence of $PPh_3$. The reaction of JYC-II-003-A with excess nBuLi yielded 1,2-bis-dodecyloxy-4-ethynyl-benzene[4] (JYC-II-005-A). The Pd-catalyzed Heck coupling reaction between 4,4'-dibromobenzil and 1,2-bis-dodecyloxy-4-ethynyl-benzene (JYC-II-005-A) generated 1,2-bis-[4-(3,4-bis-dodecyloxy-phenylethynyl)-phenyl]-ethane-1,2-dione (JYC-II-008-A) in 81.6% yield. An attempt to prepare bis{1,2-di-[4-(3,4-bis-dodecyloxy-phenylethynyl)-phenyl]-ethane-1,2-dithiolene}nickel from the reaction between 1,2-bis-{4-[2-(3,4-bis-dodecyloxy-phenyl)-vinyl]-phenyl}-ethane-1,2-dione and excess phosphorus pentasulfide in 1,4-dioxane at 110° C. for 5 h, followed by the reaction with $NiCl_2.6H_2O$ was unsuccessful. The reaction resulted in an undefined polymeric material (JYC-II-013-A). The synthesis of JYC-II-013-A is shown in FIG. 6. The $^1H$ NMR spectrum of JYC-II-013-A (FIG. 7) showed broad peaks indicating a polymeric material. The absorption spectrum (FIG. 8) showed a characteristic absorbance in the near-infrared region (939 nm) suggesting that nickel bis(dithiolene) complexes are indeed incorporated in this undefined polymeric material.

The absorption spectra of JYC-I-019-A, JYC-II-014-A, and JYC-II-013-A are compared in FIG. 9.

In order to have a rigid backbone and better conjugation, 3,6-bis-[2-(3,4-bis-dodecyloxy-phenyl)-vinyl]-phenanthrene-9,10-dione (JYC-II-036-A) was synthesized from the reaction of 3,6-dibromo-phenanthrene-9,10-dione with 1,2-bis-dodecyloxy-4-vinyl-benzene (JYC-II-004-A) via Heck coupling reaction. The product was isolated as a reddish brown solid. An attempt to prepare corresponding nickel bis(dithiolene) complex was difficult (FIG. 10).

Syntheses

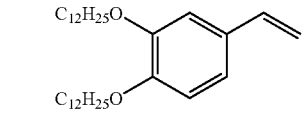

1,2-Bis-dodecyloxy-4-vinyl-benzene (JYC-II-004-A). A round bottom flask was charged with $Ph_3PMeBr$ (8.79 g, 24.6 mmol), $K_2CO_3$ (3.4 g, 24.6 mmol), and 3,4-bis-dodecyloxy-benzaldehyde (10.0 g, 21.1 mmol) in a mixture of 25 mL of 1,4-dioxane and 0.3 mL of $H_2O$. The reaction mixture was refluxed at 95° C. for 24 h. The reaction mixture was allowed to cool down to room temperature and extracted with $CH_2Cl_2$. The organic layer was washed with $H_2O$ and dried over anhydrous $MgSO_4$. The solvent was removed under reduced pressure to give an off-white solid. The crude product was purified by column chromatography (silica gel, hexanes:dichloromethane=2:1 (v/v)) to give a white solid (6.53 g, 65.6%). $^1H$ NMR (300 MHz, $CDCl_3$, δ): 6.96 (d, J=1.9 Hz, 1H), 6.90 (dd, J=8.0 Hz, 1.9 Hz, 1H), 6.80 (d, J=8.2 Hz, 1H), 6.62 (dd, J=17.3 Hz, 10.7 Hz, 1H), 5.57 (dd, J=17.6 Hz, 0.5 Hz, 1H), 5.11 (d, J=11.5 Hz, 1H), 3.98 (q, J=6.6 Hz, 4H), 1.74-1.85 (m, 4H), 1.19-1.50 (m, 36H), 0.87 (t, J=6.6 Hz, 6H). $^{13}C\{^1H\}$ NMR (75 MHz, $CDCl_3$, δ): 149.01, 148.98, 136.44, 130.63, 119.46, 113.44, 111.50, 111.18, 69.24, 32.00, 29.78, 29.72, 29.51, 29.45, 29.38, 29.34, 26.12, 22.78, 14.22. HRMS-EI (m/z): $[M]^+$ calcd for $C_{32}H_{56}O_2$, 472.4280; found, 472.4267. Anal. Calcd $C_{32}H_{56}O_2$: C, 81.29; H, 11.94. Found: C, 81.36; H, 11.99.

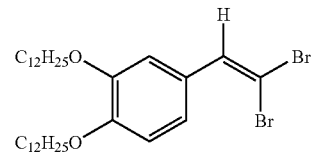

4-(2,2-Dibromo-vinyl)-1,2-bis-dodecyloxy-benzene (JYC-II-003-A). To a well stirred solution of $CBr_4$ (6.99 g, 21.1 mmol) in dry $CH_2Cl_2$ at 0° C. was added $PPh_3$ (11.05 g, 42.1 mmol) and 3,4-bis-dodecyloxy-benzaldehyde (10.0 g, 21.1 mmol). The resulting mixture was stirred for 1 h at ambient temperature. The reaction mixture was solidified during the time. The solid was dissolved in $CH_2Cl_2$, washed with $H_2O$, and dried over anhydrous $MgSO_4$. The solvent was removed under reduced pressure to give an off-white solid. The product was further purified by column chromatography (silica gel, hexanes:dichloromethane=2:1 (v/v)) to give a yellowish white solid (11.37 g, 85.6%).

$^1H$ NMR (300 MHz, $CDCl_3$, δ): 7.37 (s, 1H), 7.17 (d, J=2.2 Hz, 1H), 7.04 (dd, J=8.5 Hz, 0.6 Hz, 1H), 6.82 (d, J=8.5 Hz, 1H), 3.983 (t, J=6.6 Hz, 2H), 3.976 (t, J=6.9 Hz, 2H), 1.75-1.85 (m, 4H), 1.20-1.50 (m, 36H), 0.87 (t, J=6.6 Hz, 6H). $^{13}C\{^1H\}$ NMR (75 MHz, $CDCl_3$, δ): 149.37, 148.37, 136.38, 127.67, 121.85, 113.51, 112.72, 86.90, 69.29, 69.00, 32.00, 29.78, 29.70, 29.51, 29.45, 29.26, 26.09, 22.78, 14.24. HRMS-EI (m/z): $[M]^+$ calcd for $C_{32}H_{54}O_2Br_2$, 628.2491; found, 628.2472. Anal. Calcd for $C_{32}H_{54}O_2Br_2$: C, 60.95; H, 8.63; Br, 25.34. Found: C, 60.92; H, 8.62; Br, 25.48.

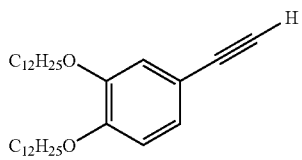

1,2-Bis-dodecyloxy-4-ethynyl-benzene (JYC-II-005-A). 4-(2,2-Dibromo-vinyl)-1,2-bis-dodecyloxy-benzene (JYC-II-003-A) (9.0 g, 14.3 mmol) in 150 mL of dry THF was cooled down to −78° C. under Ar atmosphere. nBuLi (11.4 mL of 2.5 M solution in hexanes, 28.5 mmol) was added dropwise to the mixture and the resulting mixture was stirred at −78° C. for 1 h. The reaction mixture was allowed to warm up to room temperature and stirred at room temperature for additional 2 h. The reaction was quenched with a saturated NH$_4$Cl aqueous solution and extracted with diethyl ether. The organic layer was dried over anhydrous MgSO$_4$. The solvent was removed under reduced pressure. (The reaction did not go to completion and the product has very similar R$_f$ value to that of the starting material.) The crude mixture was re-dissolved in dry THF and nBuLi (11.4 mL of 2.5 M solution in hexanes, 28.5 mmol) was added dropwise to the mixture. The mixture was stirred at room temperature for 2 h. The workup procedure was repeated. The product was further purified by column chromatography (silica gel, hexanes, then hexanes:dichloromethane=50:1 (v/v)) to give a white solid (4.38 g, 65.2%). $^1$H NMR (300 MHz, CDCl$_3$, δ): 7.04 (dd, J=8.2 Hz, J=1.9 Hz, 1H), 6.97 (d, J=1.9 Hz, 1H), 6.77 (d, J=8.2 Hz, 1H), 3.97 (t, J=6.6 Hz, 2H), 3.95 (t, J=6.6 Hz, 2H), 2.96 (s, 1H), 1.74-1.84 (m, 4H), 1.20-1.50 (m, 36H), 0.87 (t, J=6.6 Hz, 6H). $^{13}$C{$^1$H} NMR (75 MHz, CDCl$_3$, δ): 149.87, 148.45, 125.36, 116.91, 113.93, 112.91, 83.92, 75.39, 69.18, 69.05, 32.00, 29.78, 29.73, 29.70, 29.48, 29.45, 29.22, 26.08, 22.78, 14.22. HRMS-EI (m/z): [M]$^+$ calcd for C$_{32}$H$_{54}$O$_2$, 470.4124; found, 470.4113. Anal. Calcd for C$_{32}$H$_{54}$O$_2$,: C, 81.64; H, 11.56. Found: C, 81.36; H, 11.70.

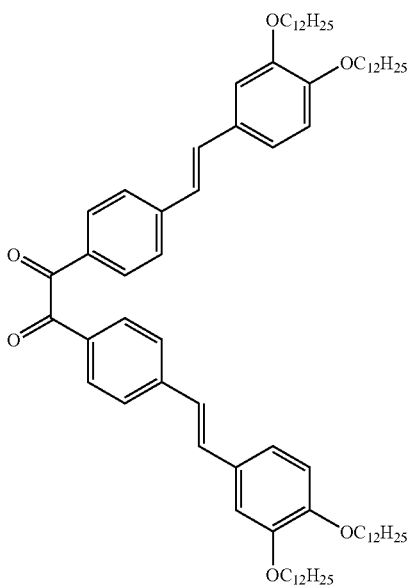

1,2-Bis-{4-[2-(3,4-bis-dodecyloxy-phenyl)-vinyl]-phenyl}-ethane-1,2-dione (JYC-II-007-A). A Schlenk tube was charged with 4,4'-dibromobenzil (1.8 g, 4.9 mmol), K$_2$CO$_3$ (3.38 g, 24.5 mmol), Bu$_4$NBr (1.58 g, 4.9 mmol), LiCl (0.21 g, 4.9 mmol), Pd(OAc)$_2$ (0.11 g, 0.49 mmol), 1,2-bis-dodecyloxy-4-vinyl-benzene (JYC-II-004-A) (5.78 g, 12.2 mmol), and 40 mL of dry DMF. The reaction mixture was heated at 100° C. under Ar over the weekend. The reaction mixture was allowed to cool down to room temperature and extracted with CH$_2$Cl$_2$. The organic phase was washed with H$_2$O and dried over anhydrous MgSO$_4$. The solvent was removed under reduced pressure. The crude product was purified by column chromatography (silica gel, dichloromethane:hexanes=1:2 (v/v), dichloromethane:hexanes=1:1 (v/v)), then dichloromethane:hexanes=3:2 (v/v)) to give a bright yellow solid. The solid was further recrystallized from CH$_2$Cl$_2$/hexanes to give a bright yellow solid (4.27 g, 75.6%).
$^1$H NMR (300 MHz, CDCl$_3$, δ): 7.94 (d, J=8.2 Hz, 2H), 7.58 (d, J=8.5 Hz, 2H), 7.18 (d, J=16.2 Hz, 2H), 7.08 (d, J=1.9 Hz, 2H), 7.05 (dd, J=8.2 Hz, 1.9 Hz, 2H), 6.96 (d, J=16.2 Hz, 2H), 6.85 (d, J=8.2 Hz, 2H), 4.03 (t, J=6.6 Hz, 4H), 4.01 (t, J=6.6 Hz, 4H), 1.76-1.88 (m, 8H), 1.20-1.53 (m, 72H), 0.86 (t, J=6.6 Hz, 12H). $^{13}$C{$^1$H} NMR (75 MHz, CDCl$_3$, δ): 193.70, 149.87, 149.12, 144.09, 132.51, 131.28, 130.40, 129.32, 126.39, 124.83, 120.81, 113.29, 111.53, 69.37, 69.15, 32.00, 29.78, 29.73, 29.52, 29.46, 29.38, 29.29, 26.14, 26.11, 22.80, 14.24. LRMS-EI (m/z): [M]$^+$ calcd for C$_{79}$H$_{118}$O$_6$, 1151.8; found, 1151.9. Anal. Calcd for C$_{78}$H$_{118}$O$_6$: C, 81.34; H, 10.33. Found: C, 81.25; H, 10.35.

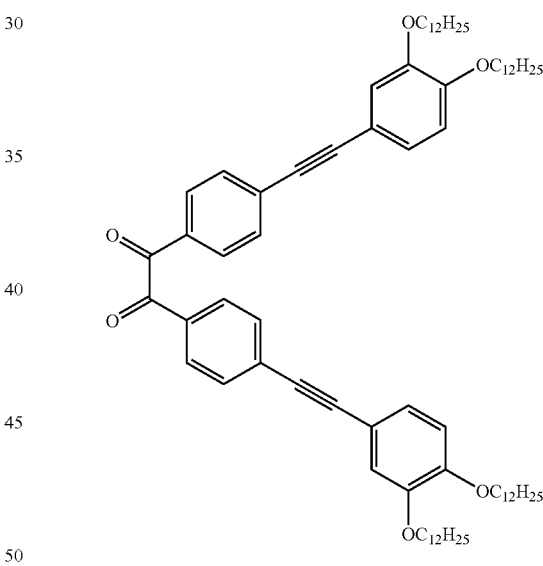

1,2-Bis-[4-(3,4-bis-dodecyloxy-phenylethynyl)-phenyl]-ethane-1,2-dione (JYC-II-008-A). A Schlenk tube was charged with Pd(PhCN)$_2$Cl$_2$ (29.4 mg, 7.7×10$^{-2}$ mmol), CuI (10 mg, 5.1×10$^{-2}$ mmol), anhydrous 1,4-dioxane (30 mL), P(t-Bu)$_3$ (0.31 g of 10 wt % in hexanes, 1.5×10$^{-1}$ mmol), HN(i-Pr)$_2$ (0.9 mL, 6.1 mmol), 4,4'-dibromobenzil (0.94 g, 2.6 mmol), and 1,2-bis-dodecyloxy-4-ethynyl-benzene (JYC-II-005-A) (3.0 g, 6.4 mmol) under Ar atmosphere. The reaction mixture was stirred at room temperature over weekend. The reaction mixture was diluted with CH$_2$Cl$_2$ and filtered through a pad of celite with CH$_2$Cl$_2$ rinsing. The solvent was removed under reduced pressure to give a yellowish brown solid. The product was purified by column chromatography (silica gel, hexanes:dichloromethane=2:1 (v/v), then hexanes:dichloromethane=1:1 (v/v)) to give a yellow solid. The solid was recrystallized from CH$_2$Cl$_2$/hexanes to give a yellow solid (2.39 g, 81.6%). $^1$H NMR (300 MHz, CDCl$_3$, δ): 7.93 (d, J=8.5 Hz, 4H), 7.60 (d, J=8.5 Hz, 4H), 7.11 (dd, J=8.5 Hz, 1.9 Hz, 2H), 7.03 (d, J=1.9 Hz, 2H), 6.82 (d, J=8.5 Hz, 2H), 4.00 (t, J=6.6 Hz, 4H), 3.99 (t, J=6.6 Hz, 4H), 1.76-1.86 (m, 8H), 1.20-1.51 (m, 72H), 0.86 (t, J=6.6 Hz, 12H). $^{13}$C{$^1$H} NMR (75 MHz, CDCl$_3$, δ): 193.09, 150.22, 148.60, 131.67, 131.45, 130.54, 129.75, 125.33, 116.51, 114.16, 112.94, 94.91, 87.16, 69.26, 69.08, 32.00, 29.78, 29.75, 29.70, 29.46, 29.26, 29.22, 26.09, 22.80, 14.24. LRMS-EI (m/z): [M]$^+$ calcd for C$_{78}$H$_{114}$O$_6$, 1147.7. found, 1147.9. Anal. Calcd for C$_{78}$H$_{114}$O$_6$: C, 81.62; H, 10.01. Found: C, 81.54; H, 10.05.

ethynyl)-phenyl]-ethane-1,2-dione (JYC-II-008-A) (1.0 g, 0.87 mmol), phosphorus pentasulfide (0.58 g, 1.3 mmol), and 20 mL of 1,4-dioxane were refluxed at 110° C. for 5 h under N$_2$ atmosphere. The reaction mixture was allowed to cool down to 60° C. and filtered through a filter to a Schlenk tube under N$_2$ counter-flow. NiCl$_2$.6H$_2$O (0.104 g, 0.44 mmol) in 1.5 mL of water was added to the filtrate. The resulting mixture was refluxed at 110° C. overnight. The reaction mixture was allowed to cool down to room temperature. A dark green solid was precipitated on the bottom of the reaction tube. The dark green solid was collected by filtration, washed with acetone and methanol, and dried under vacuum. The dark green solid was verified to be an undefined polymeric material on the basis of $^1$H NMR spectra of the solid.

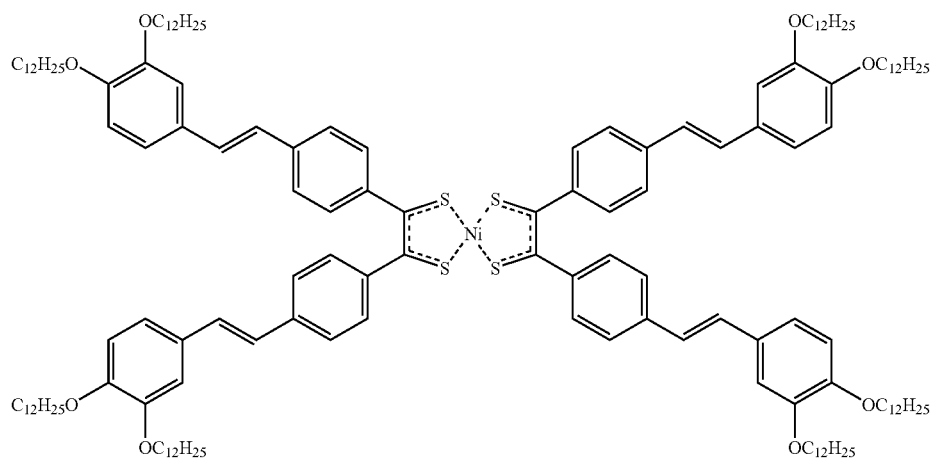

Bis[1,2-di(4-[2-(3,4-bis-dodecyloxy-phenyl)-vinyl]-phenyl)ethane-1,2-dithiolene]nickel (JYC-II-014-A). 1,2-Bis-{4-[2-(3,4-bis-dodecyloxy-phenyl)-vinyl]-phenyl}-ethane-1,2-dione (JYC-II-007-A) (1.0 g, 0.87 mmol), phosphorus pentasulfide (0.58 g, 1.3 mmol), and 20 mL of 1,4-dioxane were refluxed at 110° C. for 5 h under N$_2$ atmosphere. The reaction mixture was allowed to cool down to 60° C. and filtered through a filter to a Schlenk tube under N$_2$ counter-flow. NiCl$_2$.6H$_2$O (0.103 g, 0.43 mmol) in 1.5 mL of water was added to the filtrate. The resulting mixture was refluxed at 110° C. overnight. The reaction mixture was allowed to cool down to room temperature. A dark green solid was precipitated on the bottom of the reaction tube. The reaction mixture was extracted with CH$_2$Cl$_2$ and washed with H$_2$O. The organic phase was dried over anhydrous MgSO$_4$ and the solvent was removed under reduced pressure. The resulting dark green solid was washed with acetone and methanol. The crude product was purified by column chromatography (silica gel, hexanes:dichloromethane=1:1) to give a dark green solid (0.314 g, 30%). The $^1$H and $^{13}$C{$^1$H} NMR data and LRMS-MALDI data confirmed the formation of the desired product. $^1$H NMR (300 MHz, CDCl$_3$, δ): 6.81-7.39 (m, 36H), 4.02 (t, J=6.6 Hz, 8H), 3.99 (t, J=6.6 Hz, 8H), 1.74-1.88 (m, 16H), 1.16-1.52 (m, 144H), 0.864 (t, J=6.6 Hz, 12H), 0.861 (t, J=6.6 Hz, 12H). $^{13}$C{$^1$H} NMR (75 MHz, CDCl$_3$, δ): 180.78, 149.31, 149.12, 140.04, 138.22, 130.07, 129.76, 129.26, 126.18, 125.68, 120.25, 113.48, 111.38, 69.34, 69.20, 32.01, 29.79, 29.73, 29.54, 29.46, 29.35, 26.15, 22.80, 14.25. LRMS-MALDI (m/z): [M]$^+$ calcd for C$_{156}$H$_{236}$NiO$_8$S$_4$, 2426.5; found, 2425.4.

Undefined polymer based on bis[1,2-di(4-(3,4-bis-dodecyloxy-phenylethynyl)-phenyl)ethane-1,2-dithiolene]nickel (JYC-II-013-A). 1,2-Bis-[4-(3,4-bis-dodecyloxy-phenyl-

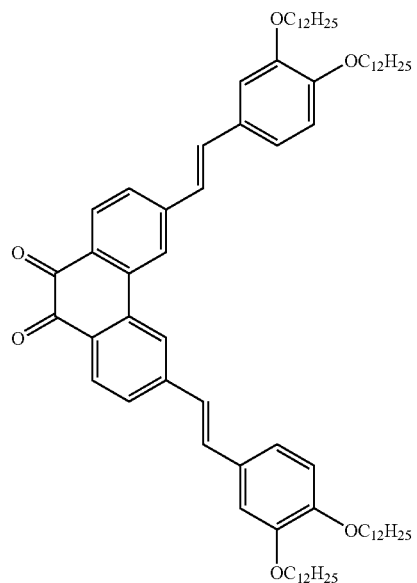

3,6-Bis-[2-(3,4-bis-dodecyloxy-phenyl)-vinyl]-phenanthrene-9,10-dione (JYC-II-036-A). A Schlenk tube was charged with 3,6-dibromo-phenanthrene-9,10-dione (2.0 g, 5.5 mmol), K$_2$CO$_3$ (3.78 g, 27.3 mmol), Bu$_4$NBr (1.76 g, 5.5 mmol), LiCl (0.23 g, 5.5 mmol), Pd(OAc)$_2$ (0.12 g, 0.55 mmol), 1,2-bis-dodecyloxy-4-vinyl-benzene (JYC-II-032-

A) (6.46 g, 13.7 mmol), and 50 mL of dry DMF. The reaction mixture was heated at 100° C. under N₂ over the weekend. The reaction mixture was allowed to cool down to room temperature and extracted with CH₂Cl₂. The organic phase was washed with H₂O and dried over anhydrous MgSO₄. The solvent was removed under reduced pressure to give a brown solid. The crude product was triturated with hot MeOH, hexanes, and ethyl acetate and filtered to give a brown solid (4.29 g, 68.3%). ¹H NMR (300 MHz, CDCl₃, δ): 8.11 (d, J=8.2 Hz, 2H), 8.02 (s, 2H), 7.54 (dd, J=8.5 Hz, J=0.8 Hz, 2H), 7.26 (d, J=15.9 Hz, 2H), 7.12 (s, 2H), 7.10 (dd, J=11.8 Hz, 3.3 Hz, 2H), 7.03 (d, J=16.2 Hz, 2H), 6.87 (d, J=8.2 Hz, 2H), 4.06 (t, J=6.6 Hz, 4H), 4.02 (t, J=6.6 Hz, 4H), 1.78-1.90 (m, 8H), 1.20-1.56 (m, 72H), 0.86 (t, J=6.6 Hz, 6H), 0.85 (t, J=6.6 Hz, 6H). ¹³C{¹H} NMR (75 MHz, CDCl₃, δ): 179.43, 150.16, 149.16, 145.00, 135.94, 133.22, 130.87, 129.52, 129.09, 126.16, 124.81, 121.81, 121.06, 113.22, 111.61, 69.40, 69.14, 32.00, 29.75, 29.55, 29.52, 29.45, 29.31, 26.18, 26.12, 22.78, 14.22. LRMS-FAB (m/z): [M]⁺ calcd for C₇₈H₁₁₆O₆, 1149.8; found, 1150.6. Anal. calcd for C₇₈H, 1606: C, 81.48; H, 10.17. Found: C, 81.27; H, 10.15.

(B) Synthesis of Side-Chain Polymers Containing Nickel Bis(dithiolene) Complexes Results and Discussions The synthesis of 1-(3,4-bis-dodecyloxy-phenyl)-2-{4-[6-(3-methyloxetan-3-ylmethoxy)hexyloxy]phenyl}ethane-1,2-dione (JYC-I-148-A).⁵ JYC-I-148-A was treated with P₄S₁₀ in 1,4-dioxane at 110° C., followed by the reaction with NiCl₂.6H₂O. The reaction yielded an undefined polymer containing nickel bis(dithiolene) complex instead of the desired precursor of the monomer for the synthesis of a side-chain polymer containing nickel bis(dithiolene) complexes as shown in FIG. 11. The presence of nickel bis(dithiolene) complexes was established by an absorption spectrum of the isolated solid which showed a characteristic absorbance in the near-infrared region and polymeric properties was identified in a ¹H NMR spectrum.

1-(3,4-Bis-dodecyloxy-phenyl)-2-(4-hydroxyphenyl) ethane-1,2-dione (JYC-II-052-A) was re-pre-pared from a multi-step process.⁵

Synthesis

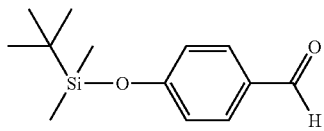

4(tert-Butyldimethylsilanyloxy)benzaldehyde (JYC-II-040-A). To a stirred solution of 4-hydroxybenzaldehyde (20.0 g, 0.16 mol) in 200 mL of CH₂Cl₂ at 0° C., imidazole (24.5 g, 0.36 mol) and ᵗBuSiMe₂Cl (27.2 g, 0.18 mol) were added. The reaction mixture was stirred at 25° C. for 1 h. The reaction mixture was poured into H₂O and extracted with CH₂Cl₂. The organic phase was dried over anhydrous MgSO₄ and the solvent was removed under reduced pressure. The crude product was purified by column chromatography (silica gel, hexanes:ethyl acetate=50:1 (v/v)) to give colorless oil (35.1 g, 90.7%). ¹H NMR (300 MHz, CDCl₃, δ): 9.86 (s, 2H), 7.77 (d, J=8.8 Hz, 2H), 6.92 (d, J=8.8 Hz, 2H), 0.97 (s, 9H), 0.23 (s, 6H). ¹³C{¹H} NMR (75 MHz, CDCl₃, δ): 190.76, 161.49, 131.87, 130.50, 120.47, 25.55, 18.25, -4.37. HRMS-FAB (m/z): [M+H]⁺ calcd for C₁₄H₂₃O₂Sᵢ, 251.1467; found, 251.1469.

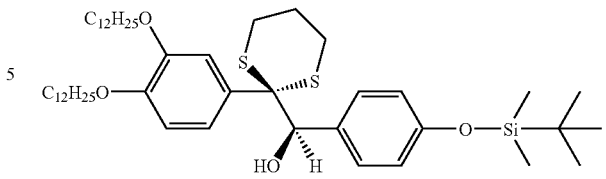

[2-(3,4-Bis-dodecyloxy-phenyl)-[1,3]dithian-2-yl][4-(tert-butyl-dimethylsilanyl-oxy)phenyl]methanol (JYC-II-042-A). JYC-II-028-A (10.0 g, 17.7 mmol) was dissolved in 80 ml of dry THF and cooled down to -78° C. ⁿBuLi (7.8 mL of 2.5 M solution in hexanes, 19.5 mmol) was added dropwise under N₂ counterflow and the reaction mixture was stirred at 0° C. for 30 min. A solution of JYC-II-040-A (4.43 g, 18.7 mmol) in dry THF was added at -78° C. via a cannula. The reaction was warmed up to room temperature over 2 h. The reaction was then quenched with H₂O and the resulting mixture was concentrated under reduced pressure. The resulting slurry was extracted with CH₂Cl₂ and washed with H₂O. The organic phase was dried over anhydrous MgSO₄. The solvent was removed under reduced pressure to give thick brown oil. The crude product was purified by column chromatography (silica gel, dichloromethane:hexanes=5:1 (v/v)) to give light yellow oil (12.82 g, 90.4%). ¹H NMR (300 MHz, CDCl₃, δ): 7.19 (dd, J=8.3 Hz, 2.4 Hz, 1H), 7.14 (d, J=2.0 Hz, 1H), 6.75 (d, J=8.3 Hz, 1H), 6.72 (d, J=8.3 Hz, 2H), 6.58 (d, J=8.3 Hz, 2H), 4.87 (d, J=3.9 Hz, 1H), 3.97 (t, J=6.8 Hz, 2H), 3.79 (t, J=6.8 Hz, 2H), 2.85 (d, 3.9 Hz, 1H), 2.67 (m, 4H), 1.88 (m, 2H), 1.67-1.85 (m, 4H), 1.20-1.52 (m, 36H), 0.93 (s, 9H), 0.86 (t, J=6.3 Hz, 6H), 0.12 (s, 6H). ¹³C{¹H} NMR (75 MHz, CDCl₃, δ): 155.46, 148.45, 130.18, 129.50, 129.26, 123.37, 118.619, 116.48, 112.74, 80.83, 69.29, 69.09, 66.66, 31.91, 29.71, 29.69, 29.63, 29.49, 29.47, 29.36, 29.29, 27.35, 27.02, 26.06, 25.64, 24.86, 22.67, 18.15, 14.08, -4.46, -4.48. HRMS-FAB (m/z): [M+H-H₂]⁺ calcd for C₄₇H₇₉O₄SᵢS₂, 799.5189; found, 799.5183. Anal. Calcd for C₄₇H₈₀O₄SᵢS₂: C, 70.44; H, 10.06; S, 8.00. Found: C, 70.55; H, 10.07; S, 8.07.

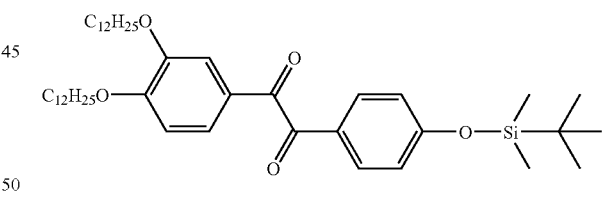

1-(3,4-Bis-dodecyloxy-phenyl)-2-[4-(tert-butyldimethylsilanyloxy)phenyl]-ethane-1,2-dione (JYC-II-050-A). A solution of JYC-II-042-A (12.32 g, 15.4 mmol) in 250 mL of acetone was added dropwise to a solution of NBS (47.61 g, 267.5 mmol) in 750 mL of solvent mixture (3% H₂O/acetone (v/v)) at 0° C. in an ice bath. The reaction mixture was stirred at 0° C. and gradually warmed up to room temperature over 30 min. The reaction mixture was poured into a saturated Na₂SO₃ aqueous solution (500 mL) and CH₂Cl₂ (800 mL). The resulting mixture was stirred at room temperature for additional 10 min. The organic phase was washed with H₂O and dried over anhydrous MgSO₄. The solvent was removed under reduced pressure to give brown oil. The crude product was purified by column chromatography (silica gel, dichloromethane:hexanes=3:7 (v/v)) to give yellow oil (2.82 g, 26.0%). ¹H NMR (300 MHz, CDCl₃, δ): 7.86 (d, J=8.8 Hz, 2H), 7.55 (d, J=2.4 Hz, 1H), 7.42 (dd, J=8.8 Hz, 2.0 Hz, 1H), 6.88 (d, J=8.8 Hz, 2H), 6.83 (d, J=8.8 Hz, 1H), 4.03 (t, J=6.8 Hz, 4H), 1.82 (m, 4H), 1.20-1.50 (m, 36H), 0.96 (s, 9H), 0.86 (t, J=6.3 Hz, 6H), 0.22 (s, 6H). $^{13}C\{^1H\}$ NMR (75 MHz, CDCl$_3$, δ): 193.55, 193.72, 161.75, 155.04, 149.33, 134.20, 132.25, 126.88, 126.08, 120.33, 112.32, 111.62, 69.23, 69.10, 31.90, 29.64, 29.60, 29.57, 29.34, 29.05, 28.91, 25.97, 25.90, 25.51, 22.66, 18.22, 14.08, −4.38. HRMS-FAB (m/z): [M+H]$^+$ calcd for $C_{44}H_{73}O_5S_i$, 709.5227; found, 709.5218.

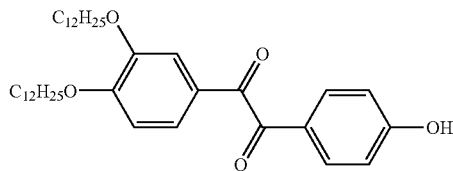

1-(3,4-Bis-dodecyloxy-phenyl)-2-(4-hydroxyphenyl) ethane-1,2-dione (JYC-II-052-A). To a solution of JYC-II-050-A (2.78 g, 3.9 mmol) in anhydrous THF (30 mL) was added Bu$_4$NF (3.9 mL of 1 M solution in THF, 3.9 mmol). The resulting orange solution was stirred at room temperature for 1 h. The reaction mixture was poured into H$_2$O and extracted with ethyl acetate. The organic phase was dried over anhydrous MgSO$_4$ and the organic solvent was removed under reduced pressure. The crude product was purified by column chromatography (silica gel, hexanes:ethyl acetate=3:1 (v/v)) to give a yellow solid (1.77 g, 76.6%). $^1$H NMR (300 MHz, CDCl$_3$, δ): 7.84 (d, J=8.8 Hz, 2H), 7.54 (d, J=2.0 Hz, 1H), 7.42 (dd, J=8.3 Hz, 2.0 Hz, 1H), 6.86 (d, J=8.8 Hz, 2H), 6.83 (d, J=8.3 Hz, 1H), 6.56 (s, 1H), 4.04 (t, J=6.8 Hz, 2H), 4.03 (t, J=6.3 Hz, 2H), 1.81 (m, 4H), 1.20-1.50 (m, 36H), 0.86 (t, J=6.3 Hz, 6H). $^{13}C\{^1H\}$ NMR (75 MHz, CDCl$_3$, δ): 194.20, 193.75, 162.14, 155.24, 149.27, 132.71, 126.44, 126.04, 125.88, 116.01, 112.34, 111.68, 69.35, 69.21, 31.89, 29.67, 29.64, 29.59, 29.56, 29.34, 28.99, 28.85, 25.95, 25.88, 22.65, 14.07. HRMS-FAB (m/z): [M+H]$^+$ calcd for $C_{38}H_{59}O_5$, 595.4363; found, 595.4340.

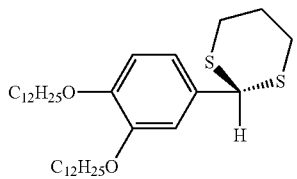

3,4-bis(dodecyloxy)benzaldehyde (JYC-II-041-A). K$_2$CO$_3$ (50.03 g, 0.362 mol) and 1-bromododecane (90.3 g, 0.362 mol) were added to a solution of 3,4-dihydroxybenzaldehyde (25.0 g, 0.181 mol) in 500 mL of DMF. The reaction mixture was heated at 100° C. for 2 days. The mixture was poured into H$_2$O and extracted with CH$_2$Cl$_2$. The organic layer was dried over anhydrous MgSO$_4$. The solvent was removed under reduced pressure. The crude product was recrystallized from MeOH to give an off-white solid (64.8 g, 72.8%). mp 69-70° C. $^1$H NMR (200 MHz, CDCl$_3$, δ): 9.80 (s, 1H), 7.36-7.41 (m, 2H), 6.92 (d, J=8.6 Hz, 1H), 4.03 (q, J=6.2 Hz, 4H), 1.81 (m, 4H), 1.44 (m, 4H), 1.24 (s, 32H), 0.85 (t, J=6.4 Hz, 6H). $^{13}C\{^1H\}$ NMR (200 MHz, CDCl$_3$, δ): 190.92, 154.65, 149.42, 129.85, 126.54, 111.72, 110.93, 69.08, 31.89, 29.58, 29.34, 29.04, 28.96, 25.92, 22.66, 14.07. IR (cm$^{-1}$): 2916, 2847, 1686, 1672, 1584, 1506, 1277, 1236, 1133, 807, 800. HRMS-FAB (m/z): [M+H]$^+$ calcd for $C_{31}H_{55}O_3$, 475.4151; found, 475.4156. Anal. Calcd for $C_{31}H_{54}O_3$: C, 78.43; H, 11.46. Found: C, 78.46; H, 11.72.

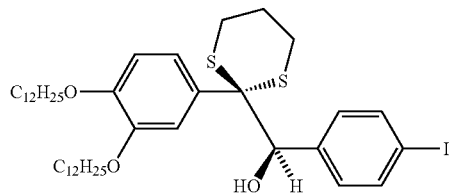

[2-(3,4-Bis-dodecyloxy-phenyl)-[1,3]dithian-2-yl]-(4-iodo-phenyl)-methanol (JYC-II-020-A). A solution of 2-(3, 4-bis-dodecyloxy-phenyl)-[1,3]dithiane (12.0 g, 21.1 mmol) in 120 mL of dry THF in a Schlenk tube was cooled down to −78° C. Under N$_2$ atmosphere, n-BuLi (9.4 mL of 2.5 M solution in hexanes, 23.4 mmol) was added dropwise to the mixture. After stirring at 0° C. for 1 h, the reaction mixture was cooled down to −78° C. and 4-iodobenzaldehyde (3.72 g, 16.0 mmol) in 100 mL of dry THF was added dropwise. The resulting mixture was allowed to warm up to room temperature and stirred at room temperature overnight. The reaction was quenched with H$_2$O and THF was removed under reduced pressure. The resulting slurry was extracted with CH$_2$Cl$_2$ and the organic layer was washed with H$_2$O and dried over anhydrous MgSO$_4$. The solvent was removed under reduced pressure. The product was purified by column chromatography (silica gel, hexanes:dichloromethane=3:2, 1:1, then 2:3 (v/v)) to give light yellow oil (8.3 g, 65%). $^1$H NMR (300 MHz, CDCl$_3$, δ): 7.44 (d, J=8.2 Hz, 2H), 7.23 (dd, J=8.5 Hz, 2.5 Hz, 1H), 7.02 (d, J=2.5 Hz, 1H), 6.78 (d, J=8.5 Hz, 1H), 6.61 (d, J=8.5 Hz, 2H), 4.84 (s, 1H), 3.98 (t, J=6.6 Hz, 2H), 3.73 (m, 2H), 3.00 (s, 1H), 2.69 (m, 4H), 1.66-1.94 (m, 6H), 1.20-1.51 (m, 36H), 0.86 (t, J=6.7 Hz, 6H). $^{13}C\{^1H\}$ NMR (75 MHz, CDCl$_3$, δ): 148.40, 148.31, 136.96, 135.88, 130.04, 128.93, 122.95, 115.99, 112.55, 93.82, 80.51, 69.29, 69.05, 66.33, 32.00, 29.78, 29.72, 29.55, 29.45, 29.32, 29.29, 27.41, 27.02, 26.12, 24.80, 22.78, 14.24. LRMS-EI (m/z): [M−H$_2$O]$^+$ calcd for $C_{41}H_{63}IO_2S_2$, 778.3; found, 778.5.

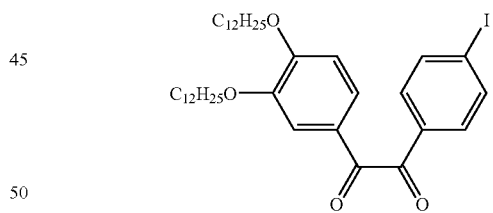

1-(3,4-Bis-dodecyloxy-phenyl)-2-(4-iodo-phenyl)-ethane-1,2-dione (JYC-II-024-A). A solution of [2-(3,4-bis-dodecyloxy-phenyl)-[1,3]dithian-2-yl]-(4-iodo-phenyl)-methanol (JYC-II-020-A) (8.2 g, 10.3 mmol) in 400 mL of acetone was added dropwise to a solution of NBS (31.86 g, 17.9 mmol) in 3% water/acetone (v/v) at 0° C. The reaction mixture was stirred at 0-25° C. for 30 min. It was then poured into a saturated aqueous Na$_2$SO$_3$ solution (400 mL) and CH$_2$Cl$_2$ (400 mL) mixture. The resulting mixture was stirred at room temperature for additional 10 min. The organic layer was washed with H$_2$O and dried over anhydrous MgSO$_4$. The solvent was removed under reduced pressure. The crude product was recrystallized from hexanes. The product was further purified by column chromatography (silica gel, hexanes:dichloromethane=2:1 (v/v)) to give a light yellow solid (1.84 g, 25.4%). $^1$H NMR (300 MHz, CDCl$_3$, δ): 7.85 (d, J=8.5 Hz, 2H), 7.65 (d, J=8.5 Hz, 2H), 7.53 (d, J=1.9 Hz, 1H), 7.38 (dd, J=8.5 Hz, 1.9 Hz, 1H), 6.83 (d, J=8.2 Hz, 1H), 4.04 (t, J=6.6 Hz, 2H), 4.03 (t, J=6.6 Hz, 2H), 1.76-1.86 (m, 4H), 1.20-1.51 (m, 36H), 0.86 (t, J=6.3 Hz, 6H). $^{13}$C {$^1$H} NMR (75 MHz, CDCl$_3$, δ): 193.77, 192.45, 155.19, 149.28, 138.17, 132.46, 130.90, 126.16, 125.47, 111.94, 111.46, 103.28, 69.21, 69.15, 32.00, 29.75, 29.70, 29.66, 29.45, 29.40, 29.10, 28.94, 26.06, 25.98, 22.78, 14.24. HRMS-EI (m/z): [M]$^+$ calcd for C$_{38}$H$_{57}$IO$_4$, 704.33016; found, 704.32941. Anal. calcd for C$_{38}$H$_{57}$IO$_4$: C, 64.76; H, 8.15. Found: C, 64.81; H, 8.15.

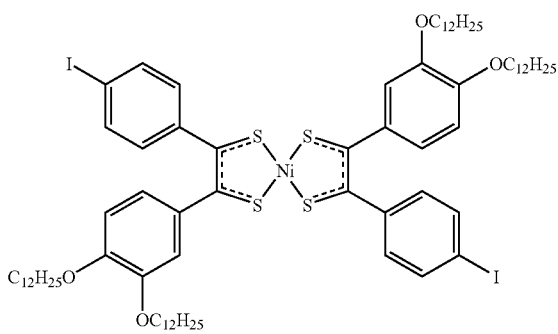

Bis[1,2-(4-iodophenyl)(3',4'-di-n-dodecyloxy-phenyl) ethane-1,2-dithiolene]nickel (JYC-II-029-A). A mixture of 1-(3,4-bis-dodecyloxy-phenyl)-2-(4-iodo-phenyl)-ethane-1,2-dione (JYC-II-024-A) (1.8 g, 2.55 mmol), phosphorus pentasulfide (1.70 g, 3.83 mmol), and 15 mL of dioxane was refluxed at 110° C. for 5 h under N$_2$ atmosphere. The reaction mixture was allowed to cool down to 50° C. and filtered to remove insoluble solid. NiCl$_2$.6H$_2$O (0.304 g, 1.28 mmol) in 1.5 mL of H$_2$O was added to the filtrate. The resulting mixture was refluxed at 110° C. for 3 h. The mixture was allowed to cool down to room temperature and extracted with CH$_2$C$_2$. The organic layer was washed with H$_2$O and dried over MgSO$_4$. The solvent was removed under reduced pressure and the crude product was purified by column chromatography (silica gel, hexanes:dichloromethane=1:1 (v/v)) to give a sticky green semi-solid (1.05 g, 53.4%).

$^1$H NMR (300 MHz, CDCl$_3$, δ): 7.61 (d, J=8.5 Hz, 2H), 7.09 (d, J=8.5 Hz, 2H), 7.03 (dd, J=8.2 Hz, 1.9 Hz, 2H), 6.78 (d, J=8.5 Hz, 2H), 6.71 (d, J=2.2 Hz, 2H), 3.99 (t, J=6.6 Hz, 4H), 3.70 (t, J=6.9 Hz, 4H), 1.62-1.88 (m, 8H), 1.20-1.52 (m, 72H), 0.86 (t, J=6.2 Hz, 12H). $^{13}$C{$^1$H} NMR (75 MHz, CDCl$_3$, δ): 181.66, 178.67, 150.15, 148.25, 140.98, 137.47, 133.30, 130.32, 122.13, 114.05, 112.61, 95.12, 69.08, 68.99, 32.00, 29.75, 29.70, 29.51, 29.46, 29.23, 29.05, 26.09, 22.78, 14.24. Anal. Calcd for C$_{76}$H$_{114}$I$_2$NiO$_4$S$_4$: C, 59.56; H, 7.50; S, 8.37. Found: C, 60.12; H, 7.60; S, 8.42.

(D) Synthesis of a Nickel Bis(dithiolene) Complex

Results and Discussions

From the structure of 4,4'-bis(diarylamino)biphenyl (TPD), which is known as a glassy material, an unsymmetrical nickel bis(dithiolene) complex (shown in FIG. 14) was targeted to synthesize. The complex is likely to be a glassy material.

The synthesis involved the preparation of 2-phenyl-[1,3] dithiane (JYC-II-051-A) from the reaction between benzaldehyde and 1,3-propanedithiol. Treatment of lithium reagent of 2-phenyl-[1,3]dithiane (JYC-II-051-A) with m-tolualdehyde at −78° C. formed (2-phenyl-[1,3]dithian-2-yl)-m-tolylmethanol (JYC-II-053-A) in 77% yield. JYC-II-053-A was converted to 1-phenyl-2-m-tolyl-ethane-1,2-dione by reacting with N-bromosuccinimide (NBS) in aqueous acetone.$^6$ Bis[1,2-(m-tolyl)(phenyl)ethane-1,2-dithiolene]nickel (JYC-II-065-A) was synthesized from the reaction between JYC-II-053-A and excess phosphorus pentasulfide in 1,4-dioxane at 110° C. for 5 h, followed by the reaction with NiCl$_2$.6H$_2$O to give a green solid in 24% yield after column chromatography (FIG. 15).

The properties of the compound was examined by thermogravimetric analysis (TGA) and differential scanning calorimetry (DSC). The thermal stability of JYC-II-065-A was determined from the thermogravimetric analysis (TGA) under nitrogen stream. The 5% weight loss temperature ($\Delta T_{5\%}$) is 265° C. (FIG. 16).

References, which are included herein by reference.
[1]Ohta, K.; Hasebe, H.,; Ema, H.; Fujimoto, T.; Yamamoto, I. *J. Chem. Soc., Chem. Commun.* 1989, 1610.
[2]van de Craats, A. M.; Warman, J. M. *Adv. Mater.* 2001, 13, 130-133.
[3]Bigot, Y. L.; Delmas, M; Gaset, A. *Synth. Comm.* 1982, 12 (2), 107-112.
[4]Pelter, A.; Ward, R. S.; Little, G. M. *J Chem. Soc., Perkin Trans.* 1, 1990, 2775-2790.
[5]Cho, J. Y. internal semi-annual report-August, 2003
[6]Page, P. C. B.; Graham A. E.; Park, B. K. *Tetrahedron* 1992, 48, 7265-7274.

EXAMPLE 4

Synthesis

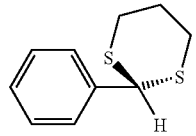

2-Phenyl-[1,3]dithiane (JYC-II-051-A). 1,3-propanedithiol (11.22 g, 103.7 mmol) was added to a solution of benzaldehyde (10.0 g, 94.2 mmol) in 150 mL of CHCl$_3$. The mixture was stirred at room temperature for 4 h. Concentrated HCl (2 mL) was added to the reaction mixture and the resulting mixture was stirred at room temperature for additional 2 h. The mixture was washed with H$_2$O and brine. The organic layer was dried over MgSO$_4$ and the organic solvent was removed under reduced pressure. The crude product was purified by column chromatography (silica gel, hexanes:dichloromethane=3:1 (v/v)) to give a colorless solid (15.29 g, 83%). $^1$H NMR (300 MHz, CDCl$_3$, δ): 7.43-7.48 (m, 2H), 7.25-7.36 (m, 3H), 5.15 (s, 1H), 2.85-3.10 (m, 4H), 2.10-2.20 (m, 1H), 1.84-1.99 (m, 1H). $^{13}$C{$^1$H} NMR (75 MHz, CDCl$_3$, δ): 138.95, 128.59, 128.29, 127.61, 51.48, 32.13, 25.15.

(2-Phenyl-[1,3]dithian-2-yl)-m-tolyl-methanol (JYC-II-053-A). A solution of

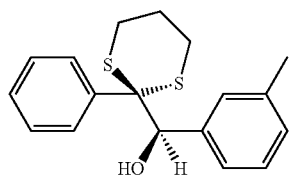

2-Phenyl-[1,3]dithiane (JYC-II-051-A) (10.0 g, 50.9 mmol) in 100 mL of anhydrous THF w a s cooled down to −78° C. nBuLi (22.4 mL of 2.5 M solution in hexanes, 56 mmol) was added dropwise and the mixture was stirred at −78° C. for 1 h. A solution of m-tolualdehyde (6.12 g, 50.9 mmol) in anhydrous THF was added to the mixture dropwise via a cannula at −78° C. under $N_2$ counterflow. The reaction was then warmed up to room temperature and stirred at room temperature overnight. The mixture was quenched with a saturated $NH_4Cl$ aqueous solution. The organic phase was washed with $H_2O$ and dried over anhydrous $MgSO_4$. The solvent was removed under reduced pressure to give brown oil. The product was purified by column chromatography (silica gel, hexanes:dichloromethane=1:2 (v/v)) to give light yellow oil (12.35 g, 76.6%). $^1H$ NMR (300 MHz, $CDCl_3$, δ): 7.66-7.70 (m, 2H), 7.25-7.33 (m, 3H), 6.98-7.02 (m, 2H), 6.64-6.68 (m, 1H), 6.56 (s, 1H), 4.94 (s, 1H), 2.86 (br s, 1H), 2.58-2.76 (m, 4H), 2.16 (s, 3H), 1.86-1.95 (m, 2H). $^{13}C\{^1H\}$ NMR (75 MHz, $CDCl_3$, δ): 136.90, 136.74, 135.67, 130.14, 128.43, 128.06, 127.41, 126.86, 126.20, 124.80, 80.39, 65.90, 26.85, 26.62, 24.42, 21.04. HRMS-EI (m/z): $[M]^+$ calcd for $C_{18}H_{20}OS_2$, 316.09556; found, 316.09640.

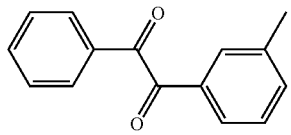

1-Phenyl-2-n-tolyl-ethane-1,2-dione (JYC-II-059-A). A solution of (2-phenyl-[1,3]dithian-2-yl)-m-tolyl-methanol (JYC-II-053-A) (7.48 g, 23.6 mmol) in 100 mL of acetone was added dropwise to a solution of NBS (73.19 g, 411 mmol) in 800 mL of (3% $H_2O$/acetone (v/v)) at 0° C. The reaction mixture was stirred at 0° C. for 30 min and it was then poured into a saturated $Na_2SO_3$ aqueous solution (500 mL) and $CH_2Cl_2$ (500 mL). The resulting mixture was stirred at room temperature for additional 10 min. The organic layer was washed with $H_2O$ and dried over anhydrous $MgSO_4$. The solvent was removed under reduced pressure. The crude product was washed with methanol and recrystallized from hexanes to give a yellow solid (2.63 g, 49.5%). $^1H$ NMR (300 MHz, $CDCl_3$, δ): 7.93-7.97 (m, 2H), 7.73-7.77 (m, 2H), 7.59-7.66 (m, 1H), 7.42-7.51 (m, 3H), 7.37 (t, J=7.4 Hz, 1H), 2.38 (s, 3H). $^{13}C\{^1H\}$ NMR (75 MHz, $CDCl_3$, δ): 194.58, 194.44, 138.81, 135.61, 134.68, 132.81, 132.78, 130.01, 129.70, 128.84, 128.76, 127.05, 21.28. HRMS-EI (m/z): $[M]^+$ calcd for $C_{15}H_{12}O_2$, 224.08373; found, 242.08461.

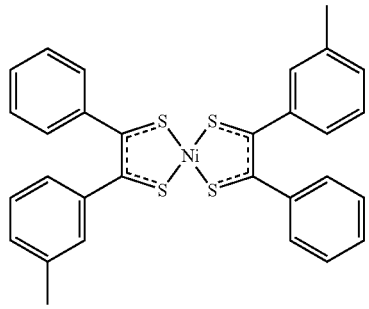

Bis[1,2-(m-tolyl)(phenyl)ethane-1,2-dithiolene]nickel (JYC-II-065-A). A mixture of 1-phenyl-2-7n-tolyl-ethane-1,2-dione (JYC-II-059-A) (1.0 g, 4.5 mmol), phosphorus pentasulfide (2.97 g, 6.7 mmol), and 15 mL of anhydrous 1,4-dioxane was refluxed at 110° C. for 5 h under an argon atmosphere. The reaction mixture was allowed to cool down to ~50° C. and filtered to remove an insoluble solid under argon counterflow. A solution of $NiCl_2.6H_2O$ (0.53 g, 2.2 mmol) in 1.5 mL of $H_2O$ was added to the filtrate. The resulting mixture was refluxed at 110° C. overnight. After cooling down to room temperature, the reaction mixture was extracted with $CH_2Cl_2$. The organic layer was washed with $H_2O$ and dried over anhydrous $MgSO_4$. The crude product was purified by column chromatography (silica gel, hexanes:dichloromethane=19:1 (v/v)) to give a green solid (0.30 g, 24%). $^1H$ NMR (300 MHz, $CDCl_3$, δ): 7.04-7.40 (m, 18H), 2.30 (s, 6H). UV ($CH_2Cl_2$) $\lambda_{max}$, nm (ε, $Lmol^{-1}cm^{-1}$): 860 (25975), 606 (980), 318 (40144), 270 (30500). HRMS-EI (m/z): $[M]^+$ calcd for $C_{30}H_{24}NiS_4$, 570.01144; found, 570.00788. Anal. Calcd for $C_{30}H_{24}NiS_4$: C, 63.05; H, 4.23; S, 22.44. Found: C, 63.30; H, 4.38; S, 22.20.

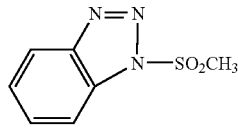

(F) Synthesis of $[Ni(S_2C_2(C_6H_4\text{-p-I})_2)_2]$

N-(1-methanesulfonyl)benzotriazole (JYC-II-054-A). To an ice-cold solution of benzotriazole (11.9 g, 0.1 mol) and pyridine (12.0 g, 0.15 mol) in dry toluene (120 mL) was added dropwise methylsulfonyl chloride (9.3 mL, 0.12 mol) in 30 mL of dry toluene. The reaction mixture was stirred at room temperature overnight. Ethyl acetate and water were added to the mixture. The organic layer was washed with $H_2O$ and brine and dried over anhydrous $MgSO_4$. The organic solvent was removed under reduced pressure. The crude product was purified by column chromatography (silica gel, hexanes:ethyl acetate=3:1 (v/v)) to give a colorless solid (18.48 g, 93.8%). $^1H$ NMR (300 MHz, $CDCl_3$, δ): 8.10 (dt, J=8.2 Hz, 1.0 Hz, 1H), 7.96 (dt, J=8.2 Hz, 1.0 Hz, 1H), 7.64 (ddd, J=8.2 Hz, 7.1 Hz, 1.1 Hz, 1H), 7.49 (ddd, J=8.2 Hz, 7.1 Hz, 1.1 Hz, 1H), 3.48 (s, 3H). $^{13}C\{^1H\}$ NMR (75 MHz, $CDCl_3$, δ): 145.03, 131.49, 130.37, 125.92, 120.49, 111.82, 42.88.

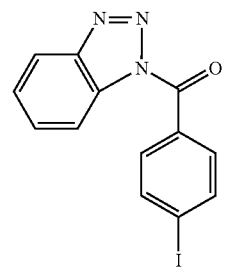

Benzotriazol-1-yl-(4-iodo-phenyl)-methanone (JYC-II-056-A). A mixture of 4-iodobenzoic acid (12.58 g, 50.7 mmol) and N-(1-methanesulfonyl)benzotriazole (JYC-II-054-A) (10.0 g, 50.7 mmol), and triethylamine (7.18 g, 71.0 mmol) were refluxed in THF overnight at 80° C. The solvent was evaporated and the residuel was extracted with $CHCl_3$. The organic layer was washed with $H_2O$ and dried over anhydrous MgSO$_4$. The solvent was removed under reduced pressure to give light yellow crystals (16.42 g, 92.8%). $^1$H NMR (300 MHz, CDCl$_3$, δ): 8.31 (dt, J=8.5 Hz, 0.8 Hz, 1H), 8.11 (dt, J=8.2 Hz, 0.8 Hz, 1H), 7.90 (s, 4H), 7.66 (ddd, J=8.2 Hz, 7.1 Hz, 1.1 Hz, 1H), 7.51 (ddd, J=8.2 Hz, 7.1 Hz, 1.1 Hz, 1H). $^{13}$C{$^1$H} NMR (75 MHz, CDCl$_3$, δ): 165.72, 145.49, 137.58, 132.81, 131.99, 130.57, 130.37, 126.30, 120.08, 114.61, 101.86.

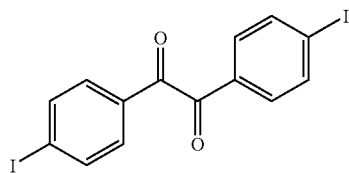

1,2-Bis(4-iodophenyl)ethane-1,2-dione (JYC-II-057-A). Under N$_2$, benzotriazol-1-yl-(4-iodo-phenyl)-methanone (JYC-II-056-A) (3.5 g, 10.0 mmol) dissolved in 40 mL of anhydrous THF was added to a THF solution of SmI$_2$ (221 mL of 0.1 M solution in THF, 22.1 mmol) at room temperature. The resulting mixture turned yellow brown in 5 min. HCl (2M, 65 mL) was added and the mixture was extracted with diethyl ether several times. The combined organic layers were washed with brine and dried over anhydrous MgSO$_4$. The solvent was removed under reduced pressure. The crude product was washed with MeOH to give a yellow solid (0.73 g, 31.5%). $^1$H NMR (300 MHz, CDCl$_3$, δ): 7.88 (d, J=8.5 Hz, 4H), 7.64 (dt, J=8.8 Hz, 4H). HRMS-EI (m/z): [M]$^+$ calcd for C$_{14}$H$_8$I$_2$O$_2$, 461.86138; found, 461.86180.

The preliminary electron mobility data of JYC-I-019-A was collected. The structure of JYC-I-019-A is shown in FIG. 1.

The device in which JYC-I-019-A was used as an electron-transport material is shown in FIG. 2. The I-V curve of ITO/JYC-I-019-A (5 μm)/ITO device at room temperature is shown in FIG. 3. The log I-log V plot of ITO/JYC-I-019-A (5 μm)/ITO device at room temperature is shown in FIG. 4.

By power fitting from 8 to 9 volts using the equation (y=ax$^b$) to get b=2.06113. The Power fitting of I-V curve of ITO/JYC-I-019-A (5 μm)/ITO device is shown in FIG. 5.

FIG. 6 shows the experimental curve (dotted line) and numerical fitting using the modified SCLC equation (The equation is shown in FIG. 7) (solid line). The preliminary electron mobility data show that the mobility of JYC-I-019-A is $3.07 \times 10^{-2}$ cm$^2$/Vs at E=$2 \times 10^4$ V/cm and the mobility of JYC-I-019-A is $3.73 \times 10^{-2}$ cm$^2$/Vs at E=$10^5$ V/cm.

EXAMPLE 5

The transition-metal charge-transport materials can be used in organic electronic devices, including, but not limited to, organic light-emitting diodes, lasers, photovoltaic cells, photodetectors, active and passive electronic devices, and memories. Active electronic devices include, but are not limited to, diodes and transistors. Passive electronic devices include, but are not limited to, resistors, capacitors, and inductors. Active and passive electronic devices can be combined to form electrical circuits with properties tailored to the need of specific applications. For example, transistors can be combined to form inverters and ring oscillators. Likewise, passive elements can be combined to form resonant circuits and various filters. Electronic devices and circuits are the foundation of modern electronics and are well known in the art. Examples of applications can be found, for instance, in P. Horowitz and W. Hill, The Art of Electronics, Cambridge University Press, Cambridge, 1989.

Organic electronic devices typically include one or several organic semiconductors that can conduct electrical charge. In devices, such as organic light-emitting diodes, transistors and memories, charges are injected into the organic semiconductor through electrical contacts formed with conductive electrodes such as metals and conductive oxides. In photovoltaic cells and photodetectors, electrical charges are produced by the optical absorption of light. These charges are then collected through electrical contacts formed with conductive electrodes such as metals and conductive oxides. In some devices and circuits it is important to combine two different organic semiconductors, one of which conducts electrons, and the other conducts holes. Preferably, the two semiconductors should have hole and electron mobilities that are comparable. Interfaces formed between such semiconductors are often called heterojunctions.

In an embodiment, the transition-metal charge-transport materials are used as electron-transport materials in organic light-emitting devices. An example of a geometry structure for such a device is shown in FIG. 1. In this device, a hole transport organic semiconductor 20 and an electron transport organic semiconductor 30 are sandwiched between an anode 10 and a cathode 40. When a voltage is applied by a power supply 50 with positive electrode applied to anode 10 and negative electrode applied to cathode 40, holes get injected into hole transport semiconductor 20 and electrons get injected into electron transport semiconductor 30. Holes and electrons form excited states at the heterojunction 60, the recombination of which leads to emission of light through at least one of the electrodes (10 or 40) that is semitransparent. The hole transport semiconductor 20 can be a triphenyldiamine (TPD) derivative thin film or other hole transport materials known in the art, the anode 10 can be indium tin oxide (ITO), the electron-transport semiconductor 30 can include of one or more of the transition-metal charge-transport materials described herein, and the cathode 40 can be a metal including, but limited to, Ca, Ag, Mg, Al, Au, or mixtures thereof.

In another embodiment, the transition-metal charge-transport materials are used as electron transport materials in photovoltaic cells. In an embodiment, a possible geometry for such a device is shown in FIG. 2. In this device, a hole-transport organic semiconductor 200 and an electron-transport organic semiconductor 300 are sandwiched between a first electrode 100 and a second electrode 400. When the device is exposed to light, optical absorption in the organic semiconductors 200 and 300 leads to the formation of excited states that diffuse to the heterojunction 600 where they separate into electron-hole pairs. Holes are transported in the semiconductor layer 200 and get collected by the electrode 100. Electrons are transported in the layer 300 and are collected by the electrode 400. The transport of the charges created optically leads to a current that can be measured by an ampmeter 500.

The hole transport semiconductor 200 can be a thin film of triphenyldiamine (TPD), a phthalocyanine, an oligoacene, an oligothiophene or any other organic hole transport material with high hole mobility known in the art. The electrode 100 can be indium tin oxide (ITO) or any other conducting oxide known in the art. The electron transport semiconductor 300 can be comprised of one or more of the transition-metal charge-transport materials described herein. The second electrode 400 can be a metal including, but limited to, Ca, Ag, Mg, Al, Au, or mixtures thereof. In some cases, an additional layer can be added between 300 and 400 to prevent the dissociation of excited states (also referred to as excitons) near the electrode 400. This layer may be called an exciton blocking layer.

In another embodiment, the transition-metal charge-transport materials are used as electron transport materials in organic field-effect transistors. In an embodiment, a possible structure for such a device is shown in FIG. 3. The organic electron-transport semiconductor 16 is deposited on top of a structure that is comprised of a conductive substrate 11 such as highly doped silicon, an insulator layer 13 such as a thermally grown silicon oxide layer, a gate electrode 12, a source electrode 15, and a drain electrode 14. A positive voltage applied to the gate electrode changes the density of electrons in the organic semiconductor 16 and will influence the current voltage characteristics measured between the source electrode 15 and the drain electrode 14. The typical electrical output characteristic of a field-effect transistor is shown in FIG. 4. When a low voltage is applied between the source electrode 15 and the drain electrode 14, a small current is measured, as shown by curve 21. In contrast, when a larger gate voltage is applied between the source electrode 15 and the drain electrode 14, a large current is measured, as shown by curve 22. For a given gate voltage, the electrical characteristics 21 and 22 have a linear regime 23 and a saturation regime 24. These electrical characteristics are similar to those measured for MOSFET transistors including inorganic semiconductors including silicon and germanium.

At low drain voltage where the response is linear (as shown by region 23 in FIG. 4), the current-voltage response is given by:

$$I_D = \frac{W C_{ox} \mu}{L}\left(V_G - V_T - \frac{V_D}{2}\right)V_D \qquad (1)$$

where W is the channel width, L the distance between source and drain electrodes (channel length), $C_{ox}$ is the capacitance per unit area of the insulator, $V_T$ is the threshold voltage and $\mu$ is the "effective" field-effect mobility, which can be calculated in this regime from the transconductance defined by:

$$g_m = \frac{\partial I_D}{\partial V_G}\bigg|_{V_D=const.} = \frac{W C_{ox}}{L}\mu V_D \qquad (2)$$

For large drain voltages (as shown by region 24 in FIG. 4), the saturated drain current $I_{Dsat}$ is given by the so-called "square-law":

$$I_{Dsat} = \frac{W C_{ox} \mu}{2L}(V_G - V_T)^2 \qquad (3)$$

In this regime, mobility can be extracted from the slope of the plot of the square root of the drain current versus gate voltage. Such a curve is called a transfer curve.

Another geometry for an organic field-effect transistor is shown in FIG. 5. The organic electron-transport semiconductor 36 is deposited on top of a structure that includes a conductive substrate 31 such as highly doped silicon, an insulator layer 33 such as a thermally grown silicon oxide layer, and a gate electrode 32. In this geometry, source electrode 15 and a drain electrode 14 are deposited on top of the semiconductor layer 36.

Another geometry for an organic field-effect transistor is shown in FIGS. 6A and 6B. In this geometry, an additional layer is introduced between the gate insulator 43 and the organic semiconductor 46. This layer modifies the properties of the surface of the gate insulator and improves its compatibility with the organic semiconductors. The surface modifier 47 can be a self-assembled monolayer leading to a thin layer. It can be deposited on top of the gate insulator 43 after the deposition of the source and drain electrodes, 45 and 44, respectively, and before the deposition of the organic semiconductor 46, as shown in FIG. 6A. Alternatively, layer 47 can be deposited on top of the gate insulator 43 before deposition of the organic semiconductor 46, as shown in FIG. 6B.

Therefore the following is claimed:

1. A charge-transport material, comprising:
a transition-metal charge-transport material monomer having a structure of Formula I:

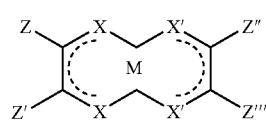

wherein M is selected from the group consisting of: nickel (II), palladium (II), platinum (II), cobalt (I), iridium (I), rhodium (I), copper (II), copper (III), silver (III), and gold (III);

wherein L and L' are each independently selected from the group consisting of a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z" and Z'" are each independently selected from a polymerizable group, wherein is R' is selected from a polymerizable group;

wherein the polymerizable group is selected from the group consisting of: vinyl; allyl; 4-styryl; acroyl; epoxide; oxetane; cyclic-carbonate; methacroyl; acrylonitrile; isocyanate; isothiocyanate; an epoxide; a strained ring olefin; $(-CH_2)_n SiCl_3$; $(-CH_2)_n Si(OCH_2CH_3)_3$; $(-CH_2)_n Si(OCH_3)_3$, where η is an integer number from 0 to 25; and a compound having the following structure:

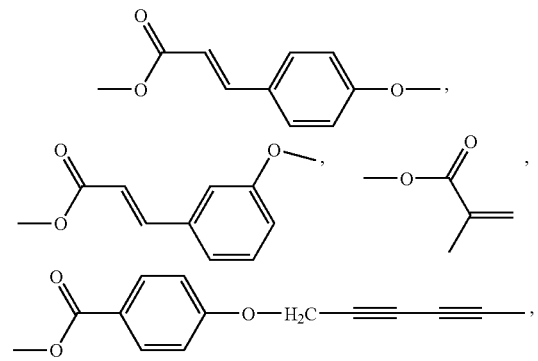

-continued

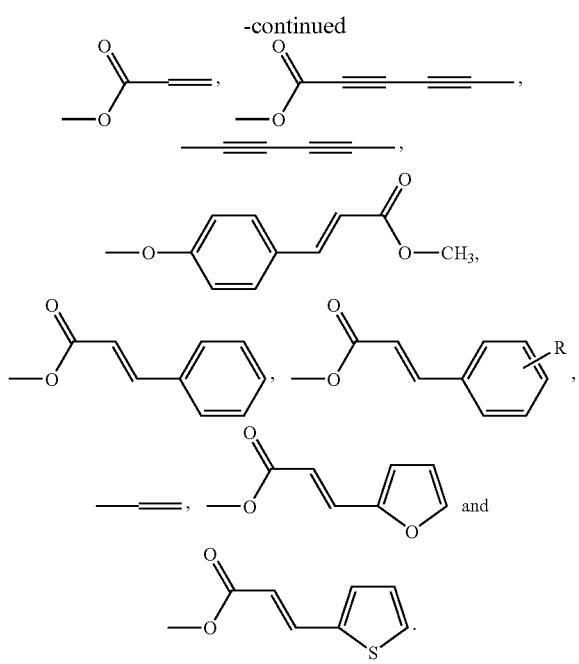

2. The charge-transport material of claim 1, wherein the aryl group is selected from the group consisting of: an aromatic ring system having 20 carbons in the aromatic ring framework not including carbons on the substituents; and an aryl represented by the following structures:

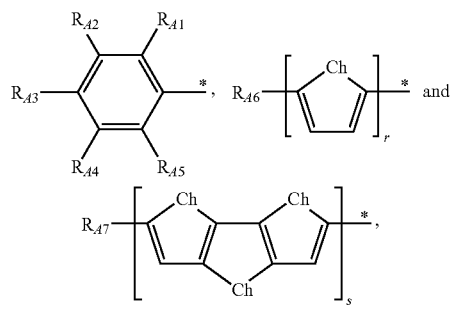

wherein Ch is selected from the group consisting of: Se, S, O, and a combination thereof; wherein $R_{A1}$, $R_{A2}$, $R_{A3}$, $R_{A4}$, $R_{A5}$, $R_{A6}$, and $R_{A7}$, are each independently selected from the group consisting of: H; a linear or branched alkyl group with up to 25 carbons;
—(CH$_2$CH$_2$O)$_\gamma$—(CH$_2$)$_\delta$OCH$_3$; —(CH$_2$CH$_2$O)$_\gamma$—(CH$_2$)$_\delta$N(CH$_3$)$_2$;
—(CH$_2$CH$_2$O)$_\gamma$—(CH$_2$)$_\delta$CON(CH$_3$)$_2$; —(CH$_2$CH$_2$O)$_\gamma$—(CH$_2$)$_\delta$CN; —(CH$_2$CH$_2$O)$_\gamma$—(CH$_2$)$_\delta$CH$_2$F;
—(CH$_2$CH$_2$O)$_\gamma$—(CH$_2$)$_\delta$NO$_2$; —(CH$_2$CH$_2$O)$_\gamma$—(CH$_2$)$_\delta$CH$_2$Cl; —(CH$_2$CH$_2$O)$_\gamma$—(CH$_2$)$_\delta$CH$_2$Br;
—(CH$_2$CH$_2$O)$_\gamma$—(CH$_2$)$_\delta$CH$_2$I; —(CH$_2$CH$_2$O)$_\gamma$—(CH$_2$)$_\delta$-Phenyl;
—(CH$_2$)$_\delta$—(OCH$_2$CH$_2$)$_\gamma$CH$_3$; —(CH$_2$)$_\delta$—(OCH$_2$CH$_2$)$_\delta$CH$_2$N(CH$_3$)$_2$;
—(CH$_2$)$_\delta$—(OCH$_2$CH$_2$)$_\gamma$CON(CH$_3$)$_2$; —(CH$_2$)$_\delta$—(OCH$_2$CH$_2$)$_\gamma$CN;
—(CH$_2$)$_\delta$—(OCH$_2$CH$_2$)$_\gamma$CH$_2$F; —(CH$_2$)$_\delta$—(OCH$_2$CH$_2$)$_\alpha$NO$_2$;
—(CH$_2$)$_\delta$—(OCH$_2$CH$_2$)$_\gamma$CH$_2$Cl; —(CH$_2$)$_\delta$—(OCH$_2$CH$_2$)$_\gamma$CH$_2$Br;
—(CH$_2$)$_\delta$—(OCH$_2$CH$_2$)$_\gamma$I; —(CH$_2$)$_\delta$—(OCH$_2$CH$_2$)$_\gamma$Phenyl; —(CF$_2$)$_\beta$OCH$_3$;
—(CF$_2$)$_\beta$CH$_2$N(CH$_3$)$_2$; —(CF$_2$)$_\beta$CF$_3$; —O(CF$_2$)$_\beta$OCH$_3$; —OCH$_2$CH$_2$(CF$_2$)$_\beta$OCH$_3$;
—OCH$_2$CH$_2$(CF$_2$)$_\beta$CH$_2$N(CH$_3$)$_2$; —O(CF$_2$)$_\beta$CH$_2$N(CH$_3$)$_2$;
—OCH$_2$CH$_2$(CF$_2$)$_\beta$CF$_3$; —(CH$_2$)$_\beta$—(OCH$_2$CH$_2$)$_\alpha$Phenyl; and —(CF$_2$)$_\beta$—(OCH$_2$CH$_2$)$_\alpha$Phenyl;

wherein subscript γ is an integer number from 0 to 25, wherein subscript δ is an integer number from 0 to 25; wherein subscript r is an integer number from 0 to 6; wherein subscript s is an integer number from 0 to 3.

3. The charge-transport material of claim 1, wherein M is nickel (II).

4. The charge-transport material of claim 1, wherein M is nickel (II), and X and X' are S.

5. A charge-transport material, comprising:
a transition-metal charge-transport material monomer having a structure of Formula II:

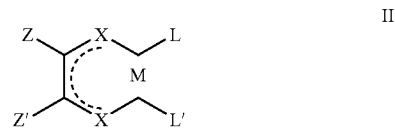

wherein M is selected from the group consisting of: nickel (II), palladium (II), platinum (II), cobalt (I), iridium (I), rhodium (I), copper(II), copper (III), silver (III), and gold (III);

wherein L and L' are each independently selected from the group consisting of: a halogen, NR$_3$, PR$_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is PR$_3$, R is an alkoxy group (R'O);

wherein X and X' are each independently selected from the group consisting of: S, Se, O, NR', and a combination thereof; and wherein Z, Z', Z" and Z'" are each independently selected from polymerizable group, wherein is R' is selected from a polymerizable group;

wherein the polymerizable group is selected from the group consisting of: vinyl; allyl; 4-styryl; acroyl; epoxide; oxetane; cyclic-carbonate; methacroyl; acrylonitrile; isocyanate; isothiocyanate; an epoxide; a strained ring olefin; (—CH$_2$)$_\eta$SiCl$_3$; (—CH$_2$)$_\eta$Si(OCH$_2$CH$_3$)$_3$; (—CH$_2$)$_\eta$Si(OCH$_3$)$_3$, where η is an integer number from 0 to 25; and a compound having the following structure:

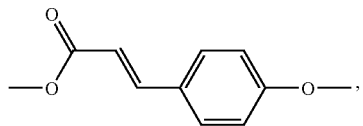

-continued

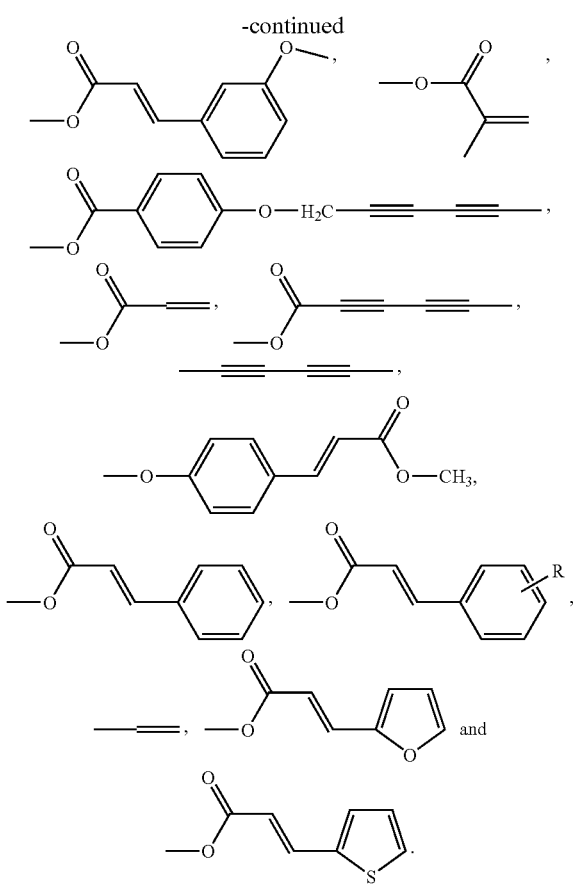

6. The charge-transport material of claim 5, wherein the aryl group is selected from the group consisting of: an aromatic ring system having 20 carbons in the aromatic ring framework not including carbons on the substituents; and an aryl represented by the following structures:

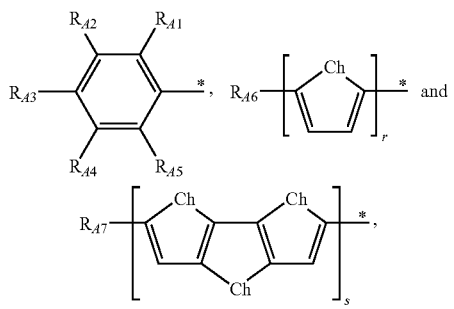

wherein Ch is selected from the group consisting of: Se, S, O, and a combination thereof; wherein $R_{A1}$, $R_{A2}$, $R_{A3}$, $R_{A4}$, $R_{A5}$, $R_{A6}$, and $R_{A7}$, are each independently selected from the group consisting of:; a linear or branched alkyl group with up to 25 carbons;
—$(CH_2CH_2O)_\gamma$—$(CH_2)_\delta OCH_3$; —$CH_2CH_2O)_\gamma$—$(CH_2)_\delta$ $(CH_3)_2$;
—$(CH_2CH_2O)_\gamma$—$(CH_2)_\delta CON(CH_3)_2$; —$(CH_2CH_2O)_\gamma$— $(CH_2)_\delta CN$; —$(CH_2CH_2O)_\gamma$—$(CH_2)_\delta CH_2F$;
—$(CH_2CH_2O)_\gamma$—$(CH_2)_\delta NO_2$; —$(CH_2CH_2O)_\gamma$— $(CH_2)_\delta CH_2Cl$; —$(CH_2CH_2O)_\gamma$—$(CH_2)_\delta CH_2Br$;
—$(CH_2CH_2O)_\gamma$—$(CH_2)_\delta CH_2I$; —$(CH_2CH_2O)_\gamma$—$(CH_2)_\delta$-Phenyl;
—$(CH_2)_\delta$—$(OCH_2CH_2)_\gamma CH_3$; —$(CH_2)_\delta$—$(OCH_2CH_2)_\delta$ $CH_2N(CH_3)_2$;
—$(CH_2)_\delta$—$(OCH_2CH_2)_\gamma CON(CH_3)_2$; —$(CH_2)_\delta$— $(OCH_2CH_2)_\gamma CN$;
—$(CH_2)_\delta$—$(OCH_2CH_2)_\gamma CH_2F$; —$(CH_2)_\delta$— $(OCH_2CH_2)_\alpha NO_2$;
—$(CH_2)_\delta$—$(OCH_2CH_2)_\gamma CH_2Cl$; —$(CH_2)_\delta$— $(OCH_2CH_2)_\gamma CH_2Br$;
—$(CH_2)_\delta$—$(OCH_2CH_2)_\gamma I$; —$(CH_2)_\delta$—$(OCH_2CH_2)_\gamma$Phenyl; —$(CF_2)_\beta OCH_3$;
—$(CF_2)_\beta CH_2N(CH_3)_2$; —$(CF_2)_\beta CF_3$; —$O(CF_2)_\beta OCH_3$; —$OCH_2CH_2(CF_2)_\beta OCH_3$;
—$OCH_2CH_2(CF_2)_\beta CH_2N(CH_3)_2$; —$O(CF_2)_\beta CH_2N(CH_3)_2$;
—$OCH_2CH_2(CF_2)_\beta CF_3$; —$(CH_2)_\beta$—$(OCH_2CH_2)_\alpha$Phenyl; and —$(CF_2)_\beta$—$(OCH_2CH_2)_\alpha$Phenyl;
wherein subscript γ is an integer number from 0 to 25, wherein subscript δ is an integer number from 0 to 25; wherein subscript r is an integer number from 0 to 6; wherein subscript s is an integer number from 0 to 3.

7. The charge-transport material of claim 5, wherein M is nickel(II).

8. A polymer comprising a monomer selected from the group consisting of: the Formula I monomer, the Formula II monomer, and a combination thereof;
wherein Formula I monomer having a structure:

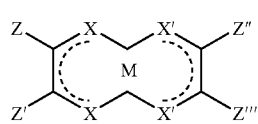

I wherein M is selected from the group consisting of: nickel (II), palladium (II), platinum (II), cobalt (I), iridium (I), rhodium (I), copper (II), copper (III), silver (III), and gold (III);
wherein L and L' are each independently selected from the group consisting of a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);
wherein X and X' are each independently selected from the group consisting of: S, Se, O, NR', and a combination thereof; and
wherein Z, Z', Z" and Z''' are each independently selected from a polymerizable group,
wherein is R' is selected from a polymerizable group;
wherein the polymerizable group is selected from a group consisting of: vinyl; allyl; 4-styryl; acroyl; epoxide; oxetane; cyclic-carbonate; methacroyl; acrylonitrile, isocyanate; isothiocyanate; an epoxide; a strained ring olefin; —$(CH)_\eta SiCl_3$; —$(CH_2)_\eta Si(OCH_2CH_3)_3$; —$(CH_2)_\eta Si(OCH_3)_3$, where η is an integer number from 0 to 25; and a compound having the following structure:

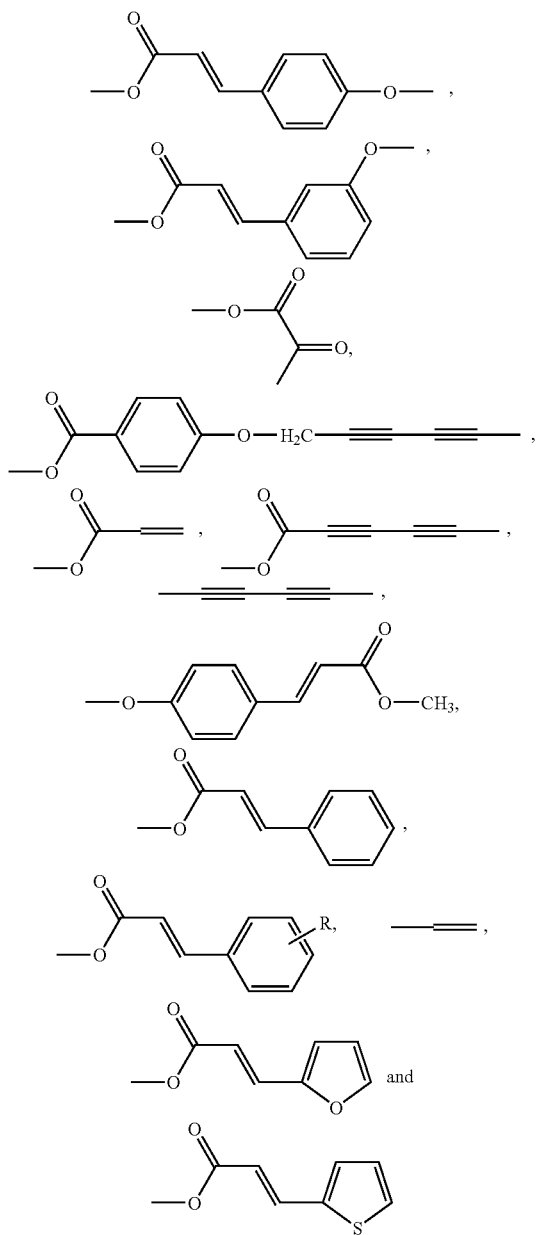

and
wherein Formula II monomer having a structure:

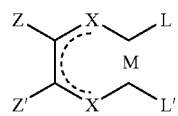

wherein M is selected from the group consisting of: nickel (II), palladium (II), platinum (II), cobalt (I), iridium (I), rhodium (I), copper(II), copper (III), silver (III), and gold (III);

wherein L and L' are each independently selected from the group consisting of: a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z" and Z'" are each independently selected from polymerizable group, wherein is R' is selected from a polymerizable group;

wherein the polymerizable group is selected from the group consisting of: vinyl; allyl; 4-styryl; acroyl; epoxide; oxetane; cyclic-carbonate; methacroyl; acrylonitrile isocyanate; isothiocyanate; an epoxide; a strained ring olefin; $(-CH_2)_nSiCl_3$; $(-CH_2)_nSi(OCH_2CH_3)_3$; $(-CH_2)_nSi(OCH_3)_3$, where $\eta$ is an integer number from 0 to 25; and a compound having the following structure:

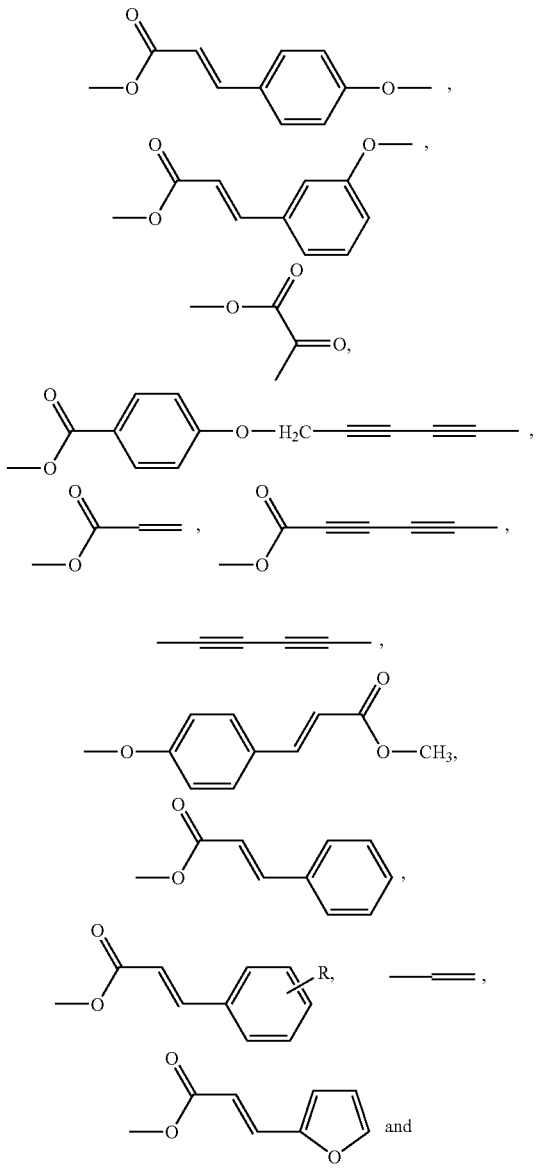

-continued

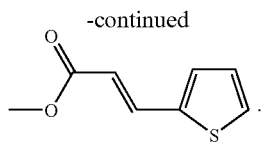

9. A homopolymer comprising a monomer selected from the group consisting of: the Formula I monomer, the Formula II monomer, and a combination thereof, wherein Formula I monomer having a structure:

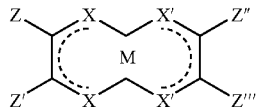

I wherein M is selected from the group consisting of: nickel (II), palladium (II), platinum (II), cobalt (I), iridium (I), rhodium (I), copper (II), copper (III), silver (III), and gold (III);

wherein L and L' are each independently selected from the group consisting of a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z" and Z''' are each independently selected from a polymerizable group, wherein is R' is selected from a polymerizable group;

wherein the polymerizable group is selected from a group consisting of: vinyl; allyl; 4-styryl; acroyl; epoxide; oxetane; cyclic-carbonate; methacroyl; acrylonitrile, isocyanate; isothiocyanate; an epoxide; a strained ring olefin; $(-CH_2)_\eta SiCl_3$; $(-CH_2)_\eta Si(OCH_2CH_3)_3$; $(-CH_2)_\eta Si(OCH_3)_3$, where $\eta$ is an integer number from 0 to 25; and a compound having the following structure:

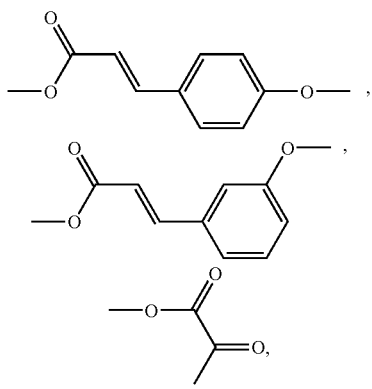

-continued

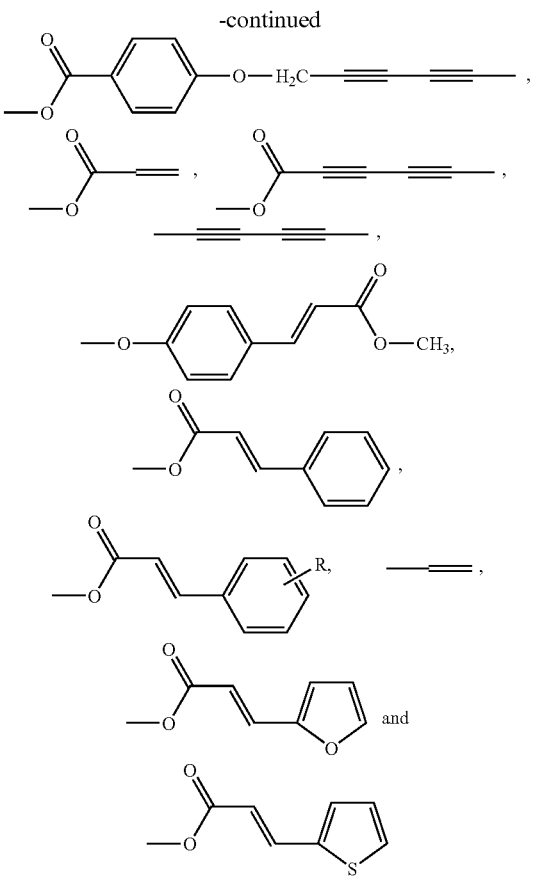

and wherein Formula II monomer having a structure:

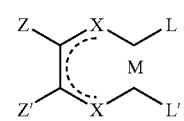

II wherein M is selected from the group consisting of: nickel (II), palladium (II), platinum (II), cobalt (I), iridium (I), rhodium (I), copper(II), copper (III), silver (III), and gold (III);

wherein L and L' are each independently selected from the group consisting of: a halogen, $NR_3PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z" and Z''' are each independently selected from polymerizable group, wherein is R' is selected from a polymerizable group;

wherein the polymerizable group is selected from the group consisting of: vinyl; allyl; 4-styryl; acroyl; epoxide; oxetane; cyclic-carbonate; methacroyl; acrylonitrile isocyanate; isothiocyanate; an epoxide; a strained ring olefin; (—CH$_2$)$_\eta$SiCl$_3$; (—CH$_2$)$_\eta$Si(OCH$_2$CH$_3$)$_3$; (—CH$_2$)$_\eta$Si(OCH$_3$)$_3$, where η is an integer number from 0 to 25; and a compound having the following structure:

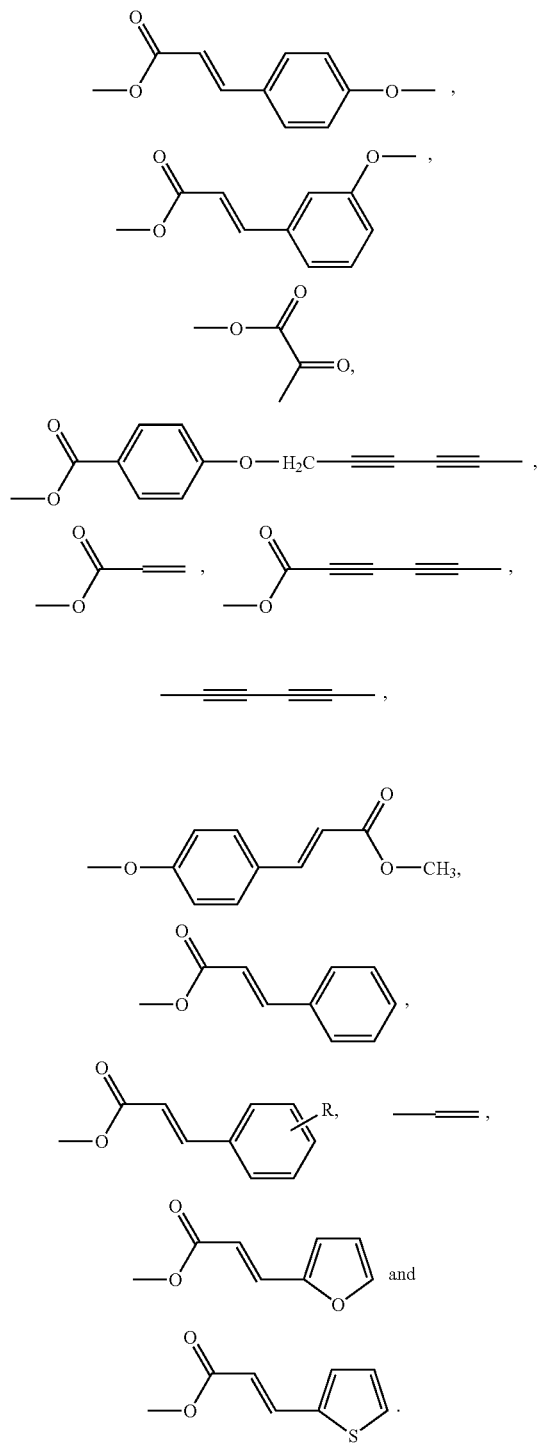

10. A copolymer comprising a monomer selected from the group consisting of: the Formula I monomer, the Formula II monomer, and a combination thereof, wherein Formula I monomer having a structure:

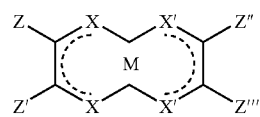

I wherein M is selected from the group consisting of: nickel (II), palladium (II), platinum (II), cobalt (I), iridium (I), rhodium (I), copper (II), copper (III), silver (III), and gold (III);

wherein L and L' are each independently selected from the group consisting of a halogen, NR$_3$, PR$_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is PR$_3$, R is an alkoxy group (R'O);

wherein X and X' are each independently selected from the group consisting of: S, Se, O, NR', and a combination thereof; and wherein Z, Z', Z" and Z"' are each independently selected from a polymerizable group, wherein is R' is selected from a polymerizable group;

wherein the polymerizable group is selected from a group consisting of: vinyl; allyl; 4-styryl; acroyl; epoxide; oxetane; cyclic-carbonate; methacroyl; acrylonitrile, isocyanate; isothiocyanate; an epoxide; a strained ring olefin; (—CH$_2$)$_\eta$SiCl$_3$; (—CH$_2$)$_\eta$Si(OCH$_2$CH$_3$)$_3$; (—CH$_2$)$_\eta$Si(OCH$_3$)$_3$, where η is an integer number from 0 to 25; and a compound having the following structure:

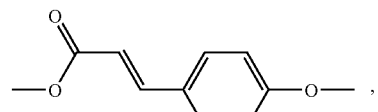

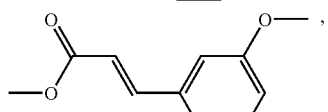

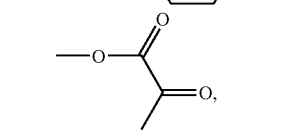

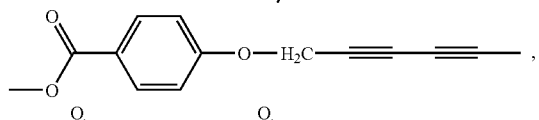

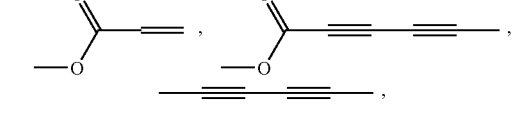

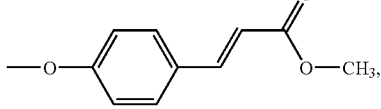

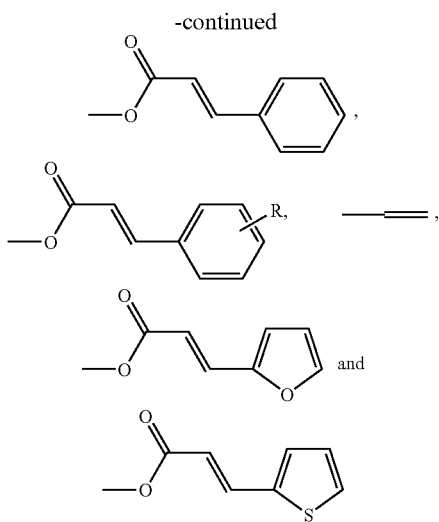

and
wherein Formula II monomer having a structure:

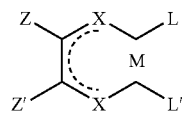

wherein M is selected from the group consisting of: nickel (II), palladium (II), platinum (II), cobalt (I), iridium (I), rhodium (I), copper(II), copper (III), silver (III), and gold (III);

wherein L and L' are each independently selected from the group consisting of: a halogen, NR₃, PR₃, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is PR₃, R is an alkoxy group (R'O);

wherein X and X' are each independently selected from the group consisting of: S, Se, O, NR', and a combination thereof; and wherein Z, Z', Z" and Z" are each independently selected from polymerizable group, wherein is R' is selected from a polymerizable group;

wherein the polymerizable group is selected from the group consisting of: vinyl; allyl; 4-styryl; acroyl; epoxide; oxetane; cyclic-carbonate; methacroyl; acrylonitrile isocyanate; isothiocyanate; an epoxide; a strained ring olefin; (—CH₂)ₙSiCl₃; (—CH₂)ₙSi(OCH₂CH₃)₃; (—CH₂)ₙSi(OCH₃)₃, where η is an integer number from 0 to 25; and a compound having the following structure:

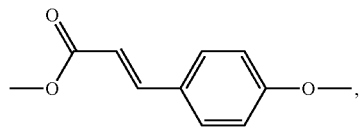

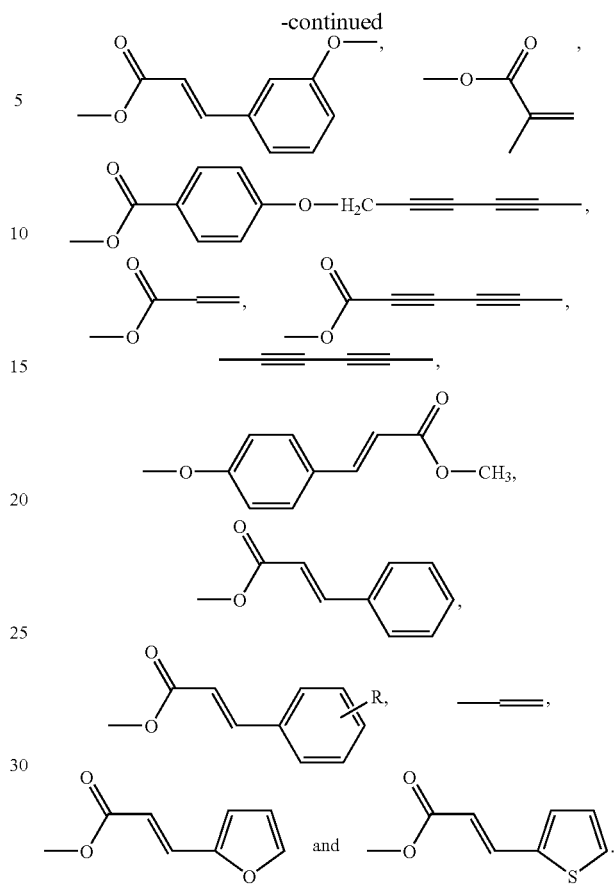

11. A device, comprising:
a polymer including a compound selected from the group consisting of: the Formula I monomer, the Formula II monomer claim, and a combination thereof,
wherein Formula I monomer having a structure:

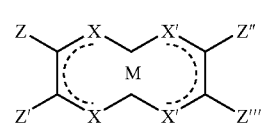

wherein M is selected from the group consisting of: nickel (II), palladium (II), platinum (II), cobalt (I), iridium (I), rhodium (I), copper (II), copper (III), silver (III), and gold (III);

wherein L and L' are each independently selected from the group consisting of a halogen, NR₃, PR₃, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is PR₃, R is an alkoxy group (R'O);

wherein X and X' are each independently selected from the group consisting of: S, Se, O, NR', and a combination thereof; and wherein Z, Z', Z" and Z'" are each independently selected from a polymerizable group, wherein is R' is selected from a polymerizable group;

wherein the polymerizable group is selected from a group consisting of: vinyl; allyl; 4-styryl; acroyl; epoxide; oxetane; cyclic-carbonate; methacroyl; acrylonitrile, isocyanate; isothiocyanate; an epoxide; a strained ring olefin; (—CH$_2$)$_\eta$SiCl$_3$; (—CH$_2$)$_\eta$Si(OCH$_2$CH$_3$)$_3$; (—CH$_2$)$_\eta$Si(OCH$_3$)$_3$, where η is an integer number from 0 to 25; and a compound having the following structure:

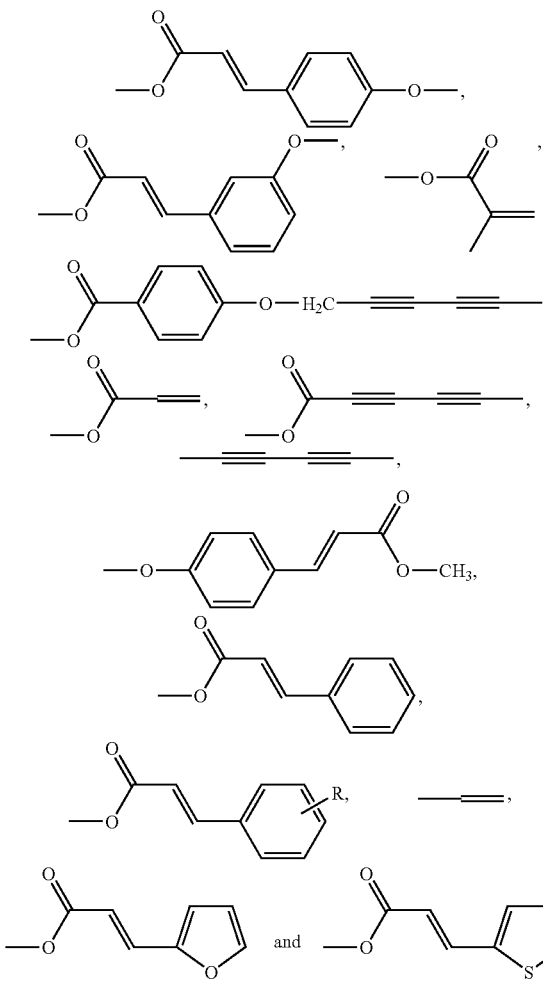

and
wherein Formula II monomer having a structure:

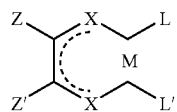

wherein M is selected from the group consisting of: nickel (II), palladium (II), platinum (II), cobalt (I), iridium (I), rhodium (I), copper(II), copper (III), silver (III), and gold (III);
wherein L and L' are each independently selected from the group consisting of: a halogen, NR$_3$, PR$_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is PR$_3$, R is an alkoxy group (R'O);
wherein X and X' are each independently selected from the group consisting of: S, Se, O, NR', and a combination thereof; and
wherein Z, Z', Z'' and Z''' are each independently selected from polymerizable group,
wherein is R' is selected from a polymerizable group;
wherein the polymerizable group is selected from the group consisting of: vinyl; allyl; 4-styryl; acroyl; epoxide; oxetane; cyclic-carbonate; methacroyl; acrylonitrile isocyanate; isothiocyanate; an epoxide; a strained ring olefin; (—CH$_2$)$_\eta$SiCl$_3$; (—CH$_2$)$_\eta$Si(OCH$_2$CH$_3$)$_3$; (—CH$_2$)$_\eta$Si(OCH$_3$)$_3$, where η is an integer number from 0 to 25; and a compound having the following structure:

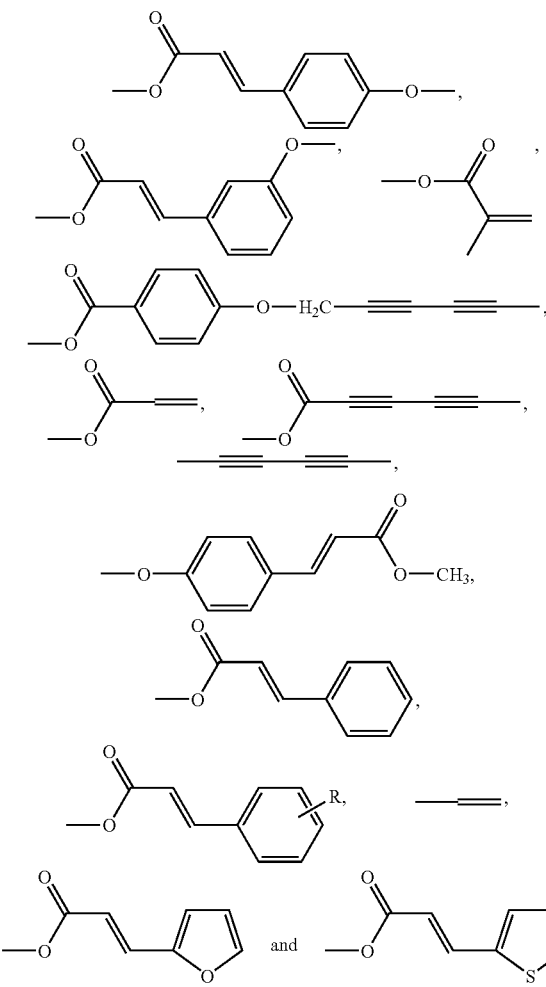

12. The device of claim 11, wherein the polymer is included in a structure selected from the group consisting of: electroluminescent (EL) devices, photovoltaic cells, light-emitting diodes, field-effect transistors, phototransistors, radio-frequency ID tags, semiconductor devices, photoconductive diodes, metal-semiconductor junctions, p-n junction diodes, p-n-p-n switching devices, photodetectors, optical sensors, phototransducers, bipolar junction transistors (BJTs), heterojunction bipolar translators, switching transistors, charge transfer devices, thin film transistors, organic radiation detectors, infra-red emitters, tunable microcavities for variable output wavelength, telecommunications devices and applications, optical computing devices, optical memory devices, chemical detectors, and combinations thereof.

13. A polymer layer, comprising:
a plurality of layers, wherein each layer includes a monomer having a central aromatic core, wherein the central aromatic cores in the layers are stacked substantially over one another to form a one-dimensional charge transport column along the stacked central aromatic cores, wherein the monomer includes a compound selected from the group consisting of: the Formula I monomer, the Formula II monomer, and a combination thereof, wherein Formula I monomer having a structure:

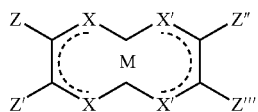
I wherein M is selected from the group consisting of: nickel (II), palladium (II), platinum (II), cobalt (I), iridium (I), rhodium (I), copper (II), copper (III), silver (III), and gold (III);
wherein L and L' are each independently selected from the group consisting of a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);
wherein X and X' are each independently selected from the group consisting of: S, Se, O, NR', and a combination thereof; and
wherein Z, Z', Z" and Z'" are each independently selected from a polymerizable group,
wherein is R' is selected from a polymerizable group;
wherein the polymerizable group is selected from a group consisting of: vinyl; allyl; 4-styryl; acroyl; epoxide; oxetane; cyclic-carbonate; methacroyl; acrylonitrile isocyanate; isothiocyanate; an epoxide; a strained ring olefin; $(-CH_2)_\eta SiCl_3$; $(-CH_2)_\eta Si(OCH_2CH_3)_3$; $(-CH_2)_\eta Si(OCH_3)_3$, where $\eta$ is an integer number from 0 to 25; and a compound having the following structure:

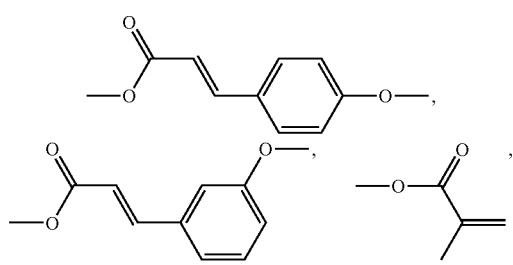

-continued

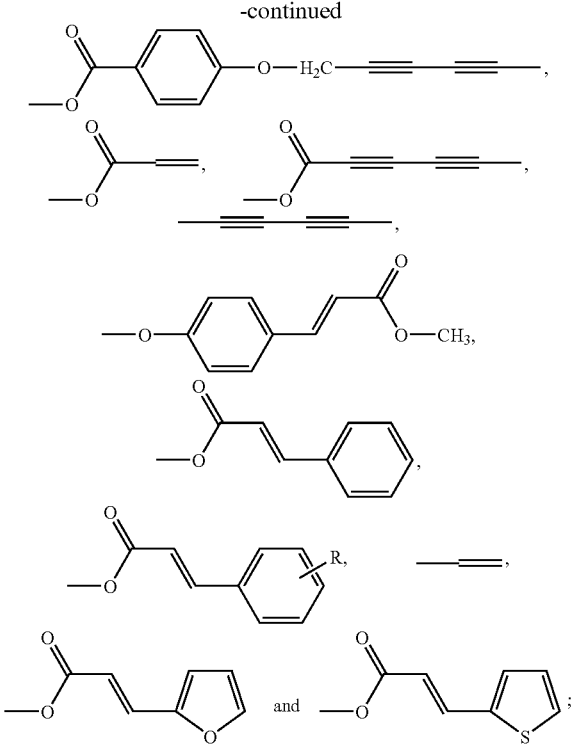

and
wherein Formula II monomer haying a structure:

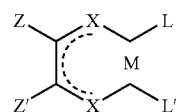
II wherein M is selected from the group consisting of: nickel (II), palladium (II), platinum (II), cobalt (I), iridium (I), rhodium (I), copper (II), copper (III), silver (III), and gold (III);
wherein L and L' are each independently selected from the group consisting of a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);
wherein X and X' are each independently selected from the group consisting of: S, Se, O, NR', and a combination thereof; and
wherein Z, Z', Z" and Z'" are each independently selected from polymerizable group,
wherein is R' is selected from a polymerizable group;
wherein the polymerizable group is selected from the group consisting of: vinyl; allyl; 4-styryl; acroyl; epoxide; oxetane; cyclic-carbonate; methacroyl; acrylonitrile, isocyanate; isothiocyanate; an epoxide; a strained ring olefin; $(-CH_2)_\eta SiCl_3$; $(-CH_2)_\eta Si(OCH_2CH_3)_3$; $(-CH_2)_\eta Si(OCH_3)_3$, where $\eta$ is an integer number from 0 to 25; and a compound having the following structure:

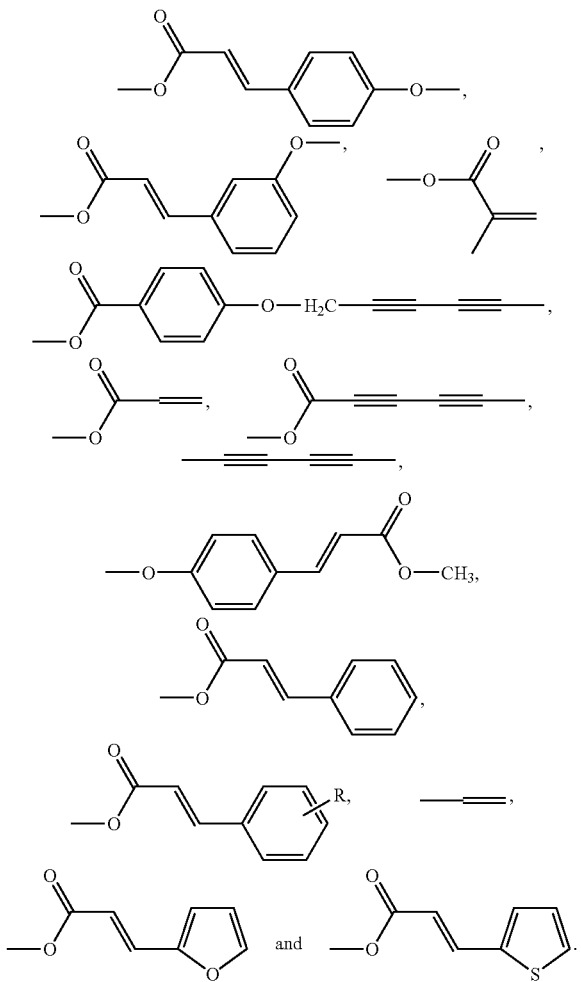

14. A device, comprising:
a first electrode;
a hole-transport layer disposed adjacent the first electrode;
an electron-transport layer disposed adjacent the hole-transport layer, and wherein the electron-transport material is selected from the group consisting of: the Formula I monomer, the Formula II monomer, and a combination thereof; and
a second electrode disposed adjacent the electron-transport layer,
wherein Formula I monomer having a structure:

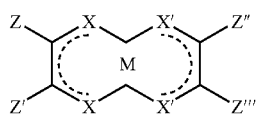

wherein M is selected from the group consisting of: nickel (II), palladium (II), platinum (II), cobalt (I), iridium (I), rhodium (I), copper (II), copper (III), silver (III), and gold (III);
wherein L and L' are each independently selected from the group consisting of a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);
wherein X and X' are each independently selected from the group consisting of: S, Se, O, NR', and a combination thereof; and
wherein Z, Z', Z" and Z'" are each independently selected from a polymerizable group,
wherein is R' is selected from a polymerizable group;
wherein the polymerizable group is selected from a group consisting of: vinyl; allyl; 4-styrol; acroyl; epoxide; oxetane; cyclic-carbonate; methacrovl; acrylonitrile; isocyanate; isothiocyanate; an epoxide; a strained ring olefin; $(-CH_2)_\eta SiCl_3$; $(-CH_2)_\eta Si(OCH_2CH_3)_3$; $(-CH_2)_\eta Si(OCH_3)_3$, where $\eta$ is an integer number from 0 to 25; and a compound having the following structure:

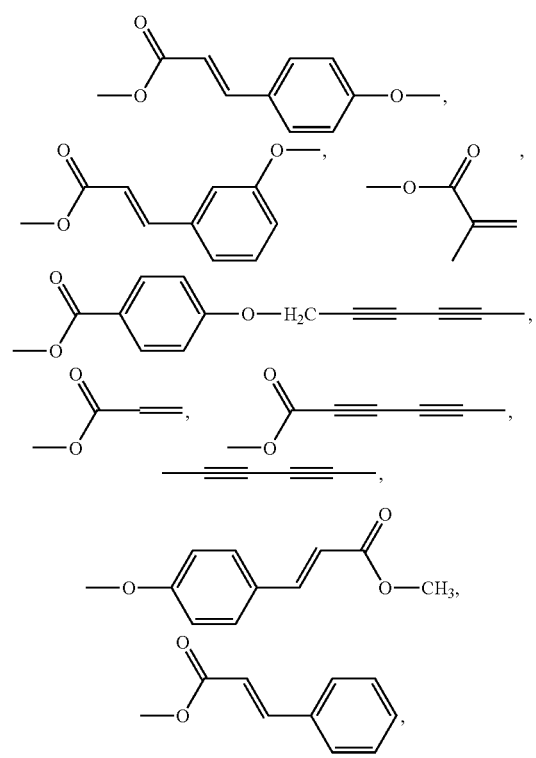

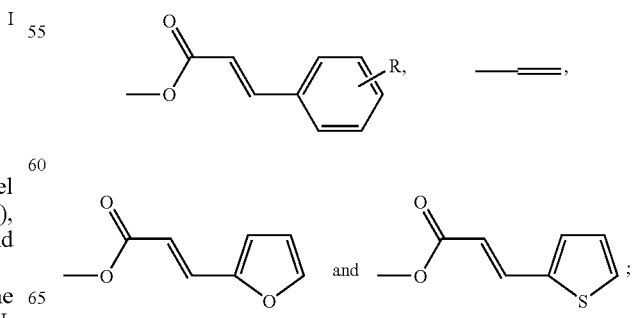

and
wherein Formula II monomer having a structure:

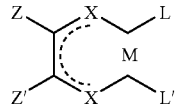

wherein M is selected from the group consisting of: nickel (II), palladium (II), platinum (II), cobalt (I), iridium (I), rhodium (I), copper(II), copper (III), silver (III), and gold (III):

wherein L and L' are each independently selected from the group consisting of: a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z'' and Z''' are each independently selected from polymerizable group, wherein is R' is selected from a polymerizable group;

wherein the polymerizable group is selected from the group consisting of: vinyl; allyl; 4-styryl; acroyl; epoxide; oxetane; cyclic-carbonate; methacroyl; acrylonitrile; isocyanate; isothiocyanate; an epoxide; a strained ring olefin; $(-CH_2)_n SiCl_3$; $(-CH_2)_n Si(OCH_2CH_3)_3$; $(-CH_2)_n Si(OCH_3)_3$, where η is an integer number from 0 to 25; and a compound having the following structure:

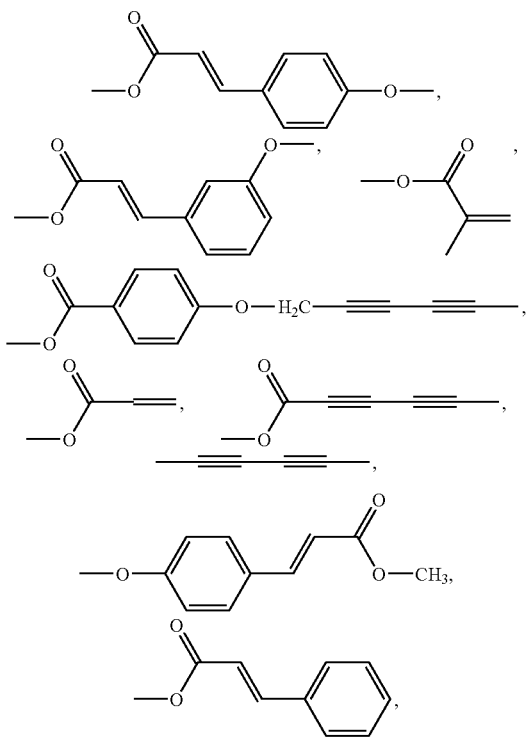

-continued

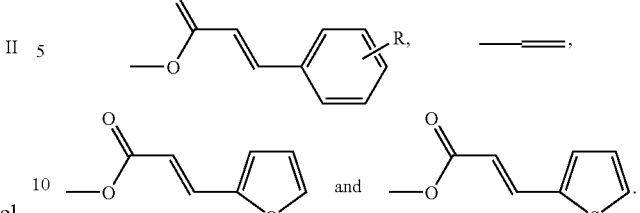

15. The device of claim 14, wherein the device is an organic light-emitting diode.

16. The device of claim 14, wherein the device is an organic photovoltaic cell.

17. An organic photovoltaic cell comprised of:
a first electrode;
a hole-transport layer disposed adjacent the first electrode;
an electron-transport layer disposed adjacent the hole-transport layer, and wherein the electron-transport material is selected from the group consisting of: the Formula I monomer, the Formula II monomer, and a combination thereof;
an exciton blocking layer disposed adjacent the electron-transport layer; and
a second electrode disposed adjacent the exciton blocking layer,
wherein Formula I monomer having a structure:

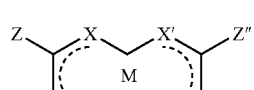

wherein M is selected from the group consisting of: nickel (II), palladium (II), platinum (II), cobalt (I), iridium (I), rhodium (I), copper (II), copper (III), silver (III), and gold (III);

wherein L and L' are each independently selected from the group consisting of a halogen, $NR_3$, $PR_3$, NCS, SCN and CN; wherein R is selected from the group consisting of: a linear or branched, unsubstituted alkyl group with up to 25 carbons; a linear or branched, substituted alkyl group with up to 25 carbons: an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z'' and Z''' are each independently selected from a polymerizable group, wherein is R' is selected from a polymerizable group;

wherein the polymerizable group is selected from a group consisting of: vinyl; allyl; 4-styryl; acroyl; epoxide; oxetane; cyclic-carbonate; methacroyl; acrylonitrile; isocyanate; isothiocyanate; an epoxide; a strained ring olefin; $(-CH_2)_n SiCl_3$; $(-CH_2)_n Si(OCH_2CH_3)_3$; $(-CH_2)_n Si(OCH_3)_3$, where η is an integer number from 0 to 25; and a compound having the following structure:

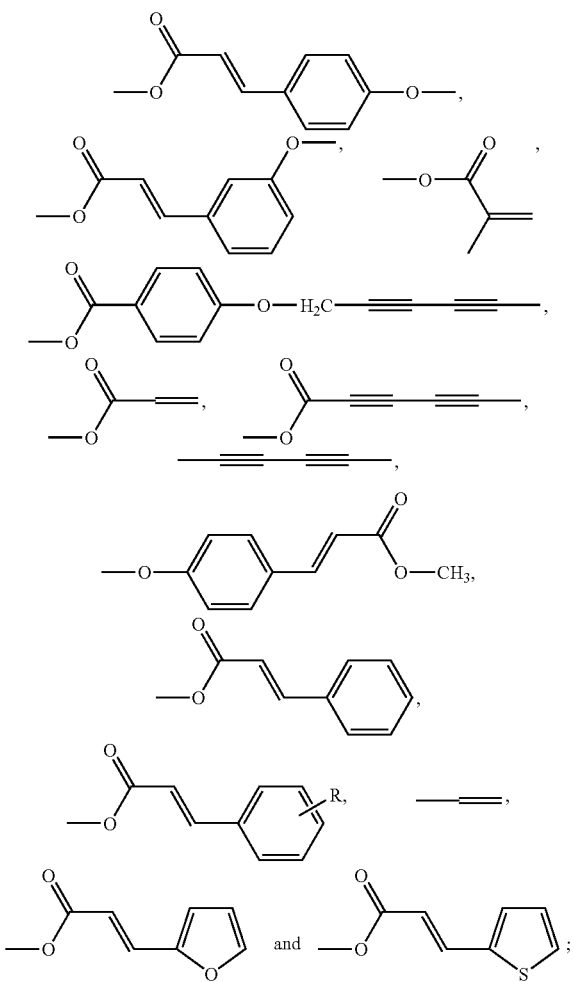

and
wherein Formula II monomer having a structure:

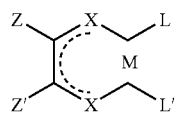
II wherein M is selected from the group consisting of: nickel (II), palladium (II), platinum (II), cobalt (I), iridium (I), rhodium (I), copper(II), copper (III), silver (III), and gold (III);

wherein L and L' are each independently selected from the group consisting of: a halogen, $NR_3$, $PR_3$, NCS, SCN and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z" and Z''' are each independently selected from polymerizable group, wherein is R' is selected from a polymerizable group;

wherein the polymerizable group is selected from the group consisting of: vinyl; allyl; 4-styryl; acroyl; epoxide; oxetane; cyclic-carbonate; methacroyl; acrylonitrile; isocyanate; isothiocyanate; an epoxide; a strained ring olefin; $(-CH_2)_nSiCl_3$; $(-CH_2)_nSi(OCH_2CH_3)_3$; $(-CH_2)_nSi(OCH_3)_3$, where $\eta$ is an integer number from 0 to 25; and a compound having the following structure:

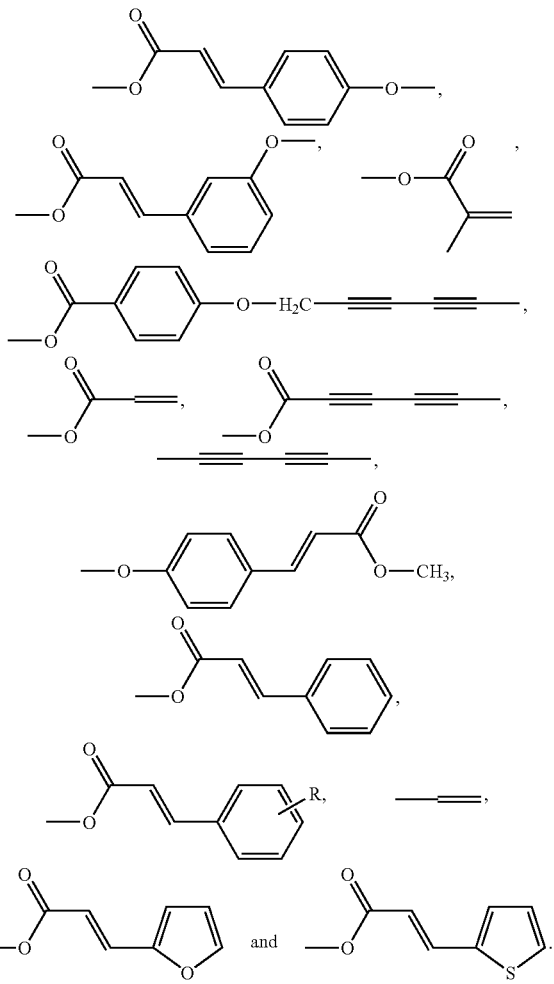

18. An organic field-effect transistor comprised of:
a substrate;
a gate electrode disposed on a first side of the substrate;
a gate insulator disposed on a second side of the substrate;
a source electrode disposed on a first portion of the gate insulator;
a drain electrode disposed on a second portion of the gate insulator; and .
an electron-transport layer disposed on a third portion of the gate insulator, the source electrode, and the drain electrode, and wherein the electron-transport material is selected from the group consisting of: the Formula I monomer, the Formula II monomer, and a combination thereof, wherein Formula I monomer having a structure:

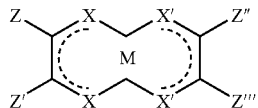

wherein M is selected from the group consisting of: nickel (II), palladium (II), platinum (II), cobalt (I), iridium (I), rhodium (I), copper (II), copper (III), silver(III), and gold (III);

wherein L and L' are each independently selected from the group consisting of a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z" and Z'" are each independently selected from a polymerizable group, wherein is R' is selected from a polymerizable group;

wherein the polymerizable group is selected from a group consisting of: vinyl; allyl; 4-styryl; acroyl: epoxide; oxetane; cyclic-carbonate; methacroyl; acrylonitrile; isocyanate; isothiocyanate; an epoxide; a strained ring olefin; $(-CH_2)_\eta SiCl_3$; $(-CH_2)_\eta Si(OCH_2CH_3)_3$; $(-CH_2)_\eta Si(OCH_3)_3$, where $\eta$ is an integer number from 0 to 25; and a compound having the following structure:

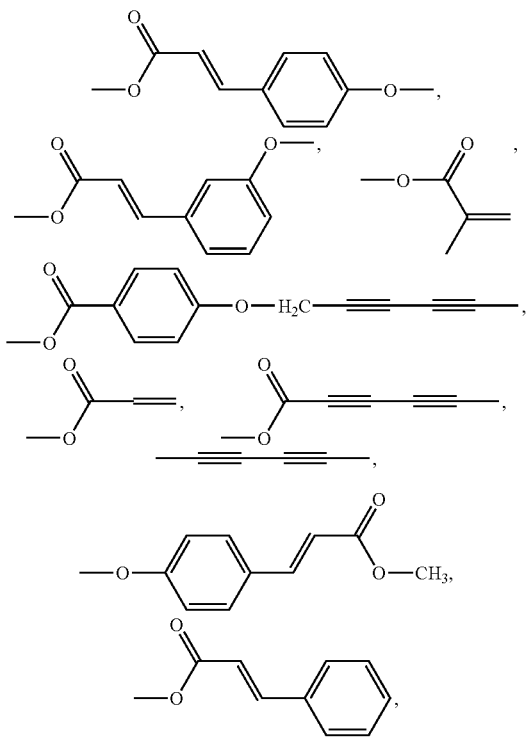

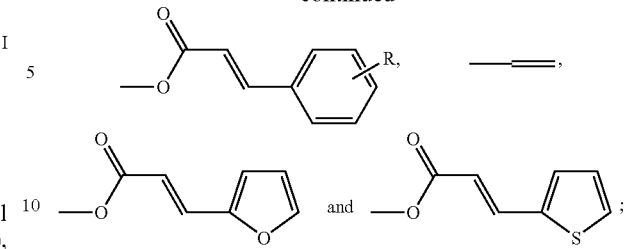

and wherein Formula II monomer having a structure:

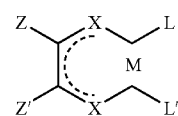

wherein M is selected from the group consisting of: nickel (II), palladium (II), platinum (II), cobalt (I), iridium (I), rhodium (I), copper(II), copper (III), silver (III), and gold (III);

wherein L and L' are each independently selected from the group consisting of: a halogen, $NR_3$, $PR_3$, NCS, SCN and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z" and Z'" are each independently selected from polymerizable group, wherein is R' is selected from a polymerizable group;

wherein the polymerizable group is selected from the group consisting of: vinyl; allyl; 4-styryl; acroyl; epoxide; oxetane; cyclic-carbonate; methacroyl; acrylonitrile; isocyanate; isothiocyanate; an epoxide; a strained ring olefin; $(-CH_2)_\eta SiCl_3$; $(-CH_2)_\eta Si(OCH_2CH_3)_3$; $(-CH_2)_\eta Si(OCH_3)_3$, where $\eta$ is an integer number from 0 to 25; and a compound having the following structure:

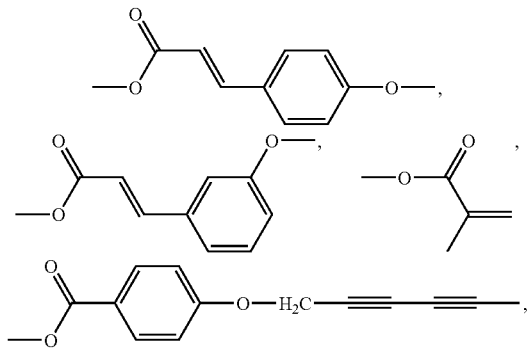

-continued

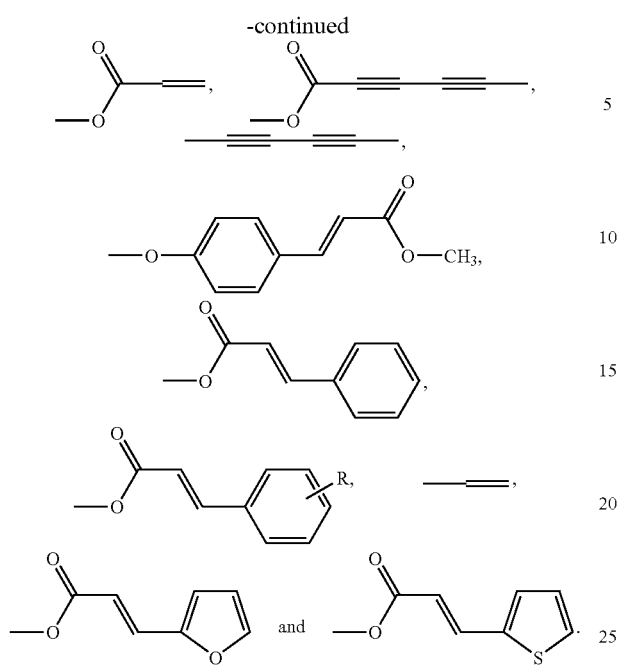

19. A material, comprising:
a mixture of components comprising a monomer, a polymer including the monomer, a co-polymer including the monomer, a homopolymer including the monomer, and combinations thereof; wherein the monomer is selected from the group consisting of: the Formula I monomer, the Formula II monomer, and a combination thereof; wherein an amount of each monomer present in the mixture is selected to control at least one property of the mixture; wherein the property is selected from one of: volatility, solubility, crystallinity, melting point, phase transitions, shelf life, charge transport ability, and combinations thereof,
wherein Formula I monomer having a structure:

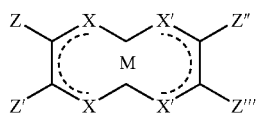

I wherein M is selected from the group consisting of: nickel (II), palladium (II), platinum (II), cobalt (I), iridium (I), rhodium (I), copper (II), copper (III), silver (III), and gold (III);
wherein L and L' are each independently selected from the group consisting of a halogen, NR$_3$, PR$_3$, NCS, SCN and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is PR$_3$, R is an alkoxy group (R'O);
wherein X and X' are each independently selected from the group consisting of: S, Se, O, NR', and a combination thereof; and
wherein Z, Z', Z" and Z''' are each independently selected from a polymerizable group, wherein is R' is selected from a polymerizable group;
wherein the polymerizable group is selected from a group consisting of: vinyl; allyl; 4-styryl; acroyl; epoxide; oxetane; cyclic-carbonate; methacroyl; acrylonitrile; isocyanate; isothiocyanate; an epoxide; a strained ring olefin; (—CH$_2$)$_\eta$SiCl$_3$; (—CH$_2$)$_\eta$Si(OCH$_2$CH$_3$)$_3$; (—CH$_2$)$_\eta$Si(OCH$_3$)$_3$, where $\eta$ is an integer number from 0 to 25; and a compound having the following structure:

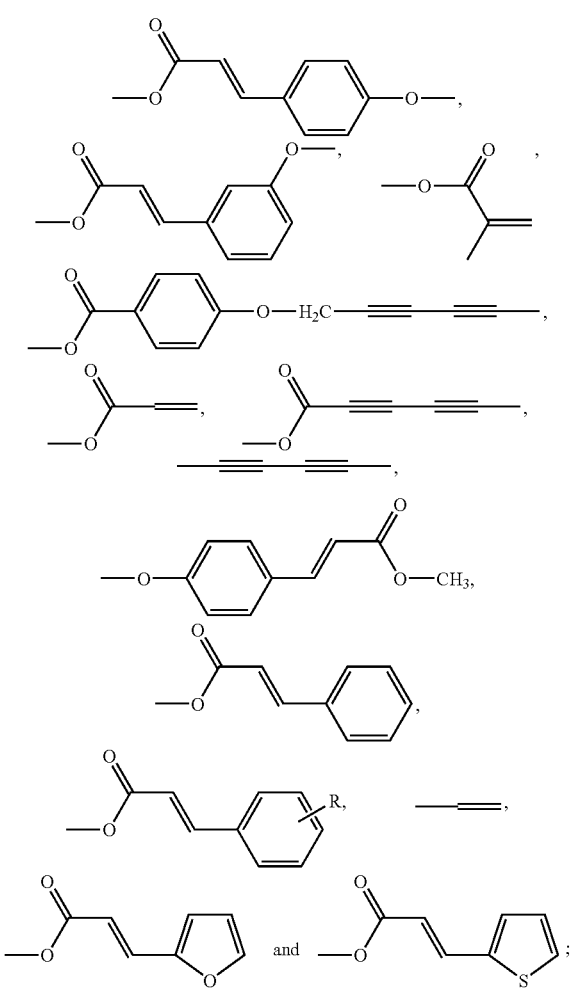

and
wherein Formula II monomer having a structure:

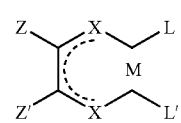

II wherein M is selected from the group consisting of: nickel (II), palladium (II), platinum (II), cobalt (I), iridium (I), rhodium (I), copper(II), copper (III), silver (III), and gold (III);
wherein L and L' are each independently selected from the group consisting of: a halogen, NR$_3$, PR$_3$, NCS, SCN, and CN; wherein R is selected from the group consisting of: a linear or branched, unsubstituted alkyl group with up to 25 carbons; a linear or branched, substituted alkyl group with up to 25 carbons: an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z", Z" and Z'" are each independently selected from polymerizable group, wherein is R' is selected from a polymerizable group;

wherein the polymerizable group is selected from the group consisting of: vinyl; allyl; 4-styryl; acroyl; epoxide; oxetane; cyclic-carbonate; methacroyl; acrylonitrile; isocyanate; isothiocyanate; an epoxide: a strained rinq olefin; $(-CH_2)_n SiCl_3$; $(-CH_2)_n Si(OCH_2CH_3)_3$; $(-CH_2)_n Si(OCH_3)_3$, where η is an integer number from 0 to 25; and a compound having the following structure:

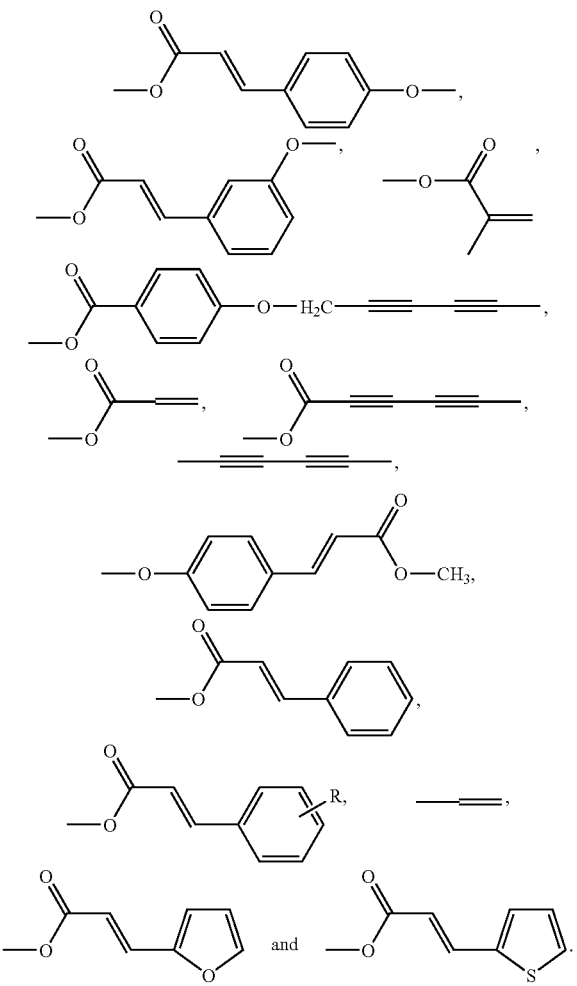

20. A material, comprising:

a mixture of components comprising a compound selected from the group consisting of: the Formula I monomer, the Formula II monomer, and a combination thereof; wherein an amount of each compound present in the mixture is selected to control at least one property of the mixture; wherein the property is selected from one of: volatility, solubility, crystallinity, melting point, phase transitions, shelf life, charge transport ability, and combinations thereof, wherein Formula I monomer having a structure:

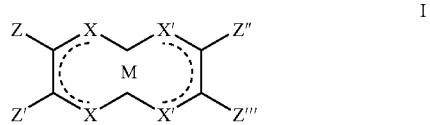

wherein M is selected from the group consisting of: nickel (II), palladium (II), platinum (II), cobalt (I), iridium (I) rhodium (I), copper (II), copper (III), silver (III), and gold (III);

wherein L and L' are each independently selected from the group consisting of a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons: an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z" and Z'" are each independently selected from a polymerizable group, wherein is R' is selected from a polymerizable group;

wherein the polymerizable group is selected from a group consisting of: vinyl; allyl; 4-styryl; acroyl; epoxide; oxetane; cyclic-carbonate; methacroyl; acrylonitrile; isocyanate; isothiocyanate; an epoxide; a strained ring olefin; $(-CH_2)_n SiCl_3$; $(-CH_2)_n Si(OCH_2CH_3)_3$; $(-CH_2)_n Si(OCH_3)_3$, where η is an integer number from 0 to 25; and a compound having the following structure:

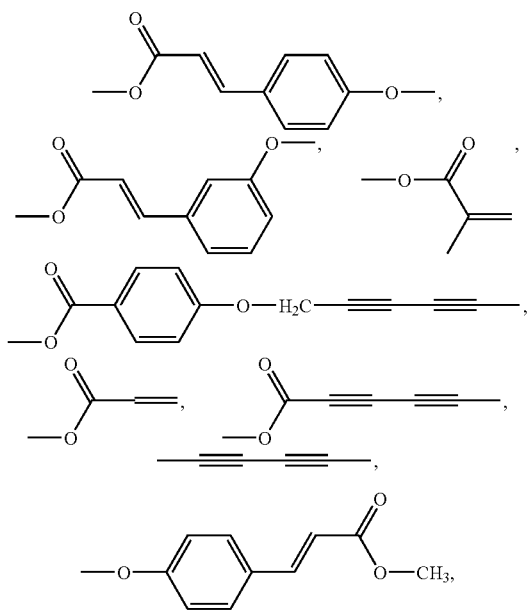

-continued

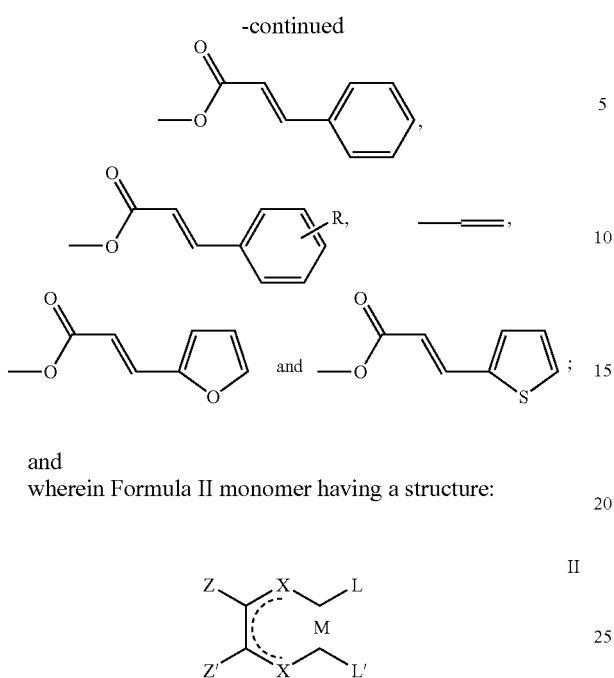

and
wherein Formula II monomer having a structure:

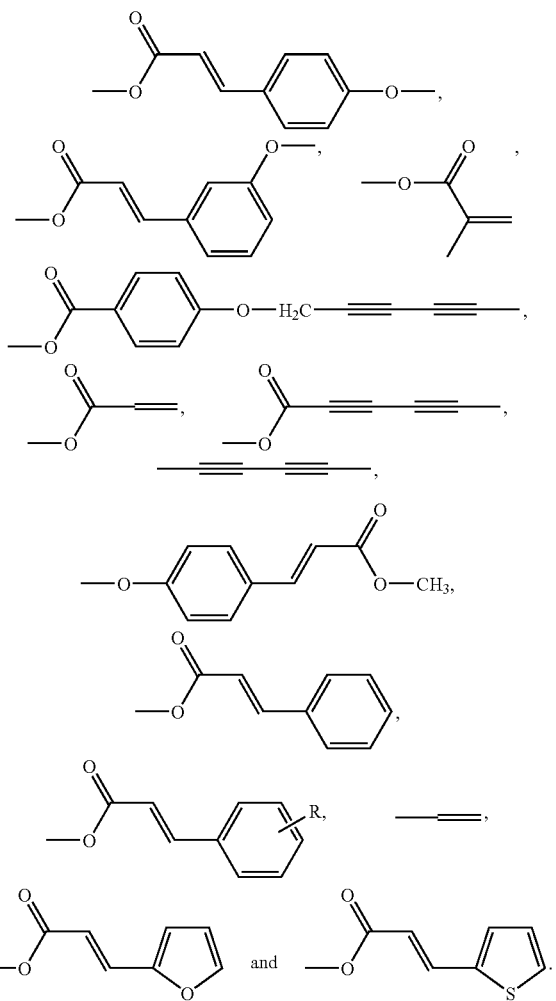

wherein M is selected from the group consisting of: nickel (II), palladium (II), platinum (II), cobalt (I), iridium (I), rhodium (I), copper(II), copper (III), silver (III), and gold (III);

wherein L and L' are each independently selected from the group consisting of: a halogen, $NR_3$, $PR_3$, NCS, SCN, and CN; wherein R is selected from the group consisting of: a linear or branched, unsubstituted alkyl group with up to 25 carbons; a linear or branched, substituted alkyl group with up to 25 carbons; an unsubstituted aryl group; a substituted aryl group; and when L is $PR_3$, R is an alkoxy group (R'O);

wherein X and X' are each independently selected from the group consisting of: S, Se, O, NR', and a combination thereof; and wherein Z, Z', Z" and Z'" are each independently selected from polymerizable group, wherein is R' is selected from a polymerizable group;

wherein the polymerizable group is selected from the group consisting of: vinyl: allyl; 4-styryl; acroyl; epoxide; oxetane; cyclic-carbonate; methacroyl; acry-lonitrile; isocyanate; isothiocyanate: an epoxide; a strained ring olefin; $(-CH_2)_n SiCl_3$; $(-CH_2)_n Si(OCH_2CH_3)_3$; $(-CH_2)_n Si(OCH_3)_3$, where η is an integer number from 0 to 25; and a compound having the following structure:

* * * * *

UNITED STATES PATENT AND TRADEMARK OFFICE
CERTIFICATE OF CORRECTION

PATENT NO.        : 7,842,830 B2
APPLICATION NO.   : 11/629268
DATED             : November 30, 2010
INVENTOR(S)       : Marder et al.

Page 1 of 2

It is certified that error appears in the above-identified patent and that said Letters Patent is hereby corrected as shown below:

Column 5, lines 36 and 37 should read:
    FIG. 14 of Example 3 illustrates a potential glassy material based on nickel bis(dithiolene) complex.

Column 10, line 55:
    Delete "the" after "to,"

Column 48, line 60:
    After "over", add "the"

Column 52, line 62:
    Add "an" before "additional"

Column 54, line 62:
    Add "an" before "additional"

Column 60, line 37:
    After "include" delete "of"

Column 60, line 39:
    After "but" add "not"

Column 60, line 65:
    After "but" add "not"

Column 64, line 50:
    After "from" add "a"

Signed and Sealed this
Twenty-fourth Day of May, 2011

David J. Kappos
*Director of the United States Patent and Trademark Office*

CERTIFICATE OF CORRECTION (continued)
U.S. Pat. No. 7,842,830 B2

Column 68, line 11:
    After "from" add "a"

Column 70, line 63:
    After "from" add "a"

Column 73, line 50:
    After "from" add "a"

Column 76, line 9:
    After "from" add "a"

Column 78, line 58:
    After "from" add "a"

Column 81, line 27:
    After "from" add "a"

Column 84, line 2:
    After "from" add "a"